(12) United States Patent
Flohr et al.

(10) Patent No.: US 8,349,824 B2
(45) Date of Patent: Jan. 8, 2013

(54) TRIAZOLOPYRIDINE COMPOUNDS

(75) Inventors: Alexander Flohr, Loerrach (DE); Luca Gobbi, Muttenz (CH); Katrin Groebke Zbinden, Liestal (CH); Matthias Koerner, Grenzach-Wyhlen (DE); Jens-Uwe Peters, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/308,588

(22) Filed: Dec. 1, 2011

(65) Prior Publication Data

US 2012/0142665 A1 Jun. 7, 2012

(30) Foreign Application Priority Data

Dec. 7, 2010 (EP) .................................. 10194014

(51) Int. Cl.
| | |
|---|---|
| A61K 31/397 | (2006.01) |
| A61K 31/55 | (2006.01) |
| A61K 31/541 | (2006.01) |
| A61K 31/5355 | (2006.01) |
| A61K 31/437 | (2006.01) |
| C07D 243/00 | (2006.01) |
| C07D 279/10 | (2006.01) |
| C07D 413/14 | (2006.01) |
| C07D 471/04 | (2006.01) |

(52) U.S. Cl. ............... 514/210.18; 514/221; 514/228.5; 514/233.2; 514/303; 540/556; 544/58.2; 544/127; 546/119

(58) Field of Classification Search ............. 514/210.18, 514/221, 228.5, 233.2, 303; 540/556; 544/58.2, 544/127; 546/119
See application file for complete search history.

(56) References Cited

FOREIGN PATENT DOCUMENTS

| WO | 2005/012485 | 2/2005 |
| WO | 2009/152825 | 12/2009 |

OTHER PUBLICATIONS

Sano, H., "J. Neurochem." 105:546-556 (2008).
Verhoest et al., "J. Med. Chem." 52:5188-5196 ( 2009).
Seeger et al., "Brain Res." 985:113-126 ( 2003).
Soderling et al., "Proc. Natl. Acad. Sci. USA" 96(12):7071-7076 ( 1999).
Coskran et al., "J. Histochem. Cytochem." 54(11):1205-1213 ( 2006).
Vandenberg et al., "Exp. Opin. Ther. Targets" 5(4):507-518 ( 2001).
Siuciak et al., "Neuropharmacology" 51(2):374-385 ( 2006).
Fujishige et al., "J. Biol. Chem." 274:18438-18445 ( 1999).
Fujishige et al., "Eur. J. Biochem." 266(3):1118-1127 ( 1999).
"International Search Report PCTEP2011071685 mailed Feb. 22, 2012".
Loughney et al., "Gene" 234(1):109-117 ( 1999).
Kehler et al., "Expert Opinion on Therapeutic Patents" 19(12):1715-1725 ( 2009).
Beavo et al., "Physiol. Rev." 75:725-748 ( 1995).
Sharma, T., "British Journal of Psychiatry" 174:44-51 ( 1999).
Rodefer et al., "Eur. J. Neuroscience" 2:1070-1076 ( 2005).
Javitt et al., "Biol. Psychiatry" 45:668-679 ( 1999).
Manallack et al., "J. Med. Chem." 48(10):3449-3462 ( 2005).
Graybiel et al., "Curr. Biol." 10:R509-R511 ( 2000).
Nakazato et al., "Exp. Opin. Ther. Patents" 10(1):75-98 ( 2000).
Soderling et al., "Curr. Opin. Cell Biol." 12:174-179 ( 2000).
Siuciak et al., "Neuropharmacology" 51(2):386-396 ( 2006).
Conti et al., "Prog. Nucleic Acid Res. Mol. Biol." 63:1-38 ( 1999).

*Primary Examiner* — Rebecca Anderson
*Assistant Examiner* — Samantha Shterengarts
(74) *Attorney, Agent, or Firm* — George W. Johnston; Patricia S. Rocha-Tramaloni; Kimberly J. Prior

(57) ABSTRACT

The invention is concerned with triazolopyridine compounds of formula (I)

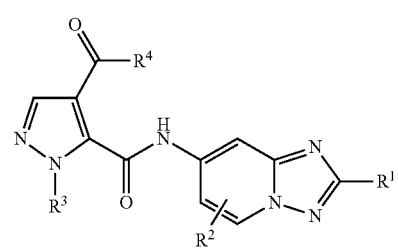

(I)

wherein $R^1$, $R^2$, $R^3$ and $R^4$ are as defined in the description and in the claims, as well as physiologically acceptable salts thereof. These compounds inhibit PDE10A and can be used as pharmaceuticals.

26 Claims, No Drawings

TRIAZOLOPYRIDINE COMPOUNDS

PRIORITY TO RELATED APPLICATION(S)

This application claims the benefit of European Patent Application No. 10194014.6, filed Dec. 7, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron,* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry,* 174(suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960's based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry,* 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididymal sperm (Coskran T. M, et al., *J. Histochem. Cytochem.* 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

SUMMARY OF THE INVENTION

The invention provides novel triazolopyridine compounds of formula (I)

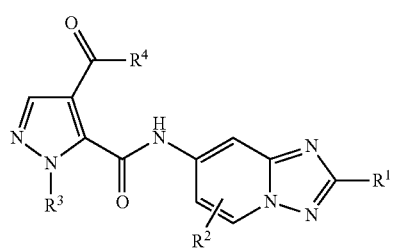

wherein
R¹ is halogen, lower-alkyl, lower-haloalkyl, lower-hydroxyalkyl, lower-alkoxy, lower-alkoxy-lower-alkyl, —C(O)—NR⁹R¹⁰, aryl, heteroaryl or NR⁷R⁸, wherein said aryl and said heteroaryl are each optionally substituted by 1 to 3 substituents independently selected from the group consisting of hydroxyl, halogen, lower-alkyl, lower-alkoxy, lower-alkoxy-lower-alkyl, lower-haloalkyl and lower-haloalkoxy;
R² is hydrogen, halogen, lower-alkyl, lower-haloalkyl, lower-hydroxyalkyl, lower-alkoxy or lower-alkoxy-lower-alkyl;
R³ is hydrogen, lower-alkyl, lower-haloalkyl, lower-hydroxyalkyl, lower-alkoxy or lower-alkoxy-lower-alkyl;
R⁴ is hydroxyl, lower-alkoxy or NR⁵R⁶;
R⁵ and R⁶ are each independently hydrogen, lower-alkyl, lower-haloalkyl, lower-hydroxyalkyl, lower-alkoxy-lower-alkyl, cycloalkyl or heterocyclyl, or R⁵ and/or R⁶ are lower-alkyl substituted by a substituent selected from the group consisting of heteroaryl, lower-alkyl-heteroaryl and lower-alkoxy-C(O)—, or
R⁵ and R⁶, together with the nitrogen atom to which they are attached, form a heterocyclyl, bicyclo-heterocyclyl or spiro-heterocyclyl, wherein said heterocyclyl is optionally substituted by 1 to 3 substituents independently selected from the group consisting of hydroxyl, halogen, lower-alkyl, lower-alkoxy, lower-alkoxy-lower-alkyl, lower-haloalkyl and oxo;
R⁷ and R⁸ are each independently hydrogen, lower-alkyl, lower-haloalkyl, lower-hydroxyalkyl, lower-alkoxy-lower-alkyl or cycloalkyl, or
R⁷ and R⁸, together with the nitrogen atom to which they are attached, form a heterocyclyl optionally substituted by a substituent selected from the group consisting of hydroxyl, halogen and oxo; and
R⁹ and R¹⁰ are each independently hydrogen, lower-alkyl, lower-haloalkyl, lower-hydroxyalkyl or lower-alkoxy-lower-alkyl,
or a pharmaceutically acceptable salt thereof.

Further, the invention provides a process for the manufacture of the above compounds, pharmaceutical compositions which contain such compounds as well as methods for the production of pharmaceutical compositions.

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

DETAILED DESCRIPTION OF THE INVENTION

Unless otherwise indicated, the following definitions are set forth to illustrate and define the meaning and scope of the various terms used to describe the invention herein.

It must be noted that, as used in the specification and the claims, the singular forms "a", "an" and "the" include plural referents unless the context clearly dictates otherwise.

When indicating the number of subsituents, the term "one or more" means from one substituent to the highest possible number of substitution, i.e. replacement of one hydrogen up to replacement of all hydrogens by substituents.

In this specification the term "lower" is used to mean a group consisting of one to seven, more specifically of one to four carbon atom(s).

The term "halogen" refers to fluorine, chlorine, bromine and iodine, more specifically fluorine, chlorine and bromine.

The term "alkyl" refers to a branched or straight-chain monovalent saturated aliphatic hydrocarbon radical of one to twenty carbon atoms, more specifically one to sixteen carbon atoms, yet more specifically one to ten carbon atoms.

The term "lower-alkyl", alone or in combination with other groups, refers to a branched or straight-chain monovalent alkyl radical of one to seven carbon atoms, more specifically one to four carbon atoms. This term is further exemplified by such radicals as methyl, ethyl, n-propyl, isopropyl, n-butyl, s-butyl, t-butyl and the like.

The term "lower-haloalkyl", alone or in combination with other groups, refers to lower-alkyl groups which are mono- or multiply substituted with halogen, particularly fluoro. Examples of lower-haloalkyl groups are —CFH₂, —CF₂H, —CF₃, CF₃CH₂—, CF₃(CH₂)₂—, (CF₃)₂CH— and CF₂H—CH₂—.

The term "lower-hydroxyalkyl" refers to lower-alkyl groups which are substituted by 1 to 3 hydroxyl groups. Examples of lower-hydroxyalkyl groups are hydroxy-methyl, 2-hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "—C(O)—NH-lower-haloalkyl" refers to groups in which one hydrogen of —C(O)—NH₂ is substituted by lower-haloalkyl.

The term "alkoxy" refers to the group R'—O—, wherein R' is an alkyl. The term "lower-alkoxy", alone or in combination with other groups, refers to the group R'—O—, wherein R' is a lower-alkyl.

The term "lower-alkoxy-lower-alkyl" refers to lower-alkyl groups which are mono- or multiply substituted with lower-alkoxy. Examples of lower-alkoxy-lower-alkyl groups are —CH$_2$—O—CH$_3$, —CH$_2$—CH$_2$—O—CH$_3$ and —CH$_2$—O—CH$_2$—CH$_3$.

The term "lower-haloalkoxy" refers to a group of the formula lower-haloalkyl-O—.

The term "amino" refers to a monovalent group that has a nitrogen atom with two hydrogen atoms (represented by —NH$_2$).

The term "oxo" when referring to substituents on heterocyclyl means that an oxygen atom is attached to the heterocyclyl ring. Thereby, the "oxo" can either replace two hydrogen atoms on a carbon atom, or it can simply be attached to sulfur, so that the sulfur exists in oxidized form, i.e. bearing one or two oxygens.

The term "cycloalkyl" refers to a monovalent carbocyclic radical of 3 to 10 carbon atoms, more specifically 3 to 6 carbon atoms, such as cyclopropyl, cyclobutyl, cyclopentyl or cyclohexyl.

The term "heterocyclyl" refers to a monovalent saturated 4- to 6-membered monocyclic ring containing one, two or three ring heteroatoms independently selected from N, O and S, the remaining ring atoms being carbon atoms, wherein the point of attachment can be through either a carbon atom or a heteroatom. Examples of heterocyclyl are morpholinyl and piperidinyl.

The term "bicyclo-heterocyclyl" refers to a monovalent saturated 7- to 10-membered bicyclic ring containing one, two or three ring heteroatoms independently selected from N, O and S, the remaining ring atoms being carbon atoms, wherein the point of attachment can be through either a carbon atom or a heteroatom. Examples of heterocyclyl are 2-oxa-5-azabicyclo[2.2.1]heptane and 1,4-diaza-bicyclo[3.2.1]octane.

The term "spiro-heterocyclyl" refers to a monovalent saturated 7- to 11-membered bicyclic moiety with the rings connected through one atom, containing one, two or three ring heteroatoms independently selected from N, O and S, the remaining ring atoms being carbon atoms, wherein the point of attachment can be through either a carbon atom or a heteroatom. An example of a spiro-heterocyclyl ring is 2-oxa-6-azaspiro[3.3]heptane.

The term "aryl" refers to a monovalent aromatic hydrocarbon ring. The aryl group more specifically includes 6 to 10 carbon atoms. An example of an aryl group is phenyl.

The term "heteroaryl" refers to an aromatic 5- or 6-membered monocyclic ring or 9- or 10-membered bicyclic ring which contains 1, 2 or 3 atoms independently selected from nitrogen, oxygen and sulphur, such as pyridinyl.

The term "lower-alkyl-heteroaryl" refers to heteroaryl which is substituted with lower-alkyl. Examples of lower-alkyl-heteroaryl are methylpyridinyl.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as a COOH group, can further form salts with bases. Examples of such salts are alkaline, earth-alkaline and ammonium salts such as Na—, K—, Ca— and trimethylammonium salt. The term "pharmaceutically acceptable salts" also refers to such salts. Particular salts are those obtained by the addition of an acid.

The term "pharmaceutically acceptable esters" embraces derivatives of the compounds of formula (I), in which a carboxy group has been converted to an ester. Lower alkyl, lower hydroxyalkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. Particular esters are methyl, ethyl, propyl, butyl and benzyl esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention provides compounds of formula (I)

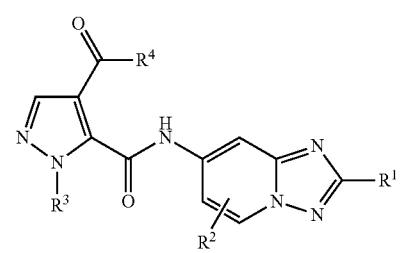

(I)

wherein

R$^1$ is halogen, lower-alkyl, lower-haloalkyl, lower-hydroxyalkyl, lower-alkoxy, lower-alkoxy-lower-alkyl, —C(O)—NR$^9$R$^{10}$, aryl, heteroaryl or NR$^7$R$^8$, wherein said aryl and said heteroaryl are each independently substituted by 1 to 3 substituents independently selected from the group consisting of hydroxyl, halogen, lower-alkyl, lower-alkoxy, lower-alkoxy-lower-alkyl, lower-haloalkyl and lower-haloalkoxy;

R$^2$ is hydrogen, halogen, lower-alkyl, lower-haloalkyl, lower-hydroxyalkyl, lower-alkoxy or lower-alkoxy-lower-alkyl;

R$^3$ is hydrogen, lower-alkyl, lower-haloalkyl, lower-hydroxyalkyl, lower-alkoxy or lower-alkoxy-lower-alkyl;

R$^4$ is hydroxyl, lower-alkoxy or NR$^5$R$^6$;

R$^5$ and R$^6$ are each independently hydrogen, lower-alkyl, lower-haloalkyl, lower-hydroxyalkyl, lower-alkoxy-lower-alkyl, cycloalkyl or heterocyclyl, or R$^5$ and/or R$^6$ are lower-alkyl substituted by a substituent selected from the group consisting of heteroaryl, lower-alkyl-heteroaryl and lower-alkoxy-C(O)—, or R$^5$ and R$^6$, together with the nitrogen atom to which they are attached, form a heterocyclyl, bicyclo-heterocyclyl or spiro-heterocyclyl, wherein said heterocyclyl is optionally substituted by 1 to 3 substituents independently selected from the group consisting of hydroxyl, halogen, lower-alkyl, lower-alkoxy, lower-alkoxy-lower-alkyl, lower-haloalkyl and oxo;

$R^7$ and $R^8$ are each independently hydrogen, lower-alkyl, lower-haloalkyl, lower-hydroxyalkyl, lower-alkoxy-lower-alkyl or cycloalkyl, or $R^7$ and $R^8$, together with the nitrogen atom to which they are attached, form a heterocyclyl optionally substituted by a substituent selected from the group consisting of hydroxyl, halogen and oxo; and $R^9$ and $R^{10}$ are each independently hydrogen, lower-alkyl, lower-haloalkyl, lower-hydroxyalkyl or lower-alkoxy-lower-alkyl, or a pharmaceutically acceptable salt thereof.

The present invention also provides compounds of formula (I)

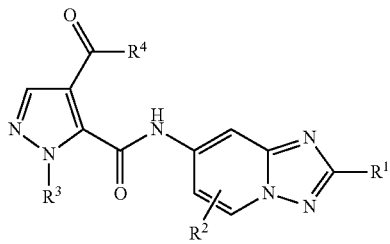

(I)

wherein
$R^1$ is lower-alkyl, —C(O)—NH-lower-haloalkyl, aryl, heteroaryl or $NR^7R^8$, wherein said aryl and said heteroaryl are each optionally substituted by 1 to 3 substituents independently selected from the group consisting of hydroxyl, halogen, lower-alkyl, lower-alkoxy and lower-haloalkyl;
$R^2$ is hydrogen, halogen or lower-alkyl;
$R^3$ is hydrogen or lower-alkyl;
$R^4$ is hydroxyl, lower-alkoxy or $NR^5R^6$;
$R^5$ and $R^6$ are each independently hydrogen, lower-alkyl, lower-haloalkyl, lower-alkoxy-lower-alkyl, lower-alkyl substituted by lower-alkyl-heteroaryl or heterocyclyl, or
$R^5$ and $R^6$, together with the nitrogen atom to which they are attached, form a heterocyclyl which is optionally substituted by 1 to 3 substituents independently selected from the group consisting of hydroxyl, halogen, lower-alkyl, lower-alkoxy, lower-haloalkyl and oxo;
$R^7$ and $R^8$ are each independently lower-alkyl or, together with the nitrogen atom to which they are attached, form a morpholinyl ring.
or pharmaceutically acceptable salts thereof.

The compounds of formula (I) can have one or more asymmetric C atoms and can therefore exist as an enantiomeric mixture, mixture of stereoisomers or as optically pure compounds. The compounds of formula (I) include all diastereomers, tautomers, racemates and mixtures thereof.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

A particular embodiment of the present invention provides compounds of formula (I) as described above, wherein $R^1$ is halogen, lower-alkyl, —C(O)—$NR^9R^{10}$, phenyl, pyridinyl or $NR^7R^8$, wherein said phenyl and said pyridinyl are each optionally substituted by 1 to 3 substituents independently selected from the group consisting of hydroxyl, halogen, lower-alkyl, lower-alkoxy, lower-haloalkyl and lower-haloalkoxy; $R^7$ and $R^8$ are each independently lower-alkyl, lower-haloalkyl or cycloalkyl, or $R^7$ and $R^8$, together with the nitrogen atom to which they are attached, form pyrrolidin-1-yl, 2-oxopyrrolidin-1-yl or morpholin-4-yl; and $R^9$ and $R^{10}$ are each independently hydrogen, lower-alkyl, lower-haloalkyl or lower-alkoxy-lower-alkyl. More specifically, $R^1$ is phenyl, 3-fluorophenyl, 2-methoxyphenyl, 3-methoxy-phenyl, pyridin-3-yl, 2-fluoropyridin-4-yl, dimethylamino, ethyl-methyl-amino cyclopropyl-methyl-amino, pyrrolidin-1-yl or morpholin-4-yl.

Another particular embodiment of the present invention provides compounds of formula (I) as described above, wherein $R^2$ is hydrogen, halogen or lower-alkyl, more specifically hydrogen.

Yet another particular embodiment of the present invention provides compounds of formula (I) as described above, wherein $R^3$ is lower-alkyl, more specifically methyl.

A particular embodiment of the present invention provides compounds of formula (I) as described above, wherein
$R^4$ is hydroxyl, lower-alkoxy or $NR^5R^6$;
$R^5$ and $R^6$ are each independently hydrogen, lower-alkyl, lower-haloalkyl, lower-hydroxyalkyl, lower-alkoxy-lower-alkyl, cyclopropyl, cyclopentyl, oxetanyl or tetrahydrofuranyl, or $R^5$ and/or $R^6$ are lower-alkyl substituted by a substituent selected from the group consisting of lower-alkyl-pyridinyl and methoxycarbonyl, or
$R^5$ and $R^6$, together with the nitrogen atom to which they are attached, form a heterocyclyl selected from the group consisting of azetidinyl, pyrrolidinyl, piperazinyl, morpholinyl and thiomorpholinyl, wherein said heterocyclyl is optionally substituted by 1 to 3 substituents independently selected from the group consisting of halogen, lower-alkyl, lower-alkoxy and oxo, or $R^5$ and $R^6$, together with the nitrogen atom to which they are attached, form 2-oxa-5-azabicyclo[2.2.1]heptanyl, 2-oxa-6-azaspiro[3.3]heptanyl or 1,4-diaza-bicyclo[3.2.1]octanyl.

Another particular embodiment of the present invention provides compounds of formula (I) as described above, wherein
$R^4$ is $NR^5R^6$;
$R^5$ and $R^6$ are each independently methyl, ethyl, 2-fluoroethyl, 2-methoxyethyl or cyclopropyl, or
$R^5$ and $R^6$, together with the nitrogen atom to which they are attached, form a heterocyclyl selected from the group consisting of azetidinyl, 3-fluoroazetidinyl, morpholin-4-yl and pyrrolidinyl, or $R^5$ and $R^6$, together with the nitrogen atom to which they are attached, form 2-oxa-6-azaspiro[3.3]heptanyl or 1,4-diaza-bicyclo[3.2.1]octanyl.

Particular compounds of formula (I) are those selected from the group consisting of:
methyl 1-methyl-5-(2-phenyl-[1,2,4]triazolo[1,5-a]pyridin-7-ylcarbamoyl)-1H-pyrazole-4-carboxylate,
1-methyl-5-(2-phenyl-[1,2,4]triazolo[1,5-a]pyridin-7-ylcarbamoyl)-1H-pyrazole-4-carboxylic acid,
4-(azetidine-1-carbonyl)-1-methyl-N-(2-phenyl-[1,2,4]triazolo[1,5-a]pyridin-7-yl)-1H-pyrazole-5-carboxamide,
N4-(2-methoxyethyl)-N4,1-dimethyl-N5-(2-phenyl-[1,2,4]triazolo[1,5-a]pyridin-7-yl)-1H-pyrazole-4,5-dicarboxamide,
N4-ethyl-N4,1-dimethyl-N5-(2-phenyl-[1,2,4]triazolo[1,5-a]pyridin-7-yl)-1H-pyrazole-4,5-dicarboxamide,
N4,N4-bis(2-methoxyethyl)-1-methyl-N5-(2-phenyl-[1,2,4]triazolo[1,5-a]pyridin-7-yl)-1H-pyrazole-4,5-dicarboxamide,
N4-ethyl-1-methyl-N5-(2-phenyl-[1,2,4]triazolo[1,5-a]pyridin-7-yl)-1H-pyrazole-4,5-dicarboxamide,
4-(azetidine-1-carbonyl)-1-methyl-N-(2-morpholino-[1,2,4]triazolo[1,5-a]pyridin-7-yl)-1H-pyrazole-5-carboxamide, 4-(azetidine-1-carbonyl)-1-methyl-N-(8-methyl-2-phenyl-[1,2,4]triazolo[1,5-a]pyridin-7-yl)-1H-pyrazole-5-carboxamide,
4-(azetidine-1-carbonyl)-1-methyl-N-(6-methyl-2-phenyl-[1,2,4]triazolo[1,5-a]pyridin-7-yl)-1H-pyrazole-5-carboxamide,
N4,N4,1-trimethyl-N5-(2-phenyl-[1,2,4]triazolo[1,5-a]pyridin-7-yl)-1H-pyrazole-4,5-dicarboxamide,
1-methyl-4-(morpholine-4-carbonyl)-N-(2-phenyl-[1,2,4]triazolo[1,5-a]pyridin-7-yl)-1H-pyrazole-5-carboxamide,
1-methyl-N-(2-phenyl-[1,2,4]triazolo[1,5-a]pyridin-7-yl)-4-(pyrrolidine-1-carbonyl)-1H-pyrazole-5-carboxamide,
(S)-1-methyl-N5-(2-phenyl-[1,2,4]triazolo[1,5-a]pyridin-7-yl)-N4-(tetrahydrofuran-3-yl)-1H-pyrazole-4,5-dicarboxamide,
(R)-1-methyl-N5-(2-phenyl-[1,2,4]triazolo[1,5-a]pyridin-7-yl)-N4-(tetrahydrofuran-3-yl)-1H-pyrazole-4,5-dicarboxamide,
N4-(3-methoxypropyl)-1-methyl-N5-(2-phenyl-[1,2,4]triazolo[1,5-a]pyridin-7-yl)-1H-pyrazole-4,5-dicarboxamide,
1-methyl-N4-(oxetan-3-yl)-N5-(2-phenyl-[1,2,4]triazolo[1,5-a]pyridin-7-yl)-1H-pyrazole-4,5-dicarboxamide,
N4,N4-diethyl-1-methyl-N5-(2-phenyl-[1,2,4]triazolo[1,5-a]pyridin-7-yl)-1H-pyrazole-4,5-dicarboxamide,
N4-isopropyl-1-methyl-N5-(2-phenyl-[1,2,4]triazolo[1,5-a]pyridin-7-yl)-1H-pyrazole-4,5-dicarboxamide,
N4,1-dimethyl-N4-((6-methylpyridin-3-yl)methyl)-N5-(2-phenyl-[1,2,4]triazolo[1,5-a]pyridin-7-yl)-1H-pyrazole-4,5-dicarboxamide,
N4-(2-fluoroethyl)-N4,1-dimethyl-N5-(2-morpholino-[1,2,4]triazolo[1,5-a]pyridin-7-yl)-1H-pyrazole-4,5-dicarboxamide,
4-(1,1-Dioxo-1lambda*6*-thiomorpholine-4-carbonyl)-2-methyl-2H-pyrazole-3-carboxylic acid (2-phenyl-[1,2,4]triazolo[1,5-a]pyridin-7-yl)-amide,
N4,1-dimethyl-N5-(2-phenyl-[1,2,4]triazolo[1,5-a]pyridin-7-yl)-1H-pyrazole-4,5-dicarboxamide,
4-(3-methoxyazetidine-1-carbonyl)-1-methyl-N-(2-phenyl-[1,2,4]triazolo[1,5-a]pyridin-7-yl)-1H-pyrazole-5-carboxamide,
4-(3-fluoroazetidine-1-carbonyl)-1-methyl-N-(2-phenyl-[1,2,4]triazolo[1,5-a]pyridin-7-yl)-1H-pyrazole-5-carboxamide,
2-Methyl-2H-pyrazole-3,4-dicarboxylic acid 4-[(2-fluoro-ethyl)-methyl-amide]3-[(2-phenyl-[1,2,4]triazolo[1,5-a]pyridin-7-yl)-amide], isopropyl 1-methyl-5-(2-phenyl-[1,2,4]triazolo[1,5-a]pyridin-7-ylcarbamoyl)-1H-pyrazole-4-carboxylate,
ethyl 1-methyl-5-(2-phenyl-[1,2,4]triazolo[1,5-a]pyridin-7-ylcarbamoyl)-1H-pyrazole-4-carboxylate,
1-methyl-4-(morpholine-4-carbonyl)-N-(2-morpholino-[1,2,4]triazolo[1,5-a]pyridin-7-yl)-1H-pyrazole-5-carboxamide,
4-(azetidine-1-carbonyl)-N-(6-fluoro-2-phenyl-[1,2,4]triazolo[1,5-a]pyridin-7-yl)-1-methyl-1H-pyrazole-5-carboxamide,
N-(6-fluoro-2-phenyl-[1,2,4]triazolo[1,5-a]pyridin-7-yl)-1-methyl-4-(pyrrolidine-1-carbonyl)-1H-pyrazole-5-carboxamide,
N-(6-fluoro-2-phenyl-[1,2,4]triazolo[1,5-a]pyridin-7-yl)-1-methyl-4-(morpholine-4-carbonyl)-1H-pyrazole-5-carboxamide,
7-(4-(azetidine-1-carbonyl)-1-methyl-1H-pyrazole-5-carboxamido)-N-(3,3,3-trifluoropropyl)-[1,2,4]triazolo[1,5-a]pyridine-2-carboxamide,
N-(2-isopropyl-[1,2,4]triazolo[1,5-a]pyridin-7-yl)-1-methyl-4-(pyrrolidine-1-carbonyl)-1H-pyrazole-5-carboxamide,
4-(azetidine-1-carbonyl)-N-(2-(dimethylamino)-[1,2,4]triazolo[1,5-a]pyridin-7-yl)-1-methyl-1H-pyrazole-5-carboxamide,
N-(2-(dimethylamino)-[1,2,4]triazolo[1,5-a]pyridin-7-yl)-1-methyl-4-(morpholine-4-carbonyl)-1H-pyrazole-5-carboxamide,
N-(2-(dimethylamino)-[1,2,4]triazolo[1,5-a]pyridin-7-yl)-1-methyl-4-(pyrrolidine-1-carbonyl)-1H-pyrazole-5-carboxamide,
N-(2-(dimethylamino)-[1,2,4]triazolo[1,5-a]pyridin-7-yl)-4-(3-fluoroazetidine-1-carbonyl)-1-methyl-1H-pyrazole-5-carboxamide,
N4,N4-diethyl-1-methyl-N5-(2-morpholino-[1,2,4]triazolo[1,5-a]pyridin-7-yl)-1H-pyrazole-4,5-dicarboxamide,
N4,N4,1-trimethyl-N5-(2-morpholino-[1,2,4]triazolo[1,5-a]pyridin-7-yl)-1H-pyrazole-4,5-dicarboxamide,
N4-ethyl-N4,1-dimethyl-N5-(2-morpholino-[1,2,4]triazolo[1,5-a]pyridin-7-yl)-1H-pyrazole-4,5-dicarboxamide,
1-methyl-N-(2-morpholino-[1,2,4]triazolo[1,5-a]pyridin-7-yl)-4-(pyrrolidine-1-carbonyl)-1H-pyrazole-5-carboxamide,
4-(3-fluoroazetidine-1-carbonyl)-1-methyl-N-(2-morpholino-[1,2,4]triazolo[1,5-a]pyridin-7-yl)-1H-pyrazole-5-carboxamide,
4-(azetidine-1-carbonyl)-1-methyl-N-(2-(pyridin-3-yl)-[1,2,4]triazolo[1,5-a]pyridin-7-yl)-1H-pyrazole-5-carboxamide,
1-methyl-4-(morpholine-4-carbonyl)-N-(2-(pyridin-3-yl)-[1,2,4]triazolo[1,5-a]pyridin-7-yl)-1H-pyrazole-5-carboxamide,
1-methyl-N-(2-(pyridin-3-yl)-[1,2,4]triazolo[1,5-a]pyridin-7-yl)-4-(pyrrolidine-1-carbonyl)-1H-pyrazole-5-carboxamide,
4-(3-fluoroazetidine-1-carbonyl)-1-methyl-N-(2-(pyridin-3-yl)-[1,2,4]triazolo[1,5-a]pyridin-7-yl)-1H-pyrazole-5-carboxamide,
N4-cyclopropyl-N4,1-dimethyl-N5-(2-phenyl-[1,2,4]triazolo[1,5-a]pyridin-7-yl)-1H-pyrazole-4,5-dicarboxamide,
N4,1-dimethyl-N5-(2-phenyl-[1,2,4]triazolo[1,5-a]pyridin-7-yl)-N4-(2,2,2-trifluoroethyl)-1H-pyrazole-4,5-dicarboxamide,
4-(azetidine-1-carbonyl)-N-(2-isopropyl-[1,2,4]triazolo[1,5-a]pyridin-7-yl)-1-methyl-1H-pyrazole-5-carboxamide,
4-(3-fluoroazetidine-1-carbonyl)-N-(2-isopropyl-[1,2,4]triazolo[1,5-a]pyridin-7-yl)-1-methyl-1H-pyrazole-5-carboxamide,
N4-cyclopentyl-N4,1-dimethyl-N5-(2-morpholino-[1,2,4]triazolo[1,5-a]pyridin-7-yl)-1H-pyrazole-4,5-dicarboxamide,
N4-cyclopropyl-N4,1-dimethyl-N5-(2-morpholino-[1,2,4]triazolo[1,5-a]pyridin-7-yl)-1H-pyrazole-4,5-dicarboxamide,
N4,1-dimethyl-N5-(2-morpholino-[1,2,4]triazolo[1,5-a]pyridin-7-yl)-N4-(2,2,2-trifluoroethyl)-1H-pyrazole-4,5-dicarboxamide,
N4-cyclopropyl-N4,1-dimethyl-N5-(2-(pyridin-3-yl)-[1,2,4]triazolo[1,5-a]pyridin-7-yl)-1H-pyrazole-4,5-dicarboxamide,
N4-(2-fluoroethyl)-N4,1-dimethyl-N5-(2-(pyridin-3-yl)-[1,2,4]triazolo[1,5-a]pyridin-7-yl)-1H-pyrazole-4,5-dicarboxamide,
4-((1S,4S)-2-oxa-5-azabicyclo[2.2.1]heptane-5-carbonyl)-1-methyl-N-(2-(pyridin-3-yl)-[1,2,4]triazolo[1,5-a]pyridin-7-yl)-1H-pyrazole-5-carboxamide, 4-(Azetidine-1-carbonyl)-2-methyl-2H-pyrazole-3-carboxylic acid [2-(ethyl-methyl-amino)-[1,2,4]triazolo[1,5-a]pyridin-7-yl]-amide, 2-Methyl-4-(morpholine-4-carbonyl)-2H-pyrazole-3-carboxylic acid [2-(ethyl-methyl-amino)-[1,2,4]triazolo[1,5-a]pyridin-7-yl]-amide, 4-(azetidine-1-carbonyl)-1-methyl-N-(2-(pyrrolidin-1-yl)-[1,2,4]triazolo[1,5-a]pyridin-7-yl)-1H-pyrazole-5-carboxamide, 1-methyl-4-(morpholine-4-carbonyl)-N-(2-(pyrrolidin-1-yl)-[1,2,4]triazolo[1,5-a]pyridin-7-yl)-1H-pyrazole-5-carboxamide, 7-(4-(azetidine-1-carbonyl)-1-methyl-1H-pyrazole-5-carboxamido)-N,N-dimethyl-[1,2,4]triazolo[1,5-a]pyridine-2-carboxamide, 7-(4-(azetidine-1-carbonyl)-1-methyl-1H-pyrazole-5-carboxamido)-N-ethyl-[1,2,4]triazolo[1,5-a]pyridine-2-carboxamide, 7-(4-(azetidine-1-carbonyl)-1-methyl-1H-pyrazole-5-carboxamido)-N-(2-methoxyethyl)-[1,2,4]triazolo[1,5-a]pyridine-2-carboxamide, 4-(azetidine-1-carbonyl)-N-(2-bromo-[1,2,4]triazolo[1,5-a]pyridin-7-yl)-1-methyl-1H-pyrazole-5-carboxamide, 4-(azetidine-1-carbonyl)-1-methyl-N-(2-(pyridin-4-yl)-[1,2,4]triazolo[1,5-a]pyridin-7-yl)-1H-pyrazole-5-carboxamide, 4-(azetidine-1-carbonyl)-1-methyl-N-(2-(2-methylpyridin-4-yl)-[1,2,4]triazolo[1,5-a]pyridin-7-yl)-1H-pyrazole-5-carboxamide, 4-(azetidine-1-carbonyl)-1-methyl-N-(2-(5-methylpyridin-3-yl)-[1,2,4]triazolo[1,5-a]pyridin-7-yl)-1H-pyrazole-5-carboxamide, N-(2-(2-methoxyphenyl)-[1,2,4]triazolo[1,5-a]pyridin-7-yl)-1-methyl-4-(morpholine-4-carbonyl)-1H-pyrazole-5-carboxamide, 4-(azetidine-1-carbonyl)-N-(2-((2-fluoroethyl)(methyl)amino)-[1,2,4]triazolo[1,5-a]pyridin-7-yl)-1-methyl-1H-pyrazole-5-carboxamide, N-(2-((2-fluoroethyl)(methyl)amino)-[1,2,4]triazolo[1,5-a]pyridin-7-yl)-1-methyl-4-(morpholine-4-carbonyl)-1H-pyrazole-5-carboxamide, N5-(2-((2-fluoroethyl)(methyl)amino)-[1,2,4]triazolo[1,5-a]pyridin-7-yl)-N4,N4,1-trimethyl-1H-pyrazole-4,5-dicarboxamide, N4-ethyl-N5-(2-((2-fluoroethyl)(methyl)amino)-[1,2,4]triazolo[1,5-a]pyridin-7-yl)-N4,1-dimethyl-1H-pyrazole-4,5-dicarboxamide, N4-cyclopropyl-N5-(2-((2-fluoroethyl)(methyl)amino)-[1,2,4]triazolo[1,5-a]pyridin-7-yl)-N4,1-dimethyl-1H-pyrazole-4,5-dicarboxamide, 4-(Azetidine-1-carbonyl)-2-methyl-2H-pyrazole-3-carboxylic acid [2-(3-methoxy-phenyl)-[1,2,4]triazolo[1,5-a]pyridin-7-yl]-amide, 2-Methyl-4-(morpholine-4-carbonyl)-2H-pyrazole-3-carboxylic acid [2-(3-methoxy-phenyl)-[1,2,4]triazolo[1,5-a]pyridin-7-yl]-amide, 2-Methyl-2H-pyrazole-3,4-dicarboxylic acid 4-[(2-methoxy-ethyl)-methyl-amide]3-{[2-(3-methoxy-phenyl)-[1,2,4]triazolo[1,5-a]pyridin-7-yl]-amide}, 2-Methyl-2H-pyrazole-3,4-dicarboxylic acid 4-dimethylamide 3-{[2-(3-methoxy-phenyl)[1,2,4]triazolo[1,5-a]pyridin-7-yl]-amide}, 2-Methyl-2H-pyrazole-3,4-dicarboxylic acid 4-(ethyl-methyl-amide) 3-{[2-(3-methoxy-phenyl)-[1,2,4]triazolo[1,5-a]pyridin-7-yl]-amide}, 2-Methyl-4-(morpholine-4-carbonyl)-2H-pyrazole-3-carboxylic acid [2-(3-hydroxy-phenyl)-[1,2,4]triazolo[1,5-a]pyridin-7-yl]-amide, 2-Methyl-4-(morpholine-4-carbonyl)-2H-pyrazole-3-carboxylic acid {2-[3-(2-fluoro-ethoxy)-phenyl]-[1,2,4]triazolo[1,5-a]pyridin-7-yl}-amide, 2-Methyl-4-(morpholine-4-carbonyl)-2H-pyrazole-3-carboxylic acid [2-(3-fluoromethoxy-phenyl)-[1,2,4]triazolo[1,5-a]pyridin-7-yl]-amide, 2-Methyl-2H-pyrazole-3,4-dicarboxylic acid 4-(ethyl-methyl-amide)3-({2-[3-(2-fluoro-ethoxy)-phenyl]-[1,2,4]triazolo[1,5-a]pyridin-7-yl}-amide), 2-Methyl-2H-pyrazole-3,4-dicarboxylic acid 4-(ethyl-methyl-amide)3-{[2-(3-fluoromethoxy-phenyl)-[1,2,4]triazolo[1,5-a]pyridin-7-yl]-amide}, 2-Methyl-2H-pyrazole-3,4-dicarboxylic acid 4-dimethylamide 3-({2-[3-(2-fluoro-ethoxy)-phenyl]-[1,2,4]triazolo[1,5-a]pyridin-7-yl}-amide), 2-Methyl-2H-pyrazole-3,4-dicarboxylic acid 4-dimethylamide 3-{[2-(3-fluoromethoxy-phenyl)-[1,2,4]triazolo[1,5-a]pyridin-7-yl]-amide}, 2-Methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide], 2-Methyl-2H-pyrazole-3,4-dicarboxylic acid 3-({2-[3-(2-fluoro-ethoxy)-phenyl]-[1,2,4]triazolo[1,5-a]pyridin-7-yl}-amide)4-[(2-methoxy-ethyl)-methyl-amide], 2-Methyl-2H-pyrazole-3,4-dicarboxylic acid 3-{[2-(3-fluoromethoxy-phenyl)-[1,2,4]triazolo[1,5-a]pyridin-7-yl]-amide}4-[(2-methoxy-ethyl)-methyl-amide], 4-(Azetidine-1-carbonyl)-2-methyl-2H-pyrazole-3-carboxylic acid {2-[3-(2-fluoro-ethoxy)-phenyl][1,2,4]triazolo[1,5-a]pyridin-7-yl}-amide, 4-(Azetidine-1-carbonyl)-2-methyl-2H-pyrazole-3-carboxylic acid [2-(3-fluoromethoxy-phenyl)[1,2,4]triazolo[1,5-a]pyridin-7-yl]-amide, 2-Methyl-2H-pyrazole-3,4-dicarboxylic acid 4-[(2-hydroxy-ethyl)-methyl-amide]3-[(2-phenyl-[1,2,4]triazolo[1,5-a]pyridin-7-yl)-amide], {Methyl-[1-methyl-5-(2-phenyl-[1,2,4]triazolo[1,5-a]pyridin-7-ylcarbamoyl)-1H-pyrazole-4-carbonyl]-amino}-acetic acid methyl ester, 2-Methyl-2H-pyrazole-3,4-dicarboxylic acid 4-[(2-hydroxy-ethyl)-methyl-amide]3-[(2-morpholin-4-yl-[1,2,4]triazolo[1,5-a]pyridin-7-yl)-amide], {Methyl-[1-methyl-5-(2-morpholin-4-yl-[1,2,4]triazolo[1,5-a]pyridin-7-ylcarbamoyl)-1H-pyrazole-4-carbonyl]-amino}-acetic acid methyl ester, 2-Methyl-2H-pyrazole-3,4-dicarboxylic acid 4-[(2-fluoro-ethyl)-amide]3-[(2-phenyl[1,2,4]triazolo[1,5-a]pyridin-7-yl)-amide], 2-Methyl-2H-pyrazole-3,4-dicarboxylic acid 4-dimethylamide 3-{[2-(2-methoxy-phenyl)-[1,2,4]triazolo[1,5-a]pyridin-7-yl]-amide}, 2-Methyl-2H-pyrazole-3,4-dicarboxylic acid 4-(ethyl-methyl-amide)3-{[2-(2-methoxy-phenyl)-[1,2,4]triazolo[1,5-a]pyridin-7-yl]-amide}, 2-Methyl-2H-pyrazole-3,4-dicarboxylic acid 4-[(2-methoxy-ethyl)-methyl-amide]3-{[2-(2-methoxy-phenyl)-[1,2,4]triazolo[1,5-a]pyridin-7-yl]-amide}, 2-Methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl]-amide), 2-Methyl-2H-pyrazole-3,4-dicarboxylic acid 4-(ethyl-methyl-amide)3-({2-[2-(2-fluoro-ethoxy)-phenyl]-[1,2,4]triazolo[1,5-a]pyridin-7-yl}-amide), 4-(azetidine-1-carbonyl)-N-(2-(2-methoxyphenyl)-[1,2,4]triazolo[1,5-a]pyridin-7-yl)-1-methyl-1H-pyrazole-5-carboxamide, N4-cyclopropyl-N5-(2-(2-methoxyphenyl)-[1,2,4]triazolo[1,5-a]pyridin-7-yl)-N4,1-dimethyl-1H-pyrazole-4,5-dicarboxamide, N5-(2-(3-fluorophenyl)-[1,2,4]triazolo[1,5-a]pyridin-7-yl)-N4,N4,1-trimethyl-1H-pyrazole-4,5-dicarboxamide, 4-(azetidine-1-carbonyl)-N-(2-(3-fluorophenyl)-[1,2,4]triazolo[1,5-a]pyridin-7-yl)-1-methyl-1H-pyrazole-5-carboxamide, N-(2-(3-fluorophenyl)-[1,2,4]triazolo[1,5-a]pyridin-7-yl)-1-methyl-4-(morpholine-4-carbonyl)-1H-pyrazole-5-carboxamide, N-(2-(3-fluorophenyl)-[1,2,4]triazolo[1,5-a]pyridin-7-yl)-4-(3-methoxyazetidine-1-carbonyl)-1-methyl-1H-pyrazole-5-carboxamide, N-(2-(3-fluorophenyl)-[1,2,4]triazolo[1,5-a]pyridin-7-yl)-1-methyl-4-(4-methylpiperazine-1-carbonyl)-1H-pyrazole-5-carboxamide, N5-(2-(2-fluoropyridin-3-yl)-[1,2,4]triazolo[1,5-a]pyridin-7-yl)-N4,N4,1-trimethyl-1H-pyrazole-4,5-dicarboxamide, 4-(azetidine-1-carbonyl)-N-(2-(2-fluoropyridin-3-yl)-[1,2,4]triazolo[1,5-a]pyridin-7-yl)-1-methyl-1H-pyrazole-5-carboxamide, N-(2-(2-fluoropyridin-3-yl)-[1,2,4]triazolo[1,5-a]pyridin-7-yl)-1-methyl-4-(morpholine-4-carbonyl)-1H-pyrazole-5-carboxamide, 1-methyl-N-(2-morpholino-[1,2,4]triazolo[1,5-a]pyridin-7-yl)-4-(2-oxa-6-azaspiro[3.3]heptane-6-carbonyl)-1H-pyrazole-5-carboxamide, N4-cyclopropyl-1-methyl-N5-(2-morpholino-[1,2,4]triazolo[1,5-a]pyridin-7-yl)-1H-pyrazole-4,5-dicarboxamide, 4-(3-fluoroazetidine-1-carbonyl)-N-(2-(2-fluoroethyl)(methyl)amino)-[1,2,4]triazolo[1,5-a]pyridin-7-yl)-1-methyl-1H-pyrazole-5-carboxamide, N-(2-((2-fluoroethyl)(methyl)amino)-[1,2,4]triazolo[1,5-a]pyridin-7-yl)-1-methyl-4-(pyrrolidine-1-carbonyl)-1H-pyrazole-5-carboxamide, N4-ethyl-N4,1-dimethyl-N5-(2-(pyridin-3-yl)-[1,2,4]triazolo[1,5-a]pyridin-7-yl)-1H-pyrazole-4,5-dicarboxamide, N-(2-(2-fluoropyridin-4-yl)-[1,2,4]triazolo[1,5-a]pyridin-7-yl)-1-methyl-4-(morpholine-4-carbonyl)-1H-pyrazole-5-carboxamide, 4-(azetidine-1-carbonyl)-N-(2-(2-fluoropyridin-4-yl)-[1,2,4]triazolo[1,5-a]pyridin-7-yl)-1-methyl-1H-pyrazole-5-carboxamide, 4-(azetidine-1-carbonyl)-N-(2-(6-fluoropyridin-2-yl)-[1,2,4]triazolo[1,5-a]pyridin-7-yl)-1-methyl-1H-pyrazole-5-carboxamide, N5-(2-(6-fluoropyridin-2-yl)-[1,2,4]triazolo[1,5-a]pyridin-7-yl)-N4,N4,1-trimethyl-1H-pyrazole-4,5-dicarboxamide, N-(2-(6-fluoropyridin-2-yl)-[1,2,4]triazolo[1,5-a]pyridin-7-yl)-1-methyl-4-(morpholine-4-carbonyl)-1H-pyrazole-5-carboxamide, 2-Methyl-4-(2-oxa-6-aza-spiro[3.3]heptane-6-carbonyl)-2H-pyrazole-3-carboxylic acid (2-pyrrolidin-1-yl-[1,2,4]triazolo[1,5-a]pyridin-7-yl)-amide, 2-Methyl-2H-pyrazole-3,4-dicarboxylic acid 4-(cyclopropyl-methyl-amide)3-[(2-pyrrolidin-1-yl-[1,2,4]triazolo[1,5-a]pyridin-7-yl)-amide], 2-Methyl-2H-pyrazole-3,4-dicarboxylic acid 4-(ethyl-methyl-amide)3-[(2-pyrrolidin-1-yl-[1,2,4]triazolo[1,5-a]pyridin-7-yl)-amide], 5-[2-(Cyclopropyl-methyl-amino)-[1,2,4]triazolo[1,5-a]pyridin-7-ylcarbamoyl]-1-methyl-1H-pyrazole-4-carboxylic acid, 2-Methyl-2H-pyrazole-3,4-dicarboxylic acid 4-(cyclopropyl-methyl-amide)3-{[2-(cyclopropyl-methyl-amino)-[1,2,4]triazolo[1,5-a]pyridin-7-yl]-amide}, 4-(Azetidine-1-carbonyl)-2-methyl-2H-pyrazole-3-carboxylic acid [2-(cyclopropyl-methyl-amino)-[1,2,4]triazolo[1,5-a]pyridin-7-yl]-amide, 2-Methyl-4-(morpholine-4-carbonyl)-2H-pyrazole-3-carboxylic acid [2-(cyclopropyl-methyl-amino)-[1,2,4]triazolo[1,5-a]yridin-7-yl]-amide, 4-(1,4-Diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide, 4-(Azetidine-1-carbonyl)-2-methyl-2H-pyrazole-3-carboxylic acid {2-[2-(2-fluoro-ethoxy)-phenyl]-[1,2,4]triazolo[1,5-a]pyridin-7-yl}-amide, 2-Methyl-4-(morpholine-4-carbonyl)-2H-pyrazole-3-carboxylic acid {2-[2-(2-fluoro-ethoxy)-phenyl]-[1,2,4]triazolo[1,5-a]pyridin-7-yl}-amide, 2-Methyl-2H-pyrazole-3,4-dicarboxylic acid 3-({2-[2-(2-fluoro-ethoxy)-phenyl]-[1,2,4]triazolo[1,5-a]pyridin-7-yl}-amide)4-[(2-methoxy-ethyl)-methyl-amide], and Methyl-4-(morpholine-4-carbonyl)-N-(2-(2-oxopyrrolidin-1-yl)-[1,2,4]triazolo[1,5-a]pyridin-7-yl)-1H-pyrazole-5-carboxamide, or pharmaceutically acceptable salts thereof.

In another particular embodiment, compounds of formula (I) are those selected from the group consisting of:

4-(azetidine-1-carbonyl)-1-methyl-N-(2-phenyl-[1,2,4]triazolo[1,5-a]pyridin-7-yl)-1H-pyrazole-5-carboxamide, N4-ethyl-N4,1-dimethyl-N5-(2-phenyl-[1,2,4]triazolo[1,5-a]pyridin-7-yl)-1H-pyrazole-4,5-dicarboxamide, 4-(azetidine-1-carbonyl)-1-methyl-N-(2-morpholino-[1,2,4]triazolo[1,5-a]pyridin-7-yl)-1H-pyrazole-5-carboxamide, 1-methyl-4-(morpholine-4-carbonyl)-N-(2-phenyl-[1,2,4]triazolo[1,5-a]pyridin-7-yl)-1H-pyrazole-5-carboxamide, 1-methyl-N-(2-phenyl-[1,2,4]triazolo[1,5-a]pyridin-7-yl)-4-(pyrrolidine-1-carbonyl)-1H-pyrazole-5-carboxamide, 4-(3-fluoroazetidine-1-carbonyl)-1-methyl-N-(2-phenyl-[1,2,4]triazolo[1,5-a]pyridin-7-yl)-1H-pyrazole-5-carboxamide, 2-Methyl-2H-pyrazole-3,4-dicarboxylic acid 4-[(2-fluoroethyl)-methyl-amide]3-[(2-phenyl-[1,2,4]triazolo[1,5-a]pyridin-7-yl)-amide], 1-methyl-4-(morpholine-4-carbonyl)-N-(2-morpholino-[1,2,4]triazolo[1,5-a]pyridin-7-yl)-1H-pyrazole-5-carboxamide, 4-(azetidine-1-carbonyl)-N-(2-(dimethylamino)-[1,2,4]triazolo[1,5-a]pyridin-7-yl)-1-methyl-1H-pyrazole-5-carboxamide, N-(2-(dimethylamino)-[1,2,4]triazolo[1,5-a]pyridin-7-yl)-1-methyl-4-(pyrrolidine-1-carbonyl)-1H-pyrazole-5-carboxamide, N-(2-(dimethylamino)-[1,2,4]triazolo[1,5-a]pyridin-7-yl)-4-(3-fluoroazetidine-1-carbonyl)-1-methyl-1H-pyrazole-5-carboxamide, 4-(azetidine-1-carbonyl)-1-methyl-N-(2-(pyridin-3-yl)-[1,2,4]triazolo[1,5-a]pyridin-7-yl)-1H-pyrazole-5-carboxamide, 1-methyl-4-(morpholine-4-carbonyl)-N-(2-(pyridin-3-yl)-[1,2,4]triazolo[1,5-a]pyridin-7-yl)-1H-pyrazole-5-carboxamide, N4-cyclopropyl-N4,1-dimethyl-N5-(2-phenyl-[1,2,4]triazolo[1,5-a]pyridin-7-yl)-1H-pyrazole-4,5-dicarboxamide, N4-cyclopropyl-N4,1-dimethyl-N5-(2-morpholino-[1,2,4]triazolo[1,5-a]pyridin-7-yl)-1H-pyrazole-4,5-dicarboxamide, N4-cyclopropyl-N4,1-dimethyl-N5-(2-(pyridin-3-yl)-[1,2,4]triazolo[1,5-a]pyridin-7-yl)-1H-pyrazole-4,5-dicarboxamide, 2-Methyl-4-(morpholine-4-carbonyl)-2H-pyrazole-3-carboxylic acid [2-(ethyl-methyl-amino)-[1,2,4]triazolo[1,5-a]pyridin-7-yl]-amide, 1-methyl-4-(morpholine-4-carbonyl)-N-(2-(pyrrolidin-1-yl)-[1,2,4]triazolo[1,5-a]pyridin-7-yl)-1H-pyrazole-5-carboxamide, N-(2-(2-methoxyphenyl)-[1,2,4]triazolo[1,5-a]pyridin-7-yl)-1-methyl-4-(morpholine-4-carbonyl)-1H-pyrazole-5-carboxamide, 2-Methyl-4-(morpholine-4-carbonyl)-2H-pyrazole-3-carboxylic acid [2-(3-methoxy-phenyl)-[1,2,4]triazolo[1,5-a]pyridin-7-yl]-amide, 2-Methyl-2H-pyrazole-3,4-dicarboxylic acid 4-[(2-methoxy-ethyl)-methyl-amide]3-{[2-(3-methoxy-phenyl)-[1,2,4]triazolo[1,5-a]pyridin-7-yl]-amide}, N5-(2-(3-fluorophenyl)-[1,2,4]triazolo[1,5-a]pyridin-7-yl)-N4,N4,1-trimethyl-1H-pyrazole-4,5-dicarboxamide, 4-(azetidine-1-carbonyl)-N-(2-(2-fluoropyridin-4-yl)-[1,2,4]triazolo[1,5-a]pyridin-7-yl)-1-methyl-1H-pyrazole-5-carboxamide, 2-Methyl-4-(2-oxa-6-aza-spiro[3.3]heptane-6-carbonyl)-2H-pyrazole-3-carboxylic acid (2-pyrrolidin-1-yl-[1,2,4]triazolo[1,5-a]pyridin-7-yl)-amide, 2-Methyl-2H-pyrazole-3,4-dicarboxylic acid 4-(cyclopropyl-methyl-amide)3-[(2-pyrrolidin-1-yl-[1,2,4]triazolo[1,5-a]pyridin-7-yl)-amide], 4-(Azetidine-1-carbonyl)-2-methyl-2H-pyrazole-3-carboxylic acid [2-(cyclopropyl-methyl-amino)-[1,2,4]triazolo[1,5-a]pyridin-7-yl]-amide, and 4-(1,4-Diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide, or pharmaceutically acceptable salts thereof.

It will be appreciated that the compounds of general formula (I) in this invention can be derivatized at functional groups to provide derivatives which are capable of conversion back to the parent compound in vivo.

The invention further provides a process for the manufacture of compounds of formula (I) as defined above, which process comprises:

reacting a compound of formula (2)

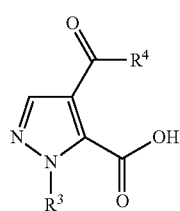

(2)

with a compound of formula (3)

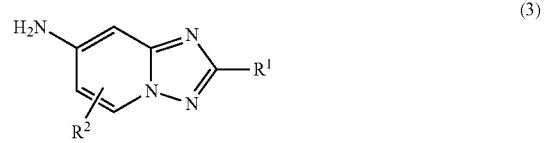

(3)

wherein $R^1$, $R^2$, $R^3$ and $R^4$ are as defined above and, if desired, converting the compounds into pharmaceutically acceptable salts thereof.

The reaction described above can be carried out under conditions as described in the description and examples or under conditions well known to the person skilled in the art.

The compounds of formula (2) and (3) can be prepared by methods known in the art or as described below or in analogy thereto.

The present invention also provides compounds of formula (I) as defined above, when prepared by a process as described above.

Compounds of formula 1 can be prepared from building blocks 2 and 3 according to Scheme 1. The conversion, commonly known as amide coupling, can be achieved in several ways. In one method, the acid 2 is activated with a coupling reagent, such as 2-(1H-benzotriazole-1-yl)-1,1,3,3-tetramethyluronium tetrafluoroborate (TBTU), or propylphosphonic anhydride, and converted by addition of amine 3 to the desired product, 1. In another method, the acid 2 is activated by transformation into an acid chloride, e.g. by reaction with thionyl chloride. The acid chloride is then converted by addition of the amine 3 to the desired product, 1. A base, e.g. diisopropylethylamine (DIPEA), is usually added to bind liberated HCl.

Scheme 1

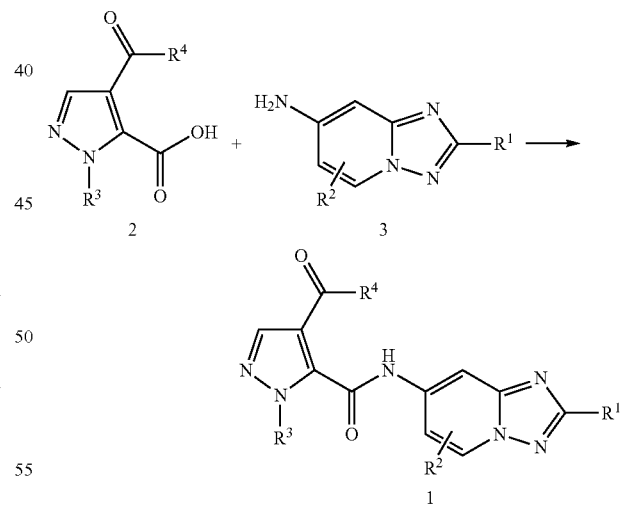

Compounds of formula 3 can be prepared according to Scheme 2: A suitably substituted 2-aminopyridine (4) is reacted with O-mesitylenesulfonyl hydroxylamine 5 to form salt 6. Salt 6 is then reacted with a compound 7 such as a (substituted) benzoic acid chloride, with a suitable base, such as pyridine, to give compound 8. Compound 8 is then converted to amine 3 by methods well known in the art. For example, if Y is bromine, 8 can be used in a palladium-catalyzed cross coupling reaction using a suitable nitrogen compound, such as carbamic acid tert-butyl ester, and a suitable ligand, such as Xantphos, to yield, after deprotection, amine 3. Alternatively, if Y is an carboxylic acid ester, compound 8 can be saponified with a suitable base such as lithium hydroxide and then be converted with diphenylphosphoryl azide to yield, after deprotection, the desired amine 3.

2-Amino-4-bromopyridine as example of 2-aminopyridines 4, carbamic acid tert-butyl ester, Xantphos and diphenylphosphoryl azide are commercially available; compounds 4, 5 and 7 are either commercially available, or can be prepared by methods well known in the art.

Selective mono-saponification of the diester 11 yields, depending on the reaction conditions, compound 2a or its isomer, compound 2b.

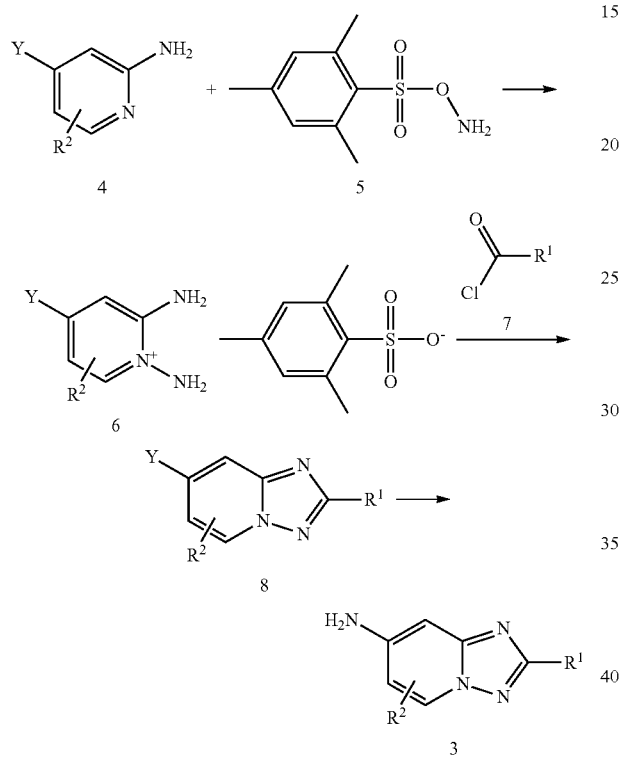

Compounds of formula 2, with —C(O)—R⁴ being a carboxylic acid derivative, can be prepared according to Scheme 3: Compound 9 is reacted with a hydrazine 10, or a salt thereof, to give a pyrazole 11 (similar to the method of A. Hanzlowsky, B. Jelencic, S. Recnik, J. Svete, A. Golobic, B. Stanovnik *J. Heterocyclic Chem.* 2003, 40(3), 487-498).

Compounds of formula 1 with —C(O)—R⁴ being a lower alkoxycarbonyl group can be further transformed according to Scheme 4. For instance, compounds of the general formula 1-COOEt can be saponified by suitable methods, e.g. by reaction with LiOH, to give 1-COOH. Upon activation with a suitable reagent such as TBTU, 1-COOH can be converted with a primary or secondary amine to 1-CONR₂. Alternatively, 1-COOEt can be directly converted into 1-CONR₂, e.g. by reaction with an amine such as methylamine.

Alternatively, compounds of formula 3 can be prepared according to Scheme 5: A suitably substituted 4-pyridinecarboxylic acid alkyl ester of formula 12 is reacted with O-mesitylenesulfonyl hydroxylamine 5 to form salt 13. Salt 13 is then reacted with a compound of formula 14 such as a (substituted) benzonitrile, with a suitable base such as potassium hydroxide and an oxidizing agent such as copper(II) acetate in a suitable solvent such as ethanol or water to form the compounds of formula 15a and 15b, which by methods well known in the art can be converted to the amines 3a and 3b.

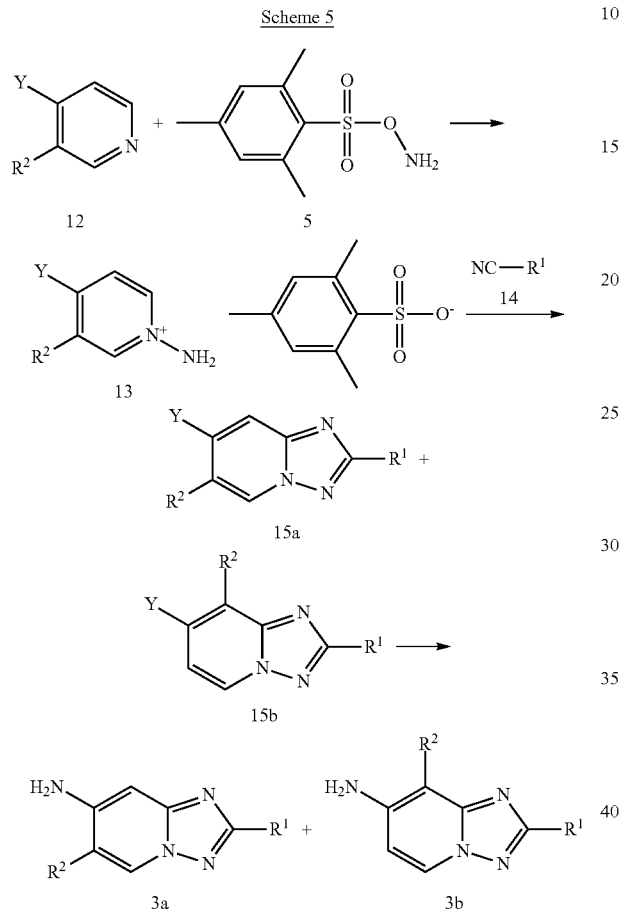

3-Methyl-4-pyridinecarboxylic acid ethyl ester and O-mesitylenesulfonyl hydroxylamine are known. Other compounds of formula 12 can be prepared by methods well known in the art. Compounds 14 are either commercially available, or can be prepared by methods well known in the art.

Alternatively, compounds of formula 3, with $R^1$ being $NR^7R^8$, can be prepared according to Scheme 6: A suitably substituted 2-aminopyridine (4) is reacted with ethoxycarbonyl-isothiocyanate (17) to form thiourea 18, which can be cyclized using hydroxylamine and a suitable base such as diisopropylethylamine to a compound of formula 19. This can be converted by methods well known in the art to compound 22 and further to the desired amine of formula 3c. For example, compounds of formula 19 can be treated with a nitrite such as sodium nitrite or alkyl nitrite such as tert-butyl nitrite and a bromide such as copper(II) bromide or benzyltriethylammonium bromide in a suitable solvent such as acetonitrile or bromoform to form bromide 20. Bromide 20 can then be reacted with an amine of formula 21 in a suitable solvent such as THF or ethanol. A base, e.g. diisopropylethylamine (DIPEA), can be added to the reaction.

2-Amino-4-bromopyrimidine, Ethoxycarbonyl-isothiocyanate and hydroxylamine are commercially available; amines 21 are either commercially available, or can be prepared by methods well known in the art.

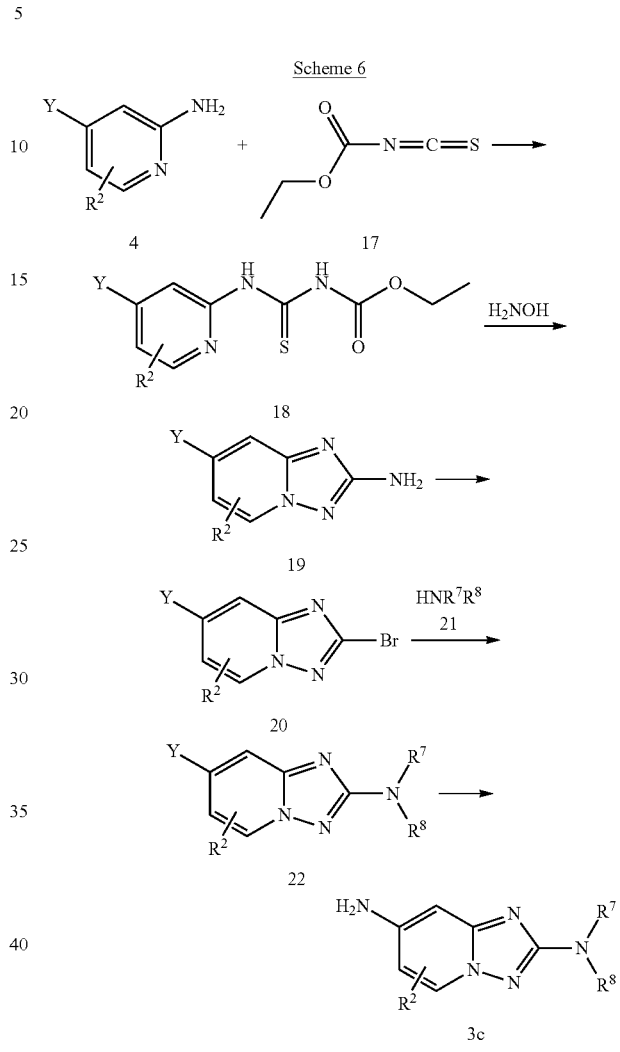

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxane or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCl) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also provides compounds as described above for use as therapeutically active substances.

The invention also provides pharmaceutical compositions comprising a compound as described above and a therapeutically inert carrier.

In another embodiment, the invention provides the use of a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention provides the use of a compound as described above for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also provides a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention further provides a compound as described above, when manufactured according to a process as described above.

In another embodiment, the invention provides a method for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer, which method comprises administering an effective amount of a compound as described above.

A particular indication is the prevention and/or treatment of schizophrenia. More particularly, the invention provides a method for the prevention and/or treatment of positive, negative and/or cognitive symptoms associated with schizophrenia.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. #A-7906), 50 nM cGMP (Sigma, cat. #G6129) and 50 nM [$^3$H]-cGMP (GE Healthcare, cat. #TRK392 S.A. 13.2Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A activity by 50%). Non-specific activity was tested without the enzyme. The reaction was initiated by the addition of the substrate solution (cGMP and [$^3$H]-cGMP) and allowed to progress for 20 minutes at room temperature. The reaction was terminated by adding 25 µl of YSi-SPA scintillation beads (GE Healthcare, cat. #RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an $IC_{50}$ value below 10 µM, more specifically below 5 µM, yet more specifically below 1 µM. The following table shows data for some examples.

| Example | PDE10A inhibition $IC_{50}$ [nM] |
|---|---|
| 1 | 14.62 |
| 2 | 24.91 |
| 3 | 0.71 |
| 4 | 0.28 |
| 5 | 0.5 |
| 6 | 0.43 |
| 7 | 1.63 |
| 8 | 1.88 |
| 9 | 16.28 |
| 10 | 0.19 |
| 11 | 0.9 |
| 12 | 0.27 |
| 13 | 0.13 |
| 14 | 12.41 |
| 15 | 4.85 |
| 16 | 2.34 |
| 17 | 11.84 |
| 18 | 0.25 |
| 19 | 5.38 |
| 20 | 1.24 |
| 21 | 26.53 |
| 22 | 9.01 |
| 23 | 4.25 |
| 24 | 21.53 |
| 25 | 0.39 |
| 26 | 0.43 |
| 27 | 7.9 |
| 28 | 7.3 |
| 29 | 40.5 |
| 30 | 1.27 |
| 31 | 0.48 |
| 32 | 0.98 |
| 33 | 28.65 |
| 34 | 28.33 |
| 35 | 7.39 |
| 36 | 43.46 |
| 37 | 4.46 |
| 38 | 19.6 |
| 39 | 22.44 |
| 40 | 7.14 |
| 41 | 6.68 |
| 42 | 5.15 |
| 43 | 3.77 |
| 44 | 5.79 |
| 45 | 4.29 |
| 46 | 1.17 |
| 47 | 1.24 |
| 48 | 0.98 |
| 49 | 0.84 |
| 50 | 47.32 |
| 51 | 41.96 |
| 52 | 57.43 |
| 53 | 1.12 |
| 54 | 80.47 |
| 55 | 0.45 |
| 56 | 3.69 |
| 57 | 51.91 |
| 58 | 7.03 |
| 59 | 7.97 |
| 60 | 3.16 |
| 61 | 0.94 |
| 62 | 112.08 |
| 63 | 93.69 |
| 64 | 103.66 |
| 65 | 67.44 |
| 66 | 1.82 |
| 67 | 2.06 |
| 68 | 11.2 |
| 69 | 0.68 |
| 70 | 5.65 |
| 71 | 6.21 |
| 72 | 20.57 |
| 73 | 11.61 |
| 74 | 1.86 |
| 75 | 0.31 |
| 76 | 5.15 |
| 77 | 0.57 |
| 78 | 0.32 |
| 79 | 1.73 |
| 80 | 0.41 |
| 81 | 0.59 |
| 82 | 0.78 |
| 83 | 0.63 |
| 84 | 0.54 |
| 85 | 0.73 |
| 86 | 0.6 |
| 87 | 0.43 |
| 88 | 0.42 |
| 89 | 0.59 |
| 90 | 1.02 |
| 91 | 0.86 |
| 92 | 0.98 |
| 93 | 2.16 |
| 94 | 20.44 |
| 95 | 50.43 |
| 96 | 2.12 |
| 97 | 0.31 |
| 98 | 0.67 |
| 99 | 0.74 |
| 101 | 0.65 |
| 102 | 0.65 |
| 103 | 0.31 |
| 104 | 1.43 |
| 105 | 1.11 |
| 106 | 1.54 |
| 107 | 4.7 |
| 108 | 15.64 |
| 109 | 3.74 |
| 110 | 4.66 |
| 111 | 6.62 |
| 112 | 57.25 |
| 113 | 19.13 |
| 114 | 5.66 |
| 115 | 2.29 |
| 116 | 1.11 |
| 117 | 14.96 |
| 118 | 6.78 |
| 119 | 1.2 |
| 120 | 1.32 |
| 121 | 5.06 |
| 122 | 6.21 |
| 123 | 0.6 |
| 124 | 0.86 |
| 125 | 54 |
| 126 | 0.49 |
| 127 | 0.73 |
| 128 | 3.37 |
| 129 | 1.1 |
| 130 | 0.34 |
| 131 | 0.9 |

| Example | PDE10A inhibition IC$_{50}$ [nM] |
|---|---|
| 132 | 1.02 |
| 133 | 16.1 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils.

The production of the pharmaceutical compositions can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage at which compounds of formula (I) can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 0.1-500 mg, more specifically 1-200 mg, of a compound of formula (I).

The following examples serve to illustrate the present invention in more detail. They are, however, not intended to limit its scope in any manner.

The examples provided below were actually prepared as described regardless of whether they are written present or past tense unless specifically indicated to the contrary.

EXAMPLES

Example 1

1-Methyl-5-(2-phenyl-[1,2,4]-triazolo[1,5-a]pyridin-7-ylcarbamoyl)-1H-pyrazole-4-carboxylate

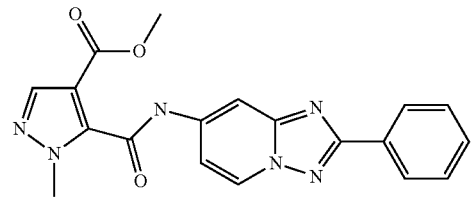 [SMILES: COC(=O)c1cnn(C)c1C(=O)Nc1ccn2nc(-c3ccccc3)nc2c1]

a) 1,2-diamino-4-bromo-pyridinium2,4,6-trimethyl-benzenesulfonate

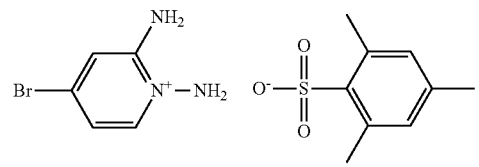

To a cooled suspension of O-(mesitylsulfonyl)hydroxylamine (11.22 g, 52.1 mmol, 1 eq) in dichloromethane (130 ml) is portionwise added 4-bromopyridin-2-amine (9.3 g, 52.1 mmol, 1 eq.) (exothermic reaction, some cooling is needed) giving a white suspension. After 1 hour the white suspension is diluted with diethyl ether (120 ml). The white solid is collected by filtration, washed with diethyl ether and dried affording 1,2-diamino-4-bromo-pyridinium 2,4,6-trimethyl-benzenesulfonate (16.74 g, 82.7%) as white crystals. mp.: 176-180° C. MS: m/z=188.2, 190.2 (M+H$^+$).

b) 7-bromo-2-phenyl-[1,2,4]triazolo[1,5-a]pyridine

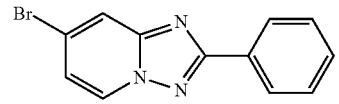 [SMILES: Brc1ccn2nc(-c3ccccc3)nc2c1]

1,2-Diamino-4-bromopyridinium 2,4,6-trimethylbenzenesulfonate (15.6 g, 40.2 mmole) in pyridine (106 ml) is heated overnight at 100° C. with benzoyl chloride (9.4 ml, 80 mmole) giving a redbrown solution and after 2 hrs a brown suspension. The reaction mixture is concentrated in vacuo and the residue is triturated for 2.5 hr in sat. aqueous ammonium chloride solution (300 ml), while neutralizing to pH 6-7 with sat. aqueous sodium bicarbonate solution. The solid is collected by filtration, washed with water (40 ml) and dried affording 7-bromo-2-phenyl-[1,2,4]triazolo[1,5-a]pyridine (6.78 g, 61.6%) as an off-white solid. mp.: 189-191° C. MS: m/z=276.1, 274.2 (M+H⁺).

c) (2-phenyl-[1,2,4]triazolor[1,5-a]pyridin-7-yl)-carbamic acid tert-butyl ester

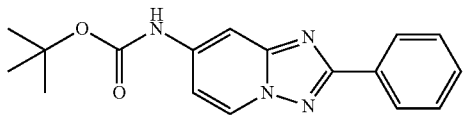 [SMILES: CC(C)(C)OC(=O)Nc1ccn2nc(-c3ccccc3)nc2c1]

To an nitrogen purged suspension of 7-bromo-2-phenyl-[1,2,4]triazolo[1,5-a]pyridine (9 g, 32.8 mmol) in dioxane (180 ml) is added successively tert-butyl carbamate (4.71 g, 39.4 mmol), tris(dibenzylidene-acetone)dipalladium(0) (601 mg, 657 umol), 4,5-bis(diphenylphos-phino)-9,9-dimethylxanthene (760 mg, 1.31 mmol) and cesium carbonate (15 g, 46 mmol). The brown mixture is then stirred for 22 hours at 100° C. under nitrogen atmosphere. The solvent is removed in vacuo and the brown residue partitioned between ethyl acetate and water. The aqueous layer is extracted twice with ethyl acetate and the combined organic layers are washed with water (3×120 ml) and with brine and dried with magnesium sulfate. The solution is concentrated in vacuo to ca 80 ml: crystallization. The suspension is stirred for 10 min in an ice bath and the solid is collected by filtration, washed with little cold ethyl acetate and dried affording (2-phenyl-[1,2,4]triazolo[1,5-a]pyridin-7-yl)-carbamic acid tert-butyl ester (7.09 g) as an off-white solid. The mother liquor is evaporated and the residue (4.79 g) is loaded on silica (16 g). The product is isolated by chromatography on a 120 g silica cartridge (eluent heptane/ethyl acetate 10-50%, 45 min) yielding a second crop of 1.748 g of a white solid. mp.: 200-201° C. dec. MS: m/z=311.3 (M+H⁺).

Total yield: 86.7%.

d) 2-phenyl-[1,2,4]triazolo[1,5-a]pyridin-7-ylamine

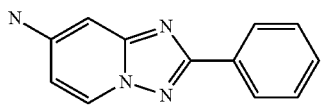

A suspension of (2-phenyl-[1,2,4]triazolo[1,5-a]pyridin-7-yl)-carbamic acid tert-butyl ester (8.5 g, 27.4 mmol) in hydrochloric acid (6 N in diethyl ether, 175 ml) is stirred overnight at room temperature. The suspension is diluted under cooling with water (ca 2 l) and ethyl acetate, the aqueous layer is washed once with ethyl acetate, made alkaline with 32% aqueous sodium hydroxide and extracted twice with ethyl acetate. The combined organic layers are dried with magnesium sulfate and the solvent is removed in vacuo affording 2-phenyl-[1,2,4]triazolo[1,5-a]pyridin-7-ylamine (5.52 g, 95.9%) as a light pink solid. mp.: 212-213° C. MS: m/z=211.2 (M+H⁺).

e) methyl 1-methyl-5-(2-phenyl-[1,2,4]triazolo[1,5-a]pyridin-7-ylcarbamoyl)-1H-pyrazole-4-carboxylate

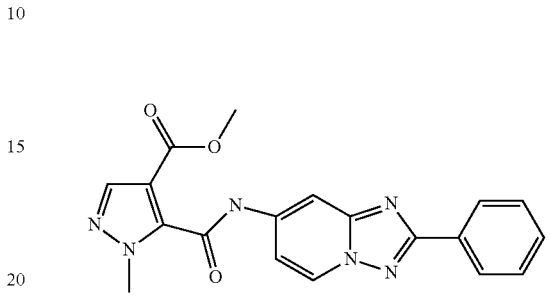

A solution of 2-phenyl-[1,2,4]triazolo[1,5-a]pyridin-7-ylamine (1.534 g, 7.3 mmol), 4-(methoxycarbonyl)-1-methyl-1H-pyrazole-5-carboxylic acid (1.61 g, 8.76 mmol), propylphosphonic anhydride (50% in ethyl acetate, 10.7 ml, 18.2 mmol) and diisopropylethylamine (5.1 ml, 29.2 mmol) in tetrahydrofurane (54 ml) is stirred at 70° C. for 1.25 hr giving a white suspension. The cooled suspension is poured in sat. aqueous sodium bicarbonate solution (200 ml), stirred at room temperature for 15 min and the solid is collected by filtration, washed with water and dried affording methyl 1-methyl-5-(2-phenyl-[1,2,4]triazolo[1,5-a]pyridin-7-ylcarbamoyl)-1H-pyrazole-4-carboxylate (2.596 g, 94.5%) as a white solid. mp.: 243-7° C. MS: m/z=377.2 (M+H⁺).

Example 2

1-Methyl-5-(2-phenyl-[1,2,4]triazolo[1,5-a]pyridin-7-ylcarbamoyl)-1H-pyrazole-4-carboxylic acid

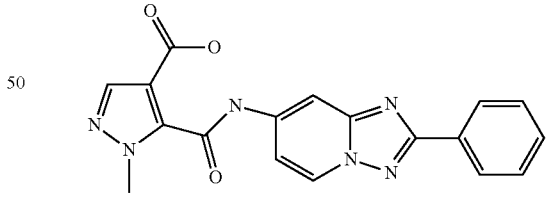

A white suspension of 1-methyl-5-(2-phenyl-[1,2,4]triazolo[1,5-a]pyridin-7-ylcarbamoyl)-1H-pyrazole-4-carboxylic acid methyl ester (2.37 g, 6.3 mmol) and lithium hydroxide monohydrate (291 mg, 6.93 mmol) in methanol (100 ml) and water (20 ml) is stirred for 5/4 hr at 70° C. giving after 20 min a colorless solution. The methanol is removed in vacuo, the residue is diluted with water and the cooled aqueous solution is neutralized with 2N aqueous hydrochloric acid (3.46 ml, 6.03 mmol). The solid is collected by filtration and dried affording 1-methyl-5-(2-phenyl-[1,2,4]triazolo[1,5-a]pyridin-7-ylcarbamoyl)-1H-pyrazole-4-carboxylic acid (2.21 g, 97%) as a white solid. mp.: >300° C. MS: m/z=361.1 (M+H⁺).

Example 3

4-(Azetidine-1-carbonyl)-2-methyl-2H-pyrazole-3-carboxylic acid (2-phenyl-[1,2,4]triazolo[1,5-a]pyridin-7-yl)-amide

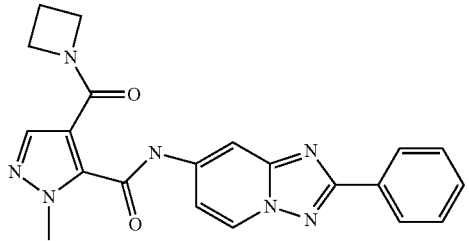 [SMILES: Cn1ncc(C(=O)N2CCC2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (4.5 g, 12.4 mmol), azetidine (2.53 ml, 37.3 mmole), N-diisopropylethylamine (6.51 ml, 37.3 mmol) and propylphosphonic anhydride (50% in ethyl acetate, 18.3 ml, 31 mmol) in tetrahydrofurane (220 ml) is stirred for 2 hours at 70° C. The turbid solution is concentrated to about 100 ml, cooled, poured on cooled sat. aqueous sodium bicarbonate solution (1000 ml) and the suspension is stirred for 20 minutes. The solid is collected by filtration, washed with little water and dried affording 4-(azetidine-1-carbonyl)-2-methyl-2H-pyrazole-3-carboxylic acid (2-phenyl-[1,2,4]triazolo[1,5-a]pyridin-7-yl)-amide (5 g, 100%) as a white solid. mp.: 243-5° C. MS: m/z=402.3 (M+H⁺).

Example 4

N4-(2-methoxyethyl)-N4,1-dimethyl-N5-(2-phenyl-[1,2,4]triazolo[1,5-a]pyridin-7-yl)-1H-pyrazole-4,5-dicarboxamide

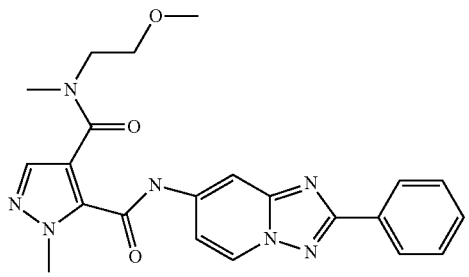 [SMILES: COCCN(C)C(=O)c1cnn(C)c1C(=O)Nc1ccn2nc(-c3ccccc3)nc2c1]

A suspension of 1-methyl-5-(2-phenyl-[1,2,4]triazolo[1,5-a]pyridin-7-ylcarbamoyl)-1H-pyrazole-4-carboxylic acid with 1 eq. lithium chloride (80 mg, 0.198 mmol), 2-methoxy-N-methylethanamine (65 ul, 0.59 mmole), diisopropylethylamine (104 ul, 0.59 mmol) and propylphosphonic anhydride (50% in ethyl acetate, 291 ul, 0.494 mmol) in tetrahydrofurane (4 ml) is stirred for 18 hours at 70° C. giving after 2 hr a light yellow solution. The cooled solution is diluted with ethyl acetate, washed once with sat. aqueous sodium bicarbonate, once with brine, dried with magnesium sulfate and the solvent is evaporated to dryness affording 2-methyl-2H-pyrazole-3,4-dicarboxylic acid 4-[(2-methoxy-ethyl)-methylamide]3-[(2-phenyl-[1,2,4]triazolo[1,5-a]pyridin-7-yl)-amide] (75 mg, 87.5%) as an off-white solid. mp.: 172-5° C. MS: m/z=434.3 (M+H⁺).

Example 5

N4-ethyl-N4,1-dimethyl-N5-(2-phenyl-[1,2,4]triazolo[1,5-a]pyridin-7-yl)-1H-pyrazole-4,5-dicarboxamide

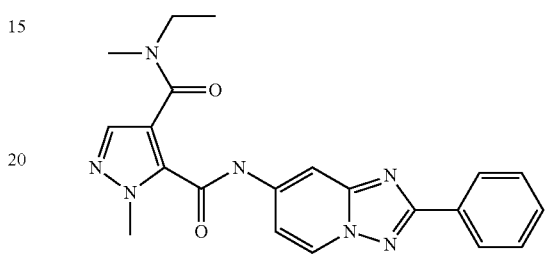

A mixture of 1-methyl-5-(2-phenyl-[1,2,4]triazolo[1,5-a]pyridin-7-ylcarbamoyl)-1H-pyrazole-4-carboxylic acid (600 mg, 1.66 mmol), N-ethylmethylamine (427 ul, 4.97 mmole), N-diisopropylethylamine (868 ul, 4.97 mmol) and propylphosphonic anhydride (50% in ethyl acetate, 2.44 ml, 4.14 mmol) in tetrahydrofurane (30 ml) is stirred for 2 hours at 70° C. The cooled solution is diluted with ethyl acetate, washed once with sat. aqueous sodium bicarbonate solution, once with brine, dried with magnesium sulfate and evaporated to dryness. Two successive crystallizations of the residue (680 mg white solid) from ethyl acetate afford N4-ethyl-N4,1-dimethyl-N5-(2-phenyl-[1,2,4]triazolo[1,5-a]pyridin-7-yl)-1H-pyrazole-4,5-dicarboxamide (365 mg, 54.6%) as a white solid. mp.: 193-4° C. MS: m/z=404.3 (M+H⁺).

Example 6

N4,N4-bis(2-methoxyethyl)-1-methyl-N5-(2-phenyl-[1,2,4]triazolo[1,5-a]pyridin-7-yl)-1H-pyrazole-4,5-dicarboxamide

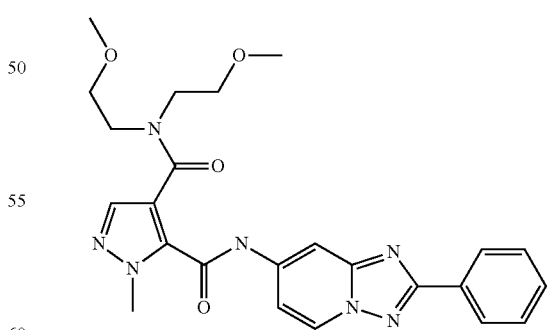

A suspension of 1-methyl-5-(2-phenyl-[1,2,4]triazolo[1,5-a]pyridin-7-ylcarbamoyl)-1H-pyrazole-4-carboxylic acid with 1 eq. lithium chloride (80 mg, 0.198 mmol), bis(2-methoxyethyl)amine (87 ul, 0.59 mmole), diisopropylethylamine (104 ul, 0.59 mmol) and propylphosphonic anhydride (50% in ethyl acetate, 291 ul, 0.494 mmol) in tetrahydrofurane (4 ml) is stirred for 2.5 hours at 70° C. giving after 20 min a light yellow solution. The cooled solution is diluted with ethyl acetate, washed once with sat. aqueous sodium carbonate solution, once with 1N aqueous hydrochloric acid, once with brine, dried with magnesium sulfate and the solvent is evaporated to dryness affording N4,N4-bis(2-methoxyethyl)-1-methyl-N5-(2-phenyl-[1,2,4]triazolo[1,5-a]pyridin-7-yl)-1H-pyrazole-4,5-dicarboxamide (80 mg, 84.8%) as a colorless waxy solid. MS: m/z=478.2 (M+H$^+$).

Example 7

N4-ethyl-1-methyl-N5-(2-phenyl-[1,2,4]triazolo[1,5-a]pyridin-7-yl)-1H-pyrazole-4,5-dicarboxamide

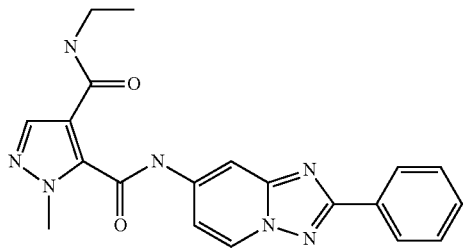 [SMILES: CCNC(=O)c1cnn(C)c1C(=O)Nc1ccn2nc(-c3ccccc3)nc2c1]

A suspension of 1-methyl-5-(2-phenyl-[1,2,4]triazolo[1,5-a]pyridin-7-ylcarbamoyl)-1H-pyrazole-4-carboxylic acid with 1 eq. lithium chloride (54 mg, 0.133 mmol), ethylamine hydrochloride (44 mg, 0.534 mmole), diisopropyl-ethylamine (93 ul, 0.534 mmol) and propylphosphonic anhydride (50% in ethyl acetate, 197 ul, 0.334 mmol) in tetrahydrofurane (3 ml) is stirred for 1.5 hours at 70° C. As no dissolution occurs after this time, ethylamine hydrochloride (87 mg, 1.07 mmol), diisopropylethylamine (186 ul, 1.07 mmol) and propylphosphonic anhydride (50% in ethyl acetate, 99 ul, 0.167 mmol) are added and the mixture is stirred overnight at room temperature. The white suspension is diluted with ethyl acetate, washed once with water, once with sat. aqueous sodium bicarbonate solution, once with brine, dried with magnesium sulfate and the solvent is evaporated to dryness affording N4-ethyl-1-methyl-N5-(2-phenyl-[1,2,4]triazolo[1,5-a]pyridin-7-yl)-1H-pyrazole-4,5-dicarboxamide (30 mg, 57.7%) as a white solid. mp.: 253-5° C. MS: m/z=390.2 (M+H$^+$).

Example 8

4-(Azetidine-1-carbonyl)-1-methyl-N-(2-morpholino-[1,2,4]triazolo[1,5-a]pyridin-7-yl)-1H-pyrazole-5-carboxamide

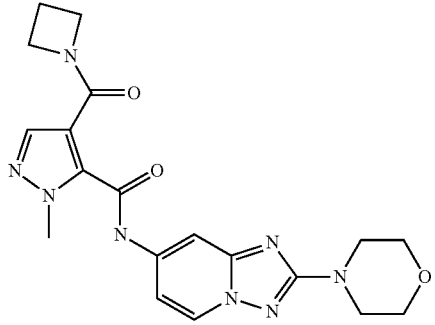 [SMILES: Cn1ncc(C(=O)N2CCC2)c1C(=O)Nc1ccn2nc(N3CCOCC3)nc2c1]

a) 1-Ethoxycarbonyl-3-(4-bromo-pyridin-2-yl)-thiourea

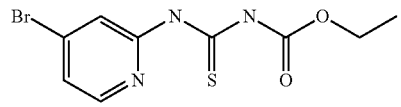 [SMILES: CCOC(=O)NC(=S)Nc1cc(Br)ccn1]

To a solution of 4-bromopyridin-2-amine (10.4 g, 60.1 mmol) in dioxane (242 ml) is added ethoxycarbonyl isothiocyanate (7.88 g, 6.8 ml, 60.1 mmol) at 25° C. The resulting mixture is stirred for 4 hours at 25° C. The solvent is evaporated, the solid yellow residue diluted with ethyl acetate and washed with water and brine. The organic layer is separated, dried over magnesium sulfate and the solvent is removed in vacuo affording 1-ethoxycarbonyl-3-(4-bromo-pyridin-2-yl)-thiourea (17.37 g, 95%) as a yellow solid. mp.: 107-110° C. MS: m/z=304.0, 305.9 (M+H$^+$).

b) 7-bromo-[1,2,4]triazolo[1,5-a]pyridin-2-amine

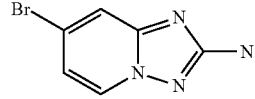 [SMILES: Nc1nc2cc(Br)ccn2n1]

A mixture of hydroxylamine hydrochloride (20.7 g, 298 mmol) and N-ethyldiisopropylamine (23.1 g, 31.2 ml, 179 mmol) in ethanol (380 ml) is stirred for a few minutes at 25° C. The mixture is then added to 1-ethoxycarbonyl-3-(4-bromo-pyridin-2-yl)-thiourea (18.13 g, 59.6 mmol) and the resulting mixture is refluxed for 1 day. The solvent is evaporated to dryness and the residue triturated for 10 minutes with water (100 ml). The solid is collected by filtration, washed with water and dried affording 7-bromo-[1,2,4]triazolo[1,5-a]pyridin-2-amine (10 g, 78.8%) as a light yellow solid. mp.: 190-2° C. MS: m/z=212.9, 215.0 (M+H$^+$).

c) 2,7-dibromo-[1,2,4]triazolo[1,5-a]pyridine

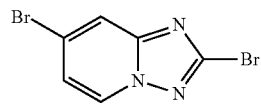 [SMILES: Brc1ccn2nc(Br)nc2c1]

A suspension of tert-butyl nitrite (4.84 g, 5.58 ml, 46.9 mmol) and copper(II) bromide (10.5 g, 46.9 mmol) in acetonitrile (350 ml) is heated to 75° C., then 7-bromo-[1,2,4]triazolo[1,5-a]pyridin-2-amine (10 g, 46.9 mmol) is added in small portions. The resulting mixture is stirred for 4 hours at 75° C. Further portions of copper(II) bromide (5.24 g, 23.5 mmol) and tert-butyl nitrite (2.42 g, 2.79 ml, 23.5 mmol) are added and refluxing is continued for 1.5 hours. The acetonitrile is evaporated and the residue (green slurry) diluted with ethyl acetate. The precipitated solid is collected by filtration, washed with ethyl acetate and dichloromethane and dried affording 2,7-dibromo-[1,2,4]triazolo[1,5-a]pyridine (13.25 g, 102%) as a light green solid. MS: m/z=275.8, 277.8, 279.8 (M+H⁺).

d) 4-(7-bromo-[1,2,4]triazolo[1,5-a]pyridin-2-yl)morpholine

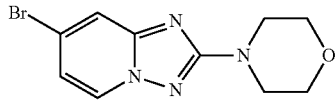 [SMILES: Brc1ccn2nc(N3CCOCC3)nc2c1]

A mixture of 2,7-dibromo-[1,2,4]triazolo[1,5-a]pyridine (1 g, 3.61 mmol) and morpholine (10.0 g, 10 ml, 115 mmol) was refluxed for 4 hours under argon atmosphere, the formerly green mixture turning to yellow. The reaction mixture is concentrated to dryness, applied on silica and purified by flash chromatography on a 20 g silica column using heptane/ethyl acetate 10-100% as eluent affording 4-(7-bromo-[1,2,4]triazolo[1,5-a]pyridin-2-yl)morpholine (367 mg, 35.9%) as a white solid. mp.: 178-9° C. MS: m/z=285.0, 283.0 (M+H⁺).

e) tert-butyl 2-morpholino-[1,2,4]triazolo[1,5-a]pyridin-7-ylcarbamate

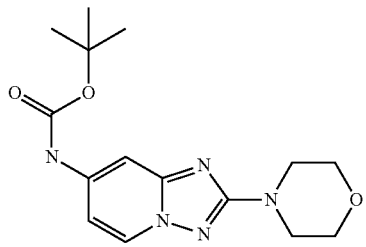 [SMILES: CC(C)(C)OC(=O)Nc1ccn2nc(N3CCOCC3)nc2c1]

To an argon purged solution of 4-(7-bromo-[1,2,4]triazolo[1,5-a]pyridin-2-yl)morpholine (321 mg, 1.13 mmol) in dioxane (8 ml) are added tert-butyl carbamate (159 mg, 1.36 mmol), tris(dibenzylideneacetone)dipalladium(0) (20.8 mg, 22.7 µmol), 4,5-bis(diphenylphosphino)-9,9-dimethylxanthene (26.2 mg, 45.4 µmol) and cesium carbonate (517 mg, 1.59 mmol). The reaction vessel is sealed and heated to 110° C. for 20 hours. The crude material is applied on silica and purified by flash chromatography on a 20 g silica column using heptane/ethyl acetate 10-70% as eluent affording tert-butyl 2-morpholino-[1,2,4]triazolo[1,5-a]pyridin-7-ylcarbamate (365 mg, 101%) as a light yellow solid. mp.: 92-3° C. MS: m/z=320.1 (M+H⁺).

f) 2-morpholino-[1,2,4]triazolo[1,5-a]pyridin-7-amine hydrochloride

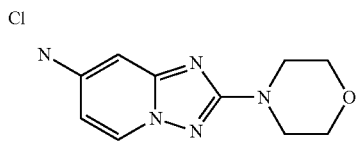 [SMILES: Cl ; Nc1ccn2nc(N3CCOCC3)nc2c1]

A mixture of tert-butyl 2-morpholino-[1,2,4]triazolo[1,5-a]pyridin-7-ylcarbamate (356 mg, 1.11 mmol) and hydrochloric acid (6N in ether, 10 ml, 60.0 mmol) is stirred for 2 hours at 25° C. The solvent is removed in vacuo affording 2-morpholino-[1,2,4]triazolo[1,5-a]pyridin-7-amine hydrochloride (308 mg, 108%) as a light yellow solid. mp.: >250° C. MS: m/z=220.3 (M+H⁺).

g) ethyl 4-(azetidine-1-carbonyl)-1-methyl-1H-pyrazole-5-carboxylate

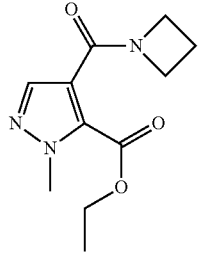 [SMILES: CCOC(=O)c1c(C(=O)N2CCC2)cnn1C]

To a cooled solution of 5-(ethoxycarbonyl)-1-methyl-1H-pyrazole-4-carboxylic acid (1.5 g, 7.57 mmole), N-ethyldiisopropylamine (3.97 ml, 22.7 mmole) and azetidine (1.02 ml, 15.1 mmole) in ethyl acetate (30 ml) is added at 0° C. propanephosphonic acid cyclic anhydride (50% in ethyl acetate, 11.4 ml, 18.9 mole). The ice-bath is removed and the light yellow solution is stirred for 3 hr at room temperature. The light yellow solution is adjusted to pH 9 with sat. aqueous sodium carbonate solution, the aqueous layer is separated and extracted twice with ethyl acetate. The combined organic layer is washed with water and brine, dried with magnesium sulfate and the solvent is removed in vacuo affording 4-(azetidine-1-carbonyl)-2-methyl-2H-pyrazole-3-carboxylic acid ethyl ester (1.09 g, 60.7%) as a light brown viscous oil. MS: m/z=238.2 (M+H⁺).

h) 4-(azetidine-1-carbonyl)-1-methyl-N-(2-morpholino-[1,2,4]triazolo[1,5-a]pyridin-7-yl)-1H-pyrazole-5-carboxamide

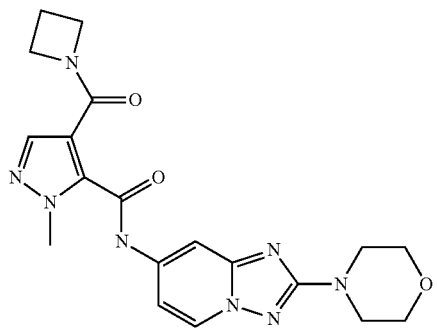 [SMILES: Cn1ncc(C(=O)N2CCC2)c1C(=O)Nc1ccn2nc(N3CCOCC3)nc2c1]

To an nitrogene purged suspension of 2-morpholino-[1,2,4]triazolo[1,5-a]pyridin-7-amine hydrochloride (80 mg, 0.313 mmol) and N-ethyldiisoppropylamine (120 ul, 0.688 mmole) in dioxane (3 ml) is added trimethyl aluminium (2 M solution in toluene, 0.47 ml, 0.94 mmol). The resulting solution is stirred for ½ hour at room temperature. Then ethyl 4-(azetidine-1-carbonyl)-1-methyl-1H-pyrazole-5-carboxylate (75 mg, 0.313 mmol) in dioxane (0.7 ml) is added and the mixture is heated to reflux in a sealed vessel and stirred for 19 hours. Purification of the reaction mixture by chromatography on a 12 g RediSep silica cartridge (eluent dichloromethane+4% methanol) affords 4-(azetidine-1-carbonyl)-1-methyl-N-(2-morpholino-[1,2,4]triazolo[1,5-a]pyridin-7-yl)-1H-pyrazole-5-carboxamide (106 mg, 82.5%) as an off-white solid. mp.: 232-4° C. MS: m/z=411.3 (M+H$^+$).

Example 9

4-(Azetidine-1-carbonyl)-1-methyl-N-(8-methyl-2-phenyl-[1,2,4]triazolo[1,5-a]pyridin-7-yl)-1H-pyrazole-5-carboxamide a) methyl 3-methylisonicotinate

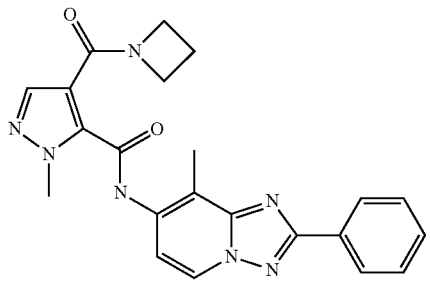 [SMILES: Cc1c(NC(=O)c2c(C(=O)N3CCC3)cnn2C)ccn2nc(-c3ccccc3)nc12]

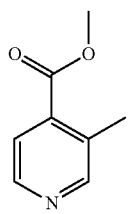

A mixture of 3-methylisonicotinic acid (7 g, 51.0 mmol) and hydrochloric acid (1 M in methanol, 200 ml, 200 mmol) is refluxed for 18 hours. The methanol is evaporated, the residue diluted with ethyl acetate and washed with sat. aqueous sodium hydrogencarbonate solution and brine. The organic layer is dried with magnesium sulfate and the solvent evaporated to dryness affording methyl 3-methylisonicotinate (5.45 g, 70.6%) as an orange oil. MS: m/z=152.1 (M$^+$).

b) 1-amino-4-(methoxycarbonyl)-3-methylpyridinium 2,4,6-trimethylbenzenesulfonate

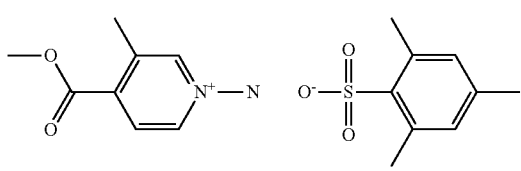

To an ice-cooled suspension (white) of O-(mesitylsulfonyl)hydroxylamine (1.75 g, 8.14 mmol) in dichloromethane (10 ml) is dropwise added a solution of methyl 3-methylisonicotinate (1.23 g, 8.14 mmol) in dichloromethane (3 ml). After the addition is completed, the resulting light yellow solution is stirred for 3 hours at 25° C. The solution is cooled to 0° C. and diluted with diethyl ether until a white solid precipitates. The suspension is stirred for 1 hour and the solid is collected by filtration, washed with ether and dried affording 1-amino-4-(methoxycarbonyl)-3-methylpyridinium 2,4,6-trimethylbenzenesulfonate (2.41 g, 80.8%) as a white solid. MS: m/z=167.2 (M$^+$).

c) methyl 8-methyl-2-phenyl-[1,2,4]triazolo[1,5-a]pyridine-7-carboxylate methyl 6-methyl-2-phenyl-[1,2,4]triazolo[1,5-a]pyridine-7-carboxylate

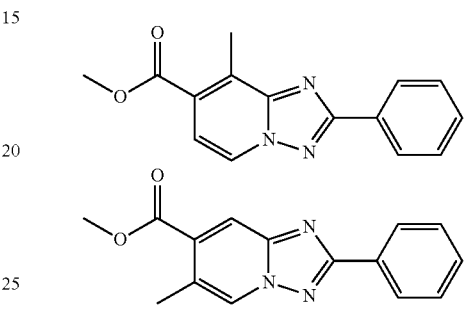

To a suspension of 1-amino-4-(methoxycarbonyl)-3-methylpyridinium 2,4,6-trimethylbenzenesulfonate (2.409 g, 6.57 mmol) in ethanol (40 ml) are added benzonitrile (675 µl, 6.57 mmol), copper(II) acetate monohydrate (1.31 g, 6.57 mmol) and finally potassium hydroxide (2M in ethanol, 3.62 ml, 7.23 mmol). The resulting mixture is heated to 90° C. and stirred for 18 hours under air atmosphere while air was slightly bubbled through the reaction mixture. The dark green mixture is poured on sat. aqueous sodium bicarbonate solution (100 ml) and stirred for 5 minutes, then extracted twice with ethyl acetate (filtration over dicalite is required because of emulsion). The combined organic layers are washed twice with water and brine, dried with magnesium sulfate and the solvent is evaporated. The crude material is loaded on silica and separated by flash chromatography on a 70 g silica column using heptane/ethyl acetate 10-30% as eluent affording methyl 8-methyl-2-phenyl-[1,2,4]triazolo[1,5-a]pyridine-7-carboxylate (634 mg, 36%) as a white solid (MS: m/z=268.1 (M+H$^+$) and methyl 6-methyl-2-phenyl-[1,2,4]triazolo[1,5-a]pyridine-7-carboxylate (112 mg, 6.37%) as a white solid. MS: m/z=268.1 (M+H$^+$).

d) 8-methyl-2-phenyl-[1,2,4]triazolo[1,5-a]pyridine-7-carboxylic acid

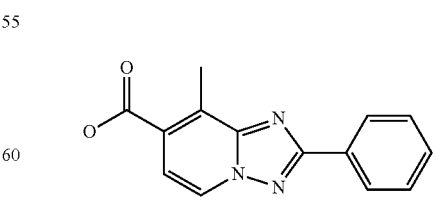

A mixture of methyl 8-methyl-2-phenyl-[1,2,4]triazolo[1,5-a]pyridine-7-carboxylate (634 mg, 2.37 mmol) and lithium hydroxide monohydrate (398 mg, 9.49 mmol) in tetrahydrofurane (15 ml) and water (5 ml) is stirred for 3 days at 25° C.

The mixture is diluted with water, acidified to pH=0 with hydrochloric acid 37% and extracted with ethyl acetate; the organic layer is washed with water and brine, dried with magnesium sulfate and the solvent is evaporated affording 8-methyl-2-phenyl-[1,2,4]triazolo[1,5-a]pyridine-7-carboxylic acid (710 mg, 118%) as a white solid. mp.: >250° C. MS: m/z=254.1 (M+H⁺).

e) 8-methyl-2-phenyl-[1,2,4]triazolo[1,5-a]pyridin-7-amine

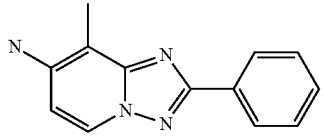 [SMILES: Cc1c(N)ccn2nc(-c3ccccc3)nc12]

To a suspension of 8-methyl-2-phenyl-[1,2,4]triazolo[1,5-a]pyridine-7-carboxylic acid (710 mg, 2.81 mmol) and triethylamine (1.17 ml, 8.42 mmol) in tert-butanol (20 ml) is added diphenyl phosphorazidate (909 µl, 4.21 mmol) at 25° C. After the addition the white suspension is refluxed for 24 hours. The crude material is loaded on silica and purified by flash chromatography on a 20 g silica column using heptane/ethyl acetate 10-100% and then ethyl acetate/methanol 10% as eluent affording 8-methyl-2-phenyl-[1,2,4]triazolo[1,5-a]pyridin-7-amine (160 mg, 25.4%) as a white solid. mp.: 213-5° C. MS: m/z=225.2 (M+H⁺).

f) 4-(azetidine-1-carbonyl)-1-methyl-N-(8-methyl-2-phenyl-[1,2,4]triazolo[1,5-a]pyridin-7-yl)-1H-pyrazole-5-carboxamide

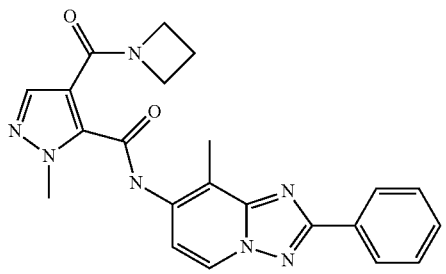 [SMILES: Cc1c(NC(=O)c2c(C(=O)N3CCC3)cnn2C)ccn2nc(-c3ccccc3)nc12]

To an argon purged solution of 8-methyl-2-phenyl-[1,2,4]triazolo[1,5-a]pyridin-7-amine (60 mg, 268 µmol) in dioxane (5 ml) is added trimethylaluminum (2M solution in toluene, 401 µl, 803 µmol). The resulting mixture is stirred for 1 hour at 25° C., then ethyl 4-(azetidine-1-carbonyl)-1-methyl-1H-pyrazole-5-carboxylate (63.5 mg, 268 µmol) is added, the mixture is heated to 100° C. and stirred for 72 hours. The crude material is loaded on silica and purified by flash chromatography on a 20 g silica column using heptane/ethyl acetate 50-100% as eluent affording 4-(azetidine-1-carbonyl)-1-methyl-N-(8-methyl-2-phenyl-[1,2,4]triazolo[1,5-a]pyridin-7-yl)-1H-pyrazole-5-carboxamide (77 mg, 69.3%) as a white solid. mp.: 243-5° C. MS: m/z=416.2 (M+H⁺).

Example 10

4-(Azetidine-1-carbonyl)-1-methyl-N-(6-methyl-2-phenyl-[1,2,4]triazolo[1,5-a]pyridin-7-yl)-1H-pyrazole-5-carboxamide

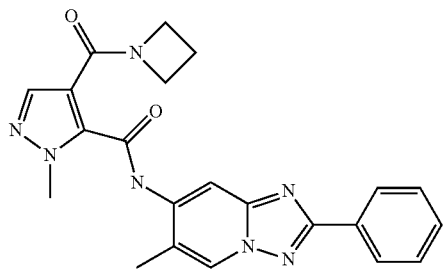 [SMILES: Cc1cn2nc(-c3ccccc3)nc2cc1NC(=O)c1c(C(=O)N2CCC2)cnn1C]

a) 6-methyl-2-phenyl-[1,2,4]triazolo[1,5-a]pyridine-7-carboxylic acid

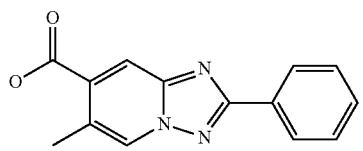 [SMILES: Cc1cn2nc(-c3ccccc3)nc2cc1C(=O)O]

A mixture of methyl 6-methyl-2-phenyl-[1,2,4]triazolo[1,5-a]pyridine-7-carboxylate (182 mg, 681 µmol) and lithium hydroxide monohydrate (114 mg, 2.72 mmol) in tetrahydrofurane (10 ml) and water (2 ml) is stirred for 4 hours at 25° C. The mixture is diluted with ethyl acetate, acidified to pH=0 with hydrochloric acid 37% and washed with water and brine. The organic layer is dried with magnesium sulfate and the solvent is evaporated to dryness affording 6-methyl-2-phenyl-[1,2,4]triazolo[1,5-a]pyridine-7-carboxylic acid (223 mg, 129%) as a light yellow solid. mp.: 228-233° C. MS: m/z=254.2 (M+H⁺).

b) 6-methyl-2-phenyl-[1,2,4]triazolo[1,5-a]pyridin-7-amine

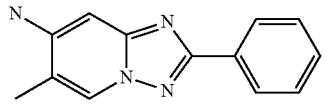 [SMILES: Cc1cn2nc(-c3ccccc3)nc2cc1N]

To a suspension of 6-methyl-2-phenyl-[1,2,4]triazolo[1,5-a]pyridine-7-carboxylic acid (172 mg, 679 µmol) and triethylamine (206 mg, 284 µl, 2.04 mmol) in tert-butanol (10 ml) is added at 25° C. diphenyl phosphorazidate (220 µl, 1.02 mmol). The resulting mixture is heated to reflux and stirred for 18 hours. The crude material is loaded on silica and purified by flash chromatography on a 20 g silica column using heptane/ethyl acetate 10-100% as eluent affording 6-methyl-2-phenyl-[1,2,4]triazolo[1,5-a]pyridin-7-ylamine (43 mg, 28%) as an off-white solid. mp.: >250° C. MS:

m/z=225.3 (M+H⁺). The hydrochloride can be prepared by stirring in tetrahydrofurane/6N hydrochloric acid in diethylether (1:6) for 2 hours and final evaporation to dryness. Light brown solid (quant.). MS: m/z=225.3 (M+H⁺).

c) 4-(azetidine-1-carbonyl)-1-methyl-N-(6-methyl-2-phenyl-[1,2,4]triazolo[1,5-a]pyridin-7-yl)-1H-pyrazole-5-carboxamide

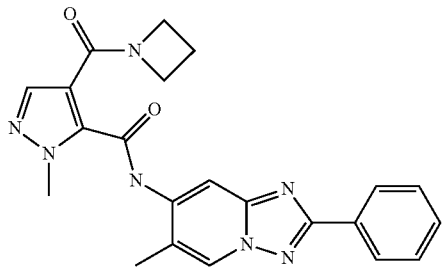 [SMILES: Cc1cn2nc(-c3ccccc3)nc2cc1NC(=O)c1c(C(=O)N2CCC2)cnn1C]

To an argon purged solution of 6-methyl-2-phenyl-[1,2,4]triazolo[1,5-a]pyridin-7-amine hydrochloride (147 mg, 564 μmol) and triethylamine (78.6 μl, 564 μmol) in dioxane (8 ml) is added trimethylaluminum (2M solution in toluene, 705 μl, 1.41 mmol). The resulting mixture is stirred for 1 hour at 25° C., then ethyl 4-(azetidine-1-carbonyl)-1-methyl-1H-pyrazole-5-carboxylate (134 mg, 564 μmol) is added; the mixture is heated to 100° C. and stirred for 18 hours. As no conversion is detected N-ethyl diisopropylamine (246 μl, 1.41 mmol) and another portion of trimethylaluminum (2M solution in toluene, 705 μl, 1.41 mmol) are added, the mixture is stirred for 1 hours at 25° C. and then for further 20 hours at 100° C. The crude material is loaded on silica and purified by flash chromatography on a 20 g silica column using heptane/ethyl acetate 10-100% as eluent affording 4-(azetidine-1-carbonyl)-1-methyl-N-(6-methyl-2-phenyl-[1,2,4]triazolo[1,5-a]pyridin-7-yl)-1H-pyrazole-5-carboxamide (57 mg, 24.3%) as a light yellow solid. mp.: 226-8° C. MS: m/z=416.2 (M+H⁺).

Example 11

2-Methyl-2H-pyrazole-3,4-dicarboxylic acid 4-dimethylamide 3-[(2-phenyl-[1,2,4]triazolo[1,5-a]pyridin-7-yl)-amide]

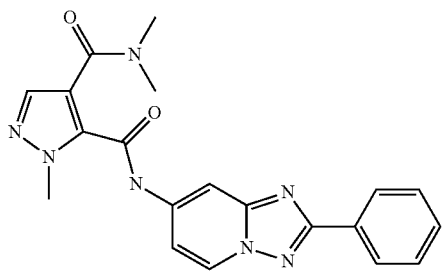 [SMILES: CN(C)C(=O)c1cnn(C)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), dimethylamine hydrochloride (158 mg, 1.93 mmol), diisopropylethylamine (434 μl, 2.48 mmol) and propylphosphonic anhydride (50% in ethyl acetate, 407 μl, 690 μmol) in tetrahydrofurane (7 ml) is stirred for 3 hours at 70° C. The suspension is diluted with ethyl acetate and washed with sat. aqueous sodium hydrogencarbonate solution and water. The organic layer is separated, dried with magnesium sulfate and the solvent is evaporated affording 2-methyl-2H-pyrazole-3,4-dicarboxylic acid 4-dimethylamide 3-[(2-phenyl-[1,2,4]triazolo[1,5-a]pyridin-7-yl)-amide] (34 mg, 31.6%) as a very insoluble white solid. mp.: >250° C. MS: m/z=390.2 (M+H⁺).

Example 12

1-Methyl-4-(morpholine-4-carbonyl)-N-(2-phenyl-[1,2,4]triazolo[1,5-a]pyridin-7-yl)-1H-pyrazole-5-carboxamide

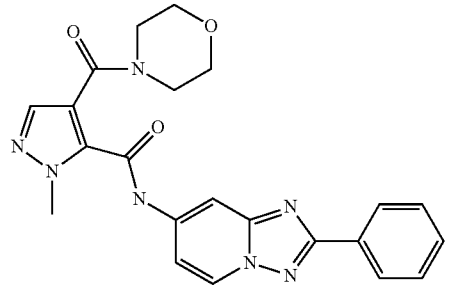 [SMILES: Cn1ncc(C(=O)N2CCOCC2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), morpholine (240 μl, 2.76 mmol) and propylphosphonic anhydride (50% in ethyl acetate, 407 μl, 690 μmol) in tetrahydrofurane (7 ml) is stirred for 3 hours at 70° C. The mixture is diluted with ethyl acetate and washed with sat. aqueous sodium hydrogencarbonate solution and brine. The organic layer is separated, dried with magnesium sulfate and the solvent is evaporated. The residue (76 mg white foam) is triturated with diethylether and ethyl acetate affording 1-methyl-4-(morpholine-4-carbonyl)-N-(2-phenyl-[1,2,4]triazolo[1,5-a]pyridin-7-yl)-1H-pyrazole-5-carboxamide (53 mg, 44.5%) as a white solid. mp.: 203-207° C. MS: m/z=432.4 (M+H⁺).

Example 13

1-Methyl-N-(2-phenyl-[1,2,4]triazolo[1,5-a]pyridin-7-yl)-4-(pyrrolidine-1-carbonyl)-1H-pyrazole-5-carboxamide

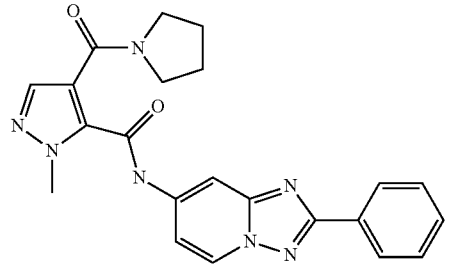 [SMILES: Cn1ncc(C(=O)N2CCCC2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), pyrrolidine (228 μl, 2.76 mmol) and propylphosphonic anhydride (50% in ethyl acetate, 407 μl, 690 μmol) in tetrahydrofurane (7 ml) is stirred for 3 hours at 70° C. The mixture is diluted with ethyl acetate and washed with sat. aqueous sodium hydrogencarbonate solution and brine. The organic layer is separated, dried with magnesium sulfate and the solvent is evaporated. The residue (65 mg white solid) is triturated with diethylether affording 2-methyl-4-(pyrrolidine-1-carbonyl)-2H-pyrazole-3-carboxylic acid (2-phenyl-[1,2,4]triazolo[1,5-a]pyridin-7-yl)-amide (24 mg, 20.9%) as a white solid. mp.: 210-215° C. MS: m/z=416.2 (M+H$^+$).

Example 14

(S)-1-Methyl-N5-(2-phenyl-[1,2,4]triazolo[1,5-a]pyridin-7-yl)-N4-(tetrahydrofuran-3-yl)-1H-pyrazole-4,5-dicarboxamide

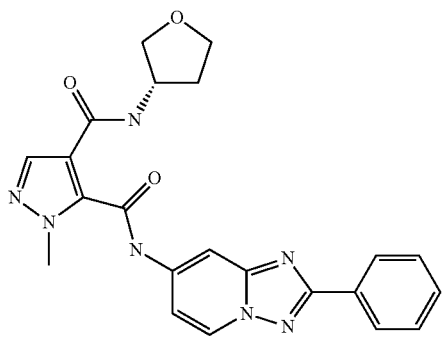 [SMILES: Cn1ncc(C(=O)N[C@H]2CCOC2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), (S)-tetrahydrofuran-3-ylamine hydrochloride (68.2 mg, 552 μmol), diisopropylethylamine (193 μl, 1.1 mmol) and propylphosphonic anhydride (50% in ethyl acetate, 407 μl, 690 μmol) in tetrahydrofurane (7 ml) is refluxed for 18 hours. The solvent is evaporated and to the residue is added sat. aqueous sodium hydrogencarbonate solution. The mixture is stirred for 20 minutes while a white solid precipitates. The solid is collected by filtration, washed with diethylether and dried affording (S)-1-methyl-N5-(2-phenyl-[1,2,4]triazolo[1,5-a]pyridin-7-yl)-N4-(tetrahydrofuran-3-yl)-1H-pyrazole-4,5-dicarboxamide (118 mg, 99.1%) as a white solid. mp.: >250° C. MS: m/z=432.4 (M+H$^+$).

Example 15

(R)-1-Methyl-N5-(2-phenyl-[1,2,4]triazolo[1,5-a]pyridin-7-yl)-N4-(tetrahydrofuran-3-yl)-1H-pyrazole-4,5-dicarboxamide

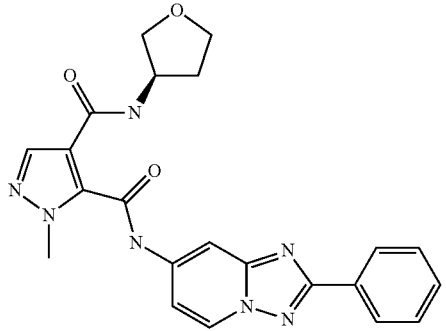 [SMILES: Cn1ncc(C(=O)N[C@@H]2CCOC2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), (R)-tetrahydrofuran-3-ylamine4-methylbenzenesulfonate (143 mg, 552 μmol), diisopropylethylamine (193 μl, 1.1 mmol) and propylphosphonic anhydride (50% in ethyl acetate, 407 μl, 690 μmol) in tetrahydrofurane (7 ml) is refluxed for 18 hours. The solvent is evaporated and to the residue is added sat. aqueous sodium hydrogencarbonate solution. The mixture is stirred for 20 minutes while a white solid precipitates. The solid is collected by filtration, washed with diethylether and dried affording (R)-1-methyl-N5-(2-phenyl-[1,2,4]triazolo[1,5-a]pyridin-7-yl)-N4-(tetrahydrofuran-3-yl)-1H-pyrazole-4,5-dicarboxamide (114 mg, 95.7%) as a white solid. mp.: >250° C. MS: m/z=432.3 (M+H$^+$).

Example 16

N4-(3-Methoxypropyl)-1-methyl-N5-(2-phenyl-[1,2,4]triazolo[1,5-a]pyridin-7-yl)-1H-pyrazole-4,5-dicarboxamide

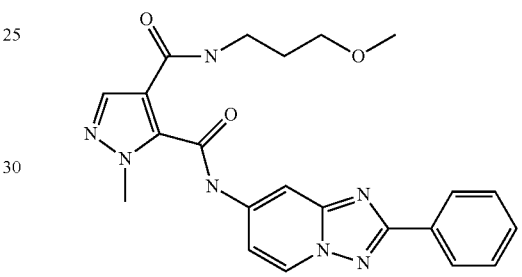

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), 3-methoxypropan-1-amine (169 μl, 1.66 mmol) and propylphosphonic anhydride (50% in ethyl acetate, 407 μl, 690 μmol) in tetrahydrofurane (7 ml) is refluxed for 18 hours. The solvent is evaporated and to the residue is added sat. aqueous sodium hydrogencarbonate solution. The mixture is stirred for 20 minutes while a white solid precipitates. The solid is collected by filtration, washed with diethylether and dried affording N4-(3-Methoxypropyl)-1-methyl-N5-(2-phenyl-[1,2,4]triazolo[1,5-a]pyridin-7-yl)-1H-pyrazole-4,5-dicarboxamide (113 mg, 94.3%) as a white solid. mp.: 191-3° C. MS: m/z=434.4 (M+H$^+$).

Example 17

1-Methyl-N4-(oxetan-3-yl)-N5-(2-phenyl-[1,2,4]triazolo[1,5-a]pyridin-7-yl)-1H-pyrazole-4,5-dicarboxamide

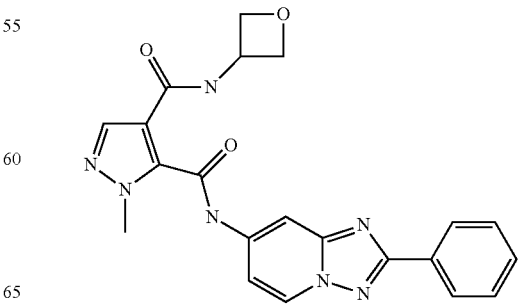

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), oxetan-3-amine hydrochloride (60.5 mg, 552 µmol), diisopropylethylamine (241 µl, 1.38 mmol) and propylphosphonic anhydride (50% in ethyl acetate, 407 µl, 690 µmol) in tetrahydrofurane (7 ml) is stirred for 20 hours at reflux under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried. The residue (94 mg white solid) is triturated with ethyl acetate, filtered and the filtrate is evaporated affording 1-methyl-N4-(oxetan-3-yl)-N5-(2-phenyl-[1,2,4]triazolo[1,5-a]pyridin-7-yl)-1H-pyrazole-4,5-dicarboxamide (44 mg, 38.2%) as a white solid. mp.: >250° C. MS: m/z=418.3 (M+H$^+$).

Example 18

N4,N4-diethyl-1-methyl-N5-(2-phenyl-[1,2,4]triazolo[1,5-a]pyridin-7-yl)-1H-pyrazole-4,5-dicarboxamide

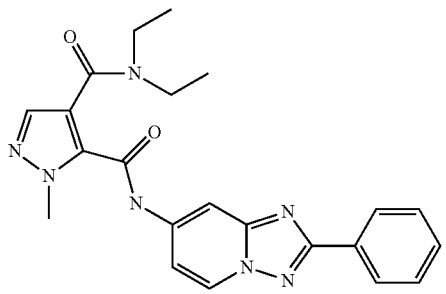 [SMILES: CCN(CC)C(=O)c1cnn(C)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), diethylamine (142 µl, 1.38 mmol) and propylphosphonic anhydride (50% in ethyl acetate, 407 µl, 690 µmol) in tetrahydrofurane (7 ml) is stirred for 20 hours at 70° C. under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried affording N4,N4-diethyl-1-methyl-N5-(2-phenyl-[1,2,4]triazolo[1,5-a]pyridin-7-yl)-1H-pyrazole-4,5-dicarboxamide (93 mg, 80.7%) as a white solid. mp.: 177-9° C. MS: m/z=418.3 (M+H$^+$).

Example 19

N4-isopropyl-1-methyl-N5-(2-phenyl-[1,2,4]triazolo[1,5-a]pyridin-7-yl)-1H-pyrazole-4,5-dicarboxamide

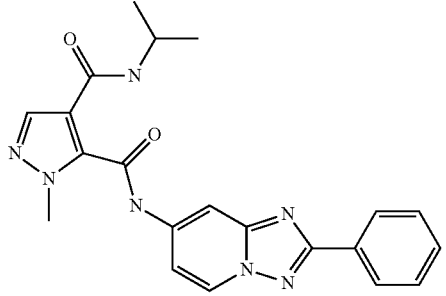 [SMILES: CC(C)NC(=O)c1cnn(C)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), isopropylamine (119 µl, 1.38 mmol) and propylphosphonic anhydride (50% in ethyl acetate, 407 ul, 318.8 mmol) in tetrahydrofurane (7.00 ml) is stirred for 20 hours at 70° C. under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried affording N4-isopropyl-1-methyl-N5-(2-phenyl-[1,2,4]triazolo[1,5-a]pyridin-7-yl)-1H-pyrazole-4,5-dicarboxamide (93 mg, 83.8%) as a white solid. mp.: >250° C. MS: m/z=404.4 (M+H$^+$).

Example 20

N4,1-dimethyl-N4-(((6-methylpyridin-3-yl)methyl)-N5-(2-phenyl-[1,2,4]triazolo[1,5-a]pyridin-7-yl)-1H-pyrazole-4,5-dicarboxamide

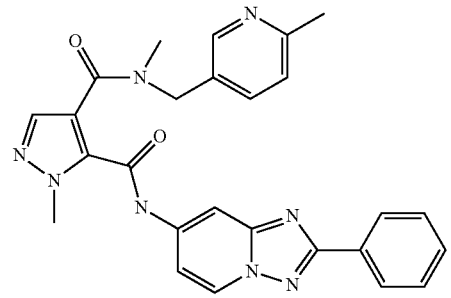 [SMILES: Cc1ccc(CN(C)C(=O)c2cnn(C)c2C(=O)Nc2ccn3nc(-c4ccccc4)nc3c2)cn1]

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), N-methyl-1-(6-methylpyridin-3-yl)methanamine (50 mg, 367 µmol), diisopropylethylamine (145 µl, 828 µmol) and propylphosphonic anhydride (50% in ethyl acetate, 407 µl, 690 µmol) in tetrahydrofurane (7.00 ml) is stirred for 20 hours at 70° C. under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried affording N4,1-dimethyl-N4-((6-methylpyridin-3-yl)methyl)-N5-(2-phenyl-[1,2,4]triazolo[1,5-a]pyridin-7-yl)-1H-pyrazole-4,5-dicarboxamide (124 mg, 93.5%) as a white solid. mp.: 110-150° C. MS: m/z=481.4 (M+H$^+$).

Example 21

N4-(2-Fluoroethyl)-N4,1-dimethyl-N5-(2-morpholino-[1,2,4]triazolo[1,5-a]pyridin-7-yl)-1H-pyrazole-4,5-dicarboxamide

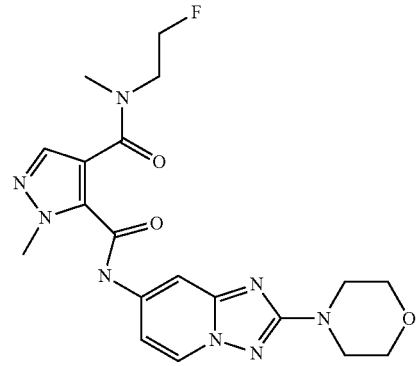 [SMILES: CN(CCF)C(=O)c1cnn(C)c1C(=O)Nc1ccn2nc(N3CCOCC3)nc2c1]

a) N-(2-Fluoroethyl)-N,1-dimethyl-1H-pyrazole-4-carboxamide

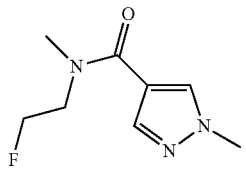

Methyl-1H-pyrazole-4-carboxylic acid (1.0 g, 7.93 mmol) was combined with DMF (10.0 ml) to give a colorless solution. Et$_3$N (3.3 ml, 23.8 mmol) and 2-(1H-benzo[d][1,2,3]triazol-1-yl)-1,1,3,3-tetramethylisouronium tetrafluoroborate (TBTU, 2.8 g, 8.72 mmol) were added and the reaction mixture was stirred at RT for 1 h. 2-Fluoroethyl-methylamine hydrochloride (991 mg, 8.72 mmol) was added and stirring was continued overnight. DMF was removed under HV and the crude product (5.93 g brown oil) was purified by chromatography with a 50 g SiO$_2$—NH$_2$ cartridge (CH$_2$Cl$_2$/MeOH 95:5). The resulting product was dried under HV at RT for 48 h. Yellow oil (1.40 g, 92%); MS: m/z=186.1 [M+H]$^+$.

b) 4-((2-Fluoroethyl)(methyl)carbamoyl)-1-methyl-1H-pyrazole-5-carboxylic acid

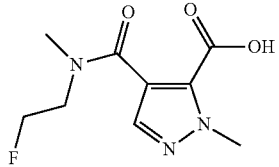

In a 50 mL three-necked flask, N-(2-fluoroethyl)-N,1-dimethyl-1H-pyrazole-4-carboxamide (500 mg, 2.7 mmol) was combined with THF (10.0 ml) to give a colorless solution. 1,1,4,7,7-Pentamethyldiethylenetriamine (621 μl, 2.97 mmol) was added, and, after cooling down to –100° C., tBuLi (1.6 M in pentane, 2.53 ml, 4.05 mmol) was added dropwise. After stirring 30 min an excess of dry ice was carefully added. After 5 min, the cooling bath was removed and the mixture was allowed to warm up to RT. H$_2$O was added and un-reacted starting material was removed by extraction with CH$_2$Cl$_2$. The aqueous layer was then acidified using 1 N HCl solution, and the acid was extracted using CH$_2$Cl$_2$. After drying over Na$_2$SO$_4$, filtration and concentration in vacuum, the viscous oil was dried in HV to yield 307 mg (50%) of product as a light brown viscous oil. MS: m/z=230.2 [M+H]$^+$.

c) N4-(2-Fluoroethyl)-N4,1-dimethyl-N5-(2-morpholino-[1,2,4]triazolo[1,5-a]pyridin-7-yl)-1H-pyrazole-4,5-dicarboxamide

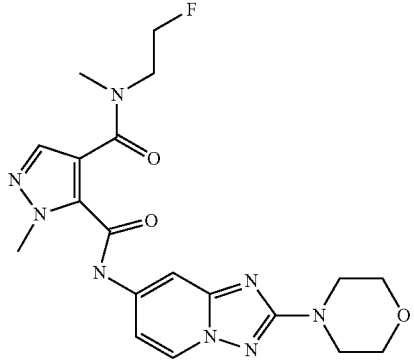 [SMILES: CN(CCF)C(=O)c1cnn(C)c1C(=O)Nc1ccn2nc(N3CCOCC3)nc2c1]

A mixture of 442-fluoroethyl)(methyl)carbamoyl)-1-methyl-1H-pyrazole-5-carboxylic acid (100 mg, 436 μmol), 2-morpholino-[1,2,4]triazolo[1,5-a]pyridin-7-amine hydrochloride (100 mg, 391 μmol), propylphosphonic anhydride (50% in ethyl acetate, 576 μl, 978 μmol) and N-ethyldiisopropylamine (273 μl, 1.56 mmol) in THF (7 ml) was stirred overnight at 75° C. The solvent was evaporated and the residue dissolved in water (10 ml, pH 3). The yellow solution was adjusted to pH 8 with sat. aqueous sodium hydrogencarbonate solution and stirred for 20 min. The solid was collected by filtration, washed with water and dried affording N4-(2-fluoroethyl)-N4,1-dimethyl-N5-(2-morpholino-[1,2,4]triazolo[1,5-a]pyridin-7-yl)-1H-pyrazole-4,5-dicarboxamide (88 mg, 52.3%) as a white solid. MS: m/z=431.2 [M+H]$^+$.

Example 22

4-(1,1-Dioxo-thiomorpholine-4-carbonyl)-2-methyl-2H-pyrazole-3-carboxylic acid (2-phenyl-[1,2,4]triazolo[1,5-a]pyridin-7-yl)-amide

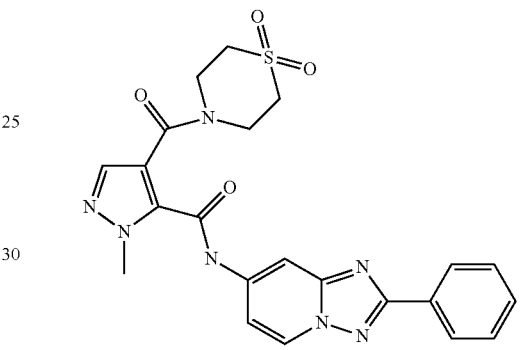

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), thiomorpholine-1,1-dioxide (44.8 mg, 331 μmol), diisopropylethylamine (145 μl, 828 μmol) and propylphosphonic anhydride (50% in ethyl acetate, 407 μl, 690 μmol) in tetrahydrofurane (7.00 ml) is stirred for 4 hours at 70° C. and then for 60 hours at 25° C. under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried affording 4-(1,1-dioxo-thiomorpholine-4-carbonyl)-2-methyl-2H-pyrazole-3-carboxylic acid (2-phenyl-[1,2,4]triazolo[1,5-a]pyridin-7-yl)-amide (112 mg, 84.7%) as a white solid. mp.: >250° C. MS: m/z=480.2 (M+H$^+$).

Example 23

N4,1-dimethyl-N5-(2-phenyl-[1,2,4]triazolo[1,5-a]pyridin-7-yl)-1H-pyrazole-4,5-dicarboxamide

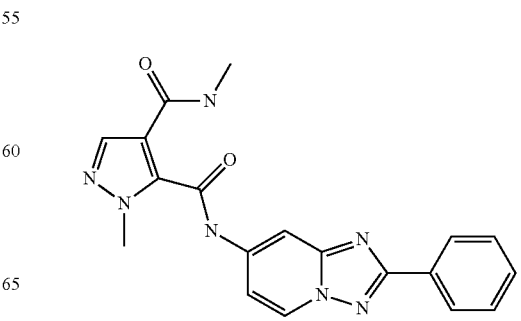

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), methanamine hydrochloride (186 mg, 2.76 mmol), diisopropylethylamine (627 μl, 3.59 mmol) and propylphosphonic anhydride (50% in ethyl acetate, 407 μl, 690 μmol) in tetrahydrofurane (7.00 ml) is stirred for 4 hours at 70° C. and then over the weekend at 25° C. under nitrogen atmosphere. The solvent is evaporated and to the residue is added sat. aqueous sodium hydrogencarbonate solution. The mixture is stirred for 20 minutes while a white solid precipitates. The solid is collected by filtration, washed with diethylether and dried affording N4,1-dimethyl-N5-(2-phenyl-[1,2,4]triazolo[1,5-a]pyridin-7-yl)-1H-pyrazole-4,5-dicarboxamide (69 mg, 66.6%) as a white solid. mp.: >250° C. MS: m/z=376.2 (M+H$^+$).

Example 24

4-(3-Methoxyazetidine-1-carbonyl)-1-methyl-N-(2-phenyl-[1,2,4]triazolo[1,5-a]pyridin-7-yl)-1H-pyrazole-5-carboxamide

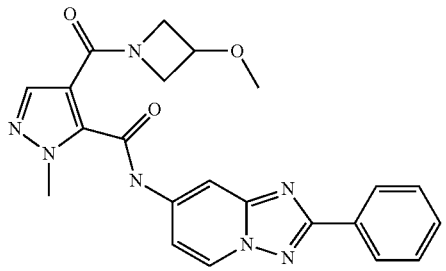 [SMILES: COC1CN(C(=O)c2cnn(C)c2C(=O)Nc2ccn3nc(-c4ccccc4)nc3c2)C1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), 3-methoxyazetidine hydrochloride (37.5 mg, 304 μmol), diisopropylethylamine (241 μl, 1.38 mmol) and propylphosphonic anhydride (50% in ethyl acetate, 407 μl, 690 μmol) in tetrahydrofurane (7.00 ml) is stirred for 3 hours at 70° C. under nitrogen atmosphere in a closed vessel, and then over the weekend at room temperature. The solvent is evaporated and to the residue is added sat. aqueous sodium hydrogencarbonate solution. The mixture is stirred for 20 minutes while a white solid precipitates. The solid is collected by filtration, washed with diethylether and dried affording 4-(3-Methoxyazetidine-1-carbonyl)-1-methyl-N-(2-phenyl-[1,2,4]triazolo[1,5-a]pyridin-7-yl)-1H-pyrazole-5-carboxamide (75 mg, 66.6%) as a very insoluble white solid. mp.: 269-270° C. MS: m/z=432.3 (M+H$^+$).

Example 25

4-(3-Fluoroazetidine-1-carbonyl)-1-methyl-N-(2-phenyl-[1,2,4]triazolo[1,5-a]pyridin-7-yl)-1H-pyrazole-5-carboxamide

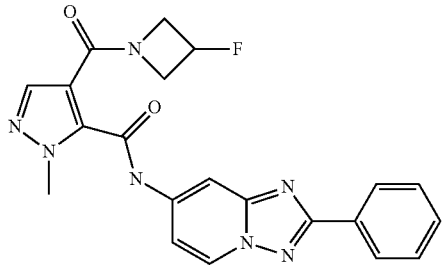 [SMILES: Cn1ncc(C(=O)N2CC(F)C2)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 μmol), 3-fluoroazetidine hydrochloride (30.8 mg, 276 mmol), diisopropylethylamine (241 μl, 1.38 mmol) and propylphosphonic anhydride (50% in ethyl acetate, 407 μl, 690 μmol) in tetrahydrofurane (7 ml) is stirred for 3 hours at 70° C. under nitrogen atmosphere in a closed vessel and then over the weekend at room temperature. The solvent is evaporated and to the residue is added sat. aqueous sodium hydrogencarbonate solution. The mixture is stirred for 20 minutes while a white solid precipitates. The solid is collected by filtration, washed with diethylether and dried affording 4-(3-fluoroazetidine-1-carbonyl)-1-methyl-N-(2-phenyl-[1,2,4]triazolo[1,5-a]pyridin-7-yl)-1H-pyrazole-5-carboxamide (111 mg, 93.3%) as an insoluble white solid. mp.: 259-262° C. MS: m/z=420.2 (M+H$^+$).

Example 26

2-Methyl-2H-pyrazole-3,4-dicarboxylic acid 4-[(2-fluoro-ethyl)-methyl-amide]3-[(2-phenyl-[1,2,4]triazolo[1,5-a]pyridin-7-yl)-amide]

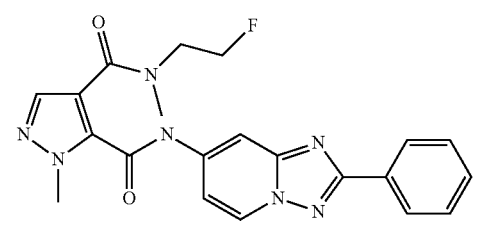 [SMILES: CN(CCF)C(=O)c1cnn(C)c1C(=O)Nc1ccn2nc(-c3ccccc3)nc2c1]

In a 20 mL sealed vessel, 4-((2-fluoroethyl)(methyl)carbamoyl)-1-methyl-1H-pyrazole-5-carboxylic acid (70 mg, 305 μmol), 2-phenyl-[1,2,4]triazolo[1,5-a]pyridin-7-amine (64 mg, 305 μmol) propylphosphonic anhydride (50% in ethyl acetate, 450 μl, 763 μmol) and N-ethyldiisopropylamine (213 μl, 1.22 mmol) are combined with tetrahydrofurane (7 ml) to give a colorless solution. The reaction mixture is stirred at 75° C. overnight. LCMS showed incomplete reaction but no side products. Propylphosphonic anhydride (50% in ethyl acetate, 450 μl, 763 mmol) is added again and the reaction mixture stirred over the weekend at 75° C. The solvent is evaporated and the residue dissolved in water (10 ml, pH 3). The yellow solution is adjusted to pH 8 with sat. aqueous sodium bicarbonate solution and stirred for 20 min. A white solid precipitates. The solid is collected by filtration (66 mg) and purified by chromatography (Si—NH2, CH2Cl2/MeOH 95:5) affording 2-methyl-2H-pyrazole-3,4-dicarboxylic acid 4-[(2-fluoro-ethyl)-methyl-amide] 3-[(2-phenyl-[1,2,4]triazolo[1,5-a]pyridin-7-yl)-amide] (50 mg, 36.9%) as a white solid. MS: m/z=422.3 (M+H).

Example 27

Isopropyl 1-methyl-5-(2-phenyl-[1,2,4]triazolo[1,5-a]pyridin-7-ylcarbamoyl)-1H-pyrazole-4-carboxylate

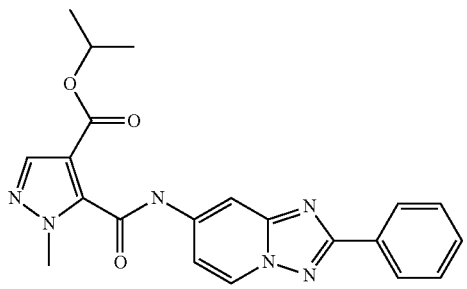 [SMILES: CC(C)OC(=O)c1cnn(C)c1C(=O)Nc1ccn2nc(-c3ccccc3)nc2c1]

A white suspension of 1-methyl-5-(2-phenyl-[1,2,4]triazolo[1,5-a]pyridin-7-ylcarbamoyl)-1H-pyrazole-4-carboxylic acid (90 mg, 248 μmol.) and 2-propanol (23 μl, 298 μmol) in N,N-dimethylformamide (2 ml) is cooled to 0° C. A solution of 4-dimethylaminopyridine (15.2 mg, 124 μmol, 0.5 eq.) and PYBROP (127 mg, 273 μmol, 1.1 eq.) in N,N-dimethylformamide (2 ml) is dropwise added at 0° C. followed after 5 min by triethylamine (105 μl, 745 μmol). The white suspension is allowed to warm to room temperature giving a colorless clear solution and stirred for 4.5 days. The colorless solution is poured on water, neutralized to pH 7-8 with aqueous 1N hydrochloric acid and extracted with dichloromethane (3×70 ml). The combined aqueous layer is washed with water (3×50 ml), dried with magnesium sulfate and the solvent is removed in vacuo. Purification of the residue (77 mg) by chromatography on a 10 g silica cartridge (eluent heptane/ethyl acetate 30-60% 25') affords isopropyl 1-methyl-5-(2-phenyl-[1,2,4]triazolo[1,5-a]pyridin-7-ylcarbamoyl)-1H-pyrazole-4-carboxylate (10 mg, 9.96%) as a white solid. MS: m/z=405.3 (M+H$^+$).

Example 28

Ethyl 1-methyl-5-(2-phenyl-[1,2,4]triazolo[1,5-a]pyridin-7-ylcarbamoyl)-1H-pyrazole-4

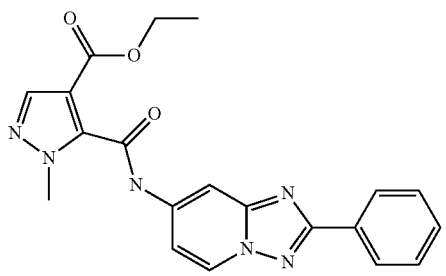 [SMILES: CCOC(=O)c1cnn(C)c1C(=O)Nc1ccn2nc(-c3ccccc3)nc2c1]

A mixture of 2-phenyl-[1,2,4]triazolo[1,5-a]pyridin-7-amine (945 mg, 4.49 mmol), 4-(ethoxycarbonyl)-1-methyl-1H-pyrazole-carboxylic acid (1.07 g, 5.39 mmol), propylphosphonic anhydride (50% in ethyl acetate, 6.62 ml, 11.2 mmol) and diisopropylethylamine (3.93 ml, 22.5 mmol) in tetrahydrofurane (50 ml) is stirred for 2.5 days at 25° C. The crude material is loaded on silicagel and purified by flash chromatography on a 50 g silica column using heptane/ethyl acetate 20-100% and then ethyl acetate/methanol 10-30% as eluent. The fractions containing product are evaporated to dryness and the residue (4.23 g light yellow solid) is dissolved in tetrahydrofurane (20 ml); sodium bicarbonate solution (30 ml) is added and the mixture is stirred for 30 minutes at 25° C. The solid is collected by filtration, washed with water and dried affording ethyl 1-methyl-5-(2-phenyl-[1,2,4]triazolo[1,5-a]pyridin-7-ylcarbamoyl)-1H-pyrazole-4-carboxylate (1.336 g, 76.1%) as an off-white solid. mp.: 242-3° C. MS: m/z=391.2 (M+H$^+$).

Example 29

1-Methyl-4-(morpholine-4-carbonyl)-N-(2-morpholino-[1,2,4]triazolo[1,5-a]pyridin-7-yl)-1H-pyrazole-5-carboxamide

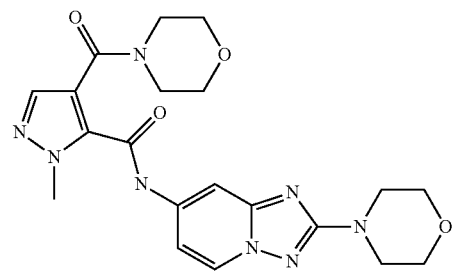 [SMILES: Cn1ncc(C(=O)N2CCOCC2)c1C(=O)Nc1ccn2nc(N3CCOCC3)nc2c1]

a) 1-methyl-5-(2-morpholino-[1,2,4]triazolo[1,5-a]pyridin-7-ylcarbamoyl)-1H-pyrazole-4-carboxylic acid

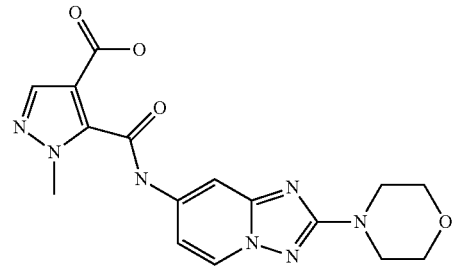 [SMILES: Cn1ncc(C(=O)O)c1C(=O)Nc1ccn2nc(N3CCOCC3)nc2c1]

A mixture of ethyl 1-methyl-5-(2-morpholino-[1,2,4]triazolo[1,5-a]pyridin-7-ylcarbamoyl)-1H-pyrazole-4-carboxylate (1.22 g, 3.05 mmol) and lithium hydroxide monohydrate (641 mg, 15.3 mmol) in methanol (30 ml) and water (5 ml) is stirred for 6 hours at 50° C. The solvent is evaporated, the residue diluted with water, acidified to pH=0 with 2N aqueous hydrochloric acid. The precipitated solid is collected by filtration, washed with ethyl acetate and dried affording 1-methyl-5-(2-morpholin-4-yl-[1,2,4]triazolo[1,5-a]pyridin-7-ylcarbamoyl)-1H-pyrazole-4-carboxylic acid (851 mg, 75%) as a light yellow solid. MS: m/z=369.9 (M−H⁺).

b) 1-methyl-4-(morpholine-4-carbonyl)-N-(2-morpholino-[1,2,4]triazolo[1,5-a]pyridin-7-yl)-1H-pyrazole-5-carboxamide

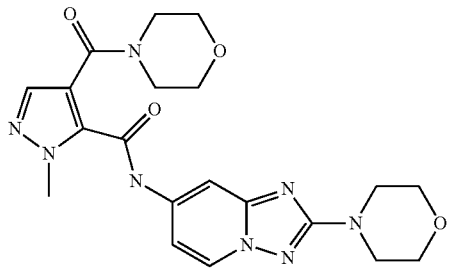 [SMILES: Cn1ncc(C(=O)N2CCOCC2)c1C(=O)Nc1ccn2nc(N3CCOCC3)nc2c1]

A mixture of 1-methyl-5-(2-morpholino-[1,2,4]triazolo[1,5-a]pyridin-7-ylcarbamoyl)-1H-pyrazole-4-carboxylic acid (100 mg, 269 µmol), morpholine (141 µl, 1.62 mmol) and propylphosphonic anhydride (50% in ethyl acetate, 397 µl, 673 µmol) in tetrahydrofurane (7 ml) is refluxed for 18 hours. The solvent is evaporated, the residue diluted with ethyl acetate and washed with sat. aqueous sodium hydrogencarbonate solution and with water. The organic layer is dried with magnesium sulfate and the solvent removed in vacuo affording 1-Methyl-4-(morpholine-4-carbonyl)-N-(2-morpholino-[1,2,4]triazolo[1,5-a]pyridin-7-yl)-1H-pyrazole-5-carboxamide (94 mg, 79.3%) as a light yellow solid. Mp.: 206-8° C. MS: m/z=441.3 (M+H⁺).

Example 30

4-(Azetidine-1-carbonyl)-N-(6-fluoro-2-phenyl-[1,2,4]triazolo[1,5-a]pyridin-7-yl)-1-methyl-1H-pyrazole-5-carboxamide

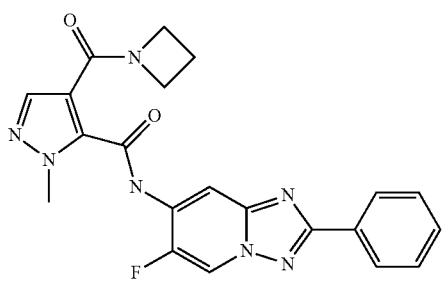 [SMILES: Cn1ncc(C(=O)N2CCC2)c1C(=O)Nc1cc2nc(-c3ccccc3)nn2cc1F]

a) methyl 2-bromo-5-fluoroisonicotinate

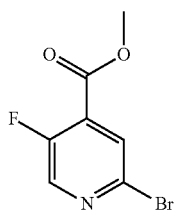

To a cooled solution of 2-bromo-5-fluoroisonicotinic acid (3.0 g, 13.6 mmol) in benzene (20 ml) and methanol (10 ml) is dropwise over a period of 15 min added under stirring and cooling (trimethylsiliyl)diazomethane (2 M in ether, 14 ml, 28 mmol). The yellow solution is stirred for 1.5 h without cooling and evaporated to dryness. Purification of the residue (3.3 g) by chromatography on a 50 g Silicycle silica cartridge using a heptane/ethyl acetate 10-50% gradient affords methyl 2-bromo-5-fluoroisonicotinate (2.82 g, 88.4%) as a light yellow solid. mp.: 43-6° C. MS: m/z=233.9 (M+H⁺).

b) methyl 2-(tert-butoxycarbonylamino)-5-fluoroisonicotinate

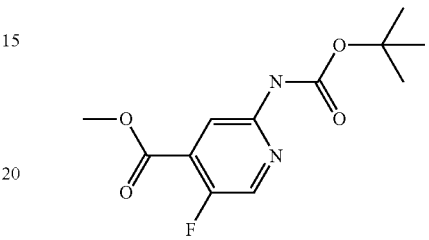

To an nitrogen purged suspension of methyl 2-bromo-5-fluoroisonicotinate (2.8 g, 12 mmol) in dioxane (55 ml) is added successively tert-butyl carbamate (1.68 g, 14.4 mmol), tris(dibenzylidene-acetone)dipalladium(0) (219 mg, 239 umol), 4,5-bis(diphenylphos-phino)-9,9-dimethylxanthene (277 mg, 479 mmol) and cesium carbonate (5.46 g, 16.8 mmol). The mixture is then stirred for 5.5 hrs at 100° C. under nitrogen atmosphere. After 5 min at 100° C. the redbrown suspension has turned green. The mixture is diluted with ethyl acetate, washed twice with water, once with brine, dried with magnesium sulfate and the solvent is removed in vacuo. The product is isolated by chromatography of the residue (3.85 g) on a 70 g Silicycle silica cartridge using a heptane/ethyl acetate 10-40% gradient affording methyl 2-(tert-butoxycarbonylamino)-5-fluoroisonicotinate (1.8 g, 55.7%) as a light yellow solid. MS: m/z=271.2 (M+H⁺).

c) methyl 2-amino-5-fluoroisonicotinate

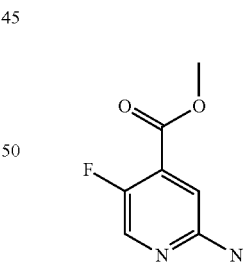

A mixture of methyl 2-(tert-butoxycarbonylamino)-5-fluoroisonicotinate (1.80 g, 6.66 mmol) and hydrochloric acid (6N in ether, 40 ml, 240 mmol) is stirred for 20 hours at 25° C. The solvent is evaporated and the light brown slurry is diluted with ethyl acetate, cooled to 0° C. and adjusted to pH 8 with sat. aqueous sodium carbonate solution. The organic layer is washed with brine, dried with magnesium sulfate and the solvent is removed under reduced pressure affording methyl 2-amino-5-fluoroisonicotinate (932 mg, 82.2%) as a brown waxy solid. MS: m/z=171.0 (M+H⁺).

d) 1,2-diamino-5-fluoro-4-(methoxycarbonyl)pyridinium 2,4,6-trimethylbenzenesulfonate

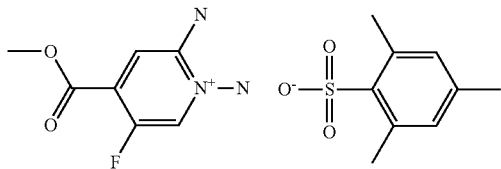

To an ice-cooled white suspension of O-(mesitylsulfonyl)hydroxylamine (1.18 g, 5.48 mmol) in dichloromethane (8.44 ml) is added dropwise a solution of methyl 2-amino-5-fluoroisonicotinate (932 mg, 5.48 mmol) in dichloromethane (2.53 ml). The resulting light brown suspension is stirred for 2 hours at room temperature. The suspension is cooled to −5-0° C., diluted with diethylether (15 ml) and stirred for 30 minutes. The solid is collected by filtration, washed with diethyl ether and dried affording 1,2-diamino-5-fluoro-4-(methoxycarbonyl)pyridinium 2,4,6-trimethylbenzenesulfonate (1.72 g, 81.4%) as a light brown solid. MS: m/z=186.0 (M+).

e) methyl 6-fluoro-2-phenyl-[1,2,4]triazolo[1,5-a]pyridine-7-carboxylate

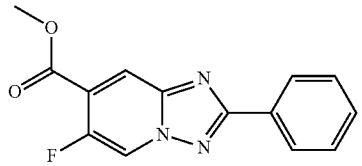 [SMILES: COC(=O)c1cc2nc(-c3ccccc3)nn2cc1F]

A mixture of 1,2-diamino-5-fluoro-4-(methoxycarbonyl)pyridinium 2,4,6-trimethylbenzenesulfonate (1.719 g, 4.46 mmol) and benzoyl chloride (1.03 ml, 8.92 mmol) in pyridine (12 ml) is stirred for 20 hours at 100° C. The solvent is evaporated and the residue stirred for 2.5 hours with sat. aqueous ammoniumchloride solution while neutralizing to pH 6-7 with sat. aqueous sodium bicarbonate solution. The solid is collected by filtration, washed with water and dried affording methyl 6-fluoro-2-phenyl-[1,2,4]triazolo[1,5-a]pyridine-7-carboxylate (603 mg, 49.8%) as a light brown solid. Mp.: 162-8° C. MS: m/z=272.2 (M+H+).

f) 6-fluoro-2-phenyl-[1,2,4]triazolo[1,5-a]pyridine-7-carboxylic acid

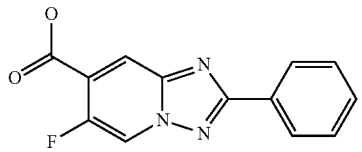 [SMILES: O=C(O)c1cc2nc(-c3ccccc3)nn2cc1F]

A mixture of methyl 6-fluoro-2-phenyl-[1,2,4]triazolo[1,5-a]pyridine-7-carboxylate (600 mg, 2.21 mmol) and lithium hydroxide monohydrate (186 mg, 4.42 mmol) in tetrahydrofurane (10 ml) and water (2.0 ml) is stirred for 3 hours at 25° C. The solvent is evaporated, the residue diluted with water (ca 10 ml) and acidified with 2N aqueous hydrochloric acid (2.2 ml), the precipitated red solid is collected by filtration, washed with water and dried affording 6-fluoro-2-phenyl-[1,2,4]triazolo[1,5-a]pyridine-7-carboxylic acid (497 mg, 87.4%) as a pink solid. Mp.: >250° C. MS: m/z=329.2 (M−H+).

g) tert-butyl 6-fluoro-2-phenyl-[1,2,4]triazolo[1,5-a]pyridin-7-ylcarbamate

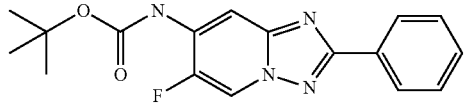 [SMILES: CC(C)(C)OC(=O)Nc1cc2nc(-c3ccccc3)nn2cc1F]

To a suspension of 6-fluoro-2-phenyl-[1,2,4]triazolo[1,5-a]pyridine-7-carboxylic acid (495 mg, 1.92 mmol) and triethylamine (805 µl, 5.77 mmol) in tert-butanol (28.9 ml) is added diphenyl phosphorazidate (623 µl, 2.89 mmol) at 25° C. The resulting mixture is heated to reflux and stirred for 18 hours. The crude material is loaded on silicagel and purified by flash chromatography on a 20 g silica column using heptane/ethyl acetate 30-100% as eluent affording tert-butyl 6-fluoro-2-phenyl-[1,2,4]triazolo[1,5-a]pyridin-7-ylcarbamate (252 mg, 39.9%) as a light yellow solid. Mp.: 180-8° C. MS: m/z=329.2 (M+H+).

h) 6-fluoro-2-phenyl-[1,2,4]triazolo[1,5-a]pyridin-7-amine

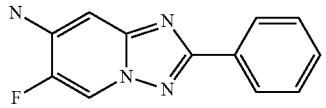 [SMILES: Nc1cc2nc(-c3ccccc3)nn2cc1F]

A mixture of tert-butyl 6-fluoro-2-phenyl-[1,2,4]triazolo[1,5-a]pyridin-7-ylcarbamate (252 mg, 767 µmol) and hydrochloric acid (5N in ether, 6 ml, 30.0 mmol) is stirred for 18 hours at 25° C. The mixture is adjusted to pH=ca 8 with sat. aqueous sodium carbonate solution and extracted twice with ethyl acetate, the organic layers are separated, dried with magnesium sulfate and the solvent is evaporated under reduced pressure affording 6-fluoro-2-phenyl-[1,2,4]triazolo[1,5-a]pyridin-7-amine (175 mg, 100%) as a light yellow solid. Mp.: >250° C. MS: m/z=229.2 (M+H+).

i) 4-(azetidine-1-carbonyl)-N-(6-fluoro-2-phenyl-[1,2,4]triazolo[1,5-a]pyridin-7-yl)-1-methyl-1H-pyrazole-5-carboxamide

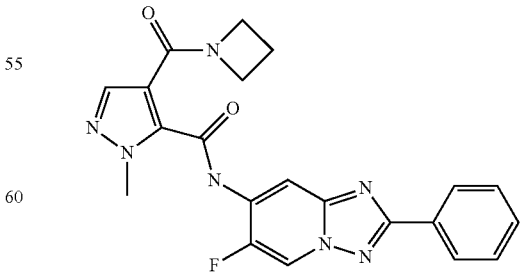

A mixture of 6-fluoro-2-phenyl-[1,2,4]triazolo[1,5-a]pyridin-7-amine (50 mg, 219 µmol), 4-(azetidine-1-carbonyl)-1-methyl-1H-pyrazole-5-carboxylic acid (45.8 mg, 219 µmol), propylphosphonic anhydride (50% in ethyl acetate, 323 µl, 548 µmol) and diisopropylethyl amine (115 µl, 657 µmol) in tetrahydrofuran (5 ml) was refluxed for 18 hours. The crude material is loaded on silica and purified by flash chromatography on a 20 g silica column using heptane/ethyl acetate 20-100% as eluent, affording 4-(azetidine-1-carbonyl)-2-methyl-2H-pyrazole-3-carboxylic acid (6-fluoro-2-phenyl-[1,2,4]triazolo[1,5-a]pyridin-7-yl)-amide (40 mg: 43.5%) as white solid. Mp.: >250° C. MS: m/z=420.3 (M+H⁺).

Example 31

N-(6-fluoro-2-phenyl-[1,2,4]triazolo[1,5-a]pyridin-7-yl)-1-methyl-4-(pyrrolidine-1-carbonyl)-1H-pyrazole-5-carboxamide

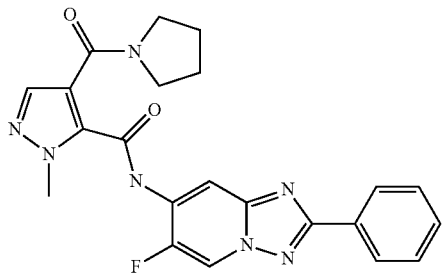 [SMILES: Cn1ncc(C(=O)N2CCCC2)c1C(=O)Nc1cc2nc(-c3ccccc3)nn2cc1F]

A mixture of 5-(6-fluoro-2-phenyl-[1,2,4]triazolo[1,5-a]pyridin-7-ylcarbamoyl)-1-methyl-1H-pyrazole-4-carboxylic acid (138 mg, 363 µmol), pyrrolidine (240 µl, 2.9 mmol), propylphosphonic anhydride (50% in ethyl acetate, 534 µl, 907 µmol) and diisopropylethylamine (190 µl, 1.09 mmol) in tetrahydrofuran (10 ml) was stirred for 2.5 days at 70° C. The solvent was evaporated; the residue was triturated with saturated aqueous sodium hydrogencarbonate solution and the precipitated solid was filtered off and dried in vacuo. The material was applied on silica and purified by flash chromatography over a 20 g silica column using heptane/EtOAc 10-100% as eluent, affording N-(6-fluoro-2-phenyl-[1,2,4]triazolo[1,5-a]pyridin-7-yl)-1-methyl-4-(pyrrolidine-1-carbonyl)-1H-pyrazole-5-carboxamide (83 mg, 52.8%) as white solid. Mp. 250-251° C. MS: m/z=434.4 (M+H⁺).

Example 32

2-Methyl-4-(morpholine-4-carbonyl)-2H-pyrazole-3-carboxylic acid (6-fluoro-2-phenyl-[1,2,4]triazolo[1,5-a]pyridin-7-yl)-amide

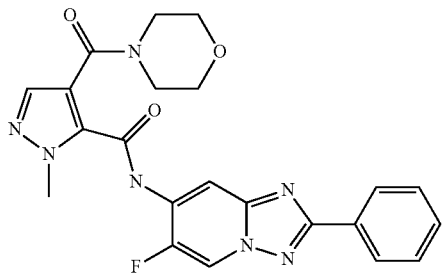 [SMILES: Cn1ncc(C(=O)N2CCOCC2)c1C(=O)Nc1cc2nc(-c3ccccc3)nn2cc1F]

A mixture of 5-(6-fluoro-2-phenyl-[1,2,4]triazolo[1,5-a]pyridin-7-ylcarbamoyl)-1-methyl-1H-pyrazole-4-carboxylic acid (138 mg, 363 µmol), morpholine (253 µl, 2.9 mmol), propylphosphonic anhydride (50% in ethyl acetate, 534 µl, 907 µmol) and diisopropylethylamine (190 µl, 1.09 mmol) in tetrahydrofuran (10 ml) was stirred for 2.5 days (weekend) at 70° C. under nitrogen atmosphere. The solvent was evaporated, the residue was triturated with saturated aqueous sodium hydrogencarbonate solution and the precipitated solid was filtered off and dried in vacuum. The crude material was applied on silica and purified by flash chromatography over a 20 g silica column using heptane/ethyl acetate 10-100% as eluent, affording 2-methyl-4-(morpholine-4-carbonyl)-2H-pyrazole-3-carboxylic acid (6-fluoro-2-phenyl-[1,2,4]triazolo[1,5-a]pyridin-7-yl)-amide (67 mg, 41.1%) as white solid. Mp.: 224-225° C. MS: m/z=450.0 (M+H⁺).

Example 33

7-(4-(Azetidine-1-carbonyl)-1-methyl-1H-pyrazole-5-carboxamido)-N-(3,3,3-trifluoropropyl)-[1,2,4]triazolo[1,5-a]pyridine-2-carboxamide

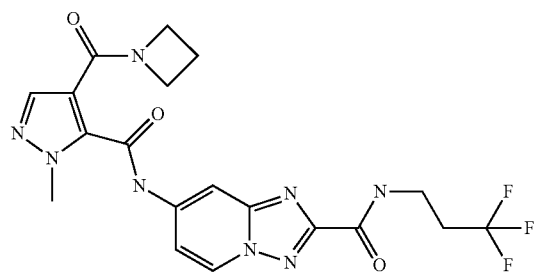 [SMILES: Cn1ncc(C(=O)N2CCC2)c1C(=O)Nc1ccn2nc(C(=O)NCCC(F)(F)F)nc2c1]

a) ethyl 7-bromo-[1,2,4]triazolo[1,5-a]pyridine-2-carboxylate

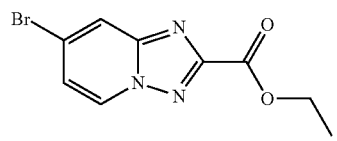

A mixture of 1,2-diamino-4-bromopyridinium 2,4,6-trimethylbenzenesulfonate (4.18 g, 10.8 mmol) and ethyl 2-chloro-2-oxoacetate (2.4 ml, 21.5 mmol) in pyridine (25 ml) is heated for 18 hours to 100° C. The solvent is evaporated and the orange residue triturated with sat. aqueous sodium hydrogencarbonate solution for 2 hours. The solid is collected by filtration, washed several times with water and dried affording ethyl 7-bromo-[1,2,4]triazolo[1,5-a]pyridine-2-carboxylate (1.759 g, 60.5%) as a light pink solid. mp.: 158-160° C. MS: m/z=270.2 (M+H⁺).

b) ethyl-7-(tert-butoxycarbonylamino)-[1,2,4]triazolo[1,5-a]pyridine-2-carboxylate

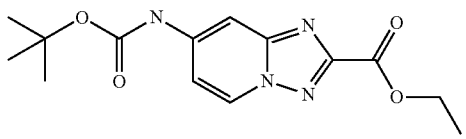 [SMILES: CCOC(=O)c1nc2cc(NC(=O)OC(C)(C)C)ccn2n1]

To an argon purged solution of ethyl 7-bromo-[1,2,4]triazolo[1,5-a]pyridine-2-carboxylate (1.76 g, 6.52 mmol) in dioxane (45 ml) are added tert-butyl carbamate (916 mg, 7.82 mmol), tris(dibenzylideneacetone)dipalladium(0) (119 mg, 130 μmol), 4,5-bis(diphenylphosphino)-9,9-dimethylxanthene (151 mg, 261 μmol) and cesium carbonate (2.97 g, 9.12 mmol). The resulting mixture is heated to 110° C. and stirred for 20 hours. The reaction mixture is loaded on silica and purified by flash chromatography on a 50 g silica column using heptane/ethyl acetate 30-100% as eluent affording ethyl 7-(tert-butoxycarbonylamino)-[1,2,4]triazolo[1,5-a]pyridine-2-carboxylate (1.07 g, 54%) as a light yellow solid. mp.: 220-2° C. MS: m/z=307.3 (M+H+).

c) ethyl 7-amino-[1,2,4]triazolo[1,5-a]pyridine-2-carboxylate

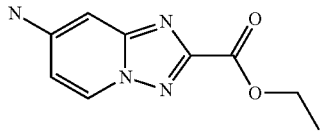

A solution of ethyl 7-(tert-butoxycarbonylamino)-[1,2,4]triazolo[1,5-a]pyridine-2-carboxylate (1.07 g, 3.49 mmol) in dichloromethane (5 ml) and trifluoroacetic acid (5.38 ml, 69.9 mmol) is stirred for 3 hours at 25° C. The mixture is made basic using sat. aqueous sodium carbonate solution and extracted with ethyl acetate. The organic layer is washed with water and brine, dried with magnesium sulfate and the solvent is removed in vacuo affording ethyl 7-amino-[1,2,4]triazolo[1,5-a]pyridine-2-carboxylate (543 mg, 75.4%) as a light yellow solid. mp.: 150-171° C. MS: m/z=207.0 (M+H+).

d) 7-{[4-(azetidine-1-carbonyl)-2-methyl-2H-pyrazole-3-carbonyl]-amino}-[1,2,4]triazolo[1,5-a]pyridine-2-carboxylic acid ethyl ester

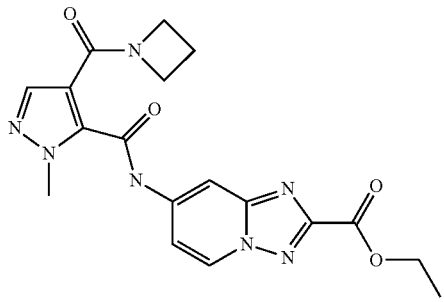 [SMILES: CCOC(=O)c1nc2cc(NC(=O)c3c(C(=O)N4CCC4)cnn3C)ccn2n1]

A mixture of ethyl 7-amino-[1,2,4]triazolo[1,5-a]pyridine-2-carboxylate (540 mg, 2.62 mmol), 4-(azetidine-1-carbonyl)-1-methyl-1H-pyrazole-5-carboxylic acid (548 mg, 2.62 mmol), propylphosphonic anhydride (50% in ethyl acetate, 3.86 ml, 6.55 mmol) and diisopropylethylamine (1.37 ml, 7.86 mmol) in tetrahydrofurane (10 ml) is refluxed for 18 hours. The solvent is evaporated and the residue triturated with sat. aqueous sodium hydrogencarbonate solution. The precipitated solid is collected by filtration, washed several times with water and dried affording 7-{[4-(azetidine-1-carbonyl)-2-methyl-2H-pyrazole-3-carbonyl]-amino}-[1,2,4]triazolo[1,5-a]pyridine-2-carboxylic acid ethyl ester (665 mg, 63.9%) as a light brown solid. mp.: 252-5° C. MS: m/z=398.2 (M+H+).

e) 7-(4-(azetidine-1-carbonyl)-1-methyl-1H-pyrazole-5-carboxamido)-N-(3,3,3-trifluoropropyl)-[1,2,4]triazolo[1,5-a]pyridine-2-carboxamide

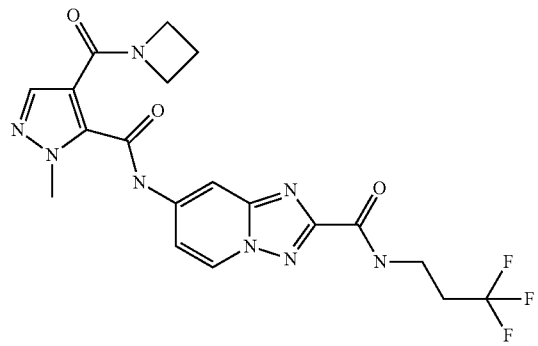 [SMILES: Cn1ncc(C(=O)N2CCC2)c1C(=O)Nc1ccn2nc(C(=O)NCCC(F)(F)F)nc2c1]

A mixture of 7-(4-(azetidine-1-carbonyl)-1-methyl-1H-pyrazole-5-carboxamido)-[1,2,4]triazolo[1,5-a]pyridine-2-carboxylic acid (140 mg, 0.379 mmole), 3,3,3-trifluoropropan-1-amine (214 mg, 1.9 mmole), N-ethyldiisopropylamine (265 ul, 1.52 mmole) and 1-propanephosphonic acid cyclic anhydride (50% in ethyl acetate, 569 ul, 0.948 mmole) in tetrahydrofurane (7 ml) is stirred for 10 h at roomtemperature. The reaction mixture is poured on sat. aqueous sodium bicarbonate solution (60 ml) and extracted with ethyl acetate (2×50 ml). The combined organic layer is washed once with water, once with brine, dried with magnesium sulfate and the solvent is removed in vacuo. Purification of the residue by chromatography on a 12 g silica cartridge (eluent dichloromethane+2% methanol) affords 7-(4-(azetidine-1-carbonyl)-1-methyl-1H-pyrazole-5-carboxamido)-N-(3,3,3-trifluoropropyl)-[1,2,4]triazolo[1,5-a]pyridine-2-carboxamide (31 mg, 17.6%) as a white foam. MS: m/z=465.3 (M+H+).

Example 34

N-(2-isopropyl-[1,2,4]triazolo[1,5-a]pyridin-7-yl)-1-methyl-4-(pyrrolidine-1-carbonyl)-1H-pyrazole-5-carboxamide

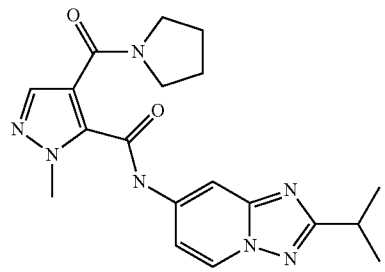 [SMILES: CC(C)c1nc2cc(NC(=O)c3c(C(=O)N4CCCC4)cnn3C)ccn2n1]

a) 7-bromo-2-isopropyl-[1,2,4]triazolo[1,5-a]pyridine

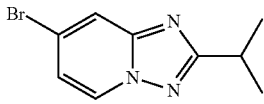

A mixture of 1,2-diamino-4-bromopyridinium 2,4,6-trimethylbenzenesulfonate (2 g, 5.15 mmol) and isobutyryl chloride (809 μl, 7.73 mmol) in pyridine (12 ml) is stirred for 18 hours at 100° C. The solvent is evaporated and the orange residue triturated for 2 hrs with sat. aqueous sodium hydrogen carbonate solution. The solid is collected by filtration, washed several times with water and dried affording 7-bromo-2-isopropyl-[1,2,4]triazolo[1,5-a]pyridine (378 mg, 30.6%) as a light brown solid. MS: m/z=240; 242 (M+H$^+$).

b) tert-butyl 2-isopropyl-[1,2,4]triazolo[1,5-a]pyridin-7-ylcarbamate

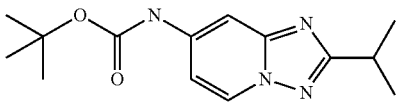 [SMILES: CC(C)c1nc2cc(NC(=O)OC(C)(C)C)ccn2n1]

To an argon purged solution of 7-bromo-2-isopropyl-[1,2,4]triazolo[1,5-a]pyridine (378 mg, 1.57 mmol) in dioxane (10 ml) are added tert-butyl carbamate (221 mg, 1.89 mmol), cesium carbonate (718 mg, 2.2 mmol), tris(dibenzylideneacetone)dipalladium(0) (28.8 mg, 31.5 μmol) and 4,5-bis(diphenylphosphino)-9,9-dimethylxanthene (36.4 mg, 63.0 μmol). The resulting mixture is refluxed for 2.5 days (weekend) under argon atmosphere. The crude material is loaded on silicagel and purified by flash chromatography on a 20 g silica column using heptane/ethyl acetate 20-70% as eluent affording tert-butyl 2-isopropyl-[1,2,4]triazolo[1,5-a]pyridin-7-ylcarbamate (405 mg, 93.1%) as a light yellow solid. Mp.: 215-8° C. MS: m/z=277.1 (M+H$^+$).

c) 2-isopropyl-[1,2,4]triazolo[1,5-a]pyridin-7-amine

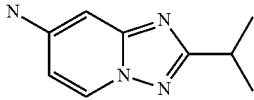

To a solution of tert-butyl 2-isopropyl-[1,2,4]triazolo[1,5-a]pyridin-7-ylcarbamate (400 mg, 1.45 mmol) in tetrahydrofurane (10 ml) is added hydrochloric acid (5 N in diethyl ether, 20 ml, 100 mmol). The resulting suspension is stirred for 18 hours at 25° C. The solvent is evaporated and the residue diluted with ethyl acetate, made basic with sodium hydroxide 2N and washed with water and brine. The organic layer is dried with magnesium sulfate and the solvent is evaporated under reduced pressure. The residue (416 mg) is purified by chromatography on a 20 g silicagel column using heptane/ethyl acetate 50-100% as eluent affording 2-isopropyl-[1,2,4]triazolo[1,5-a]pyridin-7-amine (159 mg, 62.3%) as a white solid. Mp.: 174-6° C. MS: m/z=177.2 (M+H$^+$).

d) ethyl 5-(2-isopropyl-[1,2,4]triazolo[1,5-a]pyridin-7-ylcarbamoyl)-1-methyl-1H-pyrazole-4-carboxylate

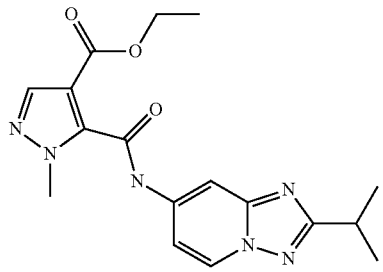 [SMILES: CCOC(=O)c1cnn(C)c1C(=O)Nc1ccn2nc(C(C)C)nc2c1]

A mixture of 2-isopropyl-[1,2,4]triazolo[1,5-a]pyridin-7-amine (159 mg, 902 μmol), 4-(ethoxycarbonyl)-1-methyl-1H-pyrazole-5-carboxylic acid (215 mg, 1.08 mmol), propylphosphonic anhydride (50% in ethyl acetate, 1.33 ml, 2.26 mmol) and diisopropylethylamine (473 μl, 2.71 mmol) in tetrahydrofurane (7 ml) is refluxed for 18 hours. The solvent is evaporated and the residue stirred for 1 hr with sat. aqueous sodium hydrogencarbonate solution. The precipitated solid is collected by filtration, washed with water and dried affording ethyl 5-(2-isopropyl-[1,2,4]triazolo[1,5-a]pyridin-7-ylcarbamoyl)-1-methyl-1H-pyrazole-4-carboxylate (332 mg, 103%) as a white solid. Mp.: 175-7° C. MS: m/z=357.2 (M+H$^+$).

e) 5-(2-isopropyl-[1,2,4]triazolo[1,5-a]pyridin-7-ylcarbamoyl)-1-methyl-1H-pyrazole-4-carboxylic acid

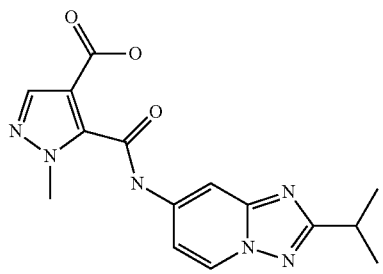 [SMILES: CC(C)c1nc2cc(NC(=O)c3c(C(=O)O)cnn3C)ccn2n1]

A mixture of ethyl 5-(2-isopropyl-[1,2,4]triazolo[1,5-a]pyridin-7-ylcarbamoyl)-1-methyl-1H-pyrazole-4-carboxylate (330 mg, 926 μmol) and lithium hydroxide monohydrate (155 mg, 3.7 mmol) in methanol (6 ml) and water (2 ml) is stirred for 18 hours at 25° C. The solvents are evaporated, the white residue is dissolved in water and acidified with 37% aqueous hydrochloric acid. The precipitated white solid is collected by filtration, washed with water and dried affording 5-(2-isopropyl-[1,2,4]triazolo[1,5-a]pyridin-7-ylcarbamoyl)-1-methyl-1H-pyrazole-4-carboxylic acid (285 mg, 93.7%) as a white solid. Mp.: >250° C. MS: m/z=327.3 (M−H$^+$).

f) N-(2-isopropyl-[1,2,4]triazolo[1,5-a]pyridin-7-yl)-1-methyl-4-(pyrrolidine-1-carbonyl)-1H-pyrazole-5-carboxamide

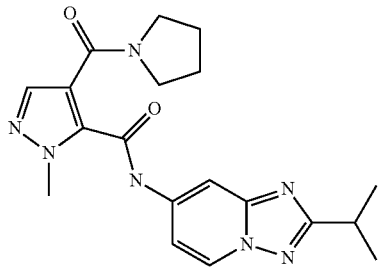 [SMILES: CC(C)c1nc2cc(NC(=O)c3c(C(=O)N4CCCC4)cnn3C)ccn2n1]

A mixture of 5-(2-isopropyl-[1,2,4]triazolo[1,5-a]pyridin-7-ylcarbamoyl)-1-methyl-1H-pyrazole-4-carboxylic acid (70 mg, 213 µmol), pyrrolidine (70.5 µl, 853 µmol), propylphosphonic anhydride (50% in ethyl acetate, 314 µl, 533 µmol) and diisopropylethylamine (112 µl, 640 µmol) in tetrahydrofurane (4 ml) is stirred for 3.5 days at 25° C. The solvent is evaporated and the residue stirred for 1 hr with sat. aqueous sodium hydrogencarbonate solution. The precipitated solid is collected by filtration, washed with water and dried affording N-(2-isopropyl-[1,2,4]triazolo[1,5-a]pyridin-7-yl)-1-methyl-4-(pyrrolidine-1-carbonyl)-1H-pyrazole-5-carboxamide (76 mg, 93.5%) as a white solid. Mp.: 141-3° C. MS: m/z=380.3 (M−H$^+$).

Example 35

4-(Azetidine-1-carbonyl)-N-(2-(dimethylamino)-[1,2,4]triazolo[1,5-a]pyridin-7-yl)-1-methyl-1H-pyrazole-5-carboxamide

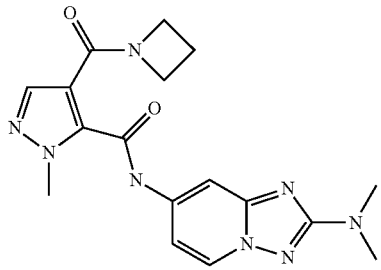 [SMILES: CN(C)c1nc2cc(NC(=O)c3c(C(=O)N4CCC4)cnn3C)ccn2n1]

a) 1-ethoxycarbonyl-3-(4-bromo-pyridin-2-yl)-thiourea

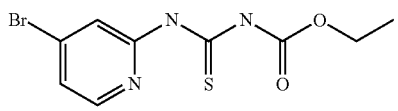

To a solution of 4-bromopyridin-2-amine (2.895 g, 16.7 mmol) in dioxane (70 ml) is added etoxycarbonyl-isothiocyanate (1.89 ml, 16.7 mmol). The resulting mixture is stirred for 18 hours at room temperature. The solvent is evaporated, the solid yellow residue diluted with ethyl acetate and washed with water and brine; the organic layer is dried with magnesium sulfate and the solvent removed under reduced pressure affording 1-ethoxycarbonyl-3-(4-bromo-pyridin-2-yl)-thiourea (4.81 g, 94.5%) as a yellow solid. Mp.: 107-110° C. MS: m/z=301.8, 303.9 (M+H$^+$).

b) 7-bromo-[1,2,4]triazolo[1,5-a]pyridin-2-amine

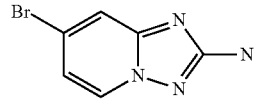 [SMILES: Nc1nc2cc(Br)ccn2n1]

A mixture of hydroxylamine hydrochloride (20.0 g, 288 mmol) and N-ethyldiisopropylamine (30.1 ml, 173 mmol) in ethanol (367 ml) is stirred for a few minutes at room temperature and the mixture is added to 1-ethoxycarbonyl-3-(4-bromo-pyridin-2-yl)-thiourea (17.5 g, 57.5 mmol). The resulting mixture is refluxed for 1 day. The solvent is evaporated and 100 ml water is added to the residue. The suspension is stirred for 10 minutes, the solid is collected by filtration, washed with water and dried affording 7-bromo-[1,2,4]triazolo[1,5-a]pyridin-2-amine (10.71 g, 87.4%) as a light yellow solid. Mp.: 190-2° C. MS: m/z=213.0, 215.0 (M+H$^+$).

c) 2,7-dibromo-[1,2,4]triazolo[1,5-a]pyridine

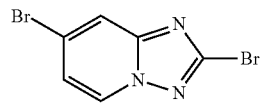

A suspension of 7-bromo-[1,2,4]triazolo[1,5-a]pyridin-2-amine (3.17 g, 14.9 mmol), benzyltriethylammonium bromide (12.2 g, 44.6 mmol) and sodium nitrite (10.3 g, 149 mmol) in bromoform (78.1 ml, 893 mmol) is stirred for 30 minutes at 25° C., then dichloroacetic acid (2.46 ml, 29.8 mmol) is added and the resulting solution (wrapped in aluminium foil to protect the mixture from light) is stirred for 18 hours at room temperature. After addition of 200 ml of water and stirring for 30 minutes, the mixture is extracted 3 times with dichloromethane, the organic layers are combined, washed with water, dried with magnesium sulfate and the solvents are evaporated under reduced pressure.

The residue (3.15 g brown solid) is purified by chromatography on a 50 g silica column using dichloromethane/methanol 5% as eluent affording 2,7-dibromo-[1,2,4]triazolo[1,5-a]pyridine (2.17 g, 52.6%) as a white solid. Mp.: 183-4° C. MS: m/z=275.8, 277.9 (M+H$^+$).

d) 7-bromo-N,N-dimethyl-[1,2,4]triazolo[1,5-a]pyridin-2-amine

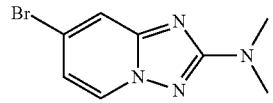

A mixture of 2,7-dibromo-[1,2,4]triazolo[1,5-a]pyridine (2.16 g, 7.8 mmol) in dimethylamine (30% in EtOH, 60 ml, 355 mmol) is heated in 4 portions a ca. 540 mg/15 ml of dimethylamine in a high pressure vessel to 100° C. for 3 hours each. The batches are combined and the solvent evaporated. The light brown crude material (4.77 g) is loaded on silicagel and purified by chromatography on a 70 g silica column using heptane/ethyl acetate 10-40% as eluent affording 7-bromo-N,N-dimethyl-[1,2,4]triazolo[1,5-a]pyridin-2-amine (1.36 g, 72.3%) as a light yellow solid. Mp.: 133-4° C. MS: m/z=243.2 (M+H⁺).

e) tert-butyl 2-(dimethylamino)-[1,2,4]-triazolo-[1,5-a]pyridine-7-ylcarbamate

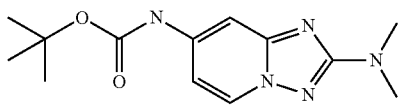 [SMILES: CN(C)c1nc2cc(NC(=O)OC(C)(C)C)ccn2n1]

To an argon purged solution of 7-bromo-N,N-dimethyl-[1,2,4]triazolo[1,5-a]pyridine-2-amine (300 mg, 1.24 mmol) in dioxane (11 ml) are added tert-butyl carbamate (175 mg, 1.49 mmol), cesium carbonate (568 mg, 1.74 mmol), tris(dibenzylideneacetone)dipalladium(0) (22.8 mg, 24.9 µmol) and 4,5-bis(diphenylphosphino)-9,9-dimethylxanthene (28.8 mg, 49.8 µmol). The resulting mixture is stirred for 18 hours at 100° C. under argon atmosphere. The crude material is loaded on silicagel and purified by chromatography on a 20 g silica column using heptane/ethyl acetate 10-70% as eluent affording tert-butyl 2-(dimethylamino)-[1,2,4]triazolo[1,5-a]pyridine-7-ylcarbamate (310 mg, 89.8%) as a yellow foam. MS: m/z=278.3 (M+H⁺).

f) N2,N2-dimethyl-[1,2,4]triazolo[1,5-a]pyridine-2,7-diamine

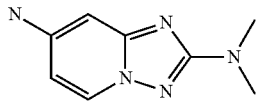

A mixture of tert-butyl 2-(dimethylamino)-[1,2,4]triazolo[1,5-a]pyridin-7-ylcarbamate (1.8 g, 6.49 mmol) in dichloromethane (15 ml) and hydrochloric acid (5N in diethyl ether, 50 ml, 250 mmol) is stirred for 18 hours at room temperature. The solvent is evaporated and the residue dissolved in water (100 ml), made basic with 32% aqueous sodium hydroxide and extracted twice with ethyl acetate. The combined organic layers are washed with water, dried with magnesium sulfate and the solvent is evaporated under reduced pressure affording N2,N2-dimethyl-[1,2,4]triazolo[1,5-a]pyridine-2,7-diamine (727 mg, 63.2%) as a yellow solid. Mp.: 236-8° C. MS: m/z=178.1 (M+H⁺).

g) ethyl 5-(2-(dimethylamino)-[1,2,4]triazolo[1,5-a]pyridin-7-ylcarbamoyl)-1-methyl-1H-pyrazole-4-carboxylate

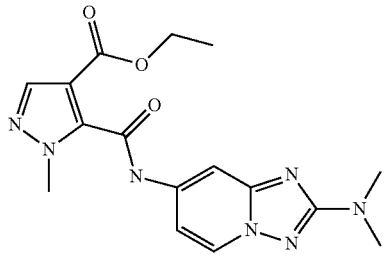 [SMILES: CCOC(=O)c1cnn(C)c1C(=O)Nc1ccn2nc(N(C)C)nc2c1]

A mixture of N2,N2-dimethyl-[1,2,4]triazolo[1,5-a]pyridine-2,7-diamine (700 mg, 3.95 mmol), 4-(ethoxycarbonyl)-1-methyl-1H-pyrazole-5-carboxylic acid (812 mg, 4.1 mmol), propylphosphonic anhydride (50% in ethyl acetate, 5.82 ml, 9.88 mmol) and diisopropylethylamine (2.07 ml, 11.9 mmol) in tetrahydrofurane (40 ml) is refluxed for 18 hours under nitrogen atmosphere. The solvent is evaporated and the residue triturated with sat. aqueous sodium hydrogencarbonate solution. The solid is collected by filtration, washed with water and dried affording ethyl 5-(2-(dimethylamino)-[1,2,4]triazolo[1,5-a]pyridin-7-ylcarbamoyl)-1-methyl-1H-pyrazole-4-carboxylate (1.26 g, 89.3%) as a light brown solid. Mp.: 193-5° C. MS: m/z=358.4 (M+H⁺).

h) 5-(2-(dimethylamino)-[1,2,4]triazolo[1,5-a]pyridin-7-ylcarbamoyl)-1-methyl-1H-pyrazole-4-carboxylic acid

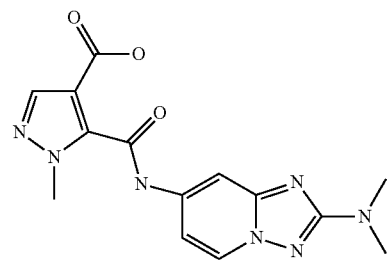 [SMILES: CN(C)c1nc2cc(NC(=O)c3c(C(=O)O)cnn3C)ccn2n1]

A mixture of ethyl 5-(2-(dimethylamino)-[1,2,4]triazolo[1,5-a]pyridin-7-ylcarbamoyl)-1-methyl-1H-pyrazole-4-carboxylate (1.24 g, 3.47 mmol) and lithium hydroxide monohydrate (291 mg, 6.94 mmol) in methanol (20 ml) and water (5 ml) is stirred for 4 hours at 50° C. The solvent is evaporated. The brown oily residue is dissolved in water and acidified to pH=5 with 2N aqueous hydrochloric acid (3.47 ml). The precipitated off-white solid is collected by filtration, dissolved in methanol and evaporated affording 5-(2-(dimethylamino)-[1,2,4]triazolo[1,5-a]pyridin-7-ylcarbamoyl)-1-methyl-1H-pyrazole-4-carboxylic acid (1.09 g, 95.3%) as an off-white solid. Mp.: >250° C. MS: m/z=328.0 (M−H⁺).

i) 4-(azetidine-1-carbonyl)-N-(2-(dimethylamino)-[1,2,4]triazolo[1,5-a]pyridin-7-yl)-1-methyl-1H-pyrazole-5-carboxamide

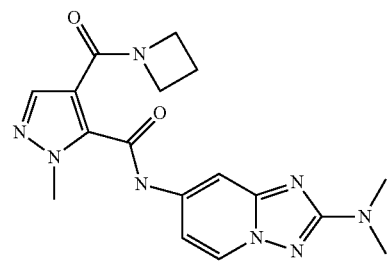 [SMILES: CN(C)c1nc2cc(NC(=O)c3c(C(=O)N4CCC4)cnn3C)ccn2n1]

A mixture of 5-(2-(dimethylamino)-[1,2,4]triazolo[1,5-a]pyridin-7-ylcarbamoyl)-1-methyl-1H-pyrazole-4-carboxylic acid (150 mg, 455 µmol), azetidine (123 µl, 1.82 mmol), propylphosphonic anhydride (50% in ethyl acetate, 671 µl, 1.14 mmol) and diisopropylethylamine (398 µl, 2.28 mmol) in tetrahydrofurane (8 ml) is stirred for 18 hours at room temperature under nitrogen atmosphere. The solvent is evaporated and the residue triturated with sat. aqueous sodium hydrogencarbonate solution. The precipitated solid is collected by filtration, washed with water and dried affording 4-(azetidine-1-carbonyl)-N-(2-(dimethylamino)-[1,2,4]triazolo[1,5-a]pyridin-7-yl)-1-methyl-1H-pyrazole-5-carboxamide (119 mg, 70.9%) as an off-white solid. Mp.: 240-1° C. MS: m/z=369.1 (M+H⁺).

Example 36

N-(2-(dimethylamino)-[1,2,4]triazolo[1,5-a]pyridin-7-yl)-1-methyl-4-(morpholine-4-carbonyl)-1H-pyrazole-5-carboxamide

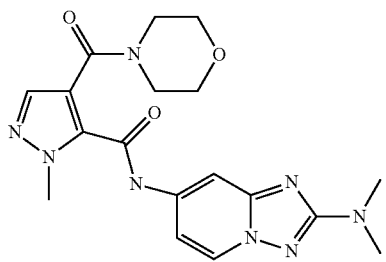 [SMILES: CN(C)c1nc2cc(NC(=O)c3c(C(=O)N4CCOCC4)cnn3C)ccn2n1]

A mixture of 5-(2-(dimethylamino)-[1,2,4]triazolo[1,5-a]pyridin-7-ylcarbamoyl)-1-methyl-1H-pyrazole-4-carboxylic acid (150 mg, 455 μmol), morpholine (317 μl, 3.64 mmol), propylphosphonic anhydride (50% in ethyl acetate, 671 μl, 1.14 mmol) and diisopropylethylamine (239 μl, 1.37 mmol) in tetrahydrofurane (8 ml) is stirred for 18 hours at 70° C. under nitrogen atmosphere. The solvent is evaporated and the residue triturated with sat. aqueous sodium hydrogencarbonate solution. The precipitated solid is collected by filtration, washed with water and dried affording N-(2-(dimethylamino)-[1,2,4]triazolo[1,5-a]pyridin-7-yl)-1-methyl-4-(morpholine-4-carbonyl)-1H-pyrazole-5-carboxamide (152 mg, 83.8%) as an off-white solid. Mp.: 196-8° C. MS: m/z=399.0 (M+H⁺).

Example 37

N-(2-(dimethylamino)-[1,2,4]triazolo[1,5-a]pyridin-7-yl)-1-methyl-4-(pyrrolidine-1-carbonyl)-1H-pyrazole-5-carboxamide

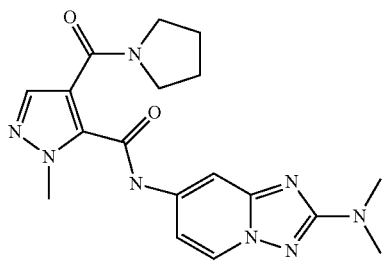 [SMILES: CN(C)c1nc2cc(NC(=O)c3c(C(=O)N4CCCC4)cnn3C)ccn2n1]

A mixture of 5-(2-(dimethylamino)-[1,2,4]triazolo[1,5-a]pyridin-7-ylcarbamoyl)-1-methyl-1H-pyrazole-4-carboxylic acid (150 mg, 455 μmol), pyrrolidine (226 μl, 2.73 mmol), propylphosphonic anhydride (50% in ethyl acetate, 671 μl, 1.14 mmol) and diisopropylethylamine (239 μl, 1.37 mmol) in tetrahydrofurane (8 ml) is stirred for 18 hours at 70° C. under nitrogen atmosphere. The solvent is evaporated and the residue triturated with sat. aqueous sodium hydrogencarbonate solution. The precipitated solid is collected by filtration, washed with water and dried affording N-(2-(dimethylamino)-[1,2,4]triazolo[1,5-a]pyridin-7-yl)-1-methyl-4-(pyrrolidine-1-carbonyl)-1H-pyrazole-5-carboxamide (155 mg, 89%) as a light brown solid. Mp.: 199-201° C. MS: m/z=383.4 (M+H⁺).

Example 38

N-(2-(dimethylamino)-[1,2,4]triazolo[1,5-a]pyridin-7-yl)-4-(3-fluoroazetidine-1-carbonyl)-1-methyl-1H-pyrazole-5-carboxamide

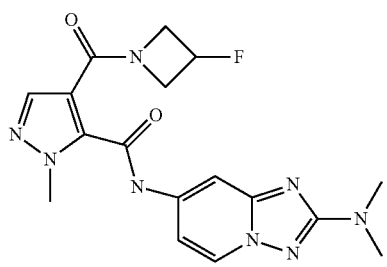 [SMILES: CN(C)c1nc2cc(NC(=O)c3c(C(=O)N4CC(F)C4)cnn3C)ccn2n1]

A mixture of 5-(2-(dimethylamino)-[1,2,4]triazolo[1,5-a]pyridin-7-ylcarbamoyl)-1-methyl-1H-pyrazole-4-carboxylic acid (150 mg, 455 μmol), 3-fluoroazetidine hydrochloride (152 mg, 1.37 mmol), propylphosphonic anhydride (50% in ethyl acetate, 671 μl, 1.14 mmol) and diisopropylethylamine (398 μl, 2.28 mmol) in tetrahydrofurane (8 ml) is stirred for 18 hours at room temperature under nitrogen atmosphere. The solvent is evaporated and the residue triturated with sat. aqueous sodium hydrogencarbonate solution; the precipitated solid is collected by filtration, washed with water and dried affording N-(2-(dimethylamino)-[1,2,4]triazolo[1,5-a]pyridin-7-yl)-4-(3-fluoroazetidine-1-carbonyl)-1-methyl-1H-pyrazole-5-carboxamide (158 mg, 89.8%) as a white solid. Mp.: 243-4° C. MS: m/z=387.2 (M+H⁺).

Example 39

N4,N4-diethyl-1-methyl-N5-(2-morpholino-[1,2,4]triazolo[1,5-a]pyridin-7-yl)-1H-pyrazole-4,5-dicarboxamide

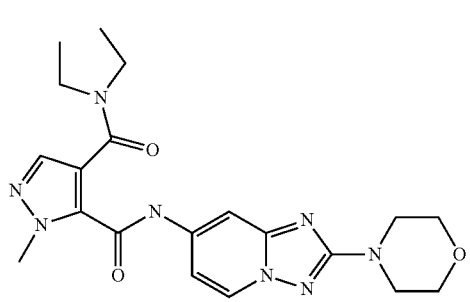 [SMILES: CCN(CC)C(=O)c1cnn(C)c1C(=O)Nc1ccn2nc(N3CCOCC3)nc2c1]

A mixture of 1-methyl-5-(2-morpholin-4-yl-[1,2,4]triazolo[1,5-a]pyridin-7-ylcarbamoyl)-1H-pyrazole-4-carboxylic acid (150 mg, 0.404 mmole), diethylamine (250 ul, 2.42 mmole), N-ethyldiisopropylamine (282 ul, 1.62 mmole) and propylphosphonic acid cyclic anhydride (50% in ethyl acetate, 606 ul, 1.01 mmole) in tetrahydrofurane (5 ml) is stirred for 22 h at 70° C. The solvent is removed under reduced pressure and the residue is triturated for 1 hr with sat. aqueous sodium bicarbonate solution (30 ml). The solid is collected by filtration, washed with water and dried affording N4,N4-diethyl-1-methyl-N5-(2-morpholino-[1,2,4]triazolo[1,5-a]pyridin-7-yl)-1H-pyrazole-4,5-dicarboxamide (140 mg, 81.3%) as a white solid. Mp.: 165-7° C. MS: m/z=427.4 (M+H$^+$).

Example 40

N4,N4,1-trimethyl-N5-(2-morpholino-[1,2,4]triazolo[1,5-a]pyridin-7-yl)-1H-pyrazole-4,5-dicarboxamide

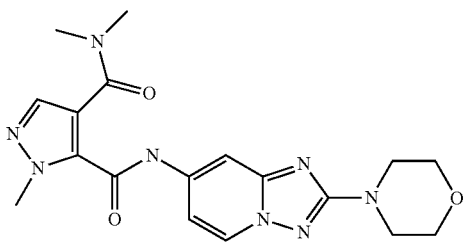 [SMILES: CN(C)C(=O)c1cnn(C)c1C(=O)Nc1ccn2nc(N3CCOCC3)nc2c1]

A mixture of 1-methyl-5-(2-morpholin-4-yl-[1,2,4]triazolo[1,5-a]pyridin-7-ylcarbamoyl)-1H-pyrazole-4-carboxylic acid (150 mg, 0.404 mmole), dimethylamine hydrochloride (198 mg, 2.42 mmole), N-ethyldiisopropylamine (564 ul, 3.23 mmole) and 1-propanephosphonic acid cyclic anhydride (50% in ethyl acetate, 606 ul, 1.01 mmole) in tetrahydrofurane (7 ml) is stirred for 22 h at 70° C. The solvent is removed under reduced pressure and the residue is triturated for 1 hr with sat. aqueous sodium bicarbonate solution (30 ml). The solid is collected by filtration, washed with water and dried affording N4,N4,1-trimethyl-N5-(2-morpholino-[1,2,4]triazolo[1,5-a]pyridin-7-yl)-1H-pyrazole-4,5-dicarboxamide (138 mg, 85.7%) as a white solid. Mp.: 237-240° C. MS: m/z=399.2 (M+H$^+$).

Example 41

N4-ethyl-N4,1-dimethyl-N5-(2-morpholino-[1,2,4]triazolo[1,5-a]pyridin-7-yl)-1H-pyrazole-4,5-dicarboxamide

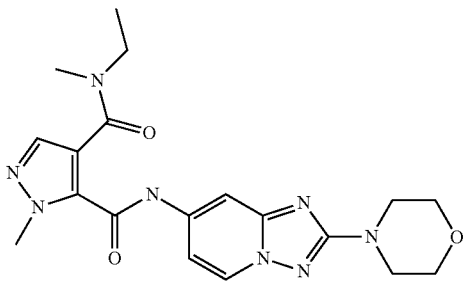 [SMILES: CCN(C)C(=O)c1cnn(C)c1C(=O)Nc1ccn2nc(N3CCOCC3)nc2c1]

A mixture of 1-methyl-5-(2-morpholin-4-yl-[1,2,4]triazolo[1,5-a]pyridin-7-ylcarbamoyl)-1H-pyrazole-4-carboxylic acid (150 mg, 0.404 mmole), N-methylethanamine (174 ul, 2.02 mmole), N-ethyldiisopropylamine (564 ul, 3.23 mmole) and 1-propanephosphonic acid cyclic anhydride (50% in ethyl acetate, 606 ul, 1.01 mmole) in tetrahydrofurane (7 ml) is stirred for at 70° C. The solvent is removed under reduced pressure and the residue is triturated for 1 hr with sat. aqueous sodium bicarbonate solution (30 ml). The solid is collected by filtration, washed with water and dried affording N4-ethyl-N4,1-dimethyl-N5-(2-morpholino-[1,2,4]triazolo[1,5-a]pyridin-7-yl)-1H-pyrazole-4,5-dicarboxamide (149 mg, 89.4%) as a white solid. Mp.: 201-3° C. MS: m/z=413.3 (M+H$^+$).

Example 42

1-Methyl-N-(2-morpholino-[1,2,4]triazolo[1,5-a]pyridin-7-yl)-4-(pyrrolidine-1-carbonyl)-1H-pyrazole-5-carboxamide

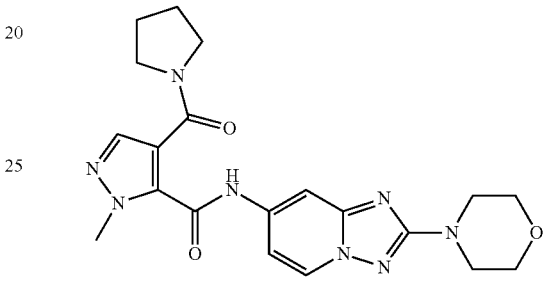

A mixture of 1-methyl-5-(2-morpholin-4-yl-[1,2,4]triazolo[1,5-a]pyridin-7-ylcarbamoyl)-1H-pyrazole-4-carboxylic acid (150 mg, 0.404 mmole), 3-fluoroazetidine hydrochloride (202 ul, 2.42 mmole), N-ethyldiisopropylamine (282 ul, 1.62 mmole) and 1-propanephosphonic acid cyclic anhydride (50% in ethyl acetate, 606 ul, 1.01 mmole) in tetrahydrofurane (7 ml) is stirred for 22 h at 70° C. The solvent is removed under reduced pressure and the residue (772 mg) is triturated for 1 hr with sat. aqueous sodium bicarbonate solution (30 ml). The solid is collected by filtration, washed with water and dried affording 1-methyl-N-(2-morpholino-[1,2,4]triazolo[1,5-a]pyridin-7-yl)-4-(pyrrolidine-1-carbonyl)-1H-pyrazole-5-carboxamide (152 mg, 88.7%) as a white solid. mp.: 210-2° C. MS: m/z=429.4 (M+H$^+$)

Example 43

4-(3-Fluoroazetidine-1-carbonyl)-1-methyl-N-(2-morpholino-[1,2,4]triazolo[1,5-a]pyridin-7-yl)-1H-pyrazole-5-carboxamide

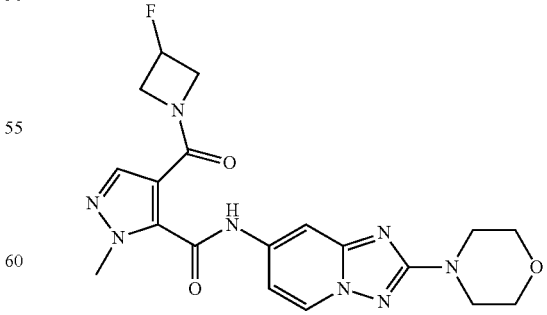

A mixture of 1-methyl-5-(2-morpholin-4-yl-[1,2,4]triazolo[1,5-a]pyridin-7-ylcarbamoyl)-1H-pyrazole-4-carboxylic acid (150 mg, 0.404 mmole), 3-fluoroazetidine hydrochloride (135 mg, 1.21 mmole), N-ethyldiisopropylamine (353 ul, 2.02 mmole) and 1-propanephosphonic acid cyclic anhydride (50% in ethyl acetate, 606 ul, 1.01 mmole) in tetrahydrofurane (7 ml) is stirred for 22 h at room temperature. The solvent is removed under reduced pressure and the residue (994 mg) is triturated for 2 hrs with sat. aqueous sodium bicarbonate solution (30 ml). The solid is collected by filtration, washed with water and dried affording 4-(3-fluoro-azetidine-1-carbonyl)-2-methyl-2H-pyrazole-3-carboxylic acid (2-morpholin-4-yl-[1,2,4]triazolo[1,5-a]pyridin-7-yl)-amide (68 mg, 39.3%) as an off-white solid. mp.: 247-250° C. MS: m/z=425.1 (M+H$^+$)

Example 44

4-(Azetidine-1-carbonyl)-1-methyl-N-(2-(pyridin-3-yl)-[1,2,4]triazolo[1,5-a]pyridin-7-yl)-1H-pyrazole-5-carboxamide

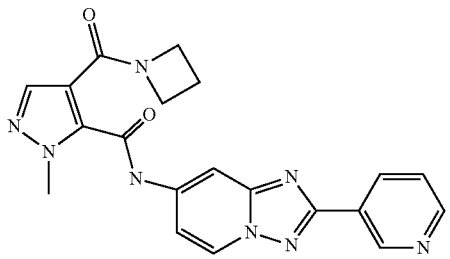 [SMILES: Cn1ncc(C(=O)N2CCC2)c1C(=O)Nc1ccn2nc(-c3cccnc3)nc2c1]

a) tert-butyl 2-bromo-[1,2,4]triazolo[1,5-a]pyridin-7-ylcarbamate

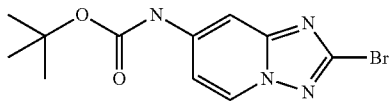 [SMILES: CC(C)(C)OC(=O)Nc1ccn2nc(Br)nc2c1]

To an argon purged solution of 2,7-dibromo-[1,2,4]triazolo[1,5-a]pyridine (1.9 g, 6.86 mmol) in dioxane (70.3 ml) are added tert-butyl carbamate (965 mg, 8.23 mmol), cesium carbonate (3.13 g, 9.61 mmol), tris(dibenzylideneacetone)dipalladium(0) (126 mg, 137 µmol) and 4,5-bis(diphenylphosphino)-9,9-dimethylxanthene (159 mg, 274 µmol). The resulting mixture is stirred for 18 hours at 100° C. under argon atmosphere. The crude material is loaded on silicagel and purified by chromatography on a 70 g silica column using heptane/ethyl acetate 10-40% as eluent affording tert-butyl 2-bromo-[1,2,4]triazolo[1,5-a]pyridin-7-ylcarbamate (1.39 g, 64.6%) as a white solid. MS: m/z=313.0; 314.9 (M+H$^+$).

b) tert-butyl 2-(pyridin-3-yl)-[1,2,4]triazolo[1,5-a]pyridin-7-ylcarbamate

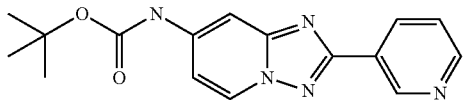 [SMILES: CC(C)(C)OC(=O)Nc1ccn2nc(-c3cccnc3)nc2c1]

Nitrogen is bubbled for 10 minutes through a mixture of tert-butyl 2-bromo-[1,2,4]triazolo[1,5-a]pyridin-7-ylcarbamate (1.39 g, 4.44 mmol) and pyridin-3-ylboronic acid (818 mg, 6.66 mmol) in dioxane (23.8 ml) and sat. aqueous sodium carbonate sol. (5.94 ml), then 1,1'-bis(diphenylphosphino)ferrocene palladium (II) chloride (181 mg, 222 µmol) is added and the resulting mixture is fluxed for 18 hours under nitrogen atmosphere. The residue is diluted with dichloromethane and washed with water; the organic layer is separated, dried with magnesium sulfate and the solvent is removed under reduced pressure. The residue is loaded on silicagel and purified by chromatography on a 50 g silica column using heptane/ethyl acetate 50-100% as eluent affording tert-butyl 2-(pyridin-3-yl)-[1,2,4]triazolo[1,5-a]pyridin-7-ylcarbamate (762 mg, 55.1%) as a light brown foam. MS: m/z=312.4 (M+H$^+$).

c) 2-(pyridin-3-yl)-[1,2,4]triazolo[1,5-a]pyridin-7-amine

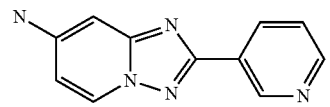 [SMILES: Nc1ccn2nc(-c3cccnc3)nc2c1]

A mixture of tert-butyl 2-(pyridin-3-yl)-[1,2,4]triazolo[1,5-a]pyridin-7-ylcarbamate (755 mg, 2.43 mmol) in hydrochloric acid (5 N in ether, 15 ml, 75.0 mmol) is stirred for 7 hours at room temperature. The solvent is evaporated and the yellowish solid is dissolved in water and made basic with sodium hydroxide 32%; the precipitated solid is collected by filtration, washed with water and dried affording 2-(pyridin-3-yl)-[1,2,4]triazolo[1,5-a]pyridin-7-amine (471 mg, 92%) as a light brown solid. mp.: 228-233° C. MS: m/z=212.1 (M+H$^+$).

d) methyl 1-methyl-5-(2-(pyridin-3-yl)-[1,2,4]triazolo[1,5-a]pyridin-7-ylcarbamoyl)-1H-pyrazole-4-carboxylate

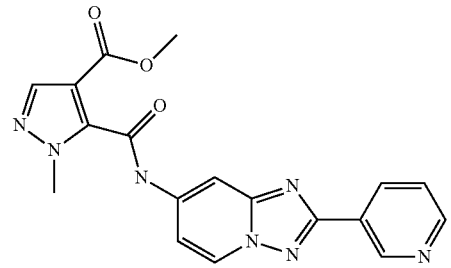 [SMILES: COC(=O)c1cnn(C)c1C(=O)Nc1ccn2nc(-c3cccnc3)nc2c1]

A mixture of 2-(pyridin-3-yl)-[1,2,4]triazolo[1,5-a]pyridin-7-amine (468 mg, 2.22 mmol), 4-(methoxycarbonyl)-1-methyl-1H-pyrazole-5-carboxylic acid (490 mg, 2.66 mmol), propylphosphonic anhydride (50% in ethyl acetate, 3.26 ml, 5.54 mmol) and N,N-diisopropylethylamine (1.51 ml, 8.86 mmol) in tetrahydrofurane (15 ml) is stirred for 18 hours at 70° C. under nitrogen atmosphere. The solvent is evaporated and the residue triturated with sat. aqueous sodium bicarbonate solution. The solid is collected by filtration, washed with water and dried affording methyl 1-methyl-5-(2-(pyridin-3-yl)-[1,2,4]triazolo[1,5-a]pyridin-7-ylcarbamoyl)-1H-pyrae) 1-methyl-5-(2-pyridin-3-yl-[1,2,4]triazolo[1,5-a]pyridin-7-ylcarbamoyl)-1H-pyrazole-4-carboxylic acid

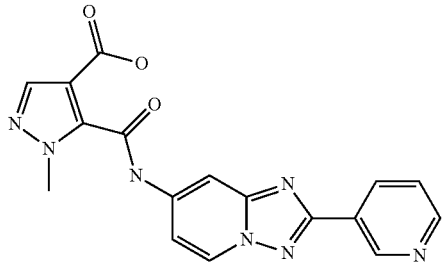 [SMILES: Cn1ncc(C(=O)O)c1C(=O)Nc1ccn2nc(-c3cccnc3)nc2c1]

A mixture of methyl 1-methyl-5-(2-(pyridin-3-yl)-[1,2,4]triazolo[1,5-a]pyridin-7-ylcarbamoyl)-1H-pyrazole-4-carboxylate (560 mg, 1.48 mmol) and lithium hydroxide monohydrate (125 mg, 2.97 mmol) in methanol (10 ml) and water (3 ml) is stirred for 18 hours at 50° C. The methanol is evaporated and the resulting suspension treated with 2N aqueous hydrochloric acid (1.485 ml, 2.97 mmol) The solvent is evaporated affording 1-methyl-5-(2-pyridin-3-yl-[1,2,4]triazolo[1,5-a]pyridin-7-ylcarbamoyl)-1H-pyrazole-4-carboxylic acid containing 2 equivalents lithium chloride (670 mg, 101%). mp.: >250° C. MS: m/z=362.0 (M+H⁺).

f) 4-(azetidine-1-carbonyl)-1-methyl-N-(2-(pyridin-3-yl)-[1,2,4]triazolo[1,5-a]pyridin-7-yl)-1H-pyrazole-5-carboxamide

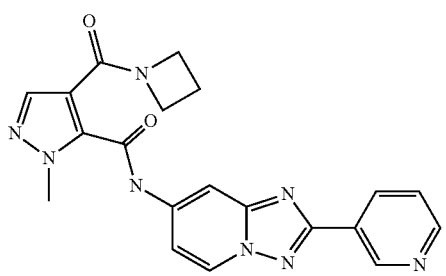 [SMILES: Cn1ncc(C(=O)N2CCC2)c1C(=O)Nc1ccn2nc(-c3cccnc3)nc2c1]

A mixture of 1-methyl-5-(2-(pyridin-3-yl)-[1,2,4]triazolo[1,5-a]pyridin-7-ylcarbamoyl)-1H-pyrazole-4-carboxylic acid (100 mg, 223 µmol), azetidine (60.2 µl, 893 µmol), propylphosphonic anhydride (50% in ethyl acetate, 329 µl, 558 µmol) and N,N-diisopropylethylamine (114 µl, 669 µmol) in tetrahydrofurane (7 ml) is stirred for 18 hours at room temperature. The solvent is evaporated and the residue triturated with sat. aqueous sodium bicarbonate solution. The solid is collected by filtration, washed with water and dried affording 4-(azetidine-1-carbonyl)-1-methyl-N-(2-(pyridin-3-yl)-[1,2,4]triazolo[1,5-a]pyridin-7-yl)-1H-pyrazole-5-carboxamide (28 mg, 31.2%) as a light brown solid. mp.: 253-4° C. MS: m/z=403.4 (M+H⁺).

Example 45

1-Methyl-4-(morpholine-4-carbonyl)-N-(2-(pyridin-3-yl)-[1,2,4]triazolo[1,5-a]pyridin-7-yl)-1H-pyrazole-5-carboxamide

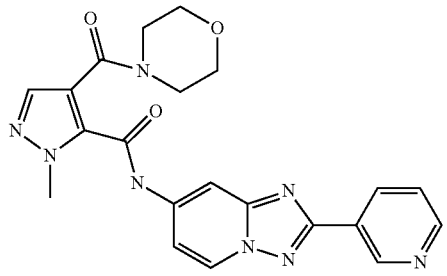 [SMILES: Cn1ncc(C(=O)N2CCOCC2)c1C(=O)Nc1ccn2nc(-c3cccnc3)nc2c1]

A mixture of 1-methyl-5-(2-(pyridin-3-yl)-[1,2,4]triazolo[1,5-a]pyridin-7-ylcarbamoyl)-1H-pyrazole-4-carboxylic acid (100 mg, 223 µmol), morpholine (156 µl, 1.79 mmol), propylphosphonic anhydride (50% in ethyl acetate, 329 µl, 558 µmol) and N,N-diisopropylethylamine (114 µl, 669 µmol) in tetrahydrofurane (7 ml) is refluxed for 18 hours. The mixture is dissolved in ethyl acetate and washed with sodium bicarbonate solution and brine. The organic layer is separated, dried with magnesium sulfate and the solvent is removed under reduced pressure. The residue is purified by chromatography on a 20 g silica column using ethyl acetate/methanol 10% as eluent affording 1-methyl-4-(morpholine-4-carbonyl)-N-(2-(pyridin-3-yl)-[1,2,4]triazolo[1,5-a]pyridin-7-yl)-1H-pyrazole-5-carboxamide (40 mg, 41.5%) as a white solid. mp.: 218-220° C. MS: m/z=433.3 (M+H⁺).

Example 46

1-Methyl-N-(2-(pyridin-3-yl)-[1,2,4]triazolo[1,5-a]pyridin-7-yl)-4-(pyrrolidine-1-carbonyl)-1H-pyrazole-5-carboxamide

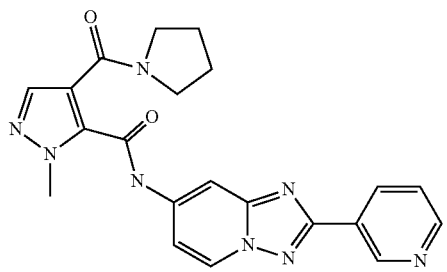 [SMILES: Cn1ncc(C(=O)N2CCCC2)c1C(=O)Nc1ccn2nc(-c3cccnc3)nc2c1]

A mixture of 1-methyl-5-(2-(pyridin-3-yl)-[1,2,4]triazolo[1,5-a]pyridin-7-ylcarbamoyl)-1H-pyrazole-4-carboxylic acid (100 mg, 223 µmol), pyrrolidine (148 µl, 1.79 mmol), propylphosphonic anhydride (50% in ethyl acetate, 329 µl, 558 µmol) and N,N-diisopropylethylamine (114 µl, 669 µmol) in tetrahydrofurane (7 ml) is refluxed for 18 hours. The solvent is evaporated and the residue triturated with sat. aqueous sodium bicarbonate solution. The solid is collected by filtration, washed with water and dried affording 1-methyl-N-(2-(pyridin-3-yl)-[1,2,4]triazolo[1,5-a]pyridin-7-yl)-4-(pyrrolidine-1-carbonyl)-1H-pyrazole-5-carboxamide (77 mg, 82.9%) as a light brown solid. mp.: 226-8° C. MS: m/z=417.3 (M+H+).

Example 47

4-(3-Fluoroazetidine-1-carbonyl)-1-methyl-N-(2-(pyridin-3-yl)-[1,2,4]triazolo[1,5-a]pyridin-7-yl)-1H-pyrazole-5-carboxamide

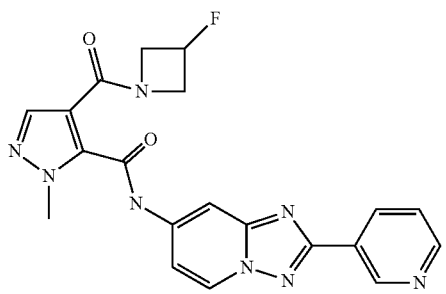 [SMILES: Cn1ncc(C(=O)N2CC(F)C2)c1C(=O)Nc1ccn2nc(-c3cccnc3)nc2c1]

A mixture of 1-methyl-5-(2-(pyridin-3-yl)-[1,2,4]triazolo[1,5-a]pyridin-7-ylcarbamoyl)-1H-pyrazole-4-carboxylic acid (100 mg, 223 µmol), 3-fluoroazetidine hydrochloride (74.7 mg, 669 µmol), propylphosphonic anhydride (50% in ethyl acetate, 329 µl, 558 µmol) and N,N-diisopropylethylamine (228 µl, 1.34 mmol) in tetrahydrofurane (7 ml) is stirred for 18 hours room temperature. The solvent is evaporated and the residue triturated with sat. aqueous sodium bicarbonate solution. The solid is collected by filtration, washed with water and dried affording 4-(3-fluoroazetidine-1-carbonyl)-1-methyl-N-(2-(pyridin-3-yl)-[1,2,4]triazolo[1,5-a]pyridin-7-yl)-1H-pyrazole-5-carboxamide (36 mg, 37.3%) as a light brown solid. mp.: 247-9° C. MS: m/z=421.1 (M+H+).

Example 48

2-Methyl-2H-pyrazole-3,4-dicarboxylic acid 4-(cyclopropyl-methyl-amide)3-[(2-phenyl-[1,2,4]triazolo[1,5-a]pyridin-7-yl)-amide]

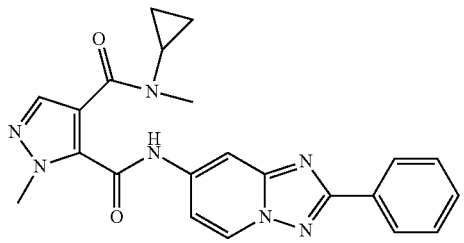 [SMILES: CN(C(=O)c1cnn(C)c1C(=O)Nc1ccn2nc(-c3ccccc3)nc2c1)C1CC1]

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), N-methylcyclopropanamine (58.9 mg, 828 µmol), N,N-diisopropylethylamine (235 µl, 1.38 mmol) and propylphosphonic anhydride (50% in ethyl acetate, 407 µl, 690 µmol) in tetrahydrofuran (5.00 ml) was stirred at 70° C. for 18 hours. The solvent was evaporated, the residue was triturated with sodium hydrogencarbonate solution. The precipitated solid was filtered off, washed with water and dried affording 2-methyl-2H-pyrazole-3,4-dicarboxylic acid 4-(cyclopropyl-methyl-amide)3-[(2-phenyl-[1,2,4]triazolo[1,5-a]pyridin-7-yl)-amide] (103 mg, 89.9%) as a light yellow solid. mp: 156-157° C., MS: m/z=416.0 (M+H+).

Example 49

2-Methyl-2H-pyrazole-3,4-dicarboxylic acid 4-[methyl-(2,2,2-trifluoro-ethyl)-amide]3-[(2-phenyl-[1,2,4]triazolo[1,5-a]pyridin-7-yl)-amide]

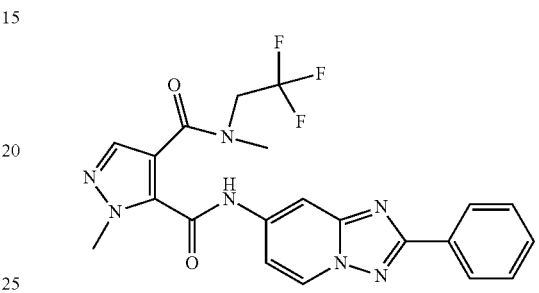

A mixture of 1-methyl-5-(2-phenyl-[1,2,4]triazolo[1,5-a]pyridin-7-ylcarbamoyl)-1H-pyrazole-4-carboxylic acid (123 mg, 339 µmol), 2,2,2-trifluoro-N-methylethanamine hydrochloride (102 mg, 679 µmol), propylphosphonic anhydride (50% in ethyl acetate, 500 µl, 849 µmol) and N,N-diisopropylethylamine (289 µl, 1.7 mmol) in tetrahydrofuran (7 ml) was stirred for 18 hours at 60° C. The solvent was evaporated and the residue was triturated with sodium hydrogencarbonate solution. The precipitated solid was filtered off, washed with water and dried affording 2-methyl-2H-pyrazole-3,4-dicarboxylic acid 4-[methyl-(2,2,2-trifluoro-ethyl)-amide]3-[(2-phenyl-[1,2,4]triazolo[1,5-a]pyridin-7-yl)-amide] (75 mg, 48.3%) as a white solid. mp: >250° C., MS: m/z=458.1 (M+H+)

Example 50

4-(Azetidine-1-carbonyl)-2-methyl-2H-pyrazole-3-carboxylic acid (2-isopropyl-[1,2,4]triazolo[1,5-a]pyridin-7-yl)-amide

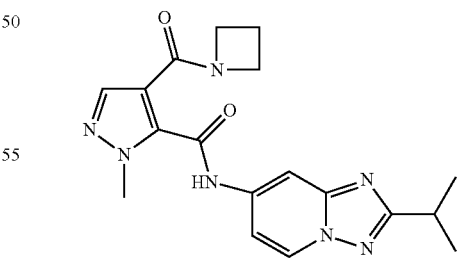

A mixture of 5-(2-isopropyl-[1,2,4]triazolo[1,5-a]pyridin-7-ylcarbamoyl)-1-methyl-1H-pyrazole-4-carboxylic acid (70 mg, 213 µmol), azetidine (71.6 µl, 1.07 mmol), propylphosphonic anhydride (50% in ethyl acetate, 314 µl, 533 µmol) and diisopropylethylamine (112 µl, 640 µmol) in tetrahydrofuran (4 ml) was stirred for 3.5 days (weekend) at 25° C. The solvent was evaporated, the residue was triturated with

Example 51

4-(3-Fluoro-azetidine-1-carbonyl)-2-methyl-2H-pyrazole-3-carboxylic acid (2-isopropyl-[1,2,4]triazolo[1,5-a]pyridin-7-yl)-amide

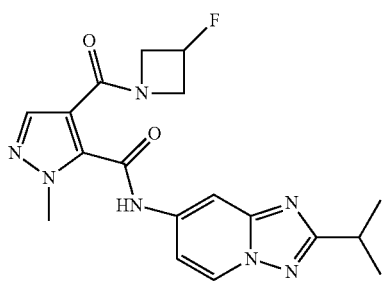 [SMILES: CC(C)c1nc2cc(NC(=O)c3c(C(=O)N4CC(F)C4)cnn3C)ccn2n1]

A mixture of 5-(2-isopropyl-[1,2,4]triazolo[1,5-a]pyridin-7-ylcarbamoyl)-1-methyl-1H-pyrazole-4-carboxylic acid (70 mg, 213 μmol), 3-fluoroazetidine hydrochloride (71.3 mg, 640 mmol), propylphosphonic anhydride (50% in ethyl acetate, 314 μl, 533 μmol) and diisopropylethylamine (223 μl, 1.28 mmol) in tetrahydrofuran (4 ml) was stirred for 2.5 days (weekend) at 25° C. The solvent was evaporated, the residue was triturated with sodium hydrogencarbonate solution. The precipitated solid was filtered off, washed with water and dried affording 4-(3-fluoro-azetidine-1-carbonyl)-2-methyl-2H-pyrazole-3-carboxylic acid (2-isopropyl-[1,2,4]triazolo[1,5-a]pyridin-7-yl)-amide (71 mg, 86.4%) as a white solid. mp: 226-227° C., MS: m/z=384.0 (M−H$^+$)

sodium hydrogencarbonate solution. The precipitated solid was filtered off, washed with water and dried affording 4-(azetidine-1-carbonyl)-2-methyl-2H-pyrazole-3-carboxylic acid (2-isopropyl-[1,2,4]triazolo[1,5-a]pyridin-7-yl)-amide (74 mg, 94.5%) as a white solid. mp: 226-227° C., MS: m/z=366.1 (M−H$^+$)

Example 52

N4-cyclopentyl-N4,1-dimethyl-N5-(2-morpholino-[1,2,4]triazolo[1,5-a]pyridin-7-yl)-1H-pyrazole-4,5-dicarboxamide

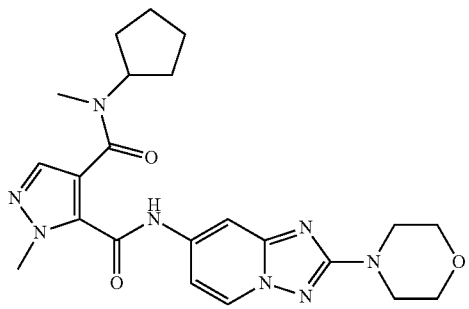 [SMILES: CN(C(=O)c1cnn(C)c1C(=O)Nc1ccn2nc(N3CCOCC3)nc2c1)C1CCCC1]

A mixture of 1-methyl-5-(2-morpholin-4-yl-[1,2,4]triazolo[1,5-a]pyridin-7-ylcarbamoyl)-1H-pyrazole-4-carboxylic acid (100 mg, 0.269 mmole), cyclopentyl-methylamine (107 mg, 1.08 mmole), N-ethyldiisopropylamine (376 ul, 2.15 mmole) and 1-propanephosphonic acid cyclic anhydride (50% in ethyl acetate, 404 ul, 0.673 mmole) in tetrahydrofurane (4 ml) was stirred for 22 hours at 70° C. The solvent was evaporated, the residue was triturated with sodium hydrogencarbonate solution. The precipitated solid was filtered off, washed with water and dried affording N4-cyclopentyl-N4,1-dimethyl-N5-(2-morpholino-[1,2,4]triazolo[1,5-a]pyridin-7-yl)-1H-pyrazole-4,5-dicarboxamide (113 mg, 92.7%) as an off-white solid. mp.: 222-4° C., MS: m/z=453.5 (M+H$^+$)

Example 53

N4-cyclopropyl-N4,1-dimethyl-N5-(2-morpholino-[1,2,4]triazolo[1,5-a]pyridin-7-yl)-1H-pyrazole-4,5-dicarboxamide

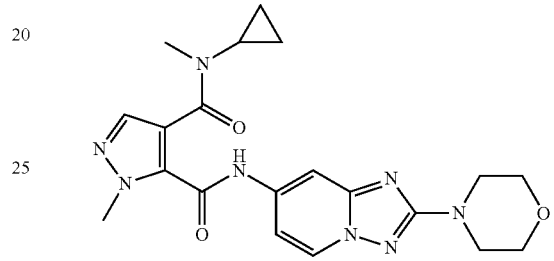

A mixture of 1-methyl-5-(2-morpholin-4-yl-[1,2,4]triazolo[1,5-a]pyridin-7-ylcarbamoyl)-1H-pyrazole-4-carboxylic acid (140 mg, 0.377 mmole), N-methyl cyclopropylamine (161 mg, 2.26 mmole), N-ethyldiisopropylamine (527 ul, 3.02 mmole) and 1-propanephosphonic acid cyclic anhydride (50% in ethyl acetate, 566 ul, 0.943 mmole) in tetrahydrofurane (5 ml) was stirred for 22 hours at 70° C. The solution is loaded on silicagel (1.5 g) and purified by chromatography on a 10 g Silicycle cartridge with ethyl acetate as eluent affording N4-cyclopropyl-N4,1-dimethyl-N5-(2-morpholino-[1,2,4]triazolo[1,5-a]pyridin-7-yl)-1H-pyrazole-4,5-dicarboxamide (139 mg, 86.9%) as a white solid. mp.: 172-5° C., MS: m/z=415.4 (M+H$^+$)

Example 54

2-Methyl-2H-pyrazole-3,4-dicarboxylic acid 4-[methyl-(2,2,2-trifluoro-ethyl)-amide]3-[(2-morpholin-4-yl-[1,2,4]triazolo[1,5-a]pyridin-7-yl)-amide]

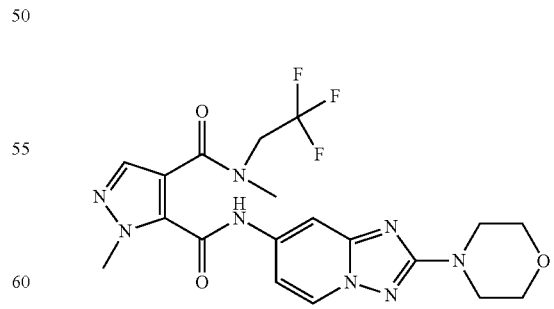

A mixture of 1-methyl-5-(2-morpholino-[1,2,4]triazolo[1,5-a]pyridin-7-ylcarbamoyl)-1H-pyrazole-4-carboxylic acid (114 mg, 307 μmol), 2,2,2-trifluoro-N-methylethanamine hydrochloride (91.8 mg, 614 μmol), propylphosphonic anhydride (50% in ethyl acetate, 452 μl, 767 μmol) and N,N- diisopropylethylamine (261 μl, 1.53 mmol) in tetrahydrofuran (6.5 ml) was stirred for 18 hours at 60° C. The solvent was evaporated, the residue was triturated with sodium hydrogencarbonate solution. The precipitated solid was filtered off, washed with water and dried affording 2-methyl-2H-pyrazole-3,4-dicarboxylic acid 4-[methyl-(2,2,2-trifluoro-ethyl)-amide]3-[(2-morpholin-4-yl-[1,2,4]triazolo[1,5-a]pyridin-7-yl)-amide] (126 mg, 88.0%) as a white solid. mp: 238.7, MS: m/z=467.0 (M+H$^+$)

Example 55

2-Methyl-2H-pyrazole-3,4-dicarboxylic acid 4-(cyclopropyl-methyl-amide)3-[(2-pyridin-3-yl-[1,2,4]triazolo[1,5-a]pyridin-7-yl)-amide]

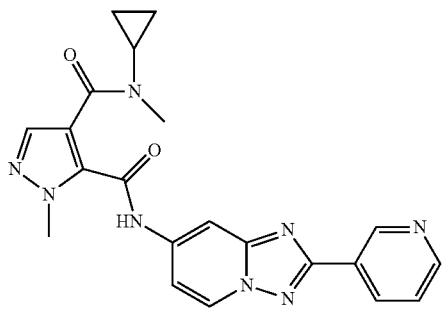 [SMILES: CN(C(=O)c1cnn(C)c1C(=O)Nc1ccn2nc(-c3cccnc3)nc2c1)C1CC1]

A mixture of 1-methyl-5-(2-pyridin-3-yl-[1,2,4]triazolo[1,5-a]pyridin-7-ylcarbamoyl)-1H-pyrazole-4-carboxylic acid (150 mg, 335 μmol), N-methylcyclopropanamine (71.4 mg, 1.00 mmol), propylphosphonic anhydride (50% in ethyl acetate, 493 μl, 837 μmol) and N,N-diisopropylethylamine (398 μl, 2.34 mmol) in tetrahydrofuran (7 ml) was stirred for 18 hours at 70° C. The solvent was evaporated and the residue was diluted with dichloromethane, the organic layer was washed with sat. sodium hydrogencarbonate solution and water, dried over magnesium sulfate, filtrated and evaporated affording 2-methyl-2H-pyrazole-3,4-dicarboxylic acid 4-(cyclopropyl-methyl-amide)3-[(2-pyridin-3-yl-[1,2,4]triazolo[1,5-a]pyridin-7-yl)-amide] (78 mg, 56.0%) as a light yellow foam. MS: m/z=417.3 (M+H$^+$)

Example 56

2-Methyl-2H-pyrazole-3,4-dicarboxylic acid 4-[(2-fluoro-ethyl)-methyl-amide]3-[(2-pyridin-3-yl-[1,2,4]triazolo[1,5-a]pyridin-7-yl)-amide]

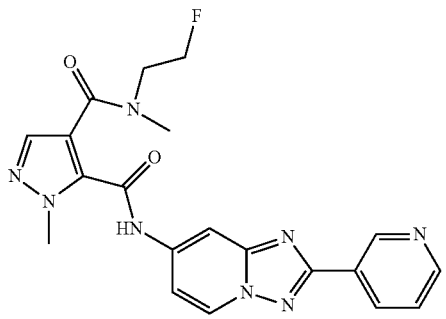 [SMILES: CN(CCF)C(=O)c1cnn(C)c1C(=O)Nc1ccn2nc(-c3cccnc3)nc2c1]

A mixture of 1-methyl-5-(2-pyridin-3-yl-[1,2,4]triazolo[1,5-a]pyridin-7-ylcarbamoyl)-1H-pyrazole-4-carboxylic acid (150 mg, 335 μmol), 2-fluoro-N-methylethanamine hydrochloride (114 mg, 1.00 mmol), propylphosphonic anhydride (50% in ethyl acetate, 493 μl, 837 μmol) and N,N-diisopropylethylamine (398 μl, 2.34 mmol) in tetrahydrofuran (7 ml) was heated for 18 hours to 70° C. The solvent was evaporated, the residue was triturated with sodium hydrogencarbonate solution. The precipitated solid was filtered off, washed with water and dried affording 2-methyl-2H-pyrazole-3,4-dicarboxylic acid 4-[(2-fluoro-ethyl)-methyl-amide]3-[(2-pyridin-3-yl-[1,2,4]triazolo[1,5-a]pyridin-7-yl)-amide (36 mg, 25.5%) as a white solid. mp: 200-208° C., MS: m/z=423.0 (M+H$^+$)

Example 57

2-Methyl-4-((1R,4R)-2-oxa-5-aza-bicyclo[2.2.1]heptane-5-carbonyl)-2H-pyrazole-3-carboxylic acid (2-pyridin-3-yl-[1,2,4]triazolo[1,5-a]pyridin-7-yl)-amide

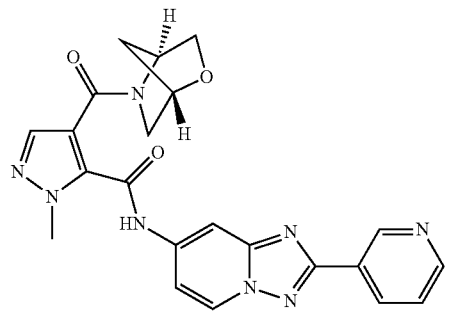 [SMILES: Cn1ncc(C(=O)N2C[C@@H]3C[C@H]2CO3)c1C(=O)Nc1ccn2nc(-c3cccnc3)nc2c1]

A mixture of 1-methyl-5-(2-pyridin-3-yl-[1,2,4]triazolo[1,5-a]pyridin-7-ylcarbamoyl)-1H-pyrazole-4-carboxylic acid (150 mg, 335 μmol), (1S,4S)-2-oxa-5-azabicyclo[2.2.1]heptane hydrochloride (136 mg, 1.00 mmol), propylphosphonic anhydride (50% in ethyl acetate, 493 μl, 837 μmol) and N,N-diisopropylethylamine (398 μl, 2.34 mmol) in tetrahydrofuran (7.00 ml) was refluxed for 2.5 days (weekend). The solvent was evaporated, the residue was triturated with sodium hydrogencarbonate solution. The precipitated solid was filtered off, washed with water and dried affording 2-methyl-4-((1R,4R)-2-oxa-5-aza-bicyclo[2.2.1]heptane-5-carbonyl)-2H-pyrazole-3-carboxylic acid (2-pyridin-3-yl-[1,2,4]triazolo[1,5-a]pyridin-7-yl)-amide (79 mg, 53.1%) as a white solid. mp: 272-273° C., MS: m/z=445.1 (M+H$^+$)

Example 58

4-(Azetidine-1-carbonyl)-2-methyl-2H-pyrazole-3-carboxylic acid [2-(ethyl-methyl-amino)-[1,2,4]triazolo[1,5-a]pyridin-7-yl]-amide

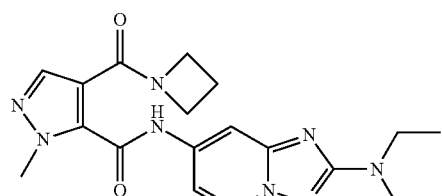

a) (7-Bromo-[1,2,4]triazolo[1,5-a]pyridin-2-yl)-ethyl-methyl-amine

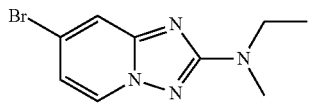

A mixture of 2,7-dibromo-[1,2,4]triazolo[1,5-a]pyridine (1 g, 3.61 mmol) and N-methylethanamine (4.00 ml, 46.6 mmol) in ethanol (4 ml) was heated for 4 hours to 120° C. in a high pressure vessel. The crude material was applied on silicagel and purified by flash chromatography over a 20 g silicagel column using heptane/ethyl acetate 10-30% as eluent affording (7-bromo-[1,2,4]triazolo[1,5-a]pyridin-2-yl)-ethyl-methyl-amine (549 mg, 59.6%) as a white solid. mp: 109-111° C., MS: m/z=255/257 (M+H$^+$)

b) [2-(Ethyl-methyl-amino)-[1,2,4]triazolo[1,5-a]pyridin-7-yl]-carbamic acid tert-butyl ester

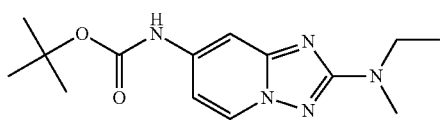 [SMILES: CCN(C)c1nc2cc(NC(=O)OC(C)(C)C)ccn2n1]

To an argon purged solution of 7-bromo-N-ethyl-N-methyl-[1,2,4]triazolo[1,5-a]pyridin-2-amine (549 mg, 2.15 mmol) in dioxane (20.6 ml) were added tert-butyl carbamate (303 mg, 2.58 mmol), cesium carbonate (982 mg, 3.01 mmol), tris(dibenzylideneacetone) dipalladium(0) (39.4 mg, 43.0 µmol) and 4,5-bis(diphenylphosphino)-9,9-dimethylxanthene (49.8 mg, 86.1 mmol). The resulting mixture was heated to 100° C. and stirred for 2.5 days (weekend) under argon atmosphere. The crude material was applied on silicagel and purified by flash chromatography over a 50 g silicagel column using heptane/ethyl acetate 10-50% as eluent affording [2-(ethyl-methyl-amino)-[1,2,4]triazolo[1,5-a]pyridin-7-yl]-carbamic acid tert-butyl ester (509 mg, 81.2%) as a white solid. mp: 181-183° C., MS: m/z=292.3 (M+H$^+$)

c) N2-Ethyl-N2-methyl-[1,2,4]triazolo[1,5-a]pyridine-2,7-diamine

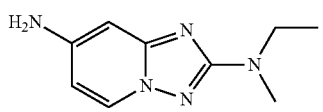

A mixture of tert-butyl 2-(ethyl(methyl)amino)-[1,2,4]triazolo[1,5-a]pyridin-7-ylcarbamate (500 mg, 1.72 mmol) in hydrochloric acid (5 N in ether, 20 ml, 658 mmol) was stirred for 18 hours at 25° C. The solvent was evaporated, the white residue was dissolved in ethyl acetate, washed with sat. sodium bicarbonate solution (pH=9) and water. The organic layer was separated, dried over magnesium sulfate, filtrated and evaporated affording N2-ethyl-N-2-methyl-[1,2,4]triazolo[1,5-a]pyridine-2,7-diamine (222 mg, 67.6%) as a white solid. mp: 216-219° C., MS: m/z=192.4 (M+H$^+$)

d) 5-[2-(Ethyl-methyl-amino)-[1,2,4]triazolo[1,5-a]pyridin-7-ylcarbamoyl]-1-methyl-1H-pyrazole-4-carboxylic acid ethyl ester

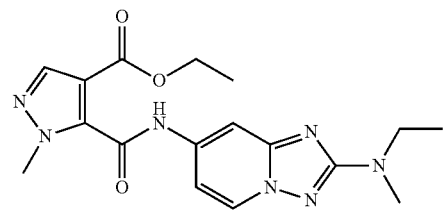 [SMILES: CCOC(=O)c1cnn(C)c1C(=O)Nc1ccn2nc(N(C)CC)nc2c1]

A mixture of N2-ethyl-N2-methyl-[1,2,4]triazolo[1,5-a]pyridine-2,7-diamine (215 mg, 1.12 mmol), 4-(ethoxycarbonyl)-1-methyl-1H-pyrazole-5-carboxylic acid (267 mg, 1.35 mmol), propylphosphonic anhydride (50% in ethyl acetate, 1.66 ml, 2.81 mmol) and N,N-diisopropylethylamine (574 µl, 3.37 mmol) in tetrahydrofuran (10 ml) was refluxed for 18 hours. The crude material was applied on silicagel and purified by flash chromatography over a 20 g silicagel column using ethyl acetate 100% as eluent affording 5-[2-(ethyl-methyl-amino)-[1,2,4]triazolo[1,5-a]pyridin-7-ylcarbamoyl]-1-methyl-1H-pyrazole-4-carboxylic acid ethyl ester (375 mg, 89.8%) as a light yellow solid. mp: 167° C., MS: m/z=372.5 (M+H$^+$)

e) 5-[2-(Ethyl-methyl-amino)-[1,2,4]triazolo[1,5-a]pyridin-7-ylcarbamoyl]-1-methyl-1H-pyrazole-4-carboxylic acid

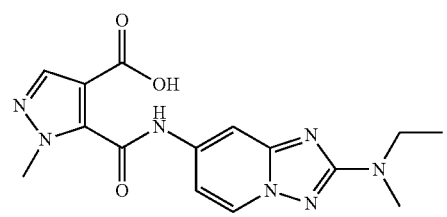 [SMILES: CCN(C)c1nc2cc(NC(=O)c3c(C(=O)O)cnn3C)ccn2n1]

A mixture of ethyl 5-(2-(ethyl(methyl)amino)-[1,2,4]triazolo[1,5-a]pyridin-7-ylcarbamoyl)-1-methyl-1H-pyrazole-4-carboxylate (366 mg, 985 µmol) and lithium hydroxide hydrate (82.7 mg, 1.97 mmol) in methanol (15 ml) and water (5 ml) was stirred for 5 hours at 50° C. The methanol was evaporated, the residue was diluted with water and was then neutralized with hydrochloric acid 1N (1.97 ml, 1.97 mmol). The precipitated white solid was filtered off, washed with water several times and dried affording 5-[2-(ethyl-methyl-amino)-[1,2,4]triazolo[1,5-a]pyridin-7-ylcarbamoyl]-1-methyl-1H-pyrazole-4-carboxylic acid (306 mg, 90.4%) as a white solid.

mp: >250° C., MS: m/z=342.1 (M−H$^+$)

f) 4-(Azetidine-1-carbonyl)-2-methyl-2H-pyrazole-3-carboxylic acid [2-(ethyl-methyl-amino)-[1,2,4]triazolo[1,5-a]pyridin-7-yl]-amide

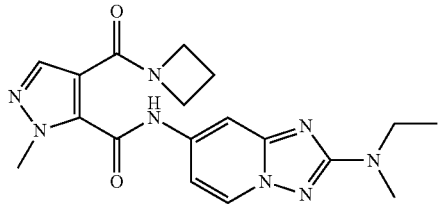 [SMILES: CCN(C)c1nc2cc(NC(=O)c3c(C(=O)N4CCC4)cnn3C)ccn2n1]

A mixture of 5-(2-(ethyl(methyl)amino)-[1,2,4]triazolo[1,5-a]pyridin-7-ylcarbamoyl)-1-methyl-1H-pyrazole-4-carboxylic acid (144 mg, 419 µmol), azetidine (84.8 µl, 1.26 mmol), propylphosphonic anhydride (50% in ethyl acetate, 618 µl, 1.05 mmol) and N,N-diisopropylethylamine (214 µl, 1.26 mmol) in tetrahydrofuran (7 ml) was refluxed for 2.5 days (weekend). The solvent was evaporated, the residue was triturated with sodium hydrogencarbonate solution. The precipitated solid was filtered off, washed with water and dried affording 4-(azetidine-1-carbonyl)-2-methyl-2H-pyrazole-3-carboxylic acid [2-(ethyl-methylamino)-[1,2,4]triazolo[1,5-a]pyridin-7-yl]-amide (151 mg white solid, 94.1%) as a white solid. mp: 229-232° C., MS: m/z=383.1 (M+H⁺)

Example 59

2-Methyl-4-(morpholine-4-carbonyl)-2H-pyrazole-3-carboxylic acid [2-(ethyl-methyl-amino)-[1,2,4]triazolo[1,5-a]pyridin-7-yl]-amide

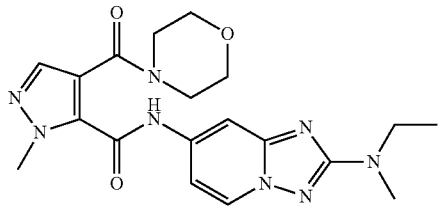 [SMILES: CCN(C)c1nc2cc(NC(=O)c3c(C(=O)N4CCOCC4)cnn3C)ccn2n1]

A mixture of 5-(2-(ethyl(methyl)amino)-[1,2,4]triazolo[1,5-a]pyridin-7-ylcarbamoyl)-1-methyl-1H-pyrazole-4-carboxylic acid (144 mg, 419 µmol), morpholine (365 mg, 4.19 mmol), propylphosphonic anhydride (50% in ethyl acetate, 618 µl, 1.05 mmol) and N,N-diisopropylethylamine (214 µL, 1.26 mmol) in tetrahydrofuran (7.00 ml) was refluxed for 2.5 days (weekend). The solvent was evaporated, the residue was triturated with sodium hydrogencarbonate solution. The precipitated solid was filtered off, washed with water and dried affording 2-methyl-4-(morpholine-4-carbonyl)-2H-pyrazole-3-carboxylic acid [2-(ethyl-methyl-amino)-[1,2,4]triazolo[1,5-a]pyridin-7-yl]-amide (141 mg, 81.5%) as a white solid. mp: 167-169° C., MS: m/z=413.4 (M+H⁺)

Example 60

4-(Azetidine-1-carbonyl)-2-methyl-2H-pyrazole-3-carboxylic acid (2-pyrrolidin-1-yl-[1,2,4]triazolo[1,5-a]pyridin-7-yl)-amide

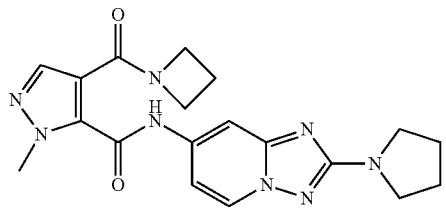 [SMILES: Cn1ncc(C(=O)N2CCC2)c1C(=O)Nc1ccn2nc(N3CCCC3)nc2c1]

a) 7-Bromo-2-pyrrolidin-1-yl-[1,2,4]triazolo[1,5-a]pyridine

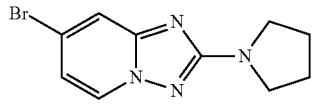 [SMILES: Brc1ccn2nc(N3CCCC3)nc2c1]

A mixture of 2,7-dibromo-[1,2,4]triazolo[1,5-a]pyridine (770 mg, 2.78 mmol) and pyrrolidine (15 ml, 181 mmol) was refluxed for 3 hours under nitrogen atmosphere. The pyrrolidine was evaporated. The residue was diluted with ethyl acetate and washed with water and brine. The organic layer was separated, dried over magnesium sulfate, filtrated and evaporated. The crude material was applied on silicagel and purified by flash chromatography over a 50 g silicagel column using heptane/ethyl acetate 10-50% as eluent affording 7-bromo-2-pyrrolidin-1-yl-[1,2,4]triazolo[1,5-a]pyridine (383 mg, 51.5%) as an off-white solid. mp: 170-172° C., MS: m/z=266.9/269 (M+H⁺)

b) (2-Pyrrolidin-1-yl-[1,2,4]triazolo[1,5-a]pyridin-7-yl)-carbamic acid tert-butyl ester

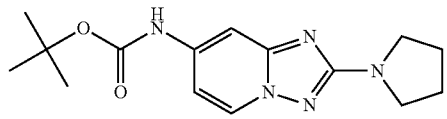 [SMILES: CC(C)(C)OC(=O)Nc1ccn2nc(N3CCCC3)nc2c1]

To an argon purged solution of 7-bromo-2-(pyrrolidin-1-yl)-[1,2,4]triazolo[1,5-a]pyridine (383 g, 1.43 mol) in dioxane (14.4 ml) were added tert-butyl carbamate (202 g, 1.72 mol), cesium carbonate (654 g, 2.01 mol), tris(dibenzylideneacetone) dipalladium(0) (26.3 g, 28.7 mmol) and 4,5-bis(diphenylphosphino)-9,9-dimethylxanthene (33.2 g, 57.4 mmol). The resulting mixture was heated to 100° C. and stirred for 18 hours under argon atmosphere. The crude material was applied on silicagel and purified by flash chromatography over a 20 g silicagel column using heptane/ethyl acetate 10-70% as eluent affording (2-pyrrolidin-1-yl-[1,2,4]triazolo

[1,5-a]pyridin-7-yl)-carbamic acid tert-butyl ester (346 mg, 79.5%) as an off-white solid. mp: 216-219° C., MS: m/z=304.1 (M+H⁺)

c) 2-Pyrrolidin-1-yl-[1,2,4]triazolo[1,5-a]pyridin-7-ylamine

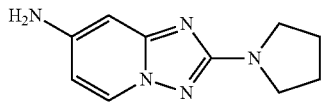 [SMILES: Nc1ccn2nc(N3CCCC3)nc2c1]

A mixture of tert-butyl 2-(pyrrolidin-1-yl)-[1,2,4]triazolo[1,5-a]pyridin-7-ylcarbamate (340 mg, 1.12 mmol) and hydrochloric acid (5N in ether, 25 ml, 125 mmol) in dichloromethane (10 ml) was stirred for 20 hours at 25° C. The solvent was evaporated, the residue was triturated with sat. sodium hydrogencarbonate solution, the solid was filtered off, washed with water several times and dried affording 2-pyrrolidin-1-yl-[1,2,4]triazolo[1,5-a]pyridin-7-ylamine (194 mg, 85.2%) as a light yellow solid. mp: 221-225° C., MS: m/z=204.4 (M+H⁺)

d) 1-Methyl-5-(2-pyrrolidin-1-yl-[1,2,4]triazolo[1,5-a]pyridin-7-ylcarbamoyl)-1H-pyrazole-4-carboxylic acid ethyl ester

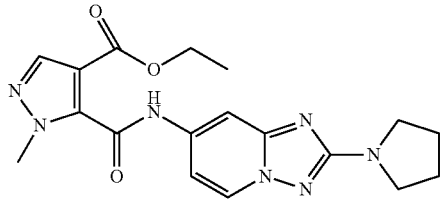 [SMILES: CCOC(=O)c1cnn(C)c1C(=O)Nc1ccn2nc(N3CCCC3)nc2c1]

A mixture of 2-(pyrrolidin-1-yl)-[1,2,4]triazolo[1,5-a]pyridin-7-amine (197 mg, 969 µmol), 4-(ethoxycarbonyl)-1-methyl-1H-pyrazole-5-carboxylic acid (231 mg, 1.16 mmol), propylphosphonic anhydride (50% in ethyl acetate, 1.43 ml, 2.42 mmol) and N,N-diisopropylethylamine (494 µl, 2.91 mmol) in tetrahydrofuran (10 ml) was refluxed for 18 hours. The solvent was evaporated, the residue was triturated with sodium hydrogencarbonate solution. The precipitated solid was filtered off, washed with water and dried affording 1-methyl-5-(2-pyrrolidin-1-yl-[1,2,4]triazolo[1,5-a]pyridin-7-ylcarbamoyl)-1H-pyrazole-4-carboxylic acid ethyl ester (327 mg, 88.0%) as a light brown solid. mp: 233-234° C., MS: m/z=384.5 (M+H⁺).

e) 1-Methyl-5-(2-pyrrolidin-1-yl-[1,2,4]triazolo[1,5-a]pyridin-7-ylcarbamoyl)-1H-pyrazole-4-carboxylic acid

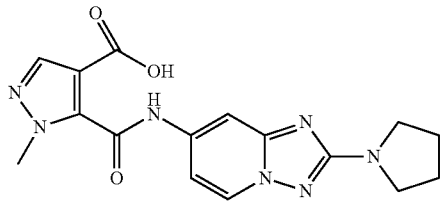 [SMILES: Cn1ncc(C(=O)O)c1C(=O)Nc1ccn2nc(N3CCCC3)nc2c1]

A mixture of ethyl 1-methyl-5-(2-(pyrrolidin-1-yl)-[1,2,4]triazolo[1,5-a]pyridin-7-ylcarbamoyl)-1H-pyrazole-4-carboxylate (322 mg, 840 µmol) and lithium hydroxide hydrate (141 mg, 3.36 mmol) in methanol (20 ml) and water (5 ml) was stirred for 2.5 days at 25° C. The solvent was evaporated, the residue was acidified with hydrochloric acid 37% to pH=0, the precipitated solid was filtered off, washed with water and dried affording 1-methyl-5-(2-pyrrolidin-1-yl-[1,2,4]triazolo[1,5-a]pyridin-7-ylcarbamoyl)-1H-pyrazole-4-carboxylic acid (316 mg, 106%) as an off-white solid. mp: >250° C., MS: m/z=356.4 (M+H⁺)

f) 4-(Azetidine-1-carbonyl)-2-methyl-2H-pyrazole-3-carboxylic acid (2-pyrrolidin-1-yl-[1,2,4]triazolo[1,5-a]pyridin-7-yl)-amide

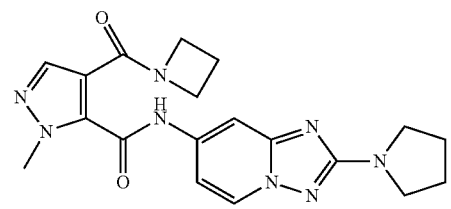 [SMILES: Cn1ncc(C(=O)N2CCC2)c1C(=O)Nc1ccn2nc(N3CCCC3)nc2c1]

A mixture of 1-methyl-5-(2-(pyrrolidin-1-yl)-[1,2,4]triazolo[1,5-a]pyridin-7-ylcarbamoyl)-1H-pyrazole-4-carboxylic acid (150 mg, 422 µmol), azetidine (85.4 µl, 1.27 mmol), propylphosphonic anhydride (50% in ethyl acetate, 622 µl, 1.06 mmol) and N,N-diisopropylethylamine (287 µl, 1.69 mmol) in tetrahydrofuran (6 ml) was stirred for 18 hours at 70°. The solvent was evaporated, the residue was triturated with sodium hydrogencarbonate solution. The precipitated solid was filtered off, washed with water and dried affording 4-(azetidine-1-carbonyl)-2-methyl-2H-pyrazole-3-carboxylic acid (2-pyrrolidin-1-yl-[1,2,4]triazolo[1,5-a]pyridin-7-yl)-amide (136 mg, 81.7%) as a light brown solid. mp: >250° C., MS: m/z=395.4 (M+H⁺).

Example 61

2-Methyl-4-(morpholine-4-carbonyl)-2H-pyrazole-3-carboxylic acid (2-pyrrolidin-1-yl-[1,2,4]triazolo[1,5-a]pyridin-7-yl)-amide

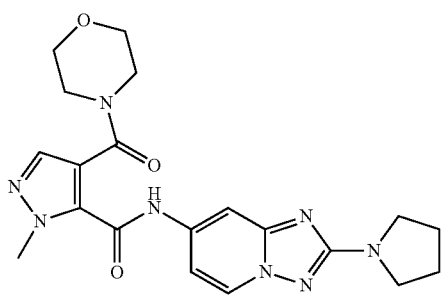 [SMILES: Cn1ncc(C(=O)N2CCOCC2)c1C(=O)Nc1ccn2nc(N3CCCC3)nc2c1]

A mixture of 1-methyl-5-(2-(pyrrolidin-1-yl)-[1,2,4]triazolo[1,5-a]pyridin-7-ylcarbamoyl)-1H-pyrazole-4-carboxylic acid (150 mg, 422 µmol), morpholine (368 µl, 4.22 mmol), propylphosphonic anhydride (50% in ethyl acetate, 622 µl, 1.06 mmol) and N,N-diisopropylethylamine (215 µl, 1.27 mmol) in tetrahydrofuran (6 ml) was stirred for 18 hours at 70° C. The solvent was evaporated, the residue was triturated with sodium hydrogencarbonate solution. The mixture was extracted with ethyl acetate, washed with water. The organic layer was separated, dried over magnesium sulfate, filtered and evaporated affording 2-methyl-4-(morpholine-4-carbonyl)-2H-pyrazole-3-carboxylic acid (2-pyrrolidin-1-yl-[1,2, 4]triazolo[1,5-a]pyridin-7-yl)-amide (109 mg, 60.8%) as a light yellow solid. mp: 194-197° C., MS: m/z=425.3 (M+H$^+$).

Example 62

7-{[4-(Azetidine-1-carbonyl)-2-methyl-2H-pyrazole-3-carbonyl]-amino}-[1,2,4]triazolo[1,5-a]pyridine-2-carboxylic acid dimethylamide

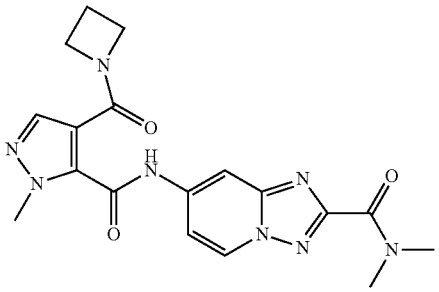 [SMILES: CN(C)C(=O)c1nc2cc(NC(=O)c3c(C(=O)N4CCC4)cnn3C)ccn2n1]

A mixture of ethyl 7-(4-(azetidine-1-carbonyl)-1-methyl-1H-pyrazole-5-carboxamido)-[1,2,4]triazolo[1,5-a]pyridine-2-carboxylate (example 33, step d) (658 mg, 1.66 mmol) and lithium hydroxide hydrate (139 mg, 3.31 mmol) in methanol (20 ml) and water (5 ml) and tetrahydrofuran (10 ml) was stirred for 6 hours at 60° C. (soluble when heated). The mixture was neutralized using hydrochloric acid 2N (1.655 ml, 3.31 mmol) and the mixture was evaporated affording 7-{[4-(azetidine-1-carbonyl)-2-methyl-2H-pyrazole-3-carbonyl]-amino}-[1,2,4]triazolo[1,5-a]pyridine-2-carboxylic acid (776 mg, 77.4%) as a light brown solid which was used in the following reactions. A mixture of 7-(4-(azetidine-1-carbonyl)-1-methyl-1H-pyrazole-5-carboxamido)-[1,2,4]triazolo[1,5-a]pyridine-2-carboxylic acid (120 mg, 244 µmol), dimethylamine hydrochloride (99.4 mg, 1.22 mmol), propylphosphonic anhydride (50% in ethyl acetate, 359 µl, 609 µmol) and diisopropylethylamine (298 µl, 1.71 mmol) in tetrahydrofuran (7 ml) was stirred for 20 hours at 25° C. The solvent was evaporated, the residue was triturated with sodium bicarbonate solution, the precipitated solid was filtered off, washed with water and dried. The material was applied on silicagel and purified by flash chromatography over a 5 g silicagel column using dichloromethane/methanol 5% as eluent affording 7-{[4-(azetidine-1-carbonyl)-2-methyl-2H-pyrazole-3-carbonyl]-amino}-[1,2,4]triazolo[1,5-a]pyridine-2-carboxylic acid dimethylamide (39 mg, 40.4%) as an off-white foam. MS: m/z=397.1 (M+H$^+$)

Example 63

7-{[4-(Azetidine-1-carbonyl)-2-methyl-2H-pyrazole-3-carbonyl]-amino}-[1,2,4]triazolo[1,5-a]pyridine-2-carboxylic acid ethylamide

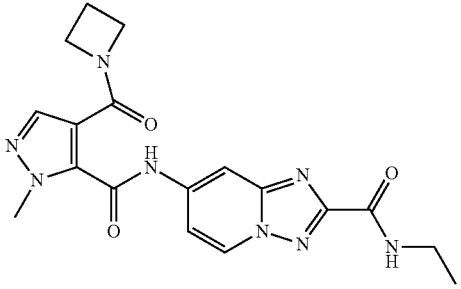 [SMILES: CCNC(=O)c1nc2cc(NC(=O)c3c(C(=O)N4CCC4)cnn3C)ccn2n1]

The product was prepared in the same manner as described in example 62 using 7-(4-(azetidine-1-carbonyl)-1-methyl-1H-pyrazole-5-carboxamido)-[1,2,4]triazolo[1,5-a]pyridine-2-carboxylic acid (130 mg, 264 µmol) and ethanamine hydrochloride (215 mg, 2.64 mmol) as starting materials. The reactions affords 7-{[4-(azetidine-1-carbonyl)-2-methyl-2H-pyrazole-3-carbonyl]-amino}-[1,2,4]triazolo[1,5-a]pyridine-2-carboxylic acid ethylamide (38 mg, 36.3%) as a white solid. mp: 217-229° C., MS: m/z=397.1 (M+H$^+$)

Example 64

7-(4-(Azetidine-1-carbonyl)-1-methyl-1H-pyrazole-5-carboxamido)-N-(2-methoxyethyl)-[1,2,4]triazolo[1,5-a]pyridine-2-carboxamide

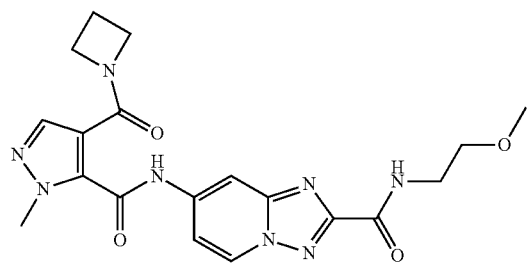 [SMILES: COCCNC(=O)c1nc2cc(NC(=O)c3c(C(=O)N4CCC4)cnn3C)ccn2n1]

The product was prepared in the same manner as described in example 62 using 7-(4-(azetidine-1-carbonyl)-1-methyl-1H-pyrazole-5-carboxamido)-[1,2,4]triazolo[1,5-a]pyridine-2-carboxylic acid (140 mg, 0.379 mmole) and 2-methoxyethanamine (163 µl, 1.9 mmole) as starting materials. The reactions affords 7-(4-(azetidine-1-carbonyl)-1-methyl-1H-pyrazole-5-carboxamido)-N-(2-methoxyethyl)-[1,2,4]triazolo[1,5-a]pyridine-2-carboxamide (32 mg, 19.8%) as a white solid. mp: 159-161° C., MS: m/z=427.3 (M+H$^+$).

Example 65

4-(Azetidine-1-carbonyl)-2-methyl-2H-pyrazole-3-carboxylic acid (2-bromo-[1,2,4]triazolo[1,5-a]pyridin-7-yl)-amide

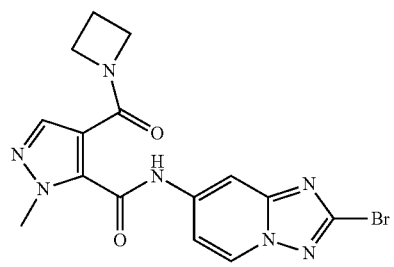 [SMILES: Cn1ncc(C(=O)N2CCC2)c1C(=O)Nc1ccn2nc(Br)nc2c1]

a) (2-Bromo-[1,2,4]triazolo[1,5-a]pyridin-7-yl)-carbamic acid tert-butyl ester

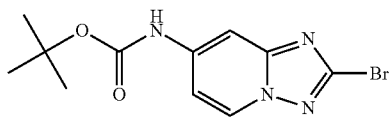 [SMILES: CC(C)(C)OC(=O)Nc1ccn2nc(Br)nc2c1]

To an argon purged solution of 2,7-dibromo-[1,2,4]triazolo[1,5-a]pyridine (6.00 g, 21.7 mmol) in dioxane (222 ml) were added tert-butyl carbamate (3.05 g, 26.0 mmol), cesium carbonate (9.88 g, 30.3 mmol), tris(dibenzylideneacetone) dipalladium(0) (397 mg, 433 mmol) and 4,5-bis(diphenylphosphino)-9,9-dimethylxanthene (501 mg, 867 µmol). The resulting mixture was heated to 100° C. and stirred for 18 hours under argon atmosphere. The material was applied on silicagel and purified by flash chromatography over a 20 g silicagel column using heptane/ethyl acetate 10-70% as eluent affording (2-bromo-[1,2,4]triazolo[1,5-a]pyridin-7-yl)-carbamic acid tert-butyl ester (5.19 g, 76.5%) as a light yellow solid. MS: m/z=313.0 (M+H$^+$).

b) 2-Bromo-[1,2,4]triazolo[1,5-a]pyridin-7-ylamine

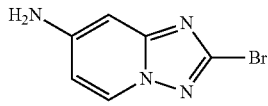

A suspension of tert-butyl 2-bromo-[1,2,4]triazolo[1,5-a]pyridin-7-ylcarbamate (5.19 g, 16.6 mmol) in dichloromethane (150 ml) and hydrochloric acid (5N in ether, 150 ml, 750 mmol) was stirred for 18 hours at 25° C. The solvents were evaporated, the residue was suspended in water (200 ml) and adjusted to pH=14 using sodium hydroxide 32%. The precipitated solid was filtered off, washed with water 4 times and dried in vacuo affording 2-bromo-[1,2,4]triazolo[1,5-a]pyridin-7-ylamine (2.39 g, 67.7&) as a light yellow solid. MS: m/z=213.0/215.1 (M+H$^+$).

c) 5-(2-Bromo-[1,2,4]triazolo[1,5-a]pyridin-7-ylcarbamoyl)-1-methyl-1H-pyrazole-4-carboxylic acid ethyl ester

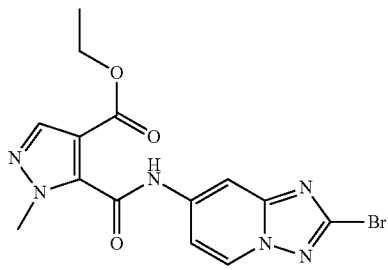 [SMILES: CCOC(=O)c1cnn(C)c1C(=O)Nc1ccn2nc(Br)nc2c1]

A mixture of 2-bromo-[1,2,4]triazolo[1,5-a]pyridin-7-amine (2.39 g, 11.2 mmol), 4-(ethoxycarbonyl)-1-methyl-1H-pyrazole-5-carboxylic acid (2.22 g, 11.2 mmol), propylphosphonic anhydride (50% in ethyl acetate, 16.5 ml, 28.0 mmol) and N,N-diisopropylethylamine (5.72 ml, 33.7 mmol) in tetrahydrofuran (80 ml) was refluxed for 18 hours under argon atmosphere. The solvent was evaporated and the resulting yellowish oil was triturated with sat. sodium hydrogencarbonate solution. The precipitated solid was filtered off, washed with water 4 times and dried in vacuo affording 5-(2-bromo-[1,2,4]triazolo[1,5-a]pyridin-7-ylcarbamoyl)-1-methyl-1H-pyrazole-4-carboxylic acid ethyl ester (3.64 g, 82.5%) as a light yellow solid. mp: 177-180° C., MS: m/z=393.0/395.0 (M+H$^+$)

d) 5-(2-Bromo-[1,2,4]triazolo[1,5-a]pyridin-7-ylcarbamoyl)-1-methyl-1H-pyrazole-4-carboxylic acid

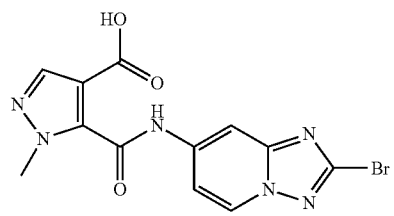 [SMILES: Cn1ncc(C(=O)O)c1C(=O)Nc1ccn2nc(Br)nc2c1]

A mixture of ethyl 5-(2-bromo-[1,2,4]triazolo[1,5-a]pyridin-7-ylcarbamoyl)-1-methyl-1H-pyrazole-4-carboxylate (1.2 g, 3.05 mmol) and lithium hydroxide hydrate (512 mg, 12.2 mmol) in methanol (40 ml) and water (10 ml) was stirred for 4 hours at 50° C. The solvent was evaporated, the residue was dissolved with water and acidified to pH=0 using hydrochloric acid 37%. The precipitated solid was filtered off and washed with water and dried in vacuo affording 5-(2-bromo-[1,2,4]triazolo[1,5-a]pyridin-7-ylcarbamoyl)-1-methyl-1H-pyrazole-4-carboxylic acid (929 mg, 83.4%) as a light brown solid. mp: >250° C., MS: m/z=362.7/364.8 (M+H$^+$)

e) 4-(Azetidine-1-carbonyl)-2-methyl-2H-pyrazole-3-carboxylic acid (2-bromo-[1,2,4]triazolo[1,5-a]pyridin-7-yl)-amide

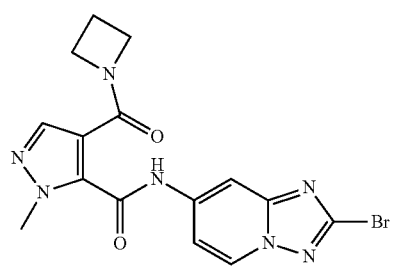 [SMILES: Cn1ncc(C(=O)N2CCC2)c1C(=O)Nc1ccn2nc(Br)nc2c1]

A mixture of 5-(2-bromo-[1,2,4]triazolo[1,5-a]pyridin-7-ylcarbamoyl)-1-methyl-1H-pyrazole-4-carboxylic acid (929 mg, 2.54 mmol), azetidine (206 µl, 3.05 mmol), propylphosphonic anhydride (50% in ethyl acetate, 3.75 ml, 6.36 mmol) and N,N-diisopropylethylamine (1.3 ml, 7.63 mmol) in tetrahydrofuran (20 ml) was stirred for 18 hours at 25° C. The solvent was evaporated, the residue was triturated with sat. sodium hydrogencarbonate solution. The solid was filtered off, washed with water and dried in vacuo affording 4-(azetidine-1-carbonyl)-2-methyl-2H-pyrazole-3-carboxylic acid (2-bromo-[1,2,4]triazolo[1,5-a]pyridin-7-yl)-amide (910 mg, 88.5%) as a light yellow solid. mp: >250° C., MS: m/z=402.2/404.0 (M−H$^+$)

Example 66

4-(Azetidine-1-carbonyl)-2-methyl-2H-pyrazole-3-carboxylic acid (2-pyridin-4-yl-[1,2,4]triazolo[1,5-a]pyridin-7-yl)-amide

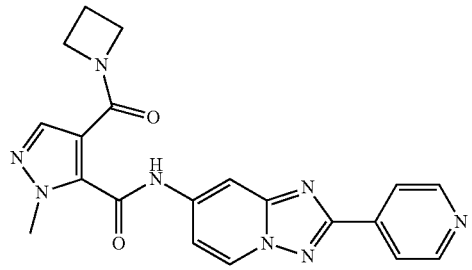 [SMILES: Cn1ncc(C(=O)N2CCC2)c1C(=O)Nc1ccn2nc(-c3ccncc3)nc2c1]

Through a mixture of 4-(azetidine-1-carbonyl)-N-(2-bromo-[1,2,4]triazolo[1,5-a]pyridin-7-yl)-1-methyl-1H-pyrazole-5-carboxamide (150 mg, 371 μmol) and pyridin-4-ylboronic acid (68.4 mg, 557 μmol) in dioxane (4 ml) and sat. sodium carbonate solution (1 ml) was bubbled nitrogen for 10 minutes, then 1,1'-bis(diphenylphosphino)ferrocene palladium (II) chloride/dppf (15.2 mg, 18.6 μmol) was added and the resulting mixture was refluxed for 18 hours under nitrogen atmosphere. The solvent was evaporated and the residue was diluted with ethyl acetate and washed with water, the organic layer was separated, dried over magnesium sulfate, filtrated and evaporated. The crude material was applied on silicagel and purified by flash chromatography over a 20 g silicagel column using ethyl acetate/methanol 2-5% as eluent affording 4-(azetidine-1-carbonyl)-2-methyl-2H-pyrazole-3-carboxylic acid (2-pyridin-4-yl-[1,2,4]triazolo[1,5-a]pyridin-7-yl)-amide (28 mg, 18.8%) as a white solid. mp: >250° C., MS: m/z=403.0 (M+H$^+$)

Example 67

4-(Azetidine-1-carbonyl)-2-methyl-2H-pyrazole-3-carboxylic acid [2-(2-methyl-pyridin-4-yl)-[1,2,4]triazolo[1,5-a]pyridin-7-yl]-amide

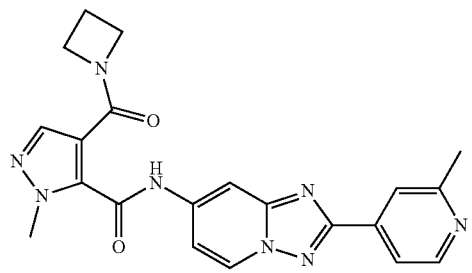 [SMILES: Cc1cc(-c2nc3cc(NC(=O)c4c(C(=O)N5CCC5)cnn4C)ccn3n2)ccn1]

The product was prepared in the same manner as described in example 66 using 4-(azetidine-1-carbonyl)-N-(2-bromo-[1,2,4]triazolo[1,5-a]pyridin-7-yl)-1-methyl-1H-pyrazole-5-carboxamide (150 mg, 371 μmol) and 2-methylpyridin-4-ylboronic acid (76.2 mg, 557 μmol) as starting materials. The crude material was applied on silicagel and purified by flash chromatography over a 20 g silicagel column using ethyl acetate/methanol 10% as eluent affording 4-(azetidine-1-carbonyl)-2-methyl-2H-pyrazole-3-carboxylic acid [2-(2-methyl-pyridin-4-yl)-[1,2,4]triazolo[1,5-a]pyridin-7-yl]-amide (34 mg, 22.0%) as an off-white solid. mp: 210-211° C., MS: m/z=417.4 (M+H$^+$)

Example 68

4-(Azetidine-1-carbonyl)-2-methyl-2H-pyrazole-3-carboxylic acid [2-(5-methyl-pyridin-3-yl)-[1,2,4]triazolo[1,5-a]pyridin-7-yl]-amide

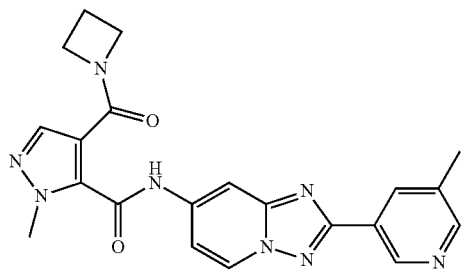 [SMILES: Cc1cncc(-c2nc3cc(NC(=O)c4c(C(=O)N5CCC5)cnn4C)ccn3n2)c1]

The product was prepared in the same manner as described in example 66 using 4-(azetidine-1-carbonyl)-N-(2-bromo-[1,2,4]triazolo[1,5-a]pyridin-7-yl)-1-methyl-1H-pyrazole-5-carboxamide (150 mg, 371 μmol) and 5-methylpyridin-3-ylboronic acid (76.2 mg, 557 μmol) as starting materials. The crude material was applied on silicagel and purified by flash chromatography over a 50 g NH2-silicagel column using heptane/ethyl acetate 20-100% as eluent affording 4-(azetidine-1-carbonyl)-2-methyl-2H-pyrazole-3-carboxylic acid [2-(5-methyl-pyridin-3-yl)-[1,2,4]triazolo[1,5-a]pyridin-7-yl]-amide (90 mg, 19.4%) as a light brown solid. mp: 262-264° C., MS: m/z=417.3 (M+H$^+$)

Example 69

2-Methyl-4-(morpholine-4-carbonyl)-2H-pyrazole-3-carboxylic acid [2-(2-methoxy-phenyl)-[1,2,4]triazolo[1,5-a]pyridin-7-yl]-amide

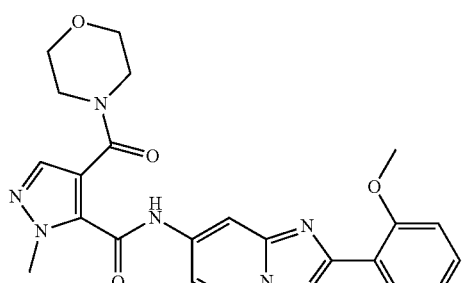

a) 2-Methyl-4-(morpholine-4-carbonyl)-2H-pyrazole-3-carboxylic acid (2-bromo-[1,2,4]triazolo[1,5-a]pyridin-7-yl)-amide

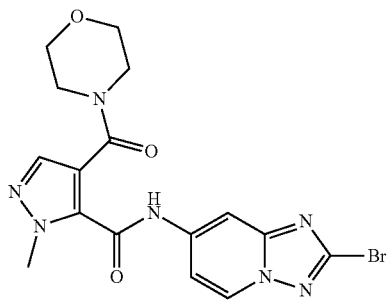 [SMILES: Cn1ncc(C(=O)N2CCOCC2)c1C(=O)Nc1ccn2nc(Br)nc2c1]

A mixture of 5-(2-bromo-[1,2,4]triazolo[1,5-a]pyridin-7-ylcarbamoyl)-1-methyl-1H-pyrazole-4-carboxylic acid (238 mg, 652 µmol), morpholine (568 µl, 6.52 mmol), propylphosphonic anhydride (50% in ethyl acetate, 960 µl, 1.63 mmol) and N,N-diisopropylethylamine (333 µl, 1.96 mmol) in tetrahydrofuran (20 ml) was refluxed for 18 hours. The solvent was evaporated, the residue was triturated with sodium hydrogencarbonate solution. The precipitated solid was filtered off, washed with water and dried in vacuo affording 2-methyl-4-(morpholine-4-carbonyl)-2H-pyrazole-3-carboxylic acid (2-bromo-[1,2,4]triazolo[1,5-a]pyridin-7-yl)-amide (220 mg, 77.7%) as a light yellow solid. mp: 198-214° C., MS: m/z=434.2/436.1 (M+H$^+$)

b) 2-Methyl-4-(morpholine-4-carbonyl)-2H-pyrazole-3-carboxylic acid [2-(2-methoxy-phenyl)-[1,2,4]triazolo[1,5-a]pyridin-7-yl]-amide

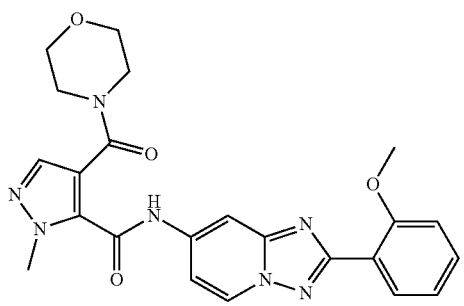 [SMILES: COc1ccccc1-c1nc2cc(NC(=O)c3c(C(=O)N4CCOCC4)cnn3C)ccn2n1]

The product was prepared in the same manner as described in example 66 using N-(2-bromo-[1,2,4]triazolo[1,5-a]pyridin-7-yl)-1-methyl-4-(morpholine-4-carbonyl)-1H-pyrazole-5-carboxamide (200 mg, 461 µmol) and 2-methoxyphenylboronic acid (140 mg, 921 µmol) as starting materials. The crude material was applied on silicagel and purified by flash chromatography over a 20 g silicagel column using ethyl acetate/methanol 10% as eluent affording 2-methyl-4-(morpholine-4-carbonyl)-2H-pyrazole-3-carboxylic acid [2-(2methoxy-phenyl)-[1,2,4]triazolo[1,5-a]pyridin-7-yl]-amide (109 mg, 51.3%) as a light brown foam. MS: m/z=462.5 (M+H$^+$). -

Example 70

4-(Azetidine-1-carbonyl)-2-methyl-2H-pyrazole-3-carboxylic acid {2-[(2-fluoro-ethyl)-methyl-amino]-[1,2,4]triazolo[1,5-a]pyridin-7-yl}-amide

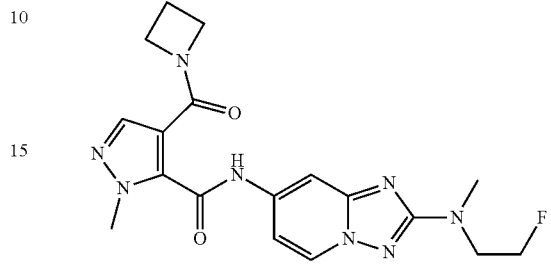

a) (7-Bromo-[1,2,4]triazolo[1,5-a]pyridin-2-yl)-(2-fluoro-ethyl)-methyl-amine

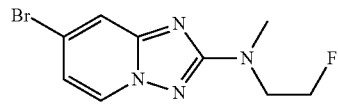

To the solution of 2,7-dibromo-[1,2,4]triazolo[1,5-a]pyridine (5 g, 18.05 mmol) and (2-fluoro-ethyl)-methyl-amine hydrochloride (20 g, 180.5 mmol) in ethanol (30 ml) was added di-isopropylethylamine (47 ml, 270.75 mmol) and the reaction mixture was heated at 130° C. in a sealed tube for 84 hours. The reaction mixture was concentrated under reduced pressure, the resulting residue was diluted with dichloromethane (100 ml). The organic layer was washed with water (2×75 ml), dried over anhydrous sodium sulfate, filtered, and concentrated under reduced pressure. The crude material was purified by column chromatography over silicagel using 0.5% methanol/dichloromethane as eluent affording (7-bromo-[1,2,4]triazolo[1,5-a]pyridin-2-yl)-(2-fluoro-ethyl)-methyl-amine (1.7 g, 34.5%) as an off white solid. MS: m/z=275.2 (M+H$^+$).

b) {2-[(2-Fluoro-ethyl)-methyl-amino]-[1,2,4]triazolo[1,5-a]pyridin-7-yl}-carbamic acid tert-butyl ester

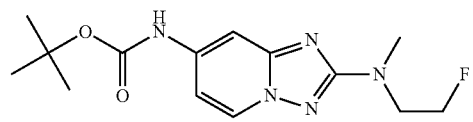 [SMILES: CN(CCF)c1nc2cc(NC(=O)OC(C)(C)C)ccn2n1]

The product was prepared in the same manner as described in example 65a) using 7-bromo-[1,2,4]triazolo[1,5-a]pyridin-2-yl)-(2-fluoro-ethyl)-methyl-amine (0.710 g, 2.6 mmol) as starting material. Volatiles were removed in vacuo and the crude residue was directly purified by column chromatography over silicagel using 2% methanol/dichloromethane as eluent affording {2-[(2-fluoro-ethyl)-methyl-amino]-[1,2,4]triazolo[1,5-a]pyridin-7-yl}-carbamic acid tert-butyl ester (710 mg, 94.5%) as a light yellow solid. MS: m/z=310.4 (M+H⁺).

c) N2-(2-Fluoro-ethyl)-N2-methyl-[1,2,4]triazolo[1,5-a]pyridine-2,7-diamine hydrochloride

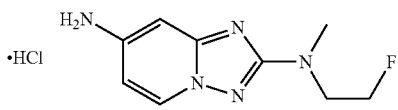

A mixture of {2-[(2-fluoro-ethyl)-methyl-amino]-[1,2,4]triazolo[1,5-a]pyridin-7-yl}-carbamic acid tert-butyl ester (1.7 g, 5.5 mmol) and hydrochloric acid in dioxane (4N, 39.2 ml, 156.7 mmol) was stirred at 25° C. for 16 h. Volatiles were removed in vacuo to afford N2-(2-Fluoro-ethyl)-N2-methyl-[1,2,4]triazolo[1,5-a]pyridine-2,7-diamine hydrochloride as a light yellow solid (1.3 g, 96.3%). MS: m/z=210.2 (M+H⁺).

d) 5-{2-[(2-Fluoro-ethyl)-methyl-amino]-[1,2,4]triazolo[1,5-a]pyridin-7-ylcarbamoyl}-1-methyl-1H-pyrazole-4-carboxylic acid ethyl ester

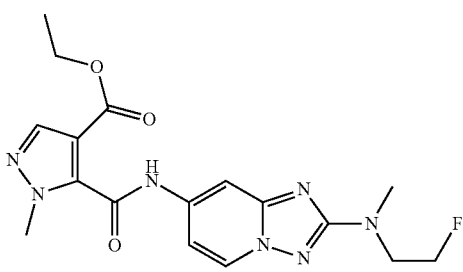 [SMILES: CCOC(=O)c1cnn(C)c1C(=O)Nc1ccn2nc(N(C)CCF)nc2c1]

The product was prepared in the same manner as described in example 65c) using N2-(2-fluoro-ethyl)-N2-methyl-[1,2,4]triazolo[1,5-a]pyridine-2,7-diamine hydrochloride (1.3 g, 5.3 mmol) and 2-methyl-2H-pyrazole-3,4-dicarboxylic acid-4-ethyl ester (1.08 g, 5.45 mmol) as starting materials. The solvent was evaporated and the resulting yellowish oil was triturated with sat. sodium hydrogencarbonate solution. The precipitated solid was filtered off, washed with water 4 times and dried in vacuo affording 5-{2-[(2-fluoro-ethyl)-methyl-amino]-[1,2,4]triazolo[1,5-a]pyridin-7-ylcarbamoyl}-1-methyl-1H-pyrazole-4-carboxylic acid ethyl ester (1.57 g, 76.2%) as a light yellow solid. MS: m/z=390.5 (M+H⁺).

e) 5-{2-[(2-Fluoro-ethyl)-methyl-amino]-[1,2,4]triazolo[1,5-a]pyridin-7-ylcarbamoyl}-1-methyl-1H-pyrazole-4-carboxylic acid

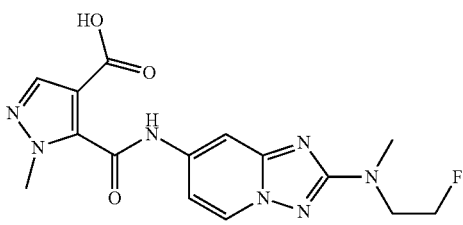 [SMILES: CN(CCF)c1nc2cc(NC(=O)c3c(C(=O)O)cnn3C)ccn2n1]

A solution of 5-{2-[(2-fluoro-ethyl)-methyl-amino]-[1,2,4]triazolo[1,5-a]pyridin-7-ylcarbamoyl}-1-methyl-1H-pyrazole-4-carboxylic acid ethyl ester (2.5 g, 6.42 mmol) and lithium hydroxide monohydrate (534 mg, 12.84 mmol) in a mixture of methanol (40 ml) and water (10 ml) was stirred for 2.5 hours at 50° C. The solvent was evaporated and the residue was dissolved in a small amount of water. Then it was acidified to pH~3 using aqueous 2N HCl solution. The resultant solid mass was filtered, washed sequentially with water (10 ml), hexane (2×10 ml), dichloromethane (2×15 ml) and finally with methanol (2×15 ml), and dried under vacuum affording 5-{2-[(2-Fluoro-ethyl)-methyl-amino]-[1,2,4]triazolo[1,5-a]pyridin-7-ylcarbamoyl}-1-methyl-1H-pyrazole-4-carboxylic acid (2.09 g, 88.8%) as an off-white solid. MS: m/z=362.4 (M+H⁺).

f) 4-(Azetidine-1-carbonyl)-2-methyl-2H-pyrazole-3-carboxylic acid {2-[(2-fluoro-ethyl)-methyl-amino]-[1,2,4]triazolo[1,5-a]pyridin-7-yl}-amide

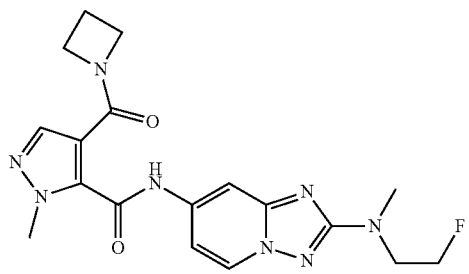 [SMILES: CN(CCF)c1nc2cc(NC(=O)c3c(C(=O)N4CCC4)cnn3C)ccn2n1]

A mixture of 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol), azetidine (74.6 µl, 1.11 mmol) and propylphosphonic anhydride (50% in ethyl acetate, 408 µl, 692 µmol) in tetrahydrofuran (5 ml) was stirred for 18 hours at 25° C. The solvent was evaporated, the residue was triturated with sodium hydrogencarbonate solution. The precipitated solid was filtered off, washed with water and dried in vacuo affording 4-(azetidine-1-carbonyl)-2-methyl-2H-pyrazole-3-carboxylic acid {2-[(2-fluoroethyl)-methyl-amino]-[1,2,4]triazolo[1,5-a]pyridin-7-yl}-amide (93 mg, 83.9%) as a white solid. mp: 236-237° C., MS: m/z=401.1 (M+H⁺)

Example 71

2-Methyl-4-(morpholine-4-carbonyl)-2H-pyrazole-3-carboxylic acid {2-[(2-fluoro-ethyl)-methyl-amino]-[1,2,4]triazolo[1,5-a]pyridin-7-yl}-amide

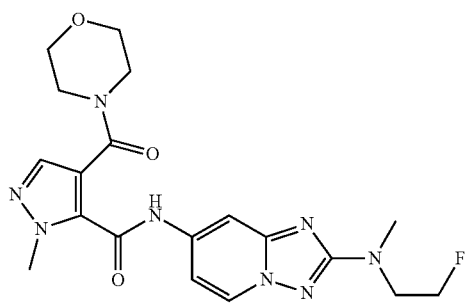 [SMILES: CN(CCF)c1nc2cc(NC(=O)c3c(C(=O)N4CCOCC4)cnn3C)ccn2n1]

A mixture of 5-(2-(2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol), morpholine (121 µl, 1.38 mmol) and propylphosphonic anhydride (50% in ethyl acetate, 408 µl, 692 µmol) in tetrahydrofuran (5.00 ml) was refluxed for 18 hours. The solvent was evaporated, the residue was triturated with sodium hydrogencarbonate solution at 5° C. The precipitated solid was filtered off, washed with water and dried in vacuo affording 2-methyl-4-(morpholine-4-carbonyl)-2H-pyrazole-3-carboxylic acid {2-[(2-fluoro-ethyl)-methyl-amino]-[1,2,4]triazolo[1,5-a]pyridin-7-yl}-amide (100 mg, 83.9%) as a white solid. mp: 144-145° C., MS: m/z=431.0 (M+H$^+$)

Example 72

2-Methyl-2H-pyrazole-3,4-dicarboxylic acid 4-dimethylamide 3-({2-[(2-fluoro-ethyl)-methyl-amino]-[1,2,4]triazolo[1,5-a]pyridin-7-yl}-amide)

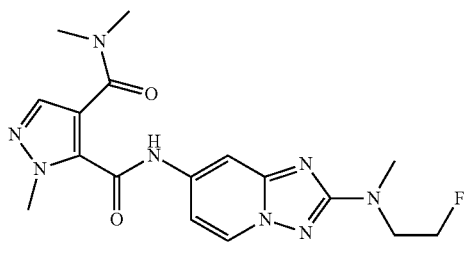 [SMILES: CN(C)C(=O)c1cnn(C)c1C(=O)Nc1ccn2nc(N(C)CCF)nc2c1]

A mixture of 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol), dimethylamine hydrochloride (113 mg, 1.38 mmol), N,N-diisopropylethylamine (377 µl, 2.21 mmol) and propylphosphonic anhydride (50% in ethyl acetate, 408 µl, 692 µmol) in tetrahydrofuran (5.00 ml) was stirred at 25° C. for 18 hours. The solvent was evaporated, the residue was triturated with sodium hydrogencarbonate solution. The precipitated solid was filtered off, washed with water and dried in vacuo affording 2-methyl-2H-pyrazole-3,4-dicarboxylic acid 4-dimethylamide 3-({2-[(2-fluoro-ethyl)-methyl-amino]-[1,2,4]triazolo[1,5-a]pyridin-7-yl}-amide) (96 mg, 89.3%) as a white solid. mp: 203-204° C., MS: m/z=389.1 (M+H$^+$)

Example 73

2-Methyl-2H-pyrazole-3,4-dicarboxylic acid 4-(ethyl-methyl-amide) 3-({2-[(2-fluoro-ethyl)-methyl-amino]-[1,2,4]triazolo[1,5-a]pyridin-7-yl}-amide)

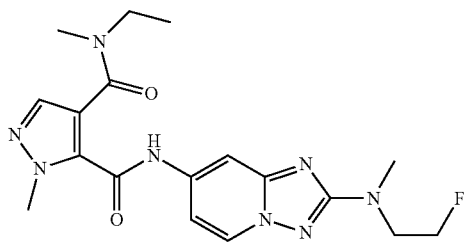 [SMILES: CCN(C)C(=O)c1cnn(C)c1C(=O)Nc1ccn2nc(N(C)CCF)nc2c1]

A mixture of 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol), N-methylethanamine (81.8 mg, 1.38 mmol), N,N-diisopropylethylamine (235 µl, 1.38 mmol) and propylphosphonic anhydride (50% in ethyl acetate, 408 µl, 692 µmol) in tetrahydrofuran (5.00 ml) was stirred at 25° C. for 18 hours. The solvent was evaporated, the residue was triturated with sodium hydrogencarbonate solution. The precipitated solid was filtered off, washed with water and dried in vacuo affording 2-methyl-2H-pyrazole-3,4-dicarboxylic acid 4-(ethyl-methyl-amide) 3-({2-[(2-fluoro-ethyl)-methyl-amino]-[1,2,4]triazolo[1,5-a]pyridin-7-yl}-amide) (90 mg, 80.8%) as a white solid. mp: 145-147° C., MS: m/z=403.3 (M+H$^+$)

Example 74

2-Methyl-2H-pyrazole-3,4-dicarboxylic acid 4-(cyclopropyl-methyl-amide)3-({2-[(2-fluoro-ethyl)-methyl-amino]-[1,2,4]triazolo[1,5-a]pyridin-7-yl}-amide)

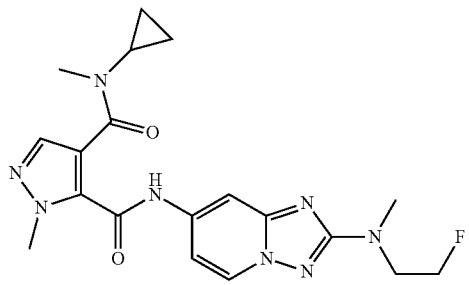 [SMILES: CN(CCF)c1nc2cc(NC(=O)c3c(C(=O)N(C)C4CC4)cnn3C)ccn2n1]

A mixture of 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol), N-methylcyclopropan-amine (19.7 mg, 277 µmol), N,N-diisopropylethylamine (235 µl, 1.38 mmol) and propylphosphonic anhydride (50% in ethyl acetate, 408 µl, 692 µmol) in tetrahydrofuran (5.00 ml) was stirred at 25° C. for 18 hours. The solvent was evaporated, the residue was triturated with sodium hydrogencarbonate solution at 0° C. The precipitated solid was filtered off, washed with water and dried in vacuo affording 2-methyl-2H-pyrazole-3,4-dicarboxylic acid 4-(cyclopropyl-methyl-amide) 3-({2-[(2-fluoroethyl)-methyl-amino]-[1,2,4]triazolo[1,5-a]pyridin-7-yl}-amide) (87 mg, 75.9%) as a white solid. mp: 148-1° C., MS: m/z=415.0 (M+H$^+$)

Example 75

4-(Azetidine-1-carbonyl)-2-methyl-2H-pyrazole-3-carboxylic acid [2-(3-methoxy-phenyl)-[1,2,4]triazolo[1,5-a]pyridin-7-yl]-amide

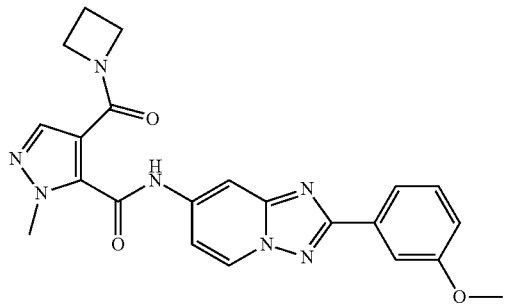 [SMILES: COc1cccc(-c2nc3cc(NC(=O)c4c(C(=O)N5CCC5)cnn4C)ccn3n2)c1]

a) 7-Bromo-2-(3-methoxy-phenyl)-[1,2,4]triazolo[1,5-a]pyridine

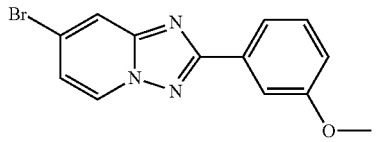 [SMILES: COc1cccc(-c2nc3cc(Br)ccn3n2)c1]

To a solution of 1,2-diamino-4-bromo-pyridinium-2,4,6-trimethyl-benzenesulfonate (Example 1, step a) (8 g, 20.7 mmol) in pyridine (50 ml) was added 3-methoxybenzoyl chloride (6 ml, 41.3 mmol). The reaction mixture was heated at 85° C. for 3 h. Volatiles were removed in vacuum, and the resultant residue was diluted with EtOAc (300 ml). The organic layer was washed successively with water (2×250 ml) and brine (100 ml), dried over anhydrous $Na_2SO_4$, filtered, and evaporated in vacuum. The crude material thus obtained was purified by column chromatography over silica gel (10-15% EtOAc/hexane) to afford 7-bromo-2-(3-methoxy-phenyl)-[1,2,4]triazolo[1,5-a]pyridine (8 g, quant) as white solid. LC-MS: m/z=303.8 $[M+H]^+$.

b) [2-(3-Methoxy-phenyl)-[1,2,4]triazolo[1,5-a]pyridin-7-yl]-carbamic acid tert-butyl ester

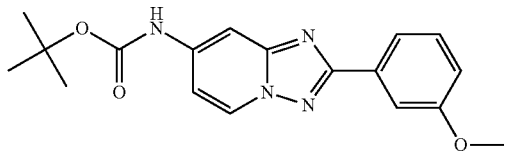 [SMILES: COc1cccc(-c2nc3cc(NC(=O)OC(C)(C)C)ccn3n2)c1]

A solution of 7-bromo-2-(3-methoxy-phenyl)-[1,2,4]triazolo[1,5-a]pyridine (5.0 g, 16.4 mmol), tert-butyl carbamate (2.88 g, 24.7 mmol) and cesium carbonate (10.6 g, 32.9 mmol) in dioxane (85 ml) was degassed well with argon for 20 min at 25° C. To this solution was then added tris(dibenzylideneacetone)dipalladium(0) (3.0 g, 3.28 mmol) and xantphos (3.8 g, 6.57 mmol), and the resulting mixture was degassed again with argon for another 20 min. The reaction mixture was heated at 100° C. under argon atmosphere for 16 h. The reaction mixture was diluted with EtOAc (500 ml). The organic layer was washed successively with water (2×250 ml) and brine (100 ml), dried over anhydrous $Na_2SO_4$, filtered, and evaporated in vacuum. The crude material thus obtained was purified by column chromatography over silica gel (20-40% EtOAc/hexane) to afford [2-(3-methoxy-phenyl)-[1,2,4]triazolo[1,5-a]pyridin-7-yl]-carbamic acid tert-butyl ester (2.8 g, 51%) as yellow solid. LC-MS: m/z=341 $[M+H]^+$.

c) 2-(3-Methoxy-phenyl)-[1,2,4]triazolo[1,5-a]pyridin-7-ylamine

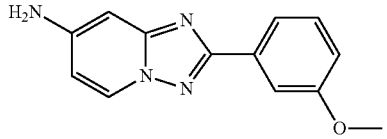 [SMILES: COc1cccc(-c2nc3cc(N)ccn3n2)c1]

To a solution of [2-(3-methoxy-phenyl)-[1,2,4]triazolo[1,5-a]pyridin-7-yl]-carbamic acid tert-butyl ester (5.5 g, 16.2 mmol) in DCM (100 ml) was added a solution of HCl in dioxane (4 N, 20 ml). The resultant reaction mixture was stirred at 25° C. for 16 h. Volatiles were removed in vacuum, and the resultant residue was dried under vacuum to give 2-(3-methoxy-phenyl)-[1,2,4]triazolo[1,5-a]pyridin-7-ylamine (5 g, quant) as light yellow solid. LC-MS: m/z=241.0 $[M+H]^+$.

d) 5-[2-(3-Methoxy-phenyl)-[1,2,4]triazolo[1,5-a]pyridin-7-ylcarbamoyl]-1-methyl-1H-pyrazole-4-carboxylic acid ethyl ester

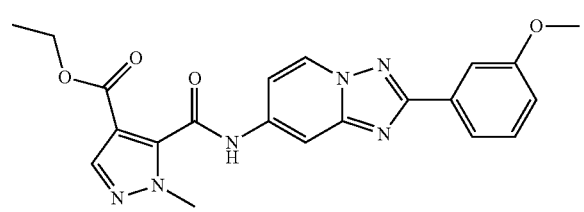 [SMILES: CCOC(=O)c1cnn(C)c1C(=O)Nc1ccn2nc(-c3cccc(OC)c3)nc2c1]

To a solution of 2-methyl-2H-pyrazole-3,4-dicarboxylic acid 4-ethyl ester (8.0 g, 40.4 mmol) in DMF (120 ml) were added HATU (34 g, 88.9 mmol), 2-(3-methoxy-phenyl)-[1,2,4]triazolo[1,5-a]pyridin-7-ylamine (10.6 g, 44.4 mmol) and DIPEA (30 ml, 161.1 mmol) at 0° C. The reaction mixture was stirred at 25° C. for 16 h. The reaction mixture was diluted with water. The resultant precipitated solid was filtered, washed with water, dried azeotropically with toluene followed by vacuum to yield 5-[2-(3-methoxy-phenyl)-[1,2,4]triazolo[1,5-a]pyridin-7-ylcarbamoyl]-1-methyl-1H-pyrazole-4-carboxylic acid ethyl ester as white solid (7.8 g, 56%). LC-MS: m/z=421.2 $[M+H]^+$.

e) 5-[2-(3-Methoxy-phenyl)-[1,2,4]triazolo[1,5-a]pyridin-7-ylcarbamoyl]-1-methyl-1H-pyrazole-4-carboxylic acid

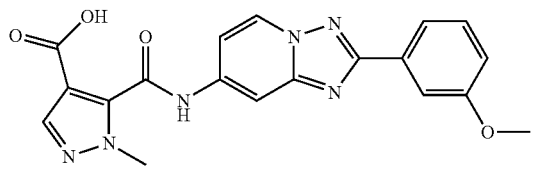 [SMILES: COc1cccc(-c2nc3cc(NC(=O)c4c(C(=O)O)cnn4C)ccn3n2)c1]

To a solution of 5-[2-(3-methoxy-phenyl)-[1,2,4]triazolo[1,5-a]pyridin-7-ylcarbamoyl]-1-methyl-1H-pyrazole-4-carboxylic acid ethyl ester (3.5 g, 8.33 mmol) in a mixture of THF (20 ml), MeOH (14 ml) and water (7 ml) was added LiOH×$H_2O$ (1.0 g, 25.0 mmol) at 0° C. The reaction mixture was stirred at 25° C. for 4 h. Solvents were removed in vacuum and the resultant crude material was diluted with water (150 ml). The aqueous layer was washed with ether (2×100 ml), cooled to 0° C., and slowly acidified (pH 5) with aqueous 1N HCl solution under stirring. The resultant precipitated solid was filtered and dried under vacuum to give 5-[2-(3-methoxy-phenyl)-[1,2,4]triazolo[1,5-a]pyridin-7-ylcarbamoyl]-1-methyl-1H-pyrazole-4-carboxylic acid as white solid (5.9 g; crude, quant). LC-MS: m/z=393.0 [M+H]⁺.

f) 4-(Azetidine-1-carbonyl)-2-methyl-2H-pyrazole-3-carboxylic acid [2-(3-methoxy-phenyl)-[1,2,4]triazolo[1,5-a]pyridin-7-yl]-amide

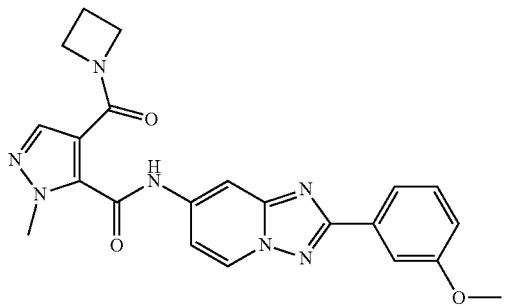 [SMILES: COc1cccc(-c2nc3cc(NC(=O)c4c(C(=O)N5CCC5)cnn4C)ccn3n2)c1]

To a solution of 5-[2-(3-methoxy-phenyl)-[1,2,4]triazolo[1,5-a]pyridin-7-ylcarbamoyl]-1-methyl-1H-pyrazole-4-carboxylic acid (4.0 g, 10.2 mmol) in DMF (50 ml) were added HATU (8.5 g, 22 mmol), azetidine hydrochloride (1.05 g, 93.5 mmol) and DIPEA (7.5 ml, 40 mmol) at 0° C. The resultant reaction mixture was stirred at 25° C. for 16 h. The mixture was diluted with water (100 ml) and stirred for 15 min. The resultant precipitated solid was filtered, washed thoroughly with water, and dried azeotropically with toluene followed by vacuum to yield 4-(azetidine-1-carbonyl)-2-methyl-2H-pyrazole-3-carboxylic acid [2-(3-methoxy-phenyl)-[1,2,4]triazolo[1,5-a]pyridin-7-yl]-amide as off-white solid (1.9 g, 44%). LC-MS: m/z=432.4 [M+H]⁺.

Example 76

2-Methyl-4-(morpholine-4-carbonyl)-2H-pyrazole-3-carboxylic acid [2-(3-methoxy-phenyl)-[1,2,4]triazolo[1,5-a]pyridin-7-yl]-amide

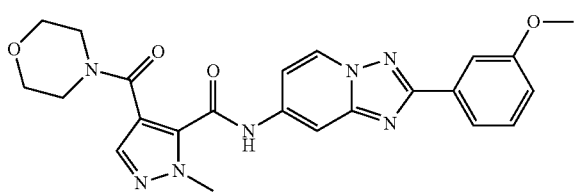 [SMILES: COc1cccc(-c2nc3cc(NC(=O)c4c(C(=O)N5CCOCC5)cnn4C)ccn3n2)c1]

This compound was prepared in the same manner as described in example 75 starting from 5-[2-(3-methoxy-phenyl)-[1,2,4]triazolo[1,5-a]pyridin-7-ylcarbamoyl]-1-methyl-1H-pyrazole-4-carboxylic acid (Example 75, step e) (1.0 g, 2.55 mmol) and morpholine (245 ul, 2.80 mmol). Off-white solid (937 mg, 80%). LC-MS: m/z=462.6 [M+H]⁺.

Example 77

2-Methyl-2H-pyrazole-3,4-dicarboxylic acid 4-[(2-methoxy-ethyl)-methyl-amide]3-{[2-(3-methoxy-phenyl)-[1,2,4]triazolo[1,5-a]pyridin-7-yl]-amide}

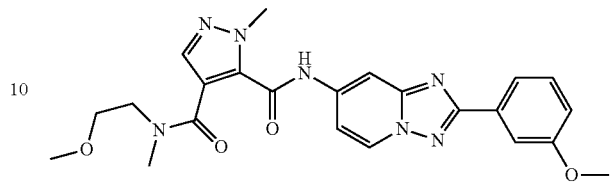

This compound was prepared in the same manner as described in example 75 starting from 5-[2-(3-methoxy-phenyl)-[1,2,4]triazolo[1,5-a]pyridin-7-ylcarbamoyl]-1-methyl-1H-pyrazole-4-carboxylic acid (Example 75, step e) (600 mg, 1.53 mmol) and (2-methoxy-ethyl)-methylamine (180 ul, 1.68 mmol). Brown solid (35 mg, 5%). LC-MS: m/z=464.2 [M+H]⁺.

Example 78

2-Methyl-2H-pyrazole-3,4-dicarboxylic acid 4-dimethylamide 3-{[2-(3-methoxy-phenyl)[1,2,4]triazolo[1,5-a]pyridin-7-yl]-amide}

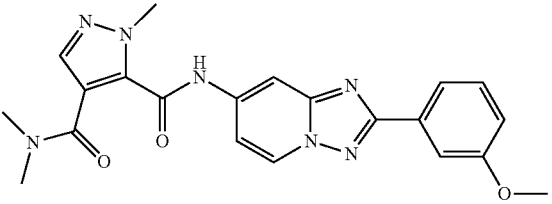

This compound was prepared in the same manner as described in example 75 starting from 5-[2-(3-methoxy-phenyl)-[1,2,4]triazolo[1,5-a]pyridin-7-ylcarbamoyl]-1-methyl-1H-pyrazole-4-carboxylic acid (example 75, step e) (600 mg, 1.53 mmol) and dimethylamine hydrochloride (137 mg, 1.68 mmol). White solid (125 mg, 19%). LC-MS: m/z=420.2 [M+H]⁺.

Example 79

2-Methyl-2H-pyrazole-3,4-dicarboxylic acid 4-(ethyl-methyl-amide)3-{[2-(3-methoxy-phenyl)-[1,2,4]triazolo[1,5-a]pyridin-7-yl]-amide}

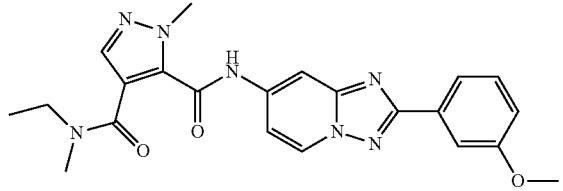 [SMILES: CCN(C)C(=O)c1cnn(C)c1C(=O)Nc1ccn2nc(-c3cccc(OC)c3)nc2c1]

This compound was prepared in the same manner as described in example 75 starting from 5-[2-(3-methoxy-phenyl)-[1,2,4]triazolo[1,5-a]pyridin-7-ylcarbamoyl]-1-methyl-1H-pyrazole-4-carboxylic acid (example 75, step e) (600 mg,

Example 80

2-Methyl-4-(morpholine-4-carbonyl)-2H-pyrazole-3-carboxylic acid [2-(3-hydroxy-phenyl)-[1,2,4]triazolo[1,5-a]pyridin-7-yl]-amide

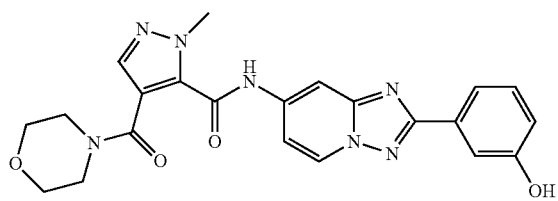 [SMILES: Cn1ncc(C(=O)N2CCOCC2)c1C(=O)Nc1ccn2nc(-c3cccc(O)c3)nc2c1]

To a solution of 2-methyl-4-(morpholine-4-carbonyl)-2H-pyrazole-3-carboxylic acid [2-(3-methoxy-phenyl)-[1,2,4]triazolo[1,5-a]pyridin-7-yl]-amide (Example 75) (2.7 g, 5.86 mmol) in DCM (50 ml) was added a solution of boron tribromide in DCM (1 M solution; 15 ml, 14.6 mmol) at 25° C. The reaction mixture was stirred at 25° C. for 4 h under nitrogen atmosphere. The mixture was diluted with water (100 ml) and stirred for 15 min. The resultant precipitated solid was filtered, washed thoroughly with water and dried azeotropically with toluene (3×100 ml) to give 2-methyl-4-(morpholine-4-carbonyl)-2H-pyrazole-3-carboxylic acid [2-(3-hydroxy-phenyl)-[1,2,4]triazolo[1,5-a]pyridin-7-yl]-amide as off-white solid (2.5 g, 96%). LC-MS: m/z=448.4 [M+H]$^+$.

Example 81

2-Methyl-4-(morpholine-4-carbonyl)-2H-pyrazole-3-carboxylic acid {2-[3-(2-fluoro-ethoxy)-phenyl]-[1,2,4]triazolo[1,5-a]pyridin-7-yl}-amide

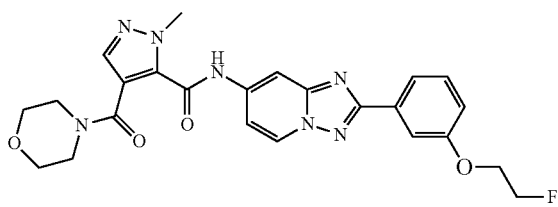 [SMILES: Cn1ncc(C(=O)N2CCOCC2)c1C(=O)Nc1ccn2nc(-c3cccc(OCCF)c3)nc2c1]

To a solution of 2-methyl-4-(morpholine-4-carbonyl)-2H-pyrazole-3-carboxylic acid [2-(3-hydroxy-phenyl)-[1,2,4]triazolo[1,5-a]pyridin-7-yl]-amide (Example 80) (350 mg, 0.782 mmol) in DMF (5 ml) was added 1-bromo-2-fluoroethane (250 mg, 1.96 mmol) and $K_2CO_3$ (108 mg, 0.782 mmol). The reaction mixture was stirred at 60° C. for 16 h. The reaction mixture was diluted with EtOAc (30 ml) and washed with water (2×10 ml) and brine (15 ml). The organic layer was dried over anhydrous $Na_2SO_4$, filtered, and evaporated off in vacuum. The crude material thus obtained was purified by column chromatography over silica gel (5% MeOH/DCM) to afford 2-methyl-4-(morpholine-4-carbonyl)-2H-pyrazole-3-carboxylic acid {2-[3-(2-fluoro-ethoxy)-phenyl]-[1,2,4]triazolo[1,5-a]pyridin-7-yl}-amide as off-white solid (90 mg, 23%). LC-MS: m/z=494.2 [M+H]$^+$.

Example 82

2-Methyl-4-(morpholine-4-carbonyl)-2H-pyrazole-3-carboxylic acid [2-(3-fluoromethoxy-phenyl)-[1,2,4]triazolo[1,5-a]pyridin-7-yl]-amide

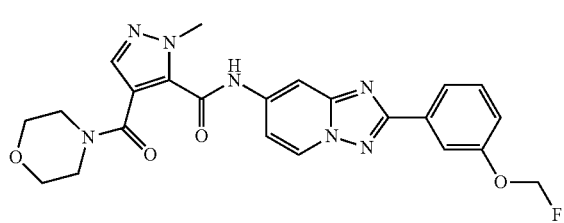 [SMILES: Cn1ncc(C(=O)N2CCOCC2)c1C(=O)Nc1ccn2nc(-c3cccc(OCF)c3)nc2c1]

This compound was prepared in the same manner as described in example 81 starting from 2-methyl-4-(morpholine-4-carbonyl)-2H-pyrazole-3-carboxylic acid [2-(3-hydroxy-phenyl)-[1,2,4]triazolo[1,5-a]pyridin-7-yl]-amide (Example 80) (250 mg, 0.559 mmol) and toluene-4-sulfonic acid fluoromethyl ester (171 mg, 0.838 mmol). White solid (10 mg, 4%). LC-MS: m/z=480.4 [M+H]$^+$.

Example 83

2-Methyl-2H-pyrazole-3,4-dicarboxylic acid 4-(ethyl-methyl-amide)3-({2-[3-(2-fluoro-ethoxy)-phenyl]-[1,2,4]triazolo[1,5-a]pyridin-7-yl}-amide)

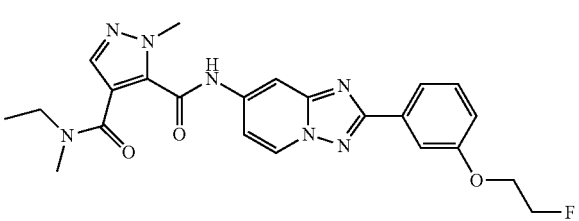 [SMILES: CCN(C)C(=O)c1cnn(C)c1C(=O)Nc1ccn2nc(-c3cccc(OCCF)c3)nc2c1]

a) 2-Methyl-2H-pyrazole-3,4-dicarboxylic acid 4-(ethyl-methyl-amide)3-{[2-(3-hydroxy-phenyl)-[1,2,4]triazolo[1,5-a]pyridin-7-yl]-amide}

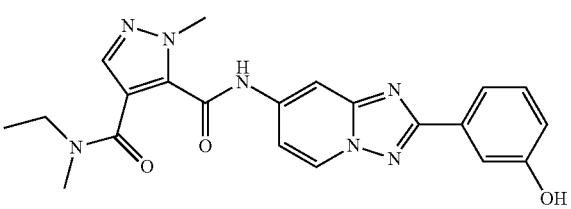 [SMILES: CCN(C)C(=O)c1cnn(C)c1C(=O)Nc1ccn2nc(-c3cccc(O)c3)nc2c1]

This compound was prepared in the same manner as described in example 80 starting from 2-methyl-2H-pyrazole-3,4-dicarboxylic acid 4-(ethyl-methyl-amide)3-{[2-(3-methoxy-phenyl)-[1,2,4]triazolo[1,5-a]pyridin-7-yl]-amide} (Example 79) (1.1 g, 2.54 mmol). White solid (210 mg, 20%). LC-MS: m/z=419.8 [M+H]⁺.

b) 2-Methyl-2H-pyrazole-3,4-dicarboxylic acid 4-(ethyl-methyl-amide)3-({2-[3-(2-fluoro-ethoxy)-phenyl]-[1,2,4]triazolo[1,5-a]pyridin-7-yl}-amide)

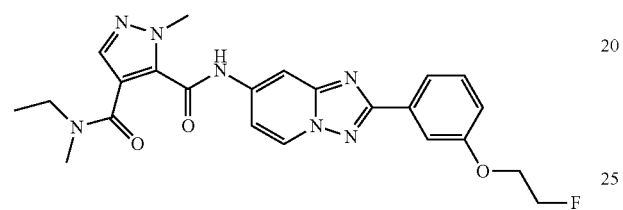

This compound was prepared in the same manner as described in example 81 starting from 2-methyl-2H-pyrazole-3,4-dicarboxylic acid 4-(ethyl-methyl-amide)3-{[2-(3-hydroxy-phenyl)-[1,2,4]triazolo[1,5-a]pyridin-7-yl]-amide} (Example 83, step a) (210 mg, 0.501 mmol) and 1-bromo-2-fluoroethane (96 mg, 0.751 mmol). White solid (30 mg, 12%). LC-MS: m/z=466.2 [M+H]⁺.

Example 84

2-Methyl-2H-pyrazole-3,4-dicarboxylic acid 4-(ethyl-methyl-amide)3-{[2-(3-fluoromethoxy-phenyl)-[1,2,4]triazolo[1,5-a]pyridin-7-yl]-amide}

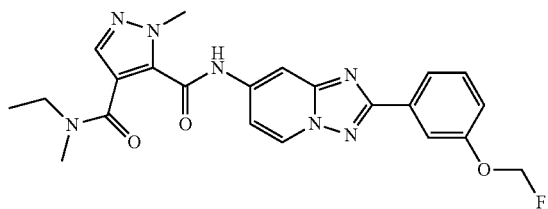 [SMILES: CCN(C)C(=O)c1cnn(C)c1C(=O)Nc1ccn2nc(-c3cccc(OCF)c3)nc2c1]

This compound was prepared in the same manner as described in example 81 starting from 2-methyl-2H-pyrazole-3,4-dicarboxylic acid 4-(ethyl-methyl-amide)3-{[2-(3-hydroxy-phenyl)-[1,2,4]triazolo[1,5-a]pyridin-7-yl]-amide} (Example 83, step a) (210 mg, 0.501 mmol) and toluene-4sulfonic acid fluoromethyl ester (182 mg, 0.894 mmol). White solid (15 mg, 5%). LC-MS: m/z=451.8 [M+H]⁺.

Example 85

2-Methyl-2H-pyrazole-3,4-dicarboxylic acid 4-dimethylamide 3-({2-[3-(2-fluoro-ethoxy)-phenyl]-[1,2,4]triazolo[1,5-a]pyridin-7-yl}-amide)

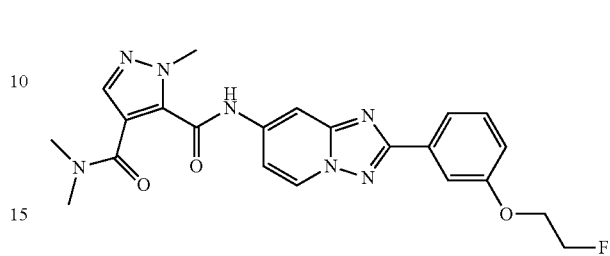

a) 2-Methyl-2H-pyrazole-3,4-dicarboxylic acid 4-dimethylamide 3-{[2-(3-hydroxy-phenyl)[1,2,4]triazolo[1,5-a]pyridin-7-yl]-amide}

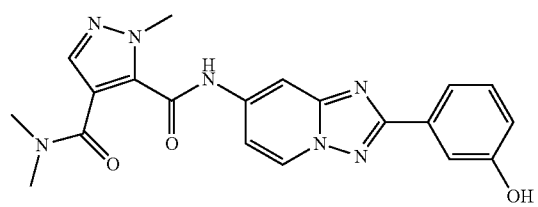 [SMILES: CN(C)C(=O)c1cnn(C)c1C(=O)Nc1ccn2nc(-c3cccc(O)c3)nc2c1]

This compound was prepared in the same manner as described in example 80 starting from 2-methyl-2H-pyrazole-3,4-dicarboxylic acid 4-dimethylamide 3-{[2-(3-methoxy-phenyl)-[1,2,4]triazolo[1,5-a]pyridin-7-yl]-amide} (Example 78) (1.0 g, 2.39 mmol). White solid (600 mg, 62%). LC-MS: m/z=406.2 [M+H]⁺.

b) 2-Methyl-2H-pyrazole-3,4-dicarboxylic acid 4-dimethylamide 3-({2-[3-(2-fluoro-ethoxy)-phenyl]-[1,2,4]triazolo[1,5-a]pyridin-7-yl}-amide)

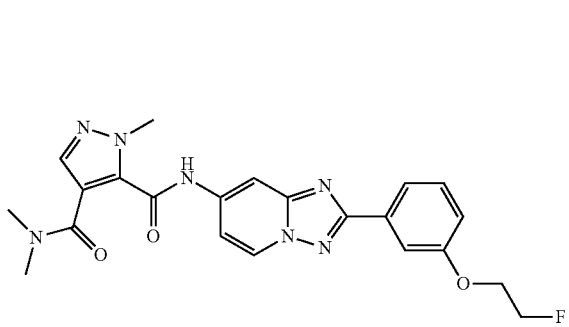 [SMILES: CN(C)C(=O)c1cnn(C)c1C(=O)Nc1ccn2nc(-c3cccc(OCCF)c3)nc2c1]

This compound was prepared in the same manner as described in example 81 starting from 2-methyl-2H-pyrazole-3,4-dicarboxylic acid 4-dimethylamide 3-{[2-(3-hydroxy-phenyl)-[1,2,4]triazolo[1,5a]pyridin-7-yl]-amide}

(500 mg, 1.23 mmol) and 1-bromo-2-fluoroethane (480 mg, 1.85 mmol). White solid (130 mg, 23%). LC-MS: m/z=452.0 [M+H]⁺.

Example 86

2-Methyl-2H-pyrazole-3,4-dicarboxylic acid 4-dimethylamide 3-{[2-(3-fluoromethoxy-phenyl)-[1,2,4]triazolo[1,5-a]pyridin-7-yl]-amide}

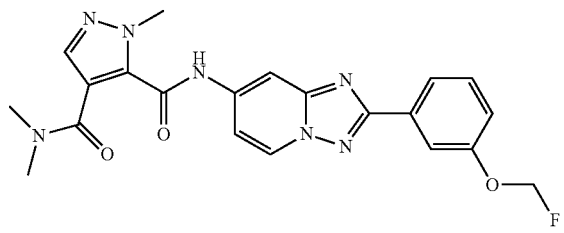 [SMILES: CN(C)C(=O)c1cnn(C)c1C(=O)Nc1ccn2nc(-c3cccc(OCF)c3)nc2c1]

This compound was prepared in the same manner as described in example 81 starting from 2-methyl-2H-pyrazole-3,4-dicarboxylic acid 4-dimethylamide 3-{[2-(3-hydroxy-phenyl)-[1,2,4]triazolo[1,5a]pyridin-7-yl]-amide} (Example 85, step a) (500 mg, 1.23 mmol) and toluene-4-sulfonic acid fluoromethyl ester. White solid (25 mg, 9%). LC-MS: m/z=438.2 [M+H]⁺.

Example 87

2-Methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide]

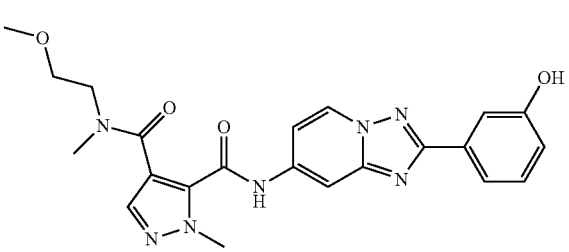 [SMILES: COCCN(C)C(=O)c1cnn(C)c1C(=O)Nc1ccn2nc(-c3cccc(O)c3)nc2c1]

a) 5-[2-(3-Hydroxy-phenyl)-[1,2,4]triazolo[1,5-a]pyridin-7-ylcarbamoyl]-1-methyl-1H-pyrazole-4-carboxylic acid

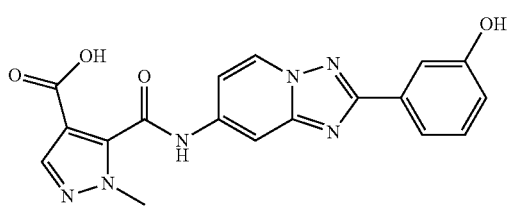 [SMILES: Cn1ncc(C(=O)O)c1C(=O)Nc1ccn2nc(-c3cccc(O)c3)nc2c1]

This compound was prepared in the same manner as described in example 80 starting from 5-[2-(3-methoxy-phenyl)-[1,2,4]triazolo[1,5-a]pyridin-7-ylcarbamoyl]-1-methyl-1H-pyrazole-4-carboxylic acid (Example 75, Step e) (500 mg, 1.27 mmol). Off-white solid (450 mg, 93%). LC-MS: m/z=379.4 [M+H]⁺.

b) 2-Methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide]

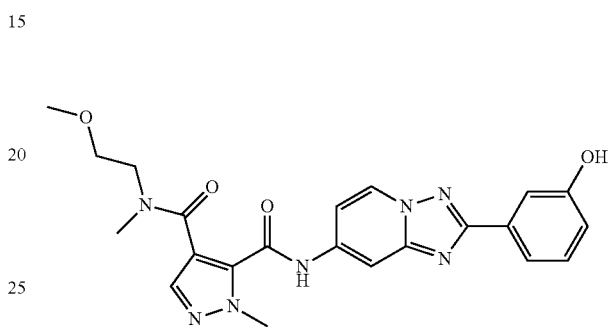

This compound was prepared in the same manner as described in example 75, step f starting from 5-[2-(3-hydroxy-phenyl)-[1,2,4]triazolo[1,5-a]pyridin-7-ylcarbamoyl]-1-methyl-1H-pyrazole-4-carboxylic acid (425 mg, 1.12 mmol) and (2-methoxy-ethyl)-methylamine (150 ul, 1.34 mmol). Brown solid (400 mg, 79%). LC-MS: m/z=449.6 [M+H]⁺.

Example 88

2-Methyl-2H-pyrazole-3,4-dicarboxylic acid 3-({2-[3-(2-fluoro-ethoxy)-phenyl]-[1,2,4]triazolo[1,5-a]pyridin-7-yl}-amide)4-[(2-methoxy-ethyl)-methyl-amide]

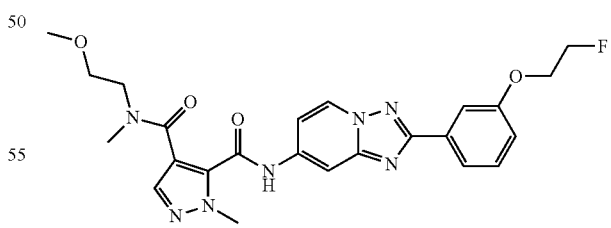

This compound was prepared in the same manner as described in example 81 starting from 2-methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide] (Example 87) (150 mg, 0.333 mmol) and 1-bromo-2-fluoroethane (42 mg, 0.333 mmol). Off white solid (40 mg, 24%). LC-MS: m/z=496.2 [M+H]⁺.

Example 89

2-Methyl-2H-pyrazole-3,4-dicarboxylic acid 3-{[2-(3-fluoromethoxy-phenyl)-[1,2,4]triazolo[1,5-a]pyridin-7-yl]-amide} 4-[(2-methoxy-ethyl)-methyl-amide]

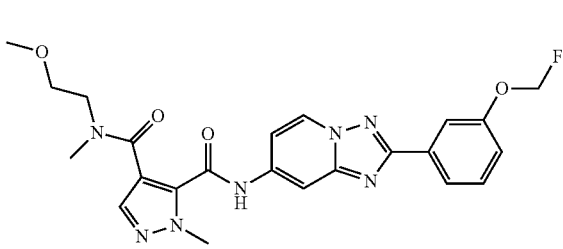 [SMILES: COCCN(C)C(=O)c1cnn(C)c1C(=O)Nc1ccn2nc(-c3cccc(OCF)c3)nc2c1]

This compound was prepared in the same manner as described in example 81 starting from 2-methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide] (Example 87) (400 mg, 0.668 mmol) and toluene-4-sulfonic acid fluoromethyl ester (186 mg, 0.668 mmol). Off white solid (20 mg, 5%). LC-MS: m/z=482.2 [M+H]$^+$.

Example 90

4-(Azetidine-1-carbonyl)-2-methyl-2H-pyrazole-3-carboxylic acid {2-[3-(2-fluoro-ethoxy)-phenyl]-[1,2,4]triazolo[1,5-a]pyridin-7-yl}-amide

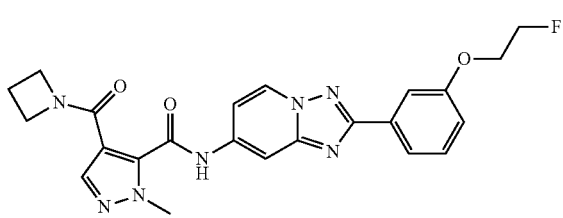 [SMILES: Cn1ncc(C(=O)N2CCC2)c1C(=O)Nc1ccn2nc(-c3cccc(OCCF)c3)nc2c1]

a) 4-(Azetidine-1-carbonyl)-2-methyl-2H-pyrazole-3-carboxylic acid [2-(3-hydroxy-phenyl)-[1,2,4]triazolo[1,5a]pyridin-7-yl]-amide

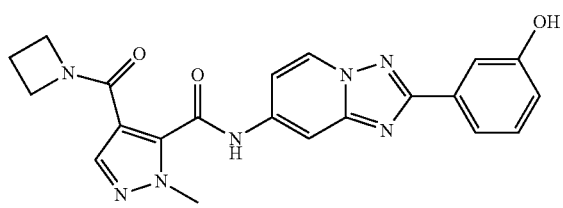 [SMILES: Cn1ncc(C(=O)N2CCC2)c1C(=O)Nc1ccn2nc(-c3cccc(O)c3)nc2c1]

This compound was prepared in the same manner as described in example 75, step f starting from 5-[2-(3-hydroxy-phenyl)-[1,2,4]triazolo[1,5-a]pyridin-7-ylcarbamoyl]-1-methyl-1H-pyrazole-4-carboxylic acid (Example 87, step a) (1.5 g, 3.97 mmol) and azetidine hydrochloride (556 mg, 5.95 mmol). Brown solid (1.0 g, 60%). LC-MS: m/z=418.2 [M+H]$^+$.

b) 4-(Azetidine-1-carbonyl)-2-methyl-2H-pyrazole-3-carboxylic acid {2-[3-(2-fluoro-ethoxy)-phenyl]-[1,2,4]triazolo[1,5-a]pyridin-7-yl}-amide

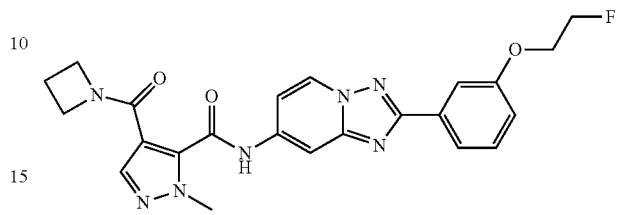

This compound was prepared in the same manner as described in example 81 starting from 4-(azetidine-1-carbonyl)-2-methyl-2H-pyrazole-3-carboxylic acid [2-(3-hydroxy-phenyl)-[1,2,4]triazolo[1,5a]pyridin-7-yl]-amide (750 mg, 1.80 mmol) and 1-bromo-2-fluoroethane (228 mg, 1.80 mmol). Off-white solid (40 mg, 5%). LC-MS: m/z=464.4 [M+H]$^+$.

Example 91

4-(Azetidine-1-carbonyl)-2-methyl-2H-pyrazole-3-carboxylic acid [2-(3-fluoromethoxy-phenyl)-[1,2,4]triazolo[1,5-a]pyridin-7-yl]-amide

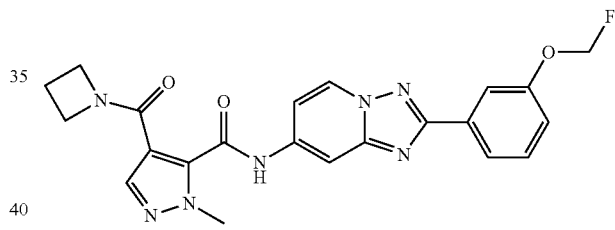

This compound was prepared in the same manner as described in example 81 starting from 4-(azetidine-1-carbonyl)-2-methyl-2H-pyrazole-3-carboxylic acid [2-(3-hydroxy-phenyl)-[1,2,4]triazolo[1,5a]pyridin-7-yl]-amide (Example 90, step a) (260 mg, 0.623 mmol) and toluene-4-sulfonic acid fluoromethyl ester (127 mg, 0.623 mmol). Off-white solid (50 mg, 18%). LC-MS: m/z=450.4 [M+H]$^+$.

Example 92

2-Methyl-2H-pyrazole-3,4-dicarboxylic acid 4-[(2-hydroxy-ethyl)-methyl-amide]3-[(2-phenyl-[1,2,4]triazolo[1,5-a]pyridin-7-yl)-amide]

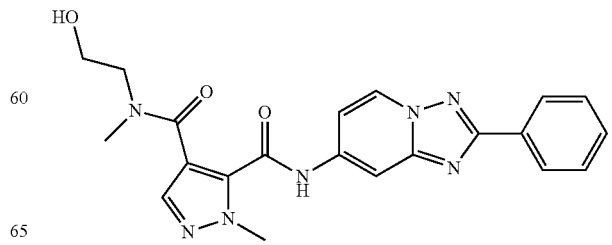

a) 1-Methyl-5-(2-phenyl-[1,2,4]triazolo[1,5-a]pyridin-7-ylcarbamoyl)-1H-pyrazole-4-carbonyl

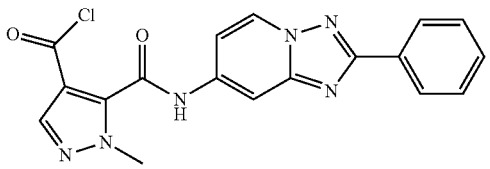 [SMILES: Cn1ncc(C(=O)Cl)c1C(=O)Nc1ccn2nc(-c3ccccc3)nc2c1]

Methyl-5-(2-phenyl-[1,2,4]triazolo[1,5-a]pyridin-7-ylcarbamoyl)-1H-pyrazole-4-carboxylic acid (Example 2) (2.0 g, 5.52 mmol) was combined with CH$_2$Cl$_2$ (54.4 ml) and DMF (272 μl) to give a white suspension. After cooling down to 0° C., oxalyl dichloride (1.87 ml, 22.1 mmol) was added and the reaction mixture stirred at 0° C. for 15 min, then at RT for 3 h. The mixture was concentrated in vacuum and the white solid obtained was dried overnight under HV. The crude material was used without further purification for the next step.

b) 2-Methyl-2H-pyrazole-3,4-dicarboxylic acid 4-[(2-hydroxy-ethyl)-methyl-amide]3-[(2-phenyl-[1,2,4]triazolo[1,5-a]pyridin-7-yl)-amide]

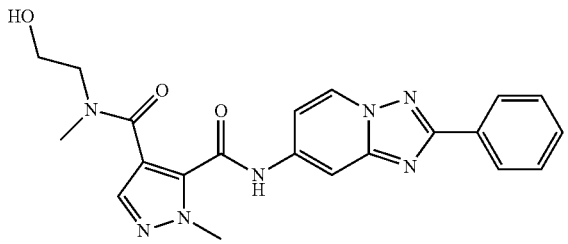 [SMILES: CN(CCO)C(=O)c1cnn(C)c1C(=O)Nc1ccn2nc(-c3ccccc3)nc2c1]

Methyl-5-(2-phenyl-[1,2,4]triazolo[1,5-a]pyridin-7-ylcarbamoyl)-1H-pyrazole-4-carbonyl chloride (2.1 g, 5.51 mmol) was combined with CH$_2$Cl$_2$ (40.0 ml) to give a white suspension. After cooling down to 0° C., 2-(methylamino)ethanol (2.07 g, 2.21 ml, 27.6 mmol) was added dropwise and a light yellow solution was obtained. After 10 min at 0° C., the stirring was continued at RT. After 2 h CH$_2$Cl$_2$ was added and the suspension was filtered. The pure product (553 mg, 24%) was obtained by recrystallization from EtOH. White solid; MS: m/z=420.2 [M+H]$^+$.

Example 93

{Methyl-[1-methyl-5-(2-phenyl-[1,2,4]triazolo[1,5-a]pyridin-7-ylcarbamoyl)-1H-pyrazole-4-carbonyl]-amino}-acetic acid methyl ester

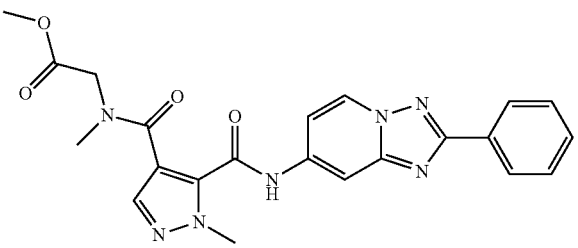 [SMILES: COC(=O)CN(C)C(=O)c1cnn(C)c1C(=O)Nc1ccn2nc(-c3ccccc3)nc2c1]

This compound was prepared in the same manner as described in example 92 starting from 1-methyl-5-(2-phenyl-[1,2,4]triazolo[1,5-a]pyridin-7-ylcarbamoyl)-1H-pyrazole-4-carbonyl chloride (Example 92, step a) (263 mg, 691 μmol) and methyl 2-(methylamino)acetate hydrochloride (482 mg, 3.45 mmol). Additional TEA (349 mg, 481 μl) was added to the reaction mixture. The final product was isolated as white solid (146 mg, 46%); MS: m/z=448.2 [M+H]$^+$.

Example 94

2-Methyl-2H-pyrazole-3,4-dicarboxylic acid 4-[(2-hydroxy-ethyl)-methyl-amide]3-[(2-morpholin-4-yl-[1,2,4]triazolo[1,5-a]pyridin-7-yl)-amide]

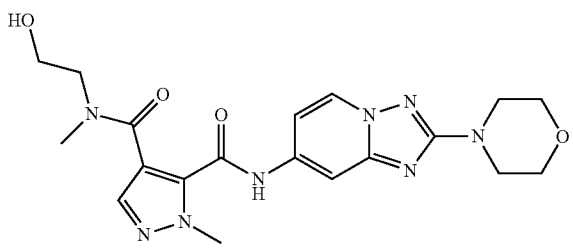 [SMILES: CN(CCO)C(=O)c1cnn(C)c1C(=O)Nc1ccn2nc(N3CCOCC3)nc2c1]

a) 1-Methyl-5-(2-morpholino-[1,2,4]triazolo[1,5-a]pyridin-7-ylcarbamoyl)-1H-pyrazole-4-carbonyl chloride

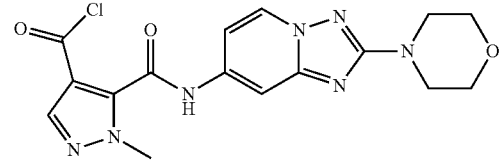 [SMILES: Cn1ncc(C(=O)Cl)c1C(=O)Nc1ccn2nc(N3CCOCC3)nc2c1]

This compound was prepared in the same manner as described in example 92, step a starting from 1-methyl-5-(2-morpholin-4-yl-[1,2,4]triazolo[1,5-a]pyridin-7-ylcarbamoyl)-1H-pyrazole-4-carboxylic acid (Example 29, step a) (250 mg, 673 μmol). The crude material was used in the following step without further purification.

b) 2-Methyl-2H-pyrazole-3,4-dicarboxylic acid 4-[(2-hydroxy-ethyl)-methyl-amide]3-[(2-morpholin-4-yl-[1,2,4]triazolo[1,5-a]pyridin-7-yl)-amide]

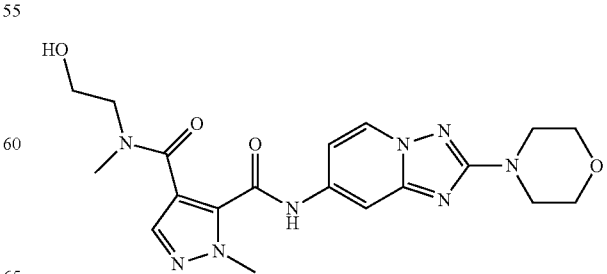

Methyl-5-(2-morpholino-[1,2,4]triazolo[1,5-a]pyridin-7-ylcarbamoyl)-1H-pyrazole-4-carbonyl chloride (262 mg, 672 μmol) was combined with CH$_2$Cl$_2$ (10 ml) to give a light brown suspension. 2-(Methylamino)ethanol (252 mg, 3.36 mmol) was added dropwise at RT and a light yellow solution was obtained. This solution was stirred overnight at RT. The precipitated product was collected by filtration and purified by HPLC to yield 101 mg (35%) of white solid. MS: m/z=429.3 [M+H]$^+$.

Example 95

{Methyl-[1-methyl-5-(2-morpholin-4-yl-[1,2,4]triazolo[1,5-a]pyridin-7-ylcarbamoyl)-1H-pyrazole-4-carbonyl]-amino}-acetic acid methyl ester

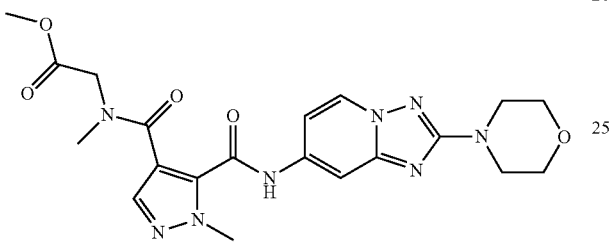

This compound was prepared in the same manner as described in example 93 starting from 1-methyl-5-(2-morpholino-[1,2,4]triazolo[1,5-a]pyridin-7-ylcarbamoyl)-1H-pyrazole-4-carbonyl chloride (Example 94, step a) (250 mg, 641 μmol). White solid (107 mg, 34%); MS: m/z=457.2 [M+H]$^+$.

Example 96

2-Methyl-2H-pyrazole-3,4-dicarboxylic acid 4-[(2-fluoro-ethyl)-amide]3-[(2-phenyl[1,2,4]triazolo[1,5-a]pyridin-7-yl)-amide]

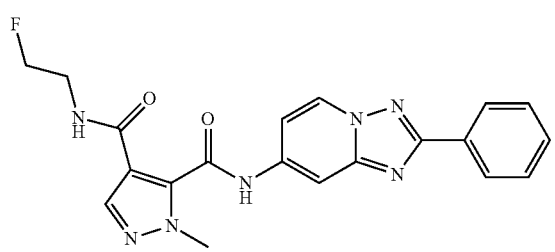 [SMILES: Cn1ncc(C(=O)NCCF)c1C(=O)Nc1ccn2nc(-c3ccccc3)nc2c1]

This compound was prepared in the same manner as described in example 93 starting from 1-methyl-5-(2-phenyl-[1,2,4]triazolo[1,5-a]pyridin-7-ylcarbamoyl)-1H-pyrazole-4-carbonyl chloride (Example 92, step a) (116 mg, 305 μmol) and 2-fluoroethanamine hydrochloride (152 mg, 1.52 mmol). Off-white solid (85 mg, 68%); MS: m/z=408.3 [M+H]$^+$.

Example 97

2-Methyl-2H-pyrazole-3,4-dicarboxylic acid 4-dimethylamide 3-{[2-(2-methoxy-phenyl)-[1,2,4]triazolo[1,5-a]pyridin-7-yl]-amide}

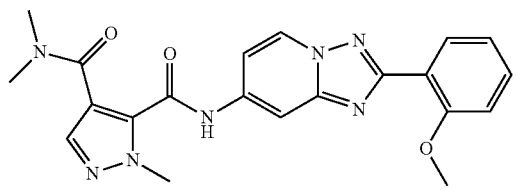 [SMILES: COc1ccccc1-c1nc2cc(NC(=O)c3c(C(=O)N(C)C)cnn3C)ccn2n1]

a) 1-Methyl-1H-pyrazole-4-carboxylic acid dimethylamide

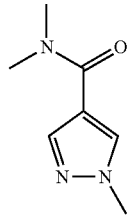

Methyl-1H-pyrazole-4-carboxylic acid (1.0 g, 7.93 mmol) was combined with DMF (10.0 ml) to give a light yellow solution. Triethylamine (3.3 ml, 23.8 mmol) and 2-(1H-benzo[d][1,2,3]triazol-1-yl)-1,1,3,3-tetramethylisouronium tetrafluoroborate (2.8 g, 8.72 mmol) were added. The reaction mixture was set under argon and stirred for 1 h at RT. Then dimethylamine hydrochloride (679 mg, 8.33 mmol) was added. The reaction mixture was stirred over night. The solvent was evaporated and the residue was absorbed on silica gel and chromatographed (amine silica gel cartridge, CH$_2$Cl$_2$). The resulting brown oil was dried at the HV over night. Yield: 1.16 g (96%); brown oil; MS: m/z=154.1 [M+H]$^+$.

b) 4-Dimethylcarbamoyl-2-methyl-2H-pyrazole-3-carboxylic acid

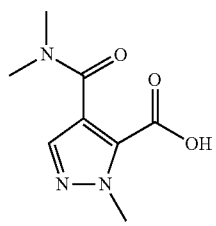

A dried 50 ml three-necked flask was set under argon and a light yellow solution of 1-methyl-1H-pyrazole-4-carboxylic acid dimethylamide (898 mg, 5.86 mmol) in THF (25.1 ml) was added. 1,1,4,7,7-Pentamethyldiethylenetriamine (1.35 ml, 6.45 mmol) was added and the reaction mixture was cooled down to −75° C. Tert-butyllithium (1.6 M in pentane, 5.5 ml, 8.79 mmol) was added dropwise. The reaction was stirred for 30 min at −75° C. Then the ice bath was removed, an excess of dry ice was added and the reaction was stirred for 2.5 h. The yellow solution was diluted with 30 ml H$_2$O and extracted with CH$_2$Cl$_2$ (2×30 ml) to remove impurities. The aqueous layer was acidified with 15 ml HCl 1N (pH=1) and extracted with CH$_2$Cl$_2$(4×40 ml). The organic layer was dried over MgSO$_4$, filtered and evaporated to yield the product as a light red solid (833 mg, 72%). MS: m/z=196.1 [M−H]$^−$.

c) 2-Methyl-2H-pyrazole-3,4-dicarboxylic acid 4-dimethylamide 3-{[2-(2-methoxy-phenyl)-[1,2,4]triazolo[1,5-a]pyridin-7-yl]-amide}

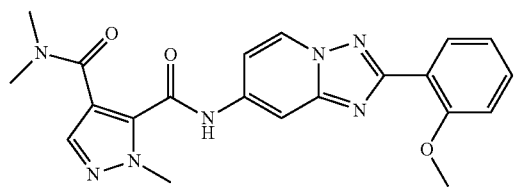 [SMILES: COc1ccccc1-c1nc2cc(NC(=O)c3c(C(=O)N(C)C)cnn3C)ccn2n1]

To a stirred solution of 4-dimethylcarbamoyl-2-methyl-2H-pyrazole-3-carboxylic acid (150 mg, 0.76 mmol) in dry THF (10 ml) was added at RT 2-(2-methoxy-phenyl)-[1,2,4]triazolo[1,5-a]pyridin-7-ylamine (110 mg, 0.46 mmol) (Example 102, step c), followed by DIPEA (dry; 0.505 ml, 3.05 mmol) and propylphosphonic anhydride (50% in ethyl acetate; 1.21 ml, 0.38 mmol). Then the reaction mixture was refluxed for 15 h. The volatiles were removed under reduced pressure to afford the crude product. This crude material was extracted with DCM and the DCM layer was washed with brine concentrated and purified via silica column chromatography eluting with 2% MeOH in DCM followed by washing with hexane to afford a white solid (150 mg, 47%). LC-MS: m/z=420.4 [M+H]$^+$.

Example 98

2-Methyl-2H-pyrazole-3,4-dicarboxylic acid 4-(ethyl-methyl-amide)3-{[2-(2-methoxy-phenyl)-[1,2,4]triazolo[1,5-a]pyridin-7-yl]-amide}

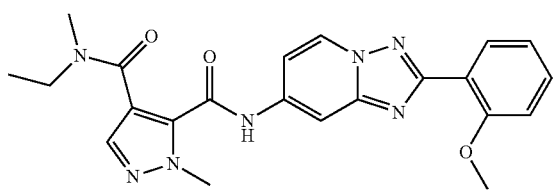 [SMILES: CCN(C)C(=O)c1cnn(C)c1C(=O)Nc1ccn2nc(-c3ccccc3OC)nc2c1]

a) 1-Methyl-1H-pyrazole-4-carboxylic acid ethyl-methyl-amide

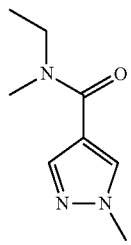

This compound was prepared in the same manner as described in example 97, step a from 1-methyl-1H-pyrazole-4-carboxylic acid (1.0 g, 7.93 mmol) and N-methylethanamine (715 µl, 8.33 mmol). Yield: 995 mg (75%); off-white solid; MS: m/z=168.1 [M+H]$^+$.

b) 4-(Ethyl-methyl-carbamoyl)-2-methyl-2H-pyrazole-3-carboxylic acid

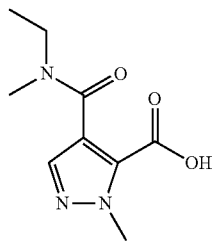

This compound was prepared in the same manner as described in example 97, step b starting from 1-methyl-1H-pyrazole-4-carboxylic acid ethyl-methyl-amide (500 mg, 2.99 mmol). Yield: 519 mg (82%); light yellow solid; MS: m/z=212.1 [M+H]$^+$.

c) 2-Methyl-2H-pyrazole-3,4-dicarboxylic acid 4-(ethyl-methyl-amide)3-{[2-(2-methoxy-phenyl)-[1,2,4]triazolo[1,5-a]pyridin-7-yl]-amide}

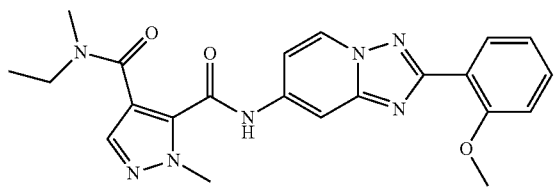 [SMILES: CCN(C)C(=O)c1cnn(C)c1C(=O)Nc1ccn2nc(-c3ccccc3OC)nc2c1]

This compound was prepared in the same manner as described in example 97, step c starting from 4-(ethyl-methyl-carbamoyl)-2-methyl-2H-pyrazole-3-carboxylic acid (150 mg, 0.71 mmol) and 2-(2-methoxy-phenyl)-[1,2,4]triazolo[1,5-a]pyridin-7-ylamine (102 mg, 0.43 mmol). Yield: 120 mg (39%); off-white solid; LC-MS: m/z=434.2 [M+H]⁺.

Example 99

2-Methyl-2H-pyrazole-3,4-dicarboxylic acid 4-[(2-methoxy-ethyl)-methyl-amide]3-{[2-(2-methoxy-phenyl)-[1,2,4]triazolo[1,5-a]pyridin-7-yl]-amide}

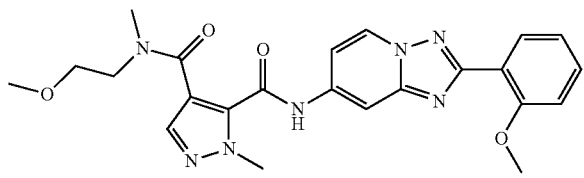 [SMILES: COCCN(C)C(=O)c1cnn(C)c1C(=O)Nc1ccn2nc(-c3ccccc3OC)nc2c1]

a) 1-Methyl-1H-pyrazole-4-carboxylic acid (2-methoxy-ethyl)-methyl-amide

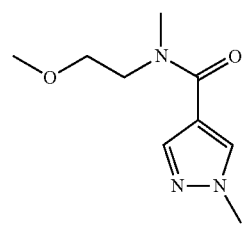

This compound was prepared in the same manner as described in example 97, step a starting from 1-methyl-1H-pyrazole-4-carboxylic acid (500 mg, 3.96 mmol) and 2-methoxy-N-methylethanamine (389 mg, 4.36 mmol). Yield: 580 mg (74%); colorless liquid; MS: m/z=198.1 [M+H]⁺.

b) 4-[(2-Methoxy-ethyl)-methyl-carbamoyl]-2-methyl-2H-pyrazole-3-carboxylic acid

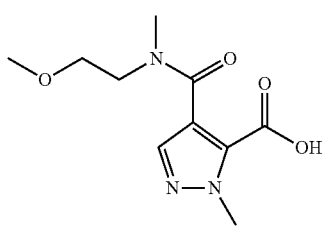 [SMILES: COCCN(C)C(=O)c1cnn(C)c1C(=O)O]

This compound was prepared in the same manner as described in example 97, step b starting from 1-methyl-1H-pyrazole-4-carboxylic acid (2-methoxy-ethyl)-methyl-amide (550 mg, 2.79 mmol). Yield: 590 mg (88%); colorless waxy solid; MS: m/z=240.1 [M−H]⁻.

c) 2-Methyl-2H-pyrazole-3,4-dicarboxylic acid 4-[(2-methoxy-ethyl)-methyl-amide]3-{[2-(2-methoxy-phenyl)-[1,2,4]triazolo[1,5-a]pyridin-7-yl]-amide}

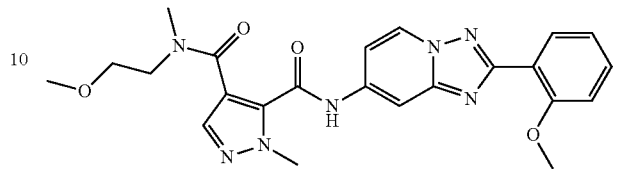

This compound was prepared in the same manner as described in example 97, step c starting from 4-[(2-methoxy-ethyl)-methyl-carbamoyl]-2-methyl-2H-pyrazole-3-carboxylic acid (150 mg, 0.62 mmol) and 2-(2-methoxy-phenyl)-[1,2,4]triazolo[1,5-a]pyridin-7-ylamine (89 mg, 0.37 mmol). Yield: 84 mg (29%); off-white solid; LC-MS: m/z=464.6 [M+H]⁺.

Example 100

2-Methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide)

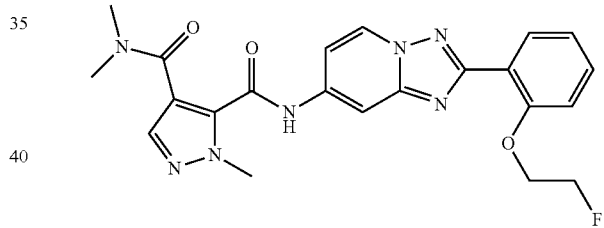

a) 2-(7-Amino-[1,2,4]triazolo[1,5-a]pyridin-2-yl)-phenol

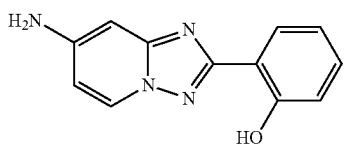 [SMILES: Nc1ccn2nc(-c3ccccc3O)nc2c1]

To a solution of 2-(2-methoxy-phenyl)-[1,2,4]triazolo[1,5-a]pyridin-7-ylamine (2.3 g, 9.6 mmol) (Example 102, step c) in DCM (60 ml) was added a solution of BBr₃ (1 M in DCM, 28.7 ml, 28.7 mmol). The mixture was allowed to warm up to 25° C. and stirring was continued for 2 h. Volatiles were removed under reduced pressure and the crude residue was extracted with DCM and washed with aq. NaHCO₃ solution. The organic layer was washed with brine, dried over Na₂SO₄ and concentrated to get the crude product which was washed with 10% DCM in hexane to afford the title compound as off-white solid (1.3 g, 60%). LC-MS: m/z=227.4 [M+H]+.

b) 2-[2-(2-Fluoro-ethoxy)-phenyl]-[1,2,4]triazolo[1,5-a]pyridin-7-ylamine

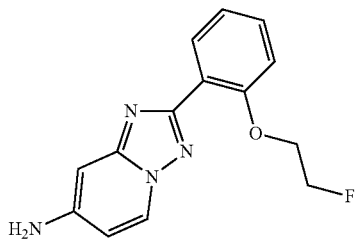 [SMILES: Nc1ccn2nc(-c3ccccc3OCCF)nc2c1]

To a solution of 2-(7-amino-[1,2,4]triazolo[1,5-a]pyridin-2-yl)-phenol (250 mg, 1.10 mmol) in dry DMF (6 ml), $K_2CO_3$ (611 mg, 4.42 mmol) was added under positive nitrogen pressure and the mixture was stirred for 20 min at rt in a sealed tube. A solution of 1-fluoro-2-bromoethane (93 mg, 0.66 mmol) in DMF was added dropwise and the reaction mixture was heated for 8 h at 90° C. On completion of reaction (monitored by TLC), the mixture was cooled, diluted with water and extracted with DCM. The organic layer was dried over $Na_2SO_4$ and concentrated under reduced pressure to get the crude product. Purification by silica gel column chromatography using 2% MeOH in DCM as eluent afforded the desired product (200 mg, 66%) as off-white solid. LC-MS: m/z=273.2 [M+H]+.

c) 2-Methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide)

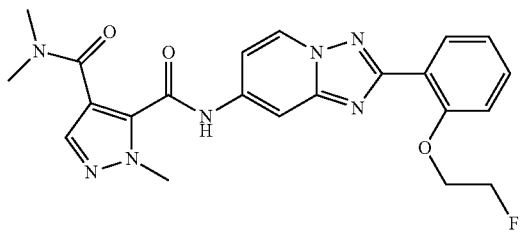 [SMILES: CN(C)C(=O)c1cnn(C)c1C(=O)Nc1ccn2nc(-c3ccccc3OCCF)nc2c1]

This compound was prepared in the same manner as described in example 97, step c starting from 2-[2-(2-fluoro-ethoxy)-phenyl]-[1,2,4]triazolo[1,5-a]pyridin-7-ylamine (159 mg, 0.58 mmol) and 4-dimethylcarbamoyl-2-methyl-2H-pyrazole-3-carboxylic acid (Example 97, step b) (150 mg, 0.78 mmol). Yield: 135 mg (38%); white solid; LC-MS: m/z=452.2 [M+H]+.

Example 101

2-Methyl-2H-pyrazole-3,4-dicarboxylic acid 4-(ethyl-methyl-amide)3-({2-[2-(2-fluoro-ethoxy)-phenyl]-[1,2,4]triazolo[1,5-a]pyridin-7-yl}-amide)

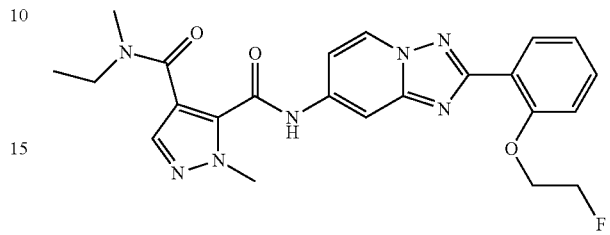

This compound was prepared in the same manner as described in example 100 starting from 2-[2-(2-fluoro-ethoxy)-phenyl]-[1,2,4]triazolo[1,5-a]pyridin-7-ylamine (126 mg, 0.46 mmol) and 4-(ethyl-methyl-carbamoyl)-2-methyl-2H-pyrazole-3-carboxylic acid (Example 98, step b) (130 mg, 0.61 mmol). Yield: 142 mg (50%); off-white solid; LC-MS: m/z=466.2 [M+H]+.

Example 102

4-(Azetidine-1-carbonyl)-2-methyl-2H-pyrazole-3-carboxylic acid [2-(2-methoxy-phenyl)-[1,2,4]triazolo[1,5-a]pyridin-7-yl]-amide

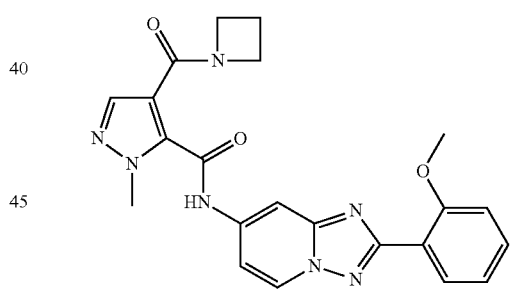

a) 7-bromo-2-(2-methoxyphenyl)-[1,2,4]triazolo[1,5-a]pyridine

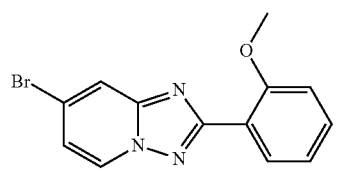 [SMILES: COc1ccccc1-c1nc2cc(Br)ccn2n1]

The product was prepared in the same manner as described in example 1b using 1,2-diamino-4-bromopyridinium 2,4,6-trimethylbenzenesulfonate (2.2 g, 5.67 mmol) and 2-methoxybenzoyl chloride (1.52 ml, 11.3 mmol) as starting materials. The reaction affords 7-bromo-2-(2-methoxyphenyl)-[1,2,4]triazolo[1,5-a]pyridine (490 mg, 28.4%) as a white solid. MS: m/z=306.0 (M+H⁺).

b) [2-(2-Methoxy-phenyl)-[1,2,4]triazolo[1,5-a]pyridin-7-yl]-carbamic acid tert-butyl ester

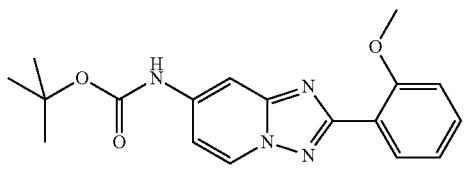 [SMILES: COc1ccccc1-c1nc2cc(NC(=O)OC(C)(C)C)ccn2n1]

The product was prepared in the same manner as described in example 1c using 7-bromo-2-(2-methoxyphenyl)-[1,2,4]triazolo[1,5-a]pyridine (490 mg, 1.61 mmol) and tert-butyl carbamate (350 mg, 2.99 mmol) as starting materials. The reaction affords [2-(2-methoxy-phenyl)-[1,2,4]triazolo[1,5-a]pyridin-7-yl]-carbamic acid tert-butyl ester (520 mg, 94.8%) as a light yellow solid. mp.: 202.8° C., MS: m/z=341.1 (M+H⁺)

c) 2-(2-Methoxy-phenyl)-[1,2,4]triazolo[1,5-a]pyridin-7-ylamine

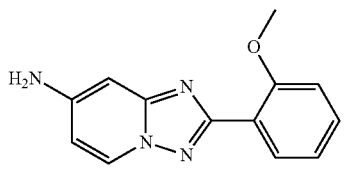 [SMILES: COc1ccccc1-c1nc2cc(N)ccn2n1]

The product was prepared in the same manner as described in example 1d using tert-butyl 2-(2-methoxyphenyl)-[1,2,4]triazolo[1,5-a]pyridin-7-ylcarbamate (510 mg, 1.5 mmol) as starting material. The reaction affords 2-(2-methoxy-phenyl)-[1,2,4]triazolo[1,5-a]pyridin-7-ylamine (370 mg, 103%) as light brown foam. MS: m/z=241.1 (M+H⁺).

d) 5-[2-(2-Methoxy-phenyl)-[1,2,4]triazolo[1,5-a]pyridin-7-ylcarbamoyl]-1-methyl-1H-pyrazole-4-carboxylic acid ethyl ester

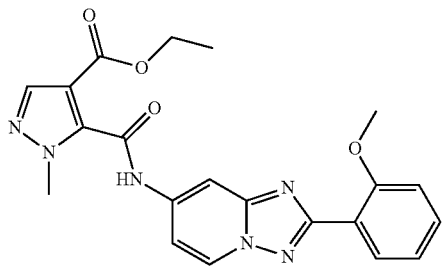 [SMILES: CCOC(=O)c1cnn(C)c1C(=O)Nc1ccn2nc(-c3ccccc3OC)nc2c1]

The product was prepared in the same manner as described in example 28 using 2-(2-methoxyphenyl)-[1,2,4]triazolo[1,5-a]pyridin-7-amine (365 mg, 1.52 mmol) and 4-(ethoxycarbonyl)-1-methyl-1H-pyrazole-5-carboxylic acid (331 mg, 1.67 mmol) as starting material. The reaction affords 5-[2-(2-methoxy-phenyl)-[1,2,4]triazolo[1,5-a]pyridin-7-ylcarbamoyl]-1-methyl-1H-pyrazole-4-carboxylic acid ethyl ester (410 mg, 64.2%) as white solid. MS: m/z=421.1 (M+H⁺).

e) 5-[2-(2-Methoxy-phenyl)-[1,2,4]triazolo[1,5-a]pyridin-7-ylcarbamoyl]-1-methyl-1H-pyrazole-4-carboxylic acid

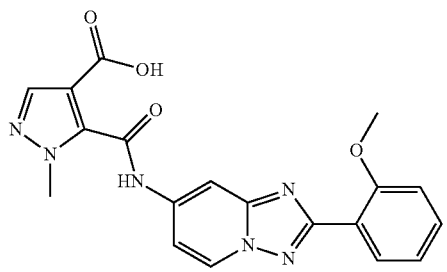 [SMILES: COc1ccccc1-c1nc2cc(NC(=O)c3c(C(=O)O)cnn3C)ccn2n1]

The product was prepared in the same manner as described in example 29a using ethyl 5-(2-(2-methoxyphenyl)-[1,2,4]triazolo[1,5-a]pyridin-7-ylcarbamoyl)-1-methyl-1H-pyrazole-4-carboxylate (400 mg, 951 µmol) as starting material. The reaction affords 5-[2-(2-methoxy-phenyl)-[1,2,4]triazolo[1,5-a]pyridin-7-ylcarbamoyl]-1-methyl-1H-pyrazole-4-carboxylic acid (405 mg, 108%) as light brown solid. mp.: 283° C., MS: m/z=393.0 (M+H⁺).

f) 4-(Azetidine-1-carbonyl)-2-methyl-2H-pyrazole-3-carboxylic acid [2-(2-methoxy-phenyl)-[1,2,4]triazolo[1,5-a]pyridin-7-yl]-amide

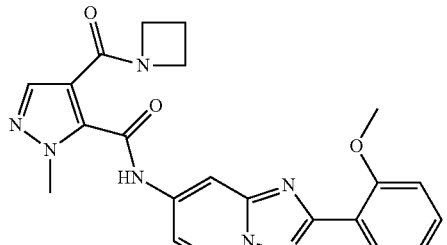

The product was prepared in the same manner as described in example 3 using 5-(2-(2-methoxyphenyl)-[1,2,4]triazolo[1,5-a]pyridin-7-ylcarbamoyl)-1-methyl-1H-pyrazole-4-carboxylic acid (75 mg, 191 µmol) and azetidine (51.5 µl, 765 µmol) as starting materials. The reaction affords 4-(azetidine-1-carbonyl)-2-methyl-2H-pyrazole-3-carboxylic acid [2-(2-methoxy-phenyl)-[1,2,4]triazolo[1,5-a]pyridin-7-yl]-amide (36.6 mg, 44.4%) off-white solid. mp.: 258.1° C., MS: m/z=432.3 (M+H⁺).

Example 103

2-Methyl-2H-pyrazole-3,4-dicarboxylic acid 4-(cyclopropyl-methyl-amide)3-{[2-(2-methoxy-phenyl)-[1,2,4]triazolo[1,5-a]pyridin-7-yl]-amide}

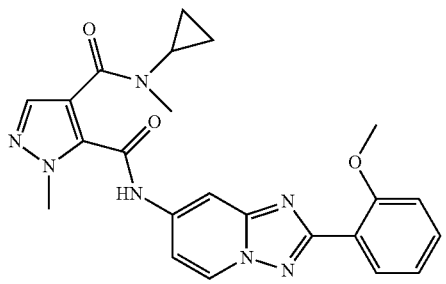 [SMILES: COc1ccccc1-c1nc2cc(NC(=O)c3c(C(=O)N(C)C4CC4)cnn3C)ccn2n1]

The product was prepared in the same manner as described in example 3 using 5-(2-(2-methoxyphenyl)-[1,2,4]triazolo[1,5-a]pyridin-7-ylcarbamoyl)-1-methyl-1H-pyrazole-4-carboxylic acid (75 mg, 191 µmol) and N-methylcyclopropanamine (54.4 mg, 765 µmol) as starting materials. The reaction affords 2-methyl-2H-pyrazole-3,4-dicarboxylic acid 4-(cyclopropyl-methyl-amide)3-{[2-(2-methoxy-phenyl)-[1,2,4]triazolo[1,5-a]pyridin-7-yl]-amide} (35 mg, 41.1%) as off-white solid. mp.: 239.2° C., MS: m/z=446.1 (M+H⁺).

Example 104

2-Methyl-2H-pyrazole-3,4-dicarboxylic acid 4-dimethylamide 3-{[2-(3-fluoro-phenyl)[1,2,4]triazolo[1,5-a]pyridin-7-yl]-amide}

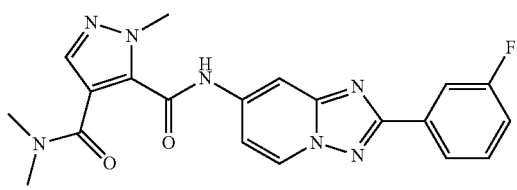 [SMILES: CN(C)C(=O)c1cnn(C)c1C(=O)Nc1ccn2nc(-c3cccc(F)c3)nc2c1]

a) 7-Bromo-2-(3-fluoro-phenyl)-[1,2,4]triazolo[1,5-a]pyridine

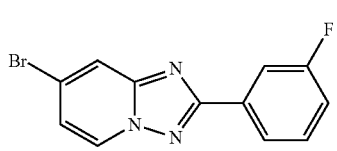 [SMILES: Fc1cccc(-c2nc3cc(Br)ccn3n2)c1]

The product was prepared in the same manner as described in example 1b using 1,2-diamino-4-bromopyridinium 2,4,6-trimethylbenzenesulfonate (2 g, 5.15 mmol) and 3-fluorobenzoyl chloride (1.24 ml, 10.3 mmol) as starting materials. The reaction affords 7-Bromo-2-(3-fluoro-phenyl)-[1,2,4]triazolo[1,5-a]pyridine (1.067 g, 70.9%) as pink solid. mp.: 186-188° C., MS: m/z=291.9/293.9 (M+H⁺).

b) [2-(3-Fluoro-phenyl)-[1,2,4]triazolo[1,5-a]pyridin-7-yl]-carbamic acid tert-butyl ester

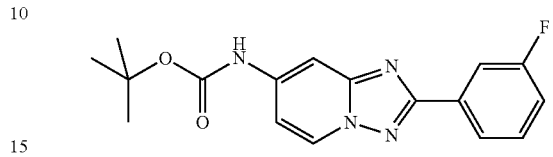

The product was prepared in the same manner as described in example 1c using 7-bromo-2-(3-fluorophenyl)-[1,2,4]triazolo[1,5-a]pyridine (1 g, 3.42 mmol) and tert-butyl carbamate (481 mg, 4.11 mmol) as starting materials. The reaction affords 2-(3-fluoro-phenyl)-[[1,2,4]triazolo[1,5-a]pyridin-7-yl]-carbamic acid tert-butyl ester (1.15 g, 102%) as light yellow foam. MS: m/z=329.0 (M+H⁺).

c) 2-(3-Fluoro-phenyl)-[1,2,4]triazolo[1,5-a]pyridin-7-ylamine

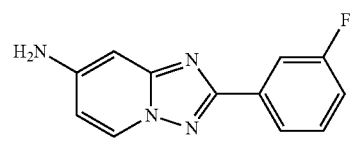

The product was prepared in the same manner as described in example 1d using tert-butyl 2-(3-fluorophenyl)-[1,2,4]triazolo[1,5-a]pyridin-7-ylcarbamate (1.0 g, 3.05 mmol) as starting material. The reaction affords 2-(3-fluoro-phenyl)-[1,2,4]triazolo[1,5-a]pyridin-7-ylamine (606 g, 87.2%) as light yellow solid. mp.: 200-203° C., MS: m/z=229.1 (M+H⁺).

d) 5-[2-(3-Fluoro-phenyl)-[1,2,4]triazolo[1,5-a]pyridin-7-ylcarbamoyl]-1-methyl-1H-pyrazole-4-carboxylic acid ethyl ester

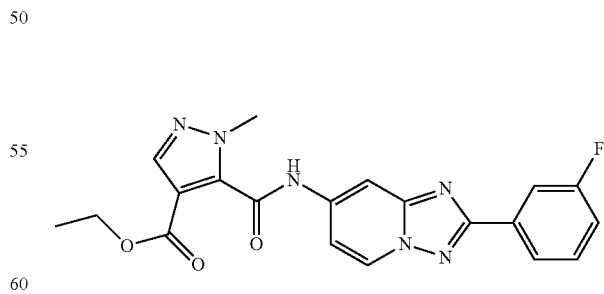

The product was prepared in the same manner as described in example 28 using 2-(3-fluorophenyl)-[1,2,4]triazolo[1,5-a]pyridin-7-amine (580 mg, 2.54 mmol) and 4-(ethoxycarbonyl)-1-methyl-1H-pyrazole-5-carboxylic acid (604 mg, 3.05 mmol) as starting materials. The reaction affords 5-[2-(3-fluoro-phenyl)-[1,2,4]triazolo[1,5-a]pyridin-7-ylcarbamoyl]-1-methyl-1H-pyrazole-4-carboxylic acid ethyl ester (600 mg, 57.8%) as white solid. mp.: 246-249° C., MS: m/z=409.3 (M+H⁺).

e) 5-[2-(3-Fluoro-phenyl)-[1,2,4]triazolo[1,5-a]pyridin-7-ylcarbamoyl]-1-methyl-1H-pyrazole-4-carboxylic acid

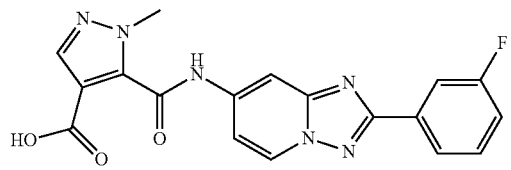

The product was prepared in the same manner as described in example 29a using 5-(2-(3-fluorophenyl)-[1,2,4]triazolo[1,5-a]pyridin-7-ylcarbamoyl)-1-methyl-1H-pyrazole-4-carboxylate (550 mg, 1.35 mmol) as starting material. The reaction affords 5-[2-(3-fluoro-phenyl)-[1,2,4]triazolo[1,5-a]pyridin-7-ylcarbamoyl]-1-methyl-1H-pyrazole-4-carboxylic acid (421 mg, 82.2%) as off white solid. mp.: >270° C., MS: m/z=381.1 (M+H⁺).

f) 2-Methyl-2H-pyrazole-3,4-dicarboxylic acid 4-dimethylamide 3-{[2-(3-fluoro-phenyl)-[1,2,4]triazolo[1,5-a]pyridin-7-yl]-amide}

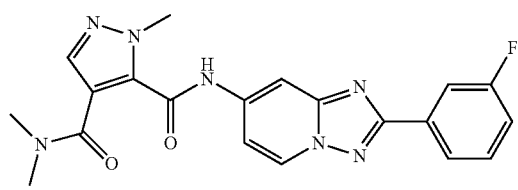

The product was prepared in the same manner as described in example 3 using 5-(2-(3-fluorophenyl)-[1,2,4]triazolo[1,5-a]pyridin-7-ylcarbamoyl)-1-methyl-1H-pyrazole-4-carboxylic acid (70 mg, 184 µmol) and dimethylamine 2M in THF (276 µl, 552 µmol) as starting materials. The reaction affords 2-methyl-2H-pyrazole-3,4-dicarboxylic acid 4-dimethylamide 3-{[2-(3-fluoro-phenyl)-[1,2,4]triazolo[1,5-a]pyridin-7-yl]-amide} (45 mg, 60%) as white solid. mp.: 255-260° C., MS: m/z=408.1 (M+H⁺).

Example 105

4-(Azetidine-1-carbonyl)-2-methyl-2H-pyrazole-3-carboxylic acid [2-(3-fluoro-phenyl)-[1,2,4]triazolo[1,5-a]pyridin-7-yl]-amide

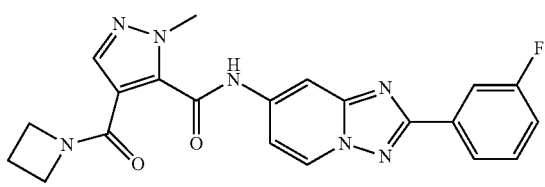

The product was prepared in the same manner as described in example 3 using 5-(2-(3-fluorophenyl)-[1,2,4]triazolo[1,5-a]pyridin-7-ylcarbamoyl)-1-methyl-1H-pyrazole-4-carboxylic acid (70 mg, 184 µmol) and azetidine (12.5 µl, 184 µmol) as starting materials. The reaction affords 4-(azetidine-1-carbonyl)-2-methyl-2H-pyrazole-3-carboxylic acid [2-(3-fluoro-phenyl)-[1,2,4]triazolo[1,5-a]pyridin-7-yl]-amide (70 mg, 90.7%) as white solid. mp.: 232-236° C., MS: m/z=420.0 (M+H⁺).

Example 106

2-Methyl-4-(morpholine-4-carbonyl)-2H-pyrazole-3-carboxylic acid [2-(3-fluoro-phenyl)-[1,2,4]triazolo[1,5-a]pyridin-7-yl]-amide

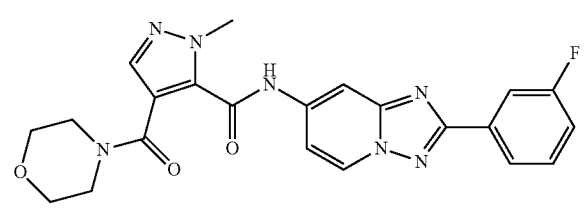 [SMILES: Cn1ncc(C(=O)N2CCOCC2)c1C(=O)Nc1ccn2nc(-c3cccc(F)c3)nc2c1]

The product was prepared in the same manner as described in example 3 using 5-(2-(3-fluorophenyl)-[1,2,4]triazolo[1,5-a]pyridin-7-ylcarbamoyl)-1-methyl-1H-pyrazole-4-carboxylic acid (70 mg, 184 µmol) and morpholine (16 µl, 184 µmol) as starting materials. The reaction affords 2-methyl-4-(morpholine-4-carbonyl)-2H-pyrazole-3-carboxylic acid [2-(3-fluoro-phenyl)-[1,2,4]triazolo[1,5-a]pyridin-7-yl]-amide (44 mg, 53.2%) as white solid. mp.: 212-214° C., MS: m/z=450.0 (M+H⁺).

Example 107

4-(3-Methoxy-azetidine-1-carbonyl)-2-methyl-2H-pyrazole-3-carboxylic acid [2-(3-fluoro-phenyl)-[1,2,4]triazolo[1,5-a]pyridin-7-yl]-amide

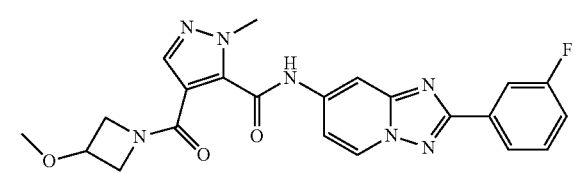 [SMILES: COC1CN(C(=O)c2cnn(C)c2C(=O)Nc2ccn3nc(-c4cccc(F)c4)nc3c2)C1]

The product was prepared in the same manner as described in example 3 using 5-(2-(3-fluorophenyl)-[1,2,4]triazolo[1,5-a]pyridin-7-ylcarbamoyl)-1-methyl-1H-pyrazole-4-carboxylic acid (60 mg, 158 µmol) and 3-methoxyazetidine hydrochloride (58.5 mg, 473 µmol) as starting materials. The reaction affords 4-(3-methoxy-azetidine-1-carbonyl)-2-methyl-2H-pyrazole-3-carboxylic acid [2-(3-fluoro-phenyl)-[1, 2,4]triazolo[1,5-a]pyridin-7-yl]-amide (10 mg, 14.1%) as white solid. mp.: 255-257° C., MS: m/z=450.0 (M+H⁺).

Example 108

2-Methyl-4-(4-methyl-piperazine-1-carbonyl)-2H-pyrazole-3-carboxylic acid [2-(3-fluoro-phenyl)-[1,2,4]triazolo[1,5-a]pyridin-7-yl]-amide

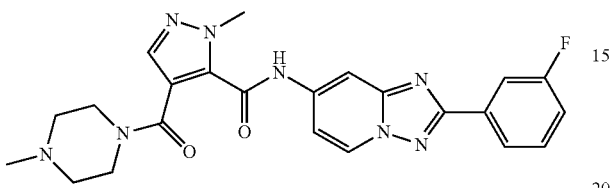

The product was prepared in the same manner as described in example 3 using 5-(2-(3-fluorophenyl)-[1,2,4]triazolo[1,5-a]pyridin-7-ylcarbamoyl)-1-methyl-1H-pyrazole-4-carboxylic acid (60 mg, 158 μmol) and 1-methylpiperazine (52.6 μl, 473 μmol) as starting materials. The reaction affords 2-methyl-4-(4-methyl-piperazine-1-carbonyl)-2H-pyrazole-3-carboxylic acid [2-(3-fluoro-phenyl)-[1,2,4]triazolo[1,5-a]pyridin-7-yl]-amide (35 mg, 48%) as light grey solid. mp.: 224-227° C., MS: m/z=263.0 (M+H⁺).

Example 109

N5-(2-(2-fluoropyridin-3-yl)-[1,2,4]triazolo[1,5-a]pyridin-7-yl)-N4,N4,1-trimethyl-1H-pyrazole-4,5-dicarboxamide

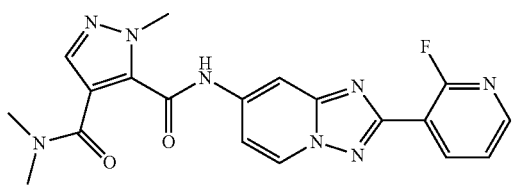 [SMILES: CN(C)C(=O)c1cnn(C)c1C(=O)Nc1ccn2nc(-c3cccnc3F)nc2c1]

a) 2-Fluoronicotinoyl chloride

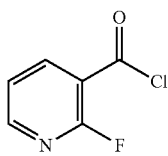

A mixture of 2-fluoronicotinic acid (5.00 g, 35.4 mmol) and thionyl chloride (35 ml, 480 mmol) was refluxed for 48 hours. The thionyl chloride was distilled off at ambient pressure, the residue was distilled under high vacuum. The reaction affords 2-fluoronicotinoyl chloride (4.45 g, 78.7%) as white solid. MS: m/z=156.1 (M+H⁺).

b) 7-Bromo-2-(2-fluoro-pyridin-3-yl)-[1,2,4]triazolo[1,5-a]pyridine

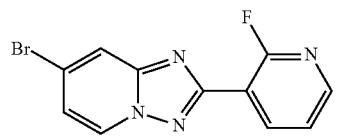 [SMILES: Fc1ncccc1-c1nc2cc(Br)ccn2n1]

The product was prepared in the same manner as described in example 1b using 1,2-diamino-4-bromopyridinium 2,4,6-trimethylbenzenesulfonate (2.2 g, 5.67 mmol) and 2-fluoronicotinoyl chloride (1.81 ml, 11.3 mmol) as starting materials. The reaction affords 7-bromo-2-(2-fluoro-pyridin-3-yl)-[1,2,4]triazolo[1,5-a]pyridine (1.175 g, 70.8%) as light brown solid. MS: m/z=294.9 (M+H⁺).

c) [2-(2-Fluoro-pyridin-3-yl)-[1,2,4]triazolo[1,5-a]pyridin-7-yl]-carbamic acid tert-butyl ester

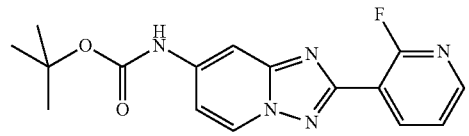 [SMILES: CC(C)(C)OC(=O)Nc1ccn2nc(-c3cccnc3F)nc2c1]

The product was prepared in the same manner as described in example 1c using 7-bromo-2-(2-fluoropyridin-3-yl)-[1,2,4]triazolo[1,5-a]pyridine (1.1 g, 3.75 mmol) and tert-butyl carbamate (528 mg, 4.5 mmol) as starting materials. The reaction affords [2-(2-fluoro-pyridin-3-yl)-[1,2,4]triazolo[1,5-a]pyridin-7-yl]-carbamic acid tert-butyl ester (870 mg, 70.4%), as light yellow solid. MS: m/z=330.1 (M+H⁺).

d) 2-(2-Fluoro-pyridin-3-yl)-[1,2,4]triazolo[1,5-a]pyridin-7-ylamine

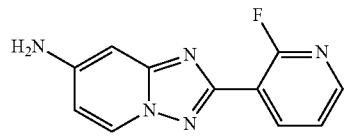 [SMILES: Nc1ccn2nc(-c3cccnc3F)nc2c1]

The product was prepared in the same manner as described in example 1d using tert-butyl 2-(2-fluoropyridin-3-yl)-[1,2,4]triazolo[1,5-a]pyridin-7-ylcarbamate (0.84 g, 2.55 mmol) as starting material. The reaction affords 2-(2-fluoro-pyridin- 3-yl)-[1,2,4]triazolo[1,5-a]pyridin-7-ylamine (547 mg, 93.6%) as light yellow solid. MS: m/z=230.1 (M+H+).

e) 5-[2-(2-Fluoro-pyridin-3-yl)-[1,2,4]triazolo[1,5-a]pyridin-7-ylcarbamoyl]-1-methyl-1H-pyrazole-4-carboxylic acid ethyl ester

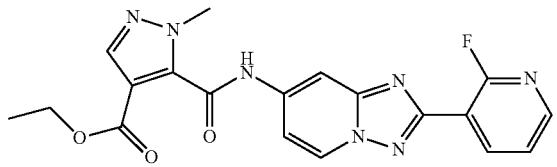 [SMILES: CCOC(=O)c1cnn(C)c1C(=O)Nc1ccn2nc(-c3cccnc3F)nc2c1]

The product was prepared in the same manner as described in example 44d using 2-(2-fluoropyridin-3-yl)-[1,2,4]triazolo[1,5-a]pyridin-7-amine (500 mg, 2.18 mmol) and 4-(ethoxycarbonyl)-1-methyl-1H-pyrazole-5-carboxylic acid (519 mg, 2.62 mmol) as starting materials. The reaction affords 5-[2-(2-fluoro-pyridin-3-yl)-[1,2,4]triazolo[1,5-a]pyridin-7-ylcarbamoyl]-1-methyl-1H-pyrazole-4-carboxylic acid ethyl ester (761 mg, 85.2%) as white solid. mp.: 249-251° C., MS: m/z=410.0 (M+H+).

f) 5-(2-(2-fluoropyridin-3-yl)-[1,2,4]triazolo[1,5-a]pyridin-7-ylcarbamoyl)-1-methyl-1H-pyrazole-4-carboxylic acid

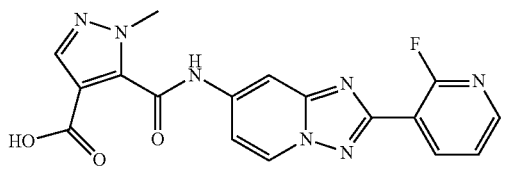 [SMILES: Cn1ncc(C(=O)O)c1C(=O)Nc1ccn2nc(-c3cccnc3F)nc2c1]

The product was prepared in the same manner as described in example 35h using 5-(2-(2-fluoropyridin-3-yl)-[1,2,4]triazolo[1,5-a]pyridin-7-ylcarbamoyl)-1-methyl-1H-pyrazole-4-carboxylate (700 mg, 1.71 mmol) as starting material. The reaction affords 5-[2-(3-fluoro-phenyl)-[1,2,4]triazolo[1,5-a]pyridin-7-ylcarbamoyl]-1-methyl-1H-pyrazole-4-carboxylic acid (420 mg, 64.4%) as white solid. mp.: >260° C., MS: m/z=382.1 (M+H+).

g) 2-Methyl-2H-pyrazole-3,4-dicarboxylic acid 4-dimethylamide 3-{[2-(2-fluoro-pyridin-3-yl)-[1,2,4]triazolo[1,5-a]pyridin-7-yl]-amide}

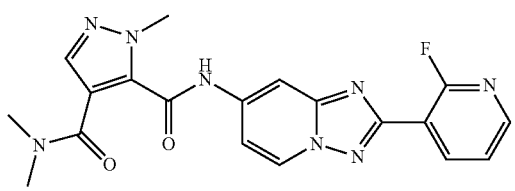 [SMILES: CN(C)C(=O)c1cnn(C)c1C(=O)Nc1ccn2nc(-c3cccnc3F)nc2c1]

The product was prepared in the same manner as described in example 3 using 5-(2-(2-fluoropyridin-3-yl)-[1,2,4]triazolo[1,5-a]pyridin-7-ylcarbamoyl)-1-methyl-1H-pyrazole-4-carboxylic acid (80 mg, 210 μmol) and dimethylamine (2M in THF, 315 μl, 629 μmol) as starting materials. The reaction affords 2-methyl-2H-pyrazole-3,4-dicarboxylic acid 4-dimethylamide 3-{[2-(2-fluoro-pyridin-3-yl)-[1,2,4]triazolo[1,5-a]pyridin-7-yl]-amide} (5.8 mg, 6.77%) as white solid. MS: m/z=409.1 (M+H+).

Example 110

4-(Azetidine-1-carbonyl)-2-methyl-2H-pyrazole-3-carboxylic acid [2-(2-fluoro-pyridin-3-yl)-[1,2,4]triazolo[1,5-a]pyridin-7-yl]-amide

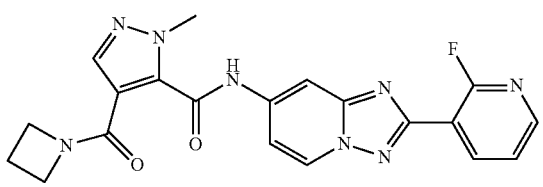 [SMILES: Cn1ncc(C(=O)N2CCC2)c1C(=O)Nc1ccn2nc(-c3cccnc3F)nc2c1]

The product was prepared in the same manner as described in example 3 using 5-(2-(2-fluoropyridin-3-yl)-[1,2,4]triazolo[1,5-a]pyridin-7-ylcarbamoyl)-1-methyl-1H-pyrazole-4-carboxylic acid (80 mg, 210 μmol) and azetidine (42.8 μl, 629 μmol) as starting materials. The reaction affords 4-(azetidine-1-carbonyl)-2-methyl-2H-pyrazole-3-carboxylic acid [2-(2-fluoro-pyridin-3-yl)-[1,2,4]triazolo[1,5-a]pyridin-7-yl]-amide (38.2 mg, 43.3%) as white solid. MS: m/z=421.0 (M+H+).

Example 111

2-Methyl-4-(morpholine-4-carbonyl)-2H-pyrazole-3-carboxylic acid [2-(2-fluoro-pyridin-3-yl)-[1,2,4]triazolo[1,5-a]pyridin-7-yl]-amide

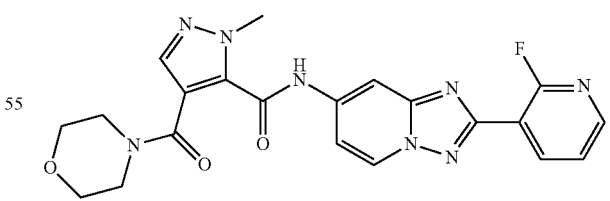

The product was prepared in the same manner as described in example 3 using 5-(2-(2-fluoropyridin-3-yl)-[1,2,4]triazolo[1,5-a]pyridin-7-ylcarbamoyl)-1-methyl-1H-pyrazole-4-carboxylic acid (80 mg, 210 μmol, 1 eq.) and morpholine (54.8 μl, 629 μmol) as starting materials. The reaction affords 2-methyl-4-(morpholine-4-carbonyl)-2H-pyrazole-3-carboxylic acid [2-(2-fluoro-pyridin-3-yl)-[1,2,4]triazolo[1,5-a]

pyridin-7-yl]-amide (48 mg, 50.8%) as white solid. mp: 267-269° C., MS: m/z=451.0 (M+H⁺).

Example 112

2-Methyl-4-(2-oxa-6-aza-spiro[3.3]heptane-6-carbonyl)-2H-pyrazole-3-carboxylic acid (2-morpholin-4-yl-[1,2,4]triazolo[1,5-a]pyridin-7-yl)-amide

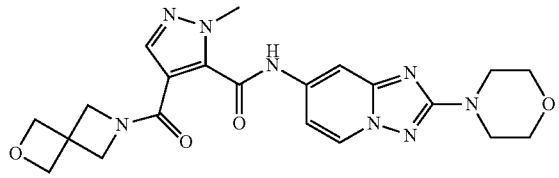 [SMILES: Cn1ncc(C(=O)N2CC3(COC3)C2)c1C(=O)Nc1ccn2nc(N3CCOCC3)nc2c1]

The product was prepared in the same manner as described in example 43 using 1-methyl-5-(2-morpholino-[1,2,4]triazolo[1,5-a]pyridin-7-ylcarbamoyl)-1H-pyrazole-4-carboxylic acid (60 mg, 162 µmol) and 2-oxa-6-azaspiro[3.3]heptane hemioxalate (69.9 mg, 242 µmol) as starting materials. The reaction affords 2-methyl-4-(2-oxa-6-aza-spiro[3.3]heptane-6-carbonyl)-2H-pyrazole-3-carboxylic acid (2-morpholin-4-yl-[1,2,4]triazolo[1,5-a]pyridin-7-yl)-amide (16.7 mg, 22.8%) as white solid. mp: >300° C., MS: m/z=453.0 (M+H⁺).

Example 113

2-Methyl-2H-pyrazole-3,4-dicarboxylic acid 4-cyclopropylamide 3-[(2-morpholin-4-yl-[1,2,4]triazolo[1,5-a]pyridin-7-yl)-amide]

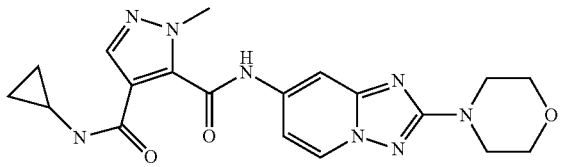 [SMILES: Cn1ncc(C(=O)NC2CC2)c1C(=O)Nc1ccn2nc(N3CCOCC3)nc2c1]

The product was prepared in the same manner as described in example 43 using 1-methyl-5-(2-morpholino-[1,2,4]triazolo[1,5-a]pyridin-7-ylcarbamoyl)-1H-pyrazole-4-carboxylic acid (80 mg, 215 µmol) and cyclopropanamine (45.3 µl, 646 µmol) as starting materials. The reaction affords 2-methyl-2H-pyrazole-3,4-dicarboxylic acid 4-cyclopropylamide 3-[(2-morpholin-4-yl-[1,2,4]triazolo[1,5-a]pyridin-7-yl)-amide] (30.8 mg, 34.8%) as off-white solid. mp: decompose >250° C., MS: m/z=411.4 (M+H⁺).

Example 114

4-(3-Fluoro-azetidine-1-carbonyl)-2-methyl-2H-pyrazole-3-carboxylic acid {2-[(2-fluoro-ethyl)-methyl-amino]-[1,2,4]triazolo[1,5-a]pyridin-7-yl}-amide

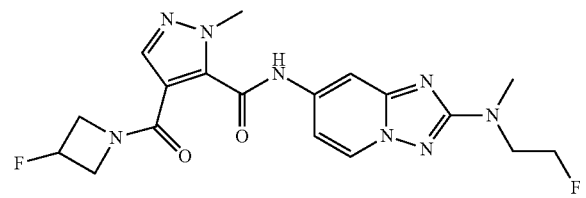 [SMILES: CN(CCF)c1nc2cc(NC(=O)c3c(C(=O)N4CC(F)C4)cnn3C)ccn2n1]

The product was prepared in the same manner as described in example 70f using 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol) and 3-fluoroazetidine hydrochloride (92.6 mg, 830 µmol) as starting materials. The reaction affords 4-(3-fluoro-azetidine-1-carbonyl)-2-methyl-2H-pyrazole-3-carboxylic acid {2-[(2-fluoro-ethyl)-methyl-amino]-[1,2,4]triazolo[1,5-a]pyridin-7-yl}-amide (98.2 mg, 84.8%) as white solid. mp: 233-236° C., MS: m/z=419.0 (M+H⁺).

Example 115

2-Methyl-4-(pyrrolidine-1-carbonyl)-2H-pyrazole-3-carboxylic acid {2-[(2-fluoro-ethyl)-methyl-amino]-[1,2,4]triazolo[1,5-a]pyridin-7-yl}-amide

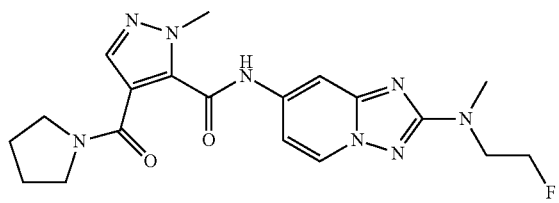 [SMILES: CN(CCF)c1nc2cc(NC(=O)c3c(C(=O)N4CCCC4)cnn3C)ccn2n1]

The product was prepared in the same manner as described in example 70f using 5-(2-((2-fluoroethyl)(methyl)amino)-[1,2,4]triazolo[1,5-a]pyridin-7-ylcarbamoyl)-1-methyl-1H-pyrazole-4-carboxylic acid (100 mg, 277 µmol) and pyrrolidine (68.7 µl, 830 µmol) as starting materials. The reaction affords 2-methyl-4-(pyrrolidine-1-carbonyl)-2H-pyrazole-3-carboxylic acid {2-[(2-fluoro-ethyl)-methyl-amino]-[1,2,4]triazolo[1,5-a]pyridin-7-yl}-amide (96.8 mg, 84.4%) as white solid. MS: m/z=415.0 (M+H⁺).

Example 116

2-Methyl-2H-pyrazole-3,4-dicarboxylic acid 4-(ethyl-methyl-amide)3-[(2-pyridin-3-yl-[1,2,4]triazolo[1,5-a]pyridin-7-yl)-amide]

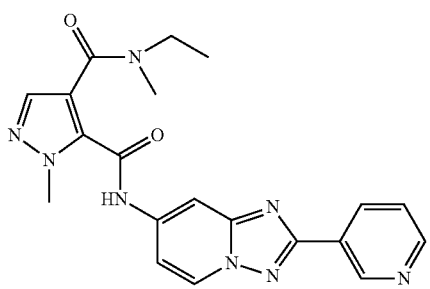 [SMILES: CCN(C)C(=O)c1cnn(C)c1C(=O)Nc1ccn2nc(-c3cccnc3)nc2c1]

The product was prepared in the same manner as described in example 45 using 1-methyl-5-(2-(pyridin-3-yl)-[1,2,4]triazolo[1,5-a]pyridin-7-ylcarbamoyl)-1H-pyrazole-4-carboxylic acid (77 mg, 172 µmol) and N-methylethanamine (59.1 µl, 687 µmol) as starting materials. The reaction affords 2-methyl-2H-pyrazole-3,4-dicarboxylic acid 4-(ethyl-methyl-amide)3-[(2-pyridin-3-yl-[1,2,4]triazolo[1,5-a]pyridin-7-yl)-amide] (7.1 mg, 10.2%) as white solid. MS: m/z=405.4 (M+H⁺).

Example 117

N-(2-(2-fluoropyridin-4-yl)-[1,2,4]triazolo[1,5-a]pyridin-7-yl)-1-methyl-4-(morpholine-4-carbonyl)-1H-pyrazole-5-carboxamide

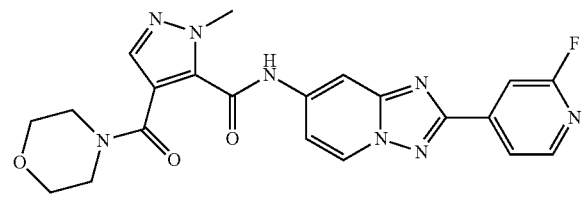 [SMILES: Cn1ncc(C(=O)N2CCOCC2)c1C(=O)Nc1ccn2nc(-c3ccnc(F)c3)nc2c1]

a) 7-bromo-2-(2-fluoropyridin-4-yl)-[1,2,4]triazolo[1,5-a]pyridine

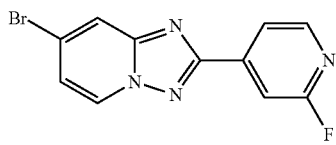 [SMILES: Fc1cc(-c2nc3cc(Br)ccn3n2)ccn1]

The product was prepared in the same manner as described in example 1b using 1,2-diamino-4-bromopyridinium 2,4,6-trimethylbenzenesulfonate (2.2 g, 5.67 mmol) and 2-fluoroisonicotinoyl chloride (1.81 g, 11.3 mmol) as starting materials. The reaction affords 7-bromo-2-(2-fluoropyridin-4-yl)-[1,2,4]triazolo[1,5-a]pyridine (1.29 g, 77.7%) as white powder. MS: m/z=294.9 (M+H⁺).

b) [2-(2-Fluoro-pyridin-4-yl)-[1,2,4]triazolo[1,5-a]pyridin-7-yl]-carbamic acid tert-butyl ester

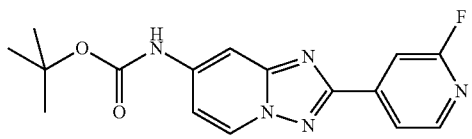 [SMILES: CC(C)(C)OC(=O)Nc1ccn2nc(-c3ccnc(F)c3)nc2c1]

The product was prepared in the same manner as described in example 1c using 7-bromo-2-(2-fluoropyridin-4-yl)-[1,2,4]triazolo[1,5-a]pyridine (1.2 g, 4.09 mmol) and tert-butyl carbamate (576 mg, 4.91 mmol) as starting materials. The reaction affords [2-(2-fluoro-pyridin-4-yl)-[1,2,4]triazolo[1,5-a]pyridin-7-yl]-carbamic acid tert-butyl ester (1.126 mg, 83.5%) as light brown powder. MS: m/z=330.0 (M+H⁺).

c) 2-(2-Fluoro-pyridin-4-yl)-[1,2,4]triazolo[1,5-a]pyridin-7-ylamine

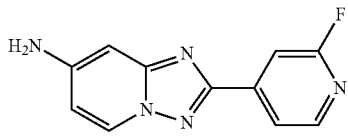 [SMILES: Nc1ccn2nc(-c3ccnc(F)c3)nc2c1]

The product was prepared in the same manner as described in example 1d using tert-butyl 2-(2-fluoropyridin-4-yl)-[1,2,4]triazolo[1,5-a]pyridin-7-ylcarbamate (1.1 g, 3.34 mmol) as starting material. The reaction affords 2-(2-fluoro-pyridin-4-yl)-[1,2,4]triazolo[1,5-a]pyridin-7-ylamine (512 mg, 66.9%) as light yellow powder. MS: m/z=230.1 (M+H⁺).

d) 5-[2-(2-Fluoro-pyridin-4-yl)-[1,2,4]triazolo[1,5-a]pyridin-7-ylcarbamoyl]-1-methyl-1H-pyrazole-4-carboxylic acid ethyl ester

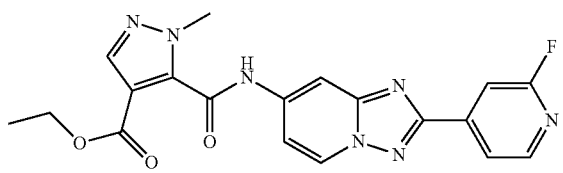

The product was prepared in the same manner as described in example 44d using 2-(2-fluoropyridin-4-yl)-[1,2,4]triazolo[1,5-a]pyridin-7-amine (0.5 g, 2.18 mmol) and 4-(ethoxycarbonyl)-1-methyl-1H-pyrazole-5-carboxylic acid (519 mg, 2.62 mmol) as starting materials. The reaction affords 5-[2-(2-fluoro-pyridin-4-yl)-[1,2,4]triazolo[1,5-a]pyridin-7-ylcarbamoyl]-1-methyl-1H-pyrazole-4-carboxylic acid ethyl ester (585 mg, 65.5%) as white solid. mp.: 220-230° C., MS: m/z=410.0 (M+H⁺).

e) 5-[2-(2-Fluoro-pyridin-4-yl)-[1,2,4]triazolo[1,5-a]pyridin-7-ylcarbamoyl]-1-methyl-1H-pyrazole-4-carboxylic acid

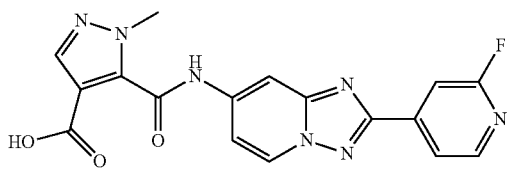 [SMILES: Cn1ncc(C(=O)O)c1C(=O)Nc1ccn2nc(-c3ccnc(F)c3)nc2c1]

The product was prepared in the same manner as described in example 35 h using ethyl 5-(2-(2-fluoropyridin-4-yl)-[1,2,4]triazolo[1,5-a]pyridin-7-ylcarbamoyl)-1-methyl-1H-pyrazole-4-carboxylate (520 mg, 1.27 mmol) as starting material. The reaction affords 5-[2-(2-fluoro-pyridin-4-yl)-[1,2,4]triazolo[1,5-a]pyridin-7-ylcarbamoyl]-1-methyl-1H-pyrazole- 4-carboxylic acid (300 mg, 61.9%) as light brown solid. mp.: >290° C., MS: m/z=382 (M+H⁺).

f) 2-Methyl-4-(morpholine-4-carbonyl)-2H-pyrazole-3-carboxylic acid [2-(2-fluoro-pyridin-4-yl)-[1,2,4]triazolo[1,5-a]pyridin-7-yl]-amide}

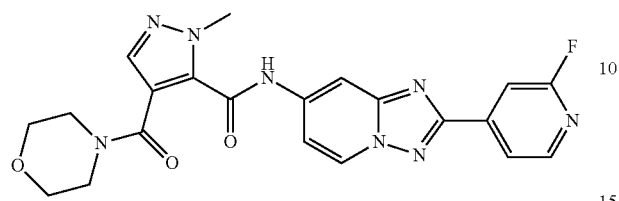

The product was prepared in the same manner as described in example 3 using 5-(2-(2-fluoropyridin-4-yl)-[1,2,4]triazolo[1,5-a]pyridin-7-ylcarbamoyl)-1-methyl-1H-pyrazole-4-carboxylic acid (60 mg, 157 µmol) and morpholine (41.1 µl, 472 µmol) as starting materials. The reaction affords 2-methyl-4-(morpholine-4-carbonyl)-2H-pyrazole-3-carboxylic acid [2-(2-fluoro-pyridin-4-yl)-[1,2,4]triazolo[1,5-a]pyridin-7-yl]-amide (33 mg, 46.6%) as white solid. mp: >280° C., MS: m/z=451.1 (M+H⁺).

Example 118

4-(Azetidine-1-carbonyl)-2-methyl-2H-pyrazole-3-carboxylic acid [2-(2-fluoro-pyridin-4-yl)-[1,2,4]triazolo[1,5-a]pyridin-7-yl]-amide

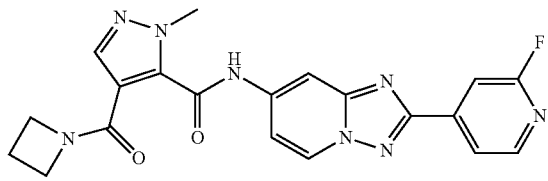 [SMILES: Cn1ncc(C(=O)N2CCC2)c1C(=O)Nc1ccn2nc(-c3ccnc(F)c3)nc2c1]

The product was prepared in the same manner as described in example 3 using 5-(2-(2-fluoropyridin-4-yl)-[1,2,4]triazolo[1,5-a]pyridin-7-ylcarbamoyl)-1-methyl-1H-pyrazole-4-carboxylic acid (60 mg, 157 µmol) and azetidine (27.0 mg, 472 µmol) as starting materials. The reaction affords 4-(azetidine-1-carbonyl)-2-methyl-2H-pyrazole-3-carboxylic acid [2-(2-fluoro-pyridin-4-yl)-[1,2,4]triazolo[1,5-a]pyridin-7-yl]-amide (48.8 mg, 73.8%) as white solid. mp: >280° C., MS: m/z=421.0 (M+H⁺).

Example 119

4-(Azetidine-1-carbonyl)-2-methyl-2H-pyrazole-3-carboxylic acid [2-(6-fluoro-pyridin-2-yl)-[1,2,4]triazolo[1,5-a]pyridin-7-yl]-amide

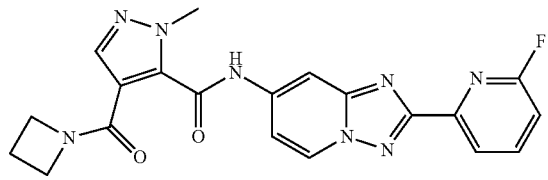 [SMILES: Cn1ncc(C(=O)N2CCC2)c1C(=O)Nc1ccn2nc(-c3cccc(F)n3)nc2c1]

a) 7-Bromo-2-(6-fluoro-pyridin-2-yl)-[1,2,4]triazolo[1,5-a]pyridine

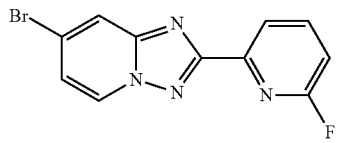 [SMILES: Fc1cccc(-c2nc3cc(Br)ccn3n2)n1]

The product was prepared in the same manner as described in example 1b using 1,2-diamino-4-bromopyridinium 2,4,6-trimethylbenzenesulfonate (2.24 g, 5.77 mmol) and 6-fluoropicolinoyl chloride (1.84 g, 11.5 mmol) as starting materials. The reaction affords 7-bromo-2-(6-fluoro-pyridin-2-yl)-[1,2,4]triazolo[1,5-a]pyridine (1.44 g, 85.4%) as brown solid. MS: m/z=294.9 (M+H⁺).

b) [2-(6-Fluoro-pyridin-2-yl)-[1,2,4]triazolo[1,5-a]pyridin-7-yl]-carbamic acid tert-butyl ester

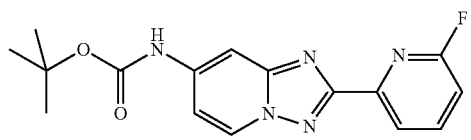 [SMILES: CC(C)(C)OC(=O)Nc1ccn2nc(-c3cccc(F)n3)nc2c1]

The product was prepared in the same manner as described in example 1c using 7-bromo-2-(6-fluoropyridin-2-yl)-[1,2,4]triazolo[1,5-a]pyridine (1.44 g, 4.91 mmol) and tert-butyl carbamate (691 mg, 5.9 mmol) as starting materials. The reaction affords [2-(6-fluoro-pyridin-2-yl)-[1,2,4]triazolo[1,5-a]pyridin-7-yl]-carbamic acid tert-butyl ester (526 mg, 32.5%), as off-white crystals. MS: m/z=330.0 (M+H⁺).

c) 2-(6-Fluoro-pyridin-2-yl)-[1,2,4]triazolo[1,5-a]pyridin-7-ylamine

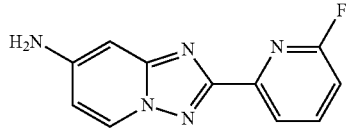

The product was prepared in the same manner as described in example 1d using tert-butyl 2-(6-fluoropyridin-2-yl)-[1,2,4]triazolo[1,5-a]pyridin-7-ylcarbamate (520 mg, 1.58 mmol) as starting material. The reaction affords 2-(6-fluoro-pyridin-2-yl)-[1,2,4]triazolo[1,5-a]pyridin-7-ylamine (350 mg, 96.7%) as white solid. MS: m/z=230.1 (M+H⁺).

d) 5-[2-(6-Fluoro-pyridin-2-yl)-[1,2,4]triazolo[1,5-a]pyridin-7-ylcarbamoyl]-1-methyl-1H-pyrazole-4-carboxylic acid ethyl ester

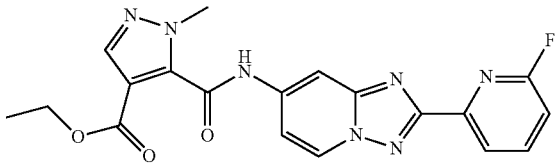 [SMILES: CCOC(=O)c1cnn(C)c1C(=O)Nc1ccn2nc(-c3cccc(F)n3)nc2c1]

The product was prepared in the same manner as described in example 44d using 2-(6-fluoropyridin-2-yl)-[1,2,4]triazolo[1,5-a]pyridin-7-amine (350 mg, 1.53 mmol) and 4-(ethoxycarbonyl)-1-methyl-1H-pyrazole-5-carboxylic acid (363 mg, 1.83 mmol) as starting materials. The reaction affords 5-[2-(6-fluoro-pyridin-2-yl)-[1,2,4]triazolo[1,5-a]pyridin-7-ylcarbamoyl]-1-methyl-1H-pyrazole-4-carboxylic acid ethyl ester (253.1 mg, 40.5%) as white solid. mp.: 290° C., MS: m/z=410.0 (M+H$^+$).

e) 5-[2-(6-Fluoro-pyridin-2-yl)-[1,2,4]triazolo[1,5-a]pyridin-7-ylcarbamoyl]-1-methyl-1H-pyrazole-4-carboxylic acid

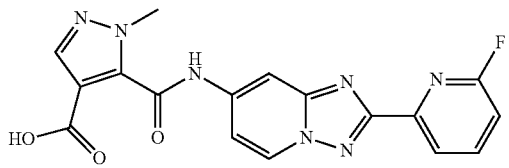 [SMILES: Cn1ncc(C(=O)O)c1C(=O)Nc1ccn2nc(-c3cccc(F)n3)nc2c1]

The product was prepared in the same manner as described in example 35 h using ethyl 5-(2-(6-fluoropyridin-2-yl)-[1,2,4]triazolo[1,5-a]pyridin-7-ylcarbamoyl)-1-methyl-1H-pyrazole-4-carboxylate (253.1 mg, 618 µmol) as starting material. The reaction affords 5-[2-(6-fluoro-pyridin-2-yl)-[1,2,4]triazolo[1,5-a]pyridin-7-ylcarbamoyl]-1-methyl-1H-pyrazole-4-carboxylic acid (192.2 mg, 81.5%) as white solid. mp.: >290° C., MS: m/z=382.1 (M+H$^+$).

f) 4-(Azetidine-1-carbonyl)-2-methyl-2H-pyrazole-3-carboxylic acid [2-(6-fluoro-pyridin-2-yl)-[1,2,4]triazolo[1,5-a]pyridin-7-yl]-amide

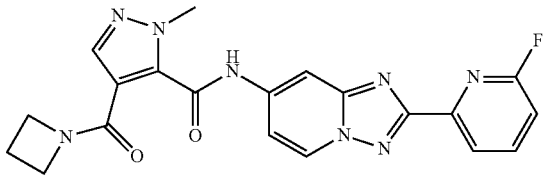 [SMILES: Cn1ncc(C(=O)N2CCC2)c1C(=O)Nc1ccn2nc(-c3cccc(F)n3)nc2c1]

The product was prepared in the same manner as described in example 3 using 5-(2-(6-fluoropyridin-2-yl)-[1,2,4]triazolo[1,5-a]pyridin-7-ylcarbamoyl)-1-methyl-1H-pyrazole-4-carboxylic acid (60 mg, 157 µmol) and azetidine (27.0 mg, 472 µmol) as starting materials. The reaction affords 4-(azetidine-1-carbonyl)-2-methyl-2H-pyrazole-3-carboxylic acid [2-(6-fluoropyridin-2-yl)-[1,2,4]triazolo[1,5-a]pyridin-7-yl]-amide (48 mg, 72.6%) as white solid. mp: 263.9° C., MS: m/z=421.0 (M+H$^+$).

Example 120

2-Methyl-2H-pyrazole-3,4-dicarboxylic acid 4-dimethylamide 3-{[2-(6-fluoro-pyridin-2-yl)-[1,2,4]triazolo[1,5-a]pyridin-7-yl]-amide}

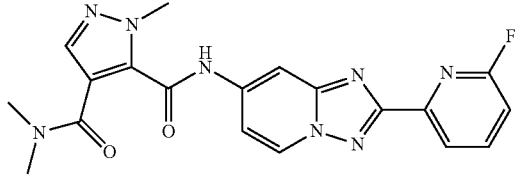 [SMILES: CN(C)C(=O)c1cnn(C)c1C(=O)Nc1ccn2nc(-c3cccc(F)n3)nc2c1]

The product was prepared in the same manner as described in example 3 using 5-(2-(6-fluoropyridin-2-yl)-[1,2,4]triazolo[1,5-a]pyridin-7-ylcarbamoyl)-1-methyl-1H-pyrazole-4-carboxylic acid (60 mg, 157 µmol) and dimethylamine (21.3 mg, 472 µmol) as starting materials. The reaction affords 2-methyl-2H-pyrazole-3,4-dicarboxylic acid 4-dimethylamide 3-{[2-(6-fluoro-pyridin-2-yl)-[1,2,4]triazolo[1,5-a]pyridin-7-yl]-amide} (33.3 mg, 51.8%) as white solid. mp: 264.4° C., MS: m/z=409.1 (M+H$^+$).

Example 121

2-Methyl-4-(morpholine-4-carbonyl)-2H-pyrazole-3-carboxylic acid [2-(6-fluoro-pyridin-2-yl)-[1,2,4]triazolo[1,5-a]pyridin-7-yl]-amide

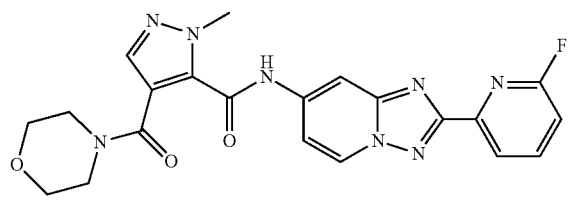 [SMILES: Cn1ncc(C(=O)N2CCOCC2)c1C(=O)Nc1ccn2nc(-c3cccc(F)n3)nc2c1]

The product was prepared in the same manner as described in example 3 using 5-(2-(6-fluoropyridin-2-yl)-[1,2,4]triazolo[1,5-a]pyridin-7-ylcarbamoyl)-1-methyl-1H-pyrazole-4-carboxylic acid (60 mg, 157 µmol) and morpholine (41.1 mg, 472 µmol) as starting materials. The reaction affords 2-methyl-4-(morpholine-4-carbonyl)-2H-pyrazole-3-carboxylic acid [2-(6-fluoropyridin-2-yl)-[1,2,4]triazolo[1,5-a]pyridin-7-yl]-amide (54.9 mg, 77.5%) as white solid. MS: m/z=451.0 (M+H$^+$).

Example 122

2-Methyl-4-(2-oxa-6-aza-spiro[3.3]heptane-6-carbonyl)-2H-pyrazole-3-carboxylic acid (2-pyrrolidin-1-yl-[1,2,4]triazolo[1,5-a]pyridin-7-yl)-amide

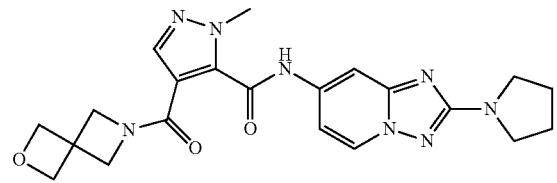 [SMILES: Cn1ncc(C(=O)N2CC3(COC3)C2)c1C(=O)Nc1ccn2nc(N3CCCC3)nc2c1]

The product was prepared in the same manner as described in example 60f using 1-methyl-5-(2-(pyrrolidin-1-yl)-[1,2,4]triazolo[1,5-a]pyridin-7-ylcarbamoyl)-1H-pyrazole-4-carboxylic acid (75 mg, 211 µmol) and 2-oxa-6-azaspiro[3.3]heptane hemioxalate (30.4 mg, 106 mmol) as starting materials. The reaction affords 2-methyl-4-(2-oxa-6-azaspiro[3.3]heptane-6-carbonyl)-2H-pyrazole-3-carboxylic acid (2-pyrrolidin-1-yl-[1,2,4]triazolo[1,5-a]pyridin-7-yl)-amide (14.5 mg, 15.7%) as off-white solid. MS: m/z=437.5 (M+H⁺).

Example 123

2-Methyl-2H-pyrazole-3,4-dicarboxylic acid 4-(cyclopropyl-methyl-amide)3-[(2-pyrrolidin-1-yl-[1,2,4]triazolo[1,5-a]pyridin-7-yl)-amide]

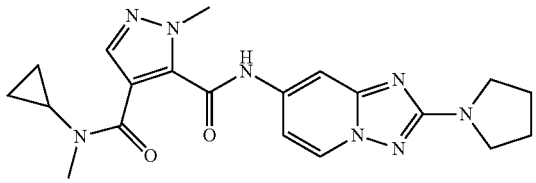 [SMILES: CN(C(=O)c1cnn(C)c1C(=O)Nc1ccn2nc(N3CCCC3)nc2c1)C1CC1]

The product was prepared in the same manner as described in example 60f using 1-methyl-5-(2-(pyrrolidin-1-yl)-[1,2,4]triazolo[1,5-a]pyridin-7-ylcarbamoyl)-1H-pyrazole-4-carboxylic acid (75 mg, 211 µmol) and N-methylcyclopropanamine (15 mg, 211 µmol) as starting materials. The reaction affords 2-methyl-2H-pyrazole-3,4-dicarboxylic acid 4-(cyclopropyl-methyl-amide) 3-[(2-pyrrolidin-1-yl-[1,2,4]triazolo[1,5-a]pyridin-7-yl)-amide] (19.8 mg, 23%) as off-white solid. mp: 274.3° C., MS: m/z=409.1 (M+H⁺).

Example 124

2-Methyl-2H-pyrazole-3,4-dicarboxylic acid 4-(ethyl-methyl-amide)3-[(2-pyrrolidin-1-yl-[1,2,4]triazolo[1,5-a]pyridin-7-yl)-amide]

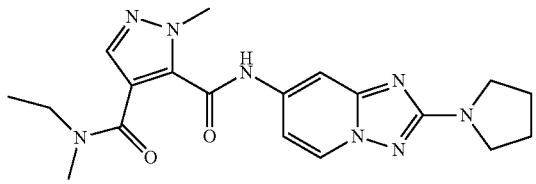 [SMILES: CCN(C)C(=O)c1cnn(C)c1C(=O)Nc1ccn2nc(N3CCCC3)nc2c1]

The product was prepared in the same manner as described in example 60f using 1-methyl-5-(2-(pyrrolidin-1-yl)-[1,2,4]triazolo[1,5-a]pyridin-7-ylcarbamoyl)-1H-pyrazole-4-carboxylic acid (75 mg, 211 µmol) and N-methylethanamine (12.5 mg, 211 µmol) as starting materials. The reaction affords 2-methyl-2H-pyrazole-3,4-dicarboxylic acid 4-(ethyl-methyl-amide)3-[(2-pyrrolidin-1-yl-[1,2,4]triazolo[1,5-a]pyridin-7-yl)-amide] (10.3 mg, 12.3%) as off-white solid. mp: 323.1° C., MS: m/z=397.1 (M+H⁺).

Example 125

5-[2-(Cyclopropyl-methyl-amino)-[1,2,4]triazolo[1,5-a]pyridin-7-ylcarbamoyl]-1-methyl-1H-pyrazole-4-carboxylic acid

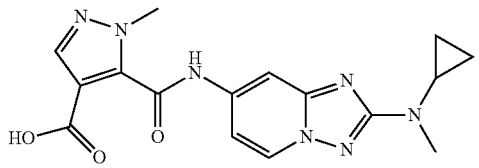 [SMILES: CN(c1nc2cc(NC(=O)c3c(C(=O)O)cnn3C)ccn2n1)C1CC1]

a) (7-Bromo-[1,2,4]triazolo[1,5-a]pyridin-2-yl)-cyclopropyl-methyl-amine

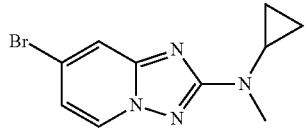

2,7-dibromo-[1,2,4]triazolo[1,5-a]pyridine (1.5 g, 5.42 mmol) was refluxed in N-methylcyclopropanamine (3.85 g, 54.2 mmol) for 4 h. The solvent was evaporated and the residue was diluted with ethyl acetate and washed with water and brine. The organic layer was dried over magnesium sulfate, filtered and applied on SiO2. Column chromatography over 70 g SiO2 using heptane/ethyl acetate affords (7-bromo-[1,2,4]triazolo[1,5-a]pyridin-2-yl)-cyclopropyl-methyl-amine (593 mg, 41%) as white powder. MS: m/z=397.1 (M+H⁺).

b) [2-(Cyclopropyl-methyl-amino)-[1,2,4]triazolo[1,5-a]pyridin-7-yl]-carbamic acid tert-butyl ester

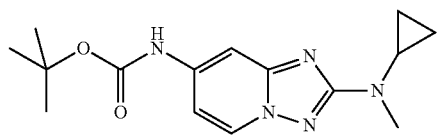 [SMILES: CN(c1nc2cc(NC(=O)OC(C)(C)C)ccn2n1)C1CC1]

The product was prepared in the same manner as described in example 8e using 7-bromo-N-cyclopropyl-N-methyl-[1,2,4]triazolo[1,5-a]pyridin-2-amine (540 mg, 2.02 mmol) and tert-butyl carbamate (284 mg, 2.43 mmol) as starting materials. The reaction affords [2-(cyclopropyl-methyl-amino)-[1,2,4]triazolo[1,5-a]pyridin-7-yl]-carbamic acid tert-butyl ester (338 mg, 55.03%) as light yellow crystals. mp: 323.1° C., MS: m/z=397.1 (M+H⁺).

b) 2-(Cyclopropyl-methyl-amino)-[1,2,4]triazolo[1,5-a]pyridin-7-yl-ammonium hydrochloride

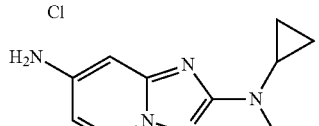

The product was prepared in the same manner as described in example 8f using tert-butyl 2-(cyclopropyl(methyl)amino)-[1,2,4]triazolo[1,5-a]pyridin-7-ylcarbamate (330 mg, 1.09 mmol) as starting material. The reaction affords 2-(cyclopropyl-methyl-amino)-[1,2,4]triazolo[1,5-a]pyridin-7-yl-ammonium hydrochloride (261 mg, 100%) as light brown solid. mp: 222.6° C., MS: m/z=397.1 (M+H⁺).

c) 5-[2-(Cyclopropyl-methyl-amino)-[1,2,4]triazolo[1,5-a]pyridin-7-ylcarbamoyl]-1-methyl-1H-pyrazole-4-carboxylic acid ethyl ester

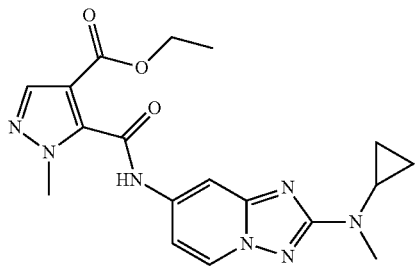 [SMILES: CCOC(=O)c1cnn(C)c1C(=O)Nc1ccn2nc(N(C)C3CC3)nc2c1]

A mixture of 2-(cyclopropyl(methyl)amino)-[1,2,4]triazolo[1,5-a]pyridin-7-ammonium chloride (260 mg, 1.08 mmol), 4-(ethoxycarbonyl)-1-methyl-1H-pyrazole-5-carboxylic acid (258 mg, 1.3 mmol), propylphosphonic anhydride (50% in ethyl acetate, 1.6 ml, 2.71 mmol) and N,N-diisopropylethylamine (738 μl, 4.34 mmol) in tetrahydrofuran (12 ml) was refluxed for 18 hours. The crude material was applied on SiO2 and purified by flash chromatography over a 10 g SiO2 column using ethyl acetate 100% as eluent. The reaction affords 5-[2-(cyclopropyl-methyl-amino)-[1,2,4]triazolo[1,5-a]pyridin-7-ylcarbamoyl]-1-methyl-1H-pyrazole-4-carboxylic acid ethyl ester (333 mg, 80.1%) as light yellow solid. mp: 210.1, MS: m/z=384.4 (M+H+).

d) 5-[2-(Cyclopropyl-methyl-amino)-[1,2,4]triazolo[1,5-a]pyridin-7-ylcarbamoyl]-1-methyl-1H-pyrazole-4-carboxylic acid

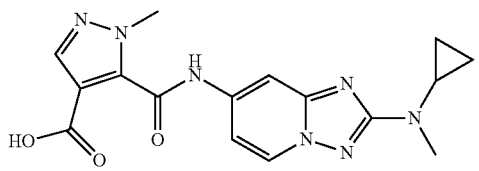 [SMILES: CN(c1nc2cc(NC(=O)c3c(C(=O)O)cnn3C)ccn2n1)C1CC1]

The product was prepared in the same manner as described in example 35h using ethyl 5-(2-(cyclopropyl(methyl)amino)-[1,2,4]triazolo[1,5-a]pyridin-7-ylcarbamoyl)-1-methyl-1H-pyrazole-4-carboxylate (325 mg, 848 μmol) as starting material. The reaction affords 5-[2-(cyclopropyl-methyl-amino)-[1,2,4]triazolo[1,5-a]pyridin-7-ylcarbamoyl]-1-methyl-1H-pyrazole-4-carboxylic acid (223 mg, 74%) as off-white solid. MS: m/z=356.3 (M+H+).

Example 126

2-Methyl-2H-pyrazole-3,4-dicarboxylic acid 4-(cyclopropyl-methyl-amide)3-{[2-(cyclopropyl-methyl-amino)-[1,2,4]triazolo[1,5-a]pyridin-7-yl]-amide}

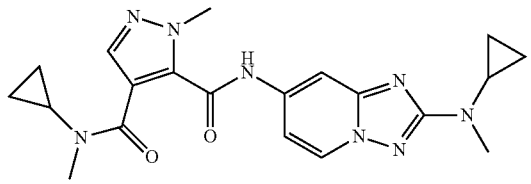 [SMILES: CN(C(=O)c1cnn(C)c1C(=O)Nc1ccn2nc(N(C)C3CC3)nc2c1)C1CC1]

The product was prepared in the same manner as described in example 70f using 5-(2-(cyclopropyl(methyl)amino)-[1,2,4]triazolo[1,5-a]pyridin-7-ylcarbamoyl)-1-methyl-1H-pyrazole-4-carboxylic acid (65 mg, 183 μmol) and N-methylcyclopropanamine (52.0 mg, 732 mmol) as starting materials. The reaction affords 2-methyl-2H-pyrazole-3,4-dicarboxylic acid 4-(cyclopropyl-methyl-amide)3-{[2-(cyclopropyl-methyl-amino)-[1,2,4]triazolo[1,5-a]pyridin-7-yl]-amide} (48 mg, 64.2%) as off-white solid. mp: 164.8, MS: m/z=409.4 (M+H+).

Example 127

4-(Azetidine-1-carbonyl)-2-methyl-2H-pyrazole-3-carboxylic acid [2-(cyclopropyl-methyl-amino)-[1,2,4]triazolo[1,5-a]pyridin-7-yl]-amide

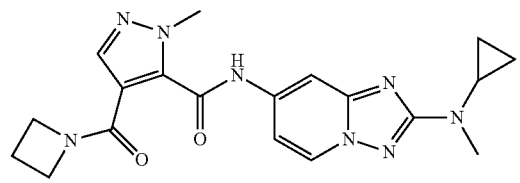 [SMILES: CN(c1nc2cc(NC(=O)c3c(C(=O)N4CCC4)cnn3C)ccn2n1)C1CC1]

The product was prepared in the same manner as described in example 70f using 5-(2-(cyclopropyl(methyl)amino)-[1,2,4]triazolo[1,5-a]pyridin-7-ylcarbamoyl)-1-methyl-1H-pyrazole-4-carboxylic acid (70 mg, 197 μmol) and azetidine (52.9 μl, 788 μmol) as starting materials. The reaction affords 4-(azetidine-1-carbonyl)-2-methyl-2H-pyrazole-3-carboxylic acid [2-(cyclopropyl-methyl-amino)-[1,2,4]triazolo[1,5-a]pyridin-7-yl]-amide (65 mg, 83.7%) as off-white solid. mp: 229.6, MS: m/z=395.0 (M+H+).

Example 128

2-Methyl-4-(morpholine-4-carbonyl)-2H-pyrazole-3-carboxylic acid [2-(cyclopropyl-methyl-amino)-[1,2,4]triazolo[1,5-a]pyridine-7-yl]-amide

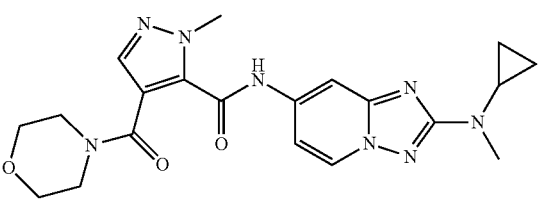 [SMILES: CN(c1nc2cc(NC(=O)c3c(C(=O)N4CCOCC4)cnn3C)ccn2n1)C1CC1]

The product was prepared in the same manner as described in example 4 using 5-(2-(cyclopropyl(methyl)amino)-[1,2,4]triazolo[1,5-a]pyridine-7-ylcarbamoyl)-1-methyl-1H-pyrazole-4-carboxylic acid (70 mg, 197 μmol) and morpholine (68.6 μl, 788 μmol) as starting materials. The reaction affords 2-Methyl-4-(morpholine-4-carbonyl)-2H-pyrazole-3-carboxylic acid [2-(cyclopropyl-methyl-amino)-[1,2,4]triazolo[1,5-a]pyridine-7-yl]-amide (82 mg, 98.1%) as off-white solid. MS: m/z=325.1 (M+H+).

Example 129

4-(1,4-Diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide

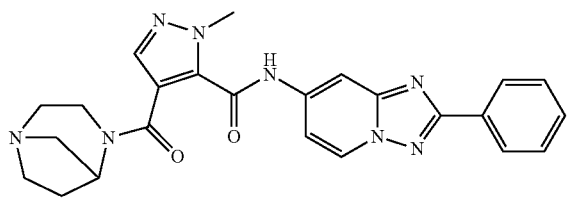 [SMILES: Cn1ncc(C(=O)N2CCN3CCC2C3)c1C(=O)Nc1ccn2nc(-c3ccccc3)nc2c1]

A mixture of 1-methyl-5-(2-phenyl-[1,2,4]triazolo[1,5-a]pyridin-7-ylcarbamoyl)-1H-pyrazole-4-carboxylic acid (100 mg, 276 µmol), 1,4-diazabicyclo[3.2.1]octane dihydrochloride (102 mg, 552 µmol), propylphosphonic anhydride (50% in ethyl acetate, 407 µl, 690 µmol) and N,N-diisopropylethylamine (469 µl, 2.76 mmol) in tetrahydrofuran (4.5 ml) was stirred overnight at 25° C. The mixture was applied on basic silica gel and purified by column chromatography using dichloromethane/methanol 19:1 as eluent to give 4-(1,4-diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide (45 mg, 35.7%) as a white solid. mp: 110.1, MS: m/z=457.2 (M+H$^+$).

Example 130

4-(Azetidine-1-carbonyl)-2-methyl-2H-pyrazole-3-carboxylic acid {2-[2-(2-fluoro-ethoxy)-phenyl]-[1,2,4]triazolo[1,5-a]pyridin-7-yl}-amide

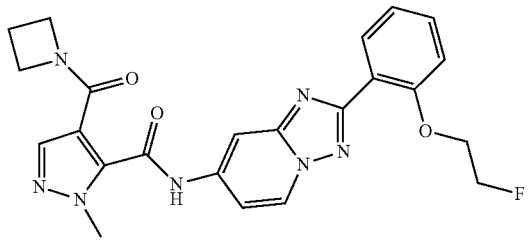 [SMILES: Cn1ncc(C(=O)N2CCC2)c1C(=O)Nc1ccn2nc(-c3ccccc3OCCF)nc2c1]

a) Azetidin-1-yl-(1-methyl-1H-pyrazol-4-yl)-methanone

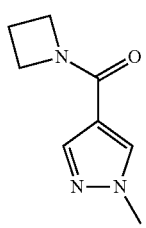

This compound was prepared in analogy to 1-methyl-1H-pyrazole-4-carboxylic acid dimethylamide (Example 97, step a) from 1-methyl-1H-pyrazole-4-carboxylic acid (1.0 g, 7.93 mmol) and azetidine (475 mg, 8.33 mmol). Yield: 1.31 g (92%); light yellow solid; MS: m/z=166.1 ([M+H]$^+$).

b) 4-(Azetidine-1-carbonyl)-2-methyl-2H-pyrazole-3-carboxylic acid

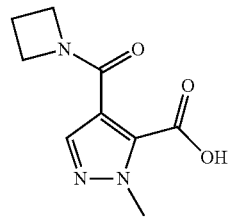

This compound was prepared in analogy to 4-dimethylcarbamoyl-2-methyl-2H-pyrazole-3-carboxylic acid (Example 97, step b) from azetidin-1-yl-(1-methyl-1H-pyrazol-4-yl)-methanone (500 mg, 3.33 mmol). Yield: 548 mg (81%); light red solid; MS: m/z=210.1 ([M+H]$^+$).

c) 4-(Azetidine-1-carbonyl)-2-methyl-2H-pyrazole-3-carboxylic acid {2-[2-(2-fluoro-ethoxy)-phenyl]-[1,2,4]triazolo[1,5-a]pyridin-7-yl}-amide

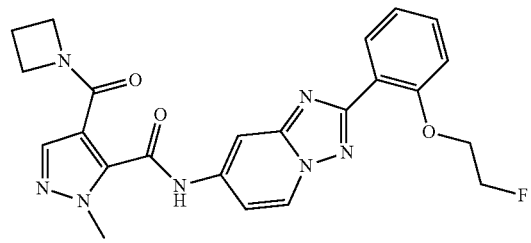 [SMILES: Cn1ncc(C(=O)N2CCC2)c1C(=O)Nc1ccn2nc(-c3ccccc3OCCF)nc2c1]

This compound was prepared in analogy to 2-methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide) (Example 100) from 2-[2-(2-fluoro-ethoxy)-phenyl]-[1,2,4]triazolo[1,5-a]pyridin-7-ylamine (127 mg, 0.47 mmol) and 4-(azetidine-1-carbonyl)-2-methyl-2H-pyrazole-3-carboxylic acid (130 mg, 0.62 mmol). Yield: 95 mg (33%); off-white solid; LC-MS: m/z=464.2 ([M+H]$^+$).

Example 131

2-Methyl-4-(morpholine-4-carbonyl)-2H-pyrazole-3-carboxylic acid {2-[2-(2-fluoro-ethoxy)-phenyl]-[1,2,4]triazolo[1,5-a]pyridin-7-yl}-amide

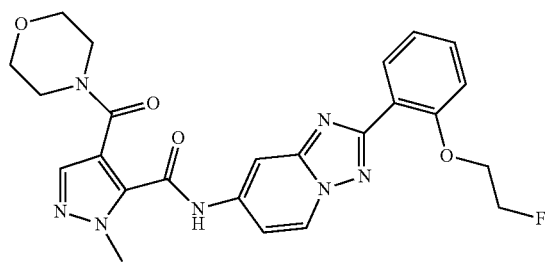 [SMILES: Cn1ncc(C(=O)N2CCOCC2)c1C(=O)Nc1ccn2nc(-c3ccccc3OCCF)nc2c1]

a) (1-Methyl-1H-pyrazol-4-yl)-morpholin-4-yl-methanone

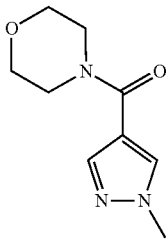

To a solution of 1-methyl-1H-pyrazole-4-carboxylic acid (2.00 g, 15.9 mmol) in DCM (100 ml) and TEA (8.80 ml, 63.5 mmol), EDCHCl (3.65 g, 19.0 mmol) and HOBt (2.57 g, 19.0 mmol) were added under a nitrogen atmosphere at rt and stirred for 30 min. Morpholine (1.68 ml, 19.0 mmol) was then added to the reaction mixture and stirring was continued for 18 h. On completion of reaction (monitored by TLC), the reaction mixture was diluted with water and DCM. The organic layer was separated, dried over $Na_2SO_4$ and concentrated to get the crude product. Column chromatography afforded the desired product as off white solid. Yield: 1.20 g (39%); MS: m/z=196.4 ([M+H]$^+$)

b) 2-Methyl-4-(morpholine-4-carbonyl)-2H-pyrazole-3-carboxylic acid

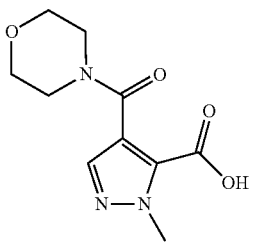 [SMILES: Cn1ncc(C(=O)N2CCOCC2)c1C(=O)O]

This compound was prepared in analogy to 4-dimethylcarbamoyl-2-methyl-2H-pyrazole-3-carboxylic acid (Example 97, step b) from (1-methyl-1H-pyrazol-4-yl)-morpholin-4-yl-methanone (1.20 g, 6.15 mmol). Yield: 1.05 g (71%); off-white solid; MS: m/z=240.2 ([M+H]$^+$)

c) 2-Methyl-4-(morpholine-4-carbonyl)-2H-pyrazole-3-carboxylic acid {2-[2-(2-fluoro-ethoxy)-phenyl]-[1,2,4]triazolo[1,5-a]pyridin-7-yl}-amide

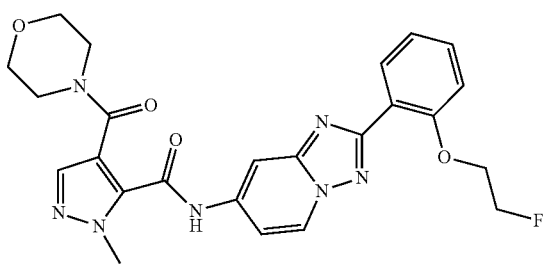 [SMILES: Cn1ncc(C(=O)N2CCOCC2)c1C(=O)Nc1ccn2nc(-c3ccccc3OCCF)nc2c1]

This compound was prepared in analogy to 2-methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide) (Example 100) from 2-[2-(2-fluoro-ethoxy)-phenyl]-[1,2,4]triazolo[1,5-a]pyridin-7-ylamine 104 mg, 0.38 mmol) and 2-methyl-4-(morpholine-4-carbonyl)-2H-pyrazole-3-carboxylic acid (130 mg, 0.54 mmol). Yield: 76 mg (28%); off-white solid; LC-MS: m/z=494.4 (M+H$^+$).

Example 132

2-Methyl-2H-pyrazole-3,4-dicarboxylic acid 3-({2-[2-(2-fluoro-ethoxy)-phenyl]-[1,2,4]triazolo[1,5-a]pyridin-7-yl}-amide) 4-[(2-methoxy-ethyl)-methyl-amide]

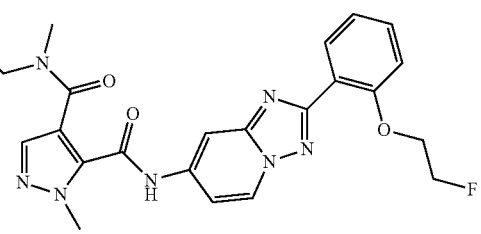

This compound was prepared in analogy to 2-methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide) (Example 100) from 2-[2-(2-fluoro-ethoxy)-phenyl]-[1,2,4]triazolo[1,5-a]pyridin-7-ylamine (110 mg, 0.40 mmol) and 4-[(2-methoxy-ethyl)-methyl-carbamoyl]-2-methyl-2H-pyrazole-3-carboxylic acid (Example 99, step b) (130 mg, 0.54 mmol). Yield: 70 mg (23%); off-white solid; LC-MS: m/z=496.4 ([M+H]$^+$).

Example 133

Methyl-4-(morpholine-4-carbonyl)-N-(2-(2-oxopyrrolidin-1-yl)-[1,2,4]triazolo[1,5-a]pyridin-7-yl)-1H-pyrazole-5-carboxamide

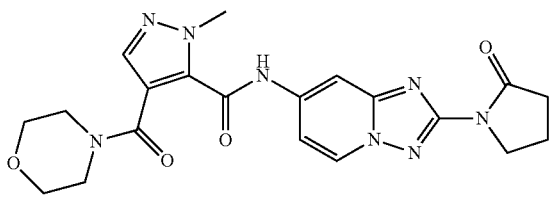 [SMILES: Cn1ncc(C(=O)N2CCOCC2)c1C(=O)Nc1ccn2nc(N3CCCC3=O)nc2c1]

To an argon purged solution of N-(2-bromo-[1,2,4]triazolo[1,5-a]pyridin-7-yl)-1-methyl-4-(morpholine-4-carbonyl)-1H-pyrazole-5-carboxamide (40 mg, 92.1 µmol) in dioxane (1.84 ml) were added pyrrolidin-2-one (8.47 µl, 111 µmol), cesium carbonate (42.0 mg, 129 µmol), tris(dibenzylideneacetone)dipalladium(0) (1.69 mg, 1.84 µmol) and 4,5-bis(diphenylphosphino)-9,9-dimethylxanthene (2.13 mg, 3.68 µmol). The resulting mixture was heated to 100° C. and stirred overnight under argon atmosphere. The crude material was applied on SiO2 and purified by flash chromatography over a 5 g SiO2 column using heptane/ethyl acetate 10-100% to ethyl acetate/methanol 2% as eluent to give 2-methyl-4-

(morpholine-4-carbonyl)-2H-pyrazole-3-carboxylic acid [2-(2-oxo-pyrrolidin-1-yl)-[1,2,4]triazolo[1,5-a]pyridin-7-yl]-amide (23 mg, 57%) as light yellow solid. mp: 269.9, MS: m/z=439.1 (M+H$^+$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:
1. A compound of formula (I)

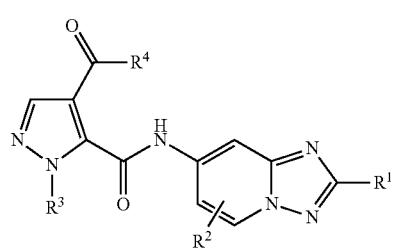

wherein
$R^1$ is halogen, lower-alkyl, lower-haloalkyl, lower-hydroxyalkyl, lower-alkoxy, lower-alkoxy-lower-alkyl, —C(O)—NR$^9$R$^{10}$, aryl, heteroaryl or NR$^7$R$^8$, wherein said aryl and said heteroaryl are each optionally substituted by 1 to 3 substituents independently selected from the group consisting of hydroxyl, halogen, lower-alkyl, lower-alkoxy, lower-alkoxy-lower-alkyl, lower-haloalkyl and lower-haloalkoxy;

R$^2$ is hydrogen, halogen, lower-alkyl, lower-haloalkyl, lower-hydroxyalkyl, lower-alkoxy or lower-alkoxy-lower-alkyl;

R$^3$ is hydrogen, lower-alkyl, lower-haloalkyl, lower-hydroxyalkyl, lower-alkoxy or lower-alkoxy-lower-alkyl;

R$^4$ is hydroxyl, lower-alkoxy or NR$^5$R$^6$;

R$^5$ and R$^6$ are each independently hydrogen, lower-alkyl, lower-haloalkyl, lower-hydroxyalkyl, lower-alkoxy-lower-alkyl, cycloalkyl or heterocyclyl, or R$^5$ and/or R$^6$ are lower-alkyl substituted by a substituent selected from the group consisting of heteroaryl, lower-alkyl-heteroaryl and lower-alkoxy-C(O)—, or R$^5$ and R$^6$, together with the nitrogen atom to which they are attached, form a heterocyclyl, bicyclo-heterocyclyl or spiro-heterocyclyl, wherein said heterocyclyl is optionally substituted by 1 to 3 substituents independently selected from the group consisting of hydroxyl, halogen, lower-alkyl, lower-alkoxy, lower-alkoxy-lower-alkyl, lower-haloalkyl and oxo;

R$^7$ and R$^8$ are each independently hydrogen, lower-alkyl, lower-haloalkyl, lower-hydroxyalkyl, lower-alkoxy-lower-alkyl or cycloalkyl, or R$^7$ and R$^8$, together with the nitrogen atom to which they are attached, form a heterocyclyl optionally substituted by a substituent selected from the group consisting of hydroxyl, halogen and oxo; and R$^9$ and R$^{10}$ are each independently hydrogen, lower-alkyl, lower-haloalkyl, lower-hydroxyalkyl or lower-alkoxy-lower-alkyl, or a pharmaceutically acceptable salt thereof.

2. The compound of claim 1,
wherein
R$^1$ is lower-alkyl, —C(O)—NH-lower-haloalkyl, aryl, heteroaryl or NR$^7$R$^8$, wherein said aryl and said heteroaryl are each optionally substituted by 1 to 3 substituents independently selected from the group consisting of hydroxyl, halogen, lower-alkyl, lower-alkoxy and lower-haloalkyl;

R$^2$ is hydrogen, halogen or lower-alkyl;

R$^3$ is hydrogen or lower-alkyl;

R$^4$ is hydroxyl, lower-alkoxy or NR$^5$R$^6$;

R$^5$ and R$^6$ are each independently hydrogen, lower-alkyl, lower-haloalkyl, lower-alkoxy-lower-alkyl, lower-alkyl substituted by lower-alkyl-heteroaryl, or heterocyclyl, or R$^5$ and R$^6$, together with the nitrogen atom to which they are attached, form a heterocyclyl which is optionally substituted by 1 to 3 substituents independently selected from the group consisting of hydroxyl, halogen, lower-alkyl, lower-alkoxy, lower-haloalkyl and oxo; and R$^7$ and R$^8$ are each independently lower-alkyl or, together with the nitrogen atom to which they are attached, form a morpholinyl ring, or a pharmaceutically acceptable salt thereof.

3. The compound of claim 1, wherein R$^1$ is halogen, lower-alkyl, —C(O)—NR$^9$R$^{10}$, phenyl, pyridinyl or NR$^7$R$^8$, wherein said phenyl and said pyridinyl are each optionally substituted by 1 to 3 substituents independently selected from the group consisting of hydroxyl, halogen, lower-alkyl, lower-alkoxy, lower-haloalkyl and lower-haloalkoxy; R$^7$ and R$^8$ are each independently lower-alkyl, lower-haloalkyl or cycloalkyl, or R$^7$ and R$^8$, together with the nitrogen atom to which they are attached, form pyrrolidin-1-yl, 2-oxopyrrolidin-1-yl or morpholin-4-yl; and R$^9$ and R$^{10}$ are each independently hydrogen, lower-alkyl, lower-haloalkyl or lower-alkoxy-lower-alkyl, or a pharmaceutically acceptable salt thereof.

4. The compound of claim 1, wherein R$^1$ is phenyl, 3-fluorophenyl, 2-methoxyphenyl, 3-methoxy-phenyl, pyridin-3-yl, 2-fluoropyridin-4-yl, dimethylamino, ethyl-methyl-amino cyclopropyl-methyl-amino, pyrrolidin-1-yl or morpholin-4-yl, or a pharmaceutically acceptable salt thereof.

5. The compound of claim 1, wherein R$^2$ is hydrogen, halogen or lower-alkyl, or a pharmaceutically acceptable salt thereof.

6. The compound of claim 5, wherein R$^2$ is hydrogen, or a pharmaceutically acceptable salt thereof.

7. The compound of claim 1, wherein R$^3$ is methyl, or a pharmaceutically acceptable salt thereof.

8. The compound of claim 1,
wherein
R$^4$ is hydroxyl, lower-alkoxy or NR$^5$R$^6$;
R$^5$ and R$^6$ are each independently hydrogen, lower-alkyl, lower-haloalkyl, lower-hydroxyalkyl, lower-alkoxy-lower-alkyl, cyclopropyl, cyclopentyl, oxetanyl or tetrahydrofuranyl, or R$^5$ and/or R$^6$ are lower-alkyl substituted by a substituent selected from the group consisting of lower-alkyl-pyridinyl and methoxycarbonyl, or R$^5$ and R$^6$, together with the nitrogen atom to which they are attached, form a heterocyclyl selected from the group consisting of azetidinyl, pyrrolidinyl, piperazinyl, morpholinyl and thiomorpholinyl, wherein said heterocyclyl is optionally substituted by 1 to 3 substituents independently selected from the group consisting of halogen, lower-alkyl, lower-alkoxy and oxo, or R$^5$ and R$^6$, together with the nitrogen atom to which they are attached, form 2-oxa-5-azabicyclo[2.2.1]heptanyl, 2-oxa-6-azaspiro[3.3]heptanyl or 1,4-diaza-bicyclo[3.2.1]octanyl, or a pharmaceutically acceptable salt thereof.

9. The compound of claim 8, wherein
R$^4$ is NR$^5$R$^6$;
R$^5$ and R$^6$ are each independently methyl, ethyl, 2-fluoroethyl, 2-methoxyethyl or cyclopropyl, or
R$^5$ and R$^6$, together with the nitrogen atom to which they are attached, form a heterocyclyl selected from the group consisting of azetidinyl, 3-fluoroazetidinyl, morpholin-4-yl and pyrrolidinyl, or R$^5$ and R$^6$, together with the nitrogen atom to which they are attached, form 2-oxa-6-azaspiro[3.3]heptanyl or 1,4-diaza-bicyclo[3.2.1]octanyl, or a pharmaceutically acceptable salt thereof.

10. The compound of claim 1, selected from the group consisting of:
methyl 1-methyl-5-(2-phenyl-[1,2,4]triazolo[1,5-a]pyridin-7-ylcarbamoyl)-1H-pyrazole-4-carboxylate,
1-methyl-5-(2-phenyl-[1,2,4]triazolo[1,5-a]pyridin-7-ylcarbamoyl)-1H-pyrazole-4-carboxylic acid,
4-(azetidine-1-carbonyl)-1-methyl-N-(2-phenyl-[1,2,4]triazolo[1,5-a]pyridin-7-yl)-1H-pyrazole-5-carboxamide,
N4-(2-methoxyethyl)-N4,1-dimethyl-N5-(2-phenyl-[1,2,4]triazolo[1,5-a]pyridin-7-yl)-1H-pyrazole-4,5-dicarboxamide,
N4-ethyl-N4,1-dimethyl-N5-(2-phenyl-[1,2,4]triazolo[1,5-a]pyridin-7-yl)-1H-pyrazole-4,5-dicarboxamide, N4,N4-bis(2-methoxyethyl)-1-methyl-N5-(2-phenyl-[1,
  2,4]triazolo[1,5-a]pyridin-7-yl)-1H-pyrazole-4,5-di-
  carboxamide,
N4-ethyl-1-methyl-N5-(2-phenyl-[1,2,4]triazolo[1,5-a]
  pyridin-7-yl)-1H-pyrazole-4,5-dicarboxamide,
4-(azetidine-1-carbonyl)-1-methyl-N-(2-morpholino-[1,
  2,4]triazolo[1,5-a]pyridin-7-yl)-1H-pyrazole-5-car-
  boxamide,
4-(azetidine-1-carbonyl)-1-methyl-N-(8-methyl-2-phe-
  nyl-[1,2,4]triazolo[1,5-a]pyridin-7-yl)-1H-pyrazole-5-
  carboxamide, and
4-(azetidine-1-carbonyl)-1-methyl-N-(6-methyl-2-phe-
  nyl-[1,2,4]triazolo[1,5-a]pyridin-7-yl)-1H-pyrazole-5-
  carboxamide,
or a pharmaceutically acceptable salt thereof.

11. The compound of claim 1, selected from the group consisting of:
N4,N4,1-trimethyl-N5-(2-phenyl-[1,2,4]triazolo[1,5-a]
  pyridin-7-yl)-1H-pyrazole-4,5-dicarboxamide,
1-methyl-4-(morpholine-4-carbonyl)-N-(2-phenyl-[1,2,4]
  triazolo[1,5-a]pyridin-7-yl)-1H-pyrazole-5-carboxam-
  ide,
1-methyl-N-(2-phenyl-[1,2,4]triazolo[1,5-a]pyridin-7-
  yl)-4-(pyrrolidine-1-carbonyl)-1H-pyrazole-5-car-
  boxamide,
(S)-1-methyl-N5-(2-phenyl-[1,2,4]triazolo[1,5-a]pyridin-
  7-yl)-N4-(tetrahydrofuran-3-yl)-1H-pyrazole-4,5-di-
  carboxamide,
(R)-1-methyl-N5-(2-phenyl-[1,2,4]triazolo[1,5-a]pyridin-
  7-yl)-N4-(tetrahydrofuran-3-yl)-1H-pyrazole-4,5-di-
  carboxamide,
N4-(3-methoxypropyl)-1-methyl-N5-(2-phenyl-[1,2,4]
  triazolo[1,5-a]pyridin-7-yl)-1H-pyrazole-4,5-dicar-
  boxamide,
1-methyl-N4-(oxetan-3-yl)-N5-(2-phenyl-[1,2,4]triazolo
  [1,5-a]pyridin-7-yl)-1H-pyrazole-4,5-dicarboxamide,
N4,N4-diethyl-1-methyl-N5-(2-phenyl-[1,2,4]triazolo[1,
  5-a]pyridin-7-yl)-1H-pyrazole-4,5-dicarboxamide,
N4-isopropyl-1-methyl-N5-(2-phenyl-[1,2,4]triazolo[1,5-
  a]pyridin-7-yl)-1H-pyrazole-4,5-dicarboxamide, and
N4,1-dimethyl-N4-(((6-methylpyridin-3-yl)methyl)-N5-
  (2-phenyl-[1,2,4]triazolo[1,5-a]pyridin-7-yl)-1H-pyra-
  zole-4,5-dicarboxamide,
or a pharmaceutically acceptable salt thereof.

12. The compound of claim 1, selected from the group consisting of:
N4-(2-fluoroethyl)-N4,1-dimethyl-N5-(2-morpholino-[1,
  2,4]triazolo[1,5-a]pyridin-7-yl)-1H-pyrazole-4,5-di-
  carboxamide,
4-(1,1-Dioxo-thiomorpholine-4-carbonyl)-2-methyl-2H-
  pyrazole-3-carboxylic acid (2-phenyl-[1,2,4]triazolo[1,
  5-a]pyridine-7-yl)-amide,
N4,1-dimethyl-N5-(2-phenyl-[1,2,4]triazolo[1,5-a]pyri-
  din-7-yl)-1H-pyrazole-4,5-dicarboxamide,
4-(3-methoxyazetidine-1-carbonyl)-1-methyl-N-(2-phe-
  nyl-[1,2,4]triazolo[1,5-a]pyridin-7-yl)-1H-pyrazole-5-
  carboxamide,
4-(3-fluoroazetidine-1-carbonyl)-1-methyl-N-(2-phenyl-
  [1,2,4]triazolo[1,5-a]pyridin-7-yl)-1H-pyrazole-5-car-
  boxamide,
2-Methyl-2H-pyrazole-3,4-dicarboxylic acid 4-[(2-
  fluoro-ethyl)-methyl-amide]3-[(2-phenyl-[1,2,4]tria-
  zolo[1,5-a]pyridin-7-yl)-amide],
isopropyl 1-methyl-5-(2-phenyl-[1,2,4]triazolo[1,5-a]py-
  ridin-7-ylcarbamoyl)-1H-pyrazole-4-carboxylate,
ethyl 1-methyl-5-(2-phenyl-[1,2,4]triazolo[1,5-a]pyridin-
  7-ylcarbamoyl)-1H-pyrazole-4-carboxylate,
1-methyl-4-(morpholine-4-carbonyl)-N-(2-morpholino-
  [1,2,4]triazolo[1,5-a]pyridin-7-yl)-1H-pyrazole-5-car-
  boxamide, and
4-(azetidine-1-carbonyl)-N-(6-fluoro-2-phenyl-[1,2,4]
  triazolo[1,5-a]pyridin-7-yl)-1-methyl-1H-pyrazole-5-
  carboxamide,
or a pharmaceutically acceptable salt thereof.

13. The compound of claim 1, selected from the group consisting of:
N-(6-fluoro-2-phenyl-[1,2,4]triazolo[1,5-a]pyridin-7-yl)-
  1-methyl-4-(pyrrolidine-1-carbonyl)-1H-pyrazole-5-
  carboxamide,
N-(6-fluoro-2-phenyl-[1,2,4]triazolo[1,5-a]pyridin-7-yl)-
  1-methyl-4-(morpholine-4-carbonyl)-1H-pyrazole-5-
  carboxamide,
7-(4-(azetidine-1-carbonyl)-1-methyl-1H-pyrazole-5-car-
  boxamido)-N-(3,3,3-trifluoropropyl)-[1,2,4]triazolo[1,
  5-a]pyridine-2-carboxamide,
N-(2-isopropyl-[1,2,4]triazolo[1,5-a]pyridin-7-yl)-1-me-
  thyl-4-(pyrrolidine-1-carbonyl)-1H-pyrazole-5-car-
  boxamide,
4-(azetidine-1-carbonyl)-N-(2-(dimethylamino)-[1,2,4]
  triazolo[1,5-a]pyridin-7-yl)-1-methyl-1H-pyrazole-5-
  carboxamide,
N-(2-(dimethylamino)-[1,2,4]triazolo[1,5-a]pyridin-7-
  yl)-1-methyl-4-(morpholine-4-carbonyl)-1H-pyrazole-
  5-carboxamide,
N-(2-(dimethylamino)-[1,2,4]triazolo[1,5-a]pyridin-7-
  yl)-1-methyl-4-(pyrrolidine-1-carbonyl)-1H-pyrazole-
  5-carboxamide,
N-(2-(dimethylamino)-[1,2,4]triazolo[1,5-a]pyridin-7-
  yl)-4-(3-fluoroazetidine-1-carbonyl)-1-methyl-1H-
  pyrazole-5-carboxamide,
N4,N4-diethyl-1-methyl-N5-(2-morpholino-[1,2,4]tria-
  zolo[1,5-a]pyridin-7-yl)-1H-pyrazole-4,5-dicarboxam-
  ide, and
N4,N4,1-trimethyl-N5-(2-morpholino-[1,2,4]triazolo[1,
  5-a]pyridin-7-yl)-1H-pyrazole-4,5-dicarboxamide, or a
  pharmaceutically acceptable salt thereof.

14. The compound of claim 1, selected from the group consisting of:
N4-ethyl-N4,1-dimethyl-N5-(2-morpholino-[1,2,4]tria-
  zolo[1,5-a]pyridin-7-yl)-1H-pyrazole-4,5-dicarboxam-
  ide,
1-methyl-N-(2-morpholino-[1,2,4]triazolo[1,5-a]pyridin-
  7-yl)-4-(pyrrolidine-1-carbonyl)-1H-pyrazole-5-car-
  boxamide,
4-(3-fluoroazetidine-1-carbonyl)-1-methyl-N-(2-mor-
  pholino-[1,2,4]triazolo[1,5-a]pyridin-7-yl)-1H-pyra-
  zole-5-carboxamide,
4-(azetidine-1-carbonyl)-1-methyl-N-(2-(pyridin-3-yl)-
  [1,2,4]triazolo[1,5-a]pyridin-7-yl)-1H-pyrazole-5-car-
  boxamide,
1-methyl-4-(morpholine-4-carbonyl)-N-(2-(pyridin-3-
  yl)-[1,2,4]triazolo[1,5-a]pyridin-7-yl)-1H-pyrazole-5-
  carboxamide,
1-methyl-N-(2-(pyridin-3-yl)-[1,2,4]triazolo[1,5-a]pyri-
  din-7-yl)-4-(pyrrolidine-1-carbonyl)-1H-pyrazole-5-
  carboxamide,
4-(3-fluoroazetidine-1-carbonyl)-1-methyl-N-(2-(pyri-
  din-3-yl)-[1,2,4]triazolo[1,5-a]pyridin-7-yl)-1H-pyra-
  zole-5-carboxamide,
N4-cyclopropyl-N4,1-dimethyl-N5-(2-phenyl-[1,2,4]tria-
  zolo[1,5-a]pyridin-7-yl)-1H-pyrazole-4,5-dicarboxam-
  ide, N4,1-dimethyl-N5-(2-phenyl-[1,2,4]triazolo[1,5-a]pyridin-7-yl)-N4-(2,2,2-trifluoroethyl)-1H-pyrazole-4,5-dicarboxamide, and 4-(azetidine-1-carbonyl)-N-(2-isopropyl-[1,2,4]triazolo[1,5-a]pyridin-7-yl)-1-methyl-1H-pyrazole-5-carboxamide, or a pharmaceutically acceptable salt thereof.

15. The compound of claim 1, selected from the group consisting of:

4-(3-fluoroazetidine-1-carbonyl)-N-(2-isopropyl-[1,2,4]triazolo[1,5-a]pyridin-7-yl)-1-methyl-1H-pyrazole-5-carboxamide, N4-cyclopentyl-N4,1-dimethyl-N5-(2-morpholino-[1,2,4]triazolo[1,5-a]pyridin-7-yl)-1H-pyrazole-4,5-dicarboxamide, N4-cyclopropyl-N4,1-dimethyl-N5-(2-morpholino-[1,2,4]triazolo[1,5-a]pyridin-7-yl)-1H-pyrazole-4,5-dicarboxamide, N4,1-dimethyl-N5-(2-morpholino-[1,2,4]triazolo[1,5-a]pyridin-7-yl)-N4-(2,2,2-trifluoroethyl)-1H-pyrazole-4,5-dicarboxamide, N4-cyclopropyl-N4,1-dimethyl-N5-(2-(pyridin-3-yl)-[1,2,4]triazolo[1,5-a]pyridin-7-yl)-1H-pyrazole-4,5-dicarboxamide, N4-(2-fluoroethyl)-N4,1-dimethyl-N5-(2-(pyridin-3-yl)-[1,2,4]triazolo[1,5-a]pyridin-7-yl)-1H-pyrazole-4,5-dicarboxamide, 4-((1S,4S)-2-oxa-5-azabicyclo[2.2.1]heptane-5-carbonyl)-1-methyl-N-(2-(pyridin-3-yl)-[1,2,4]triazolo[1,5-a]pyridin-7-yl)-1H-pyrazole-5-carboxamide, 4-(Azetidine-1-carbonyl)-2-methyl-2H-pyrazole-3-carboxylic acid [2-(ethyl-methyl-amino)-[1,2,4]triazolo[1,5-a]pyridin-7-yl]-amide, 2-Methyl-4-(morpholine-4-carbonyl)-2H-pyrazole-3-carboxylic acid [2-(ethyl-methyl-amino)-[1,2,4]triazolo[1,5-a]pyridin-7-yl]-amide, and 4-(azetidine-1-carbonyl)-1-methyl-N-(2-(pyrrolidin-1-yl)-[1,2,4]triazolo[1,5-a]pyridin-7-yl)-1H-pyrazole-5-carboxamide, or a pharmaceutically acceptable salt thereof.

16. The compound of claim 1, selected from the group consisting of:

1-methyl-4-(morpholine-4-carbonyl)-N-(2-(pyrrolidin-1-yl)-[1,2,4]triazolo[1,5-a]pyridin-7-yl)-1H-pyrazole-5-carboxamide, 7-(4-(azetidine-1-carbonyl)-1-methyl-1H-pyrazole-5-carboxamido)-N,N-dimethyl-[1,2,4]triazolo[1,5-a]pyridine-2-carboxamide, 7-(4-(azetidine-1-carbonyl)-1-methyl-1H-pyrazole-5-carboxamido)-N-ethyl-[1,2,4]triazolo[1,5-a]pyridine-2-carboxamide, 7-(4-(azetidine-1-carbonyl)-1-methyl-1H-pyrazole-5-carboxamido)-N-(2-methoxyethyl)-[1,2,4]triazolo[1,5-a]pyridine-2-carboxamide, 4-(azetidine-1-carbonyl)-N-(2-bromo-[1,2,4]triazolo[1,5-a]pyridin-7-yl)-1-methyl-1H-pyrazole-5-carboxamide, 4-(azetidine-1-carbonyl)-1-methyl-N-(2-(pyridin-4-yl)-[1,2,4]triazolo[1,5-a]pyridin-7-yl)-1H-pyrazole-5-carboxamide, 4-(azetidine-1-carbonyl)-1-methyl-N-(2-(2-methylpyridin-4-yl)-[1,2,4]triazolo[1,5-a]pyridin-7-yl)-1H-pyrazole-5-carboxamide, 4-(azetidine-1-carbonyl)-1-methyl-N-(2-(5-methylpyridin-3-yl)-[1,2,4]triazolo[1,5-a]pyridin-7-yl)-1H-pyrazole-5-carboxamide, N-(2-(2-methoxyphenyl)-[1,2,4]triazolo[1,5-a]pyridin-7-yl)-1-methyl-4-(morpholine-4-carbonyl)-1H-pyrazole-5-carboxamide, and 4-(azetidine-1-carbonyl)-N-(2-((2-fluoroethyl)(methyl)amino)-[1,2,4]triazolo[1,5-a]pyridin-7-yl)-1-methyl-1H-pyrazole-5-carboxamide, or a pharmaceutically acceptable salt thereof.

17. The compound of claim 1, selected from the group consisting of:

N-(2-((2-fluoroethyl)(methyl)amino)-[1,2,4]triazolo[1,5-a]pyridin-7-yl)-1-methyl-4-(morpholine-4-carbonyl)-1H-pyrazole-5-carboxamide, N5-(2-((2-fluoroethyl)(methyl)amino)-[1,2,4]triazolo[1,5-a]pyridin-7-yl)-N4,N4,1-trimethyl-1H-pyrazole-4,5-dicarboxamide, N4-ethyl-N5-(2-((2-fluoroethyl)(methyl)amino)-[1,2,4]triazolo[1,5-a]pyridin-7-yl)-N4,1-dimethyl-1H-pyrazole-4,5-dicarboxamide, N4-cyclopropyl-N5-(2-((2-fluoroethyl)(methyl)amino)-[1,2,4]triazolo[1,5-a]pyridin-7-yl)-N4,1-dimethyl-1H-pyrazole-4,5-dicarboxamide, 4-(Azetidine-1-carbonyl)-2-methyl-2H-pyrazole-3-carboxylic acid [2-(3-methoxy-phenyl)-[1,2,4]triazolo[1,5-a]pyridin-7-yl]-amide, 2-Methyl-4-(morpholine-4-carbonyl)-2H-pyrazole-3-carboxylic acid [2-(3-methoxy-phenyl)-[1,2,4]triazolo[1,5-a]pyridin-7-yl]-amide, 2-Methyl-2H-pyrazole-3,4-dicarboxylic acid 4-[(2-methoxy-ethyl)-methyl-amide]3-{[2-(3-methoxy-phenyl)-[1,2,4]triazolo[1,5-a]pyridin-7-yl]-amide}, 2-Methyl-2H-pyrazole-3,4-dicarboxylic acid 4-dimethylamide 3-{[2-(3-methoxy-phenyl)[1,2,4]triazolo[1,5-a]pyridin-7-yl]-amide}, 2-Methyl-2H-pyrazole-3,4-dicarboxylic acid 4-(ethyl-methyl-amide)3-{[2-(3-methoxy-phenyl)-[1,2,4]triazolo[1,5-a]pyridin-7-yl]-amide}, and 2-Methyl-4-(morpholine-4-carbonyl)-2H-pyrazole-3-carboxylic acid [2-(3-hydroxy-phenyl)-[1,2,4]triazolo[1,5-a]pyridin-7-yl]-amide, or a pharmaceutically acceptable salt thereof.

18. The compound of claim 1, selected from the group consisting of:

2-Methyl-4-(morpholine-4-carbonyl)-2H-pyrazole-3-carboxylic acid {2-[3-(2-fluoro-ethoxy)-phenyl]-[1,2,4]triazolo[1,5-a]pyridin-7-yl}-amide, 2-Methyl-4-(morpholine-4-carbonyl)-2H-pyrazole-3-carboxylic acid [2-(3-fluoromethoxy-phenyl)-[1,2,4]triazolo[1,5-a]pyridin-7-yl]-amide, 2-Methyl-2H-pyrazole-3,4-dicarboxylic acid 4-(ethyl-methyl-amide)3-({2-[3-(2-fluoro-ethoxy)-phenyl]-[1,2,4]triazolo[1,5-a]pyridin-7-yl}-amide), 2-Methyl-2H-pyrazole-3,4-dicarboxylic acid 4-(ethyl-methyl-amide)3-{[2-(3-fluoromethoxy-phenyl)-[1,2,4]triazolo[1,5-a]pyridin-7-yl]-amide}, 2-Methyl-2H-pyrazole-3,4-dicarboxylic acid 4-dimethylamide 3-({2-[3-(2-fluoro-ethoxy)-phenyl]-[1,2,4]triazolo[1,5-a]pyridin-7-yl}-amide), 2-Methyl-2H-pyrazole-3,4-dicarboxylic acid 4-dimethylamide 3-{[2-(3-fluoromethoxy-phenyl)-[1,2,4]triazolo[1,5-a]pyridin-7-yl]-amide}, 2-Methyl-2H-pyrazole-3,4-dicarboxylic acid 3-{[2-(3-hydroxy-phenyl)-[1,2,4]triazolo[1,5-a]pyridin-7-yl]-amide} 4-[(2-methoxy-ethyl)-methyl-amide], 2-Methyl-2H-pyrazole-3,4-dicarboxylic acid 3-({2-[3-(2-fluoro-ethoxy)-phenyl]-[1,2,4]triazolo[1,5-a]pyridin-7-yl}-amide)4-[(2-methoxy-ethyl)-methyl-amide], 2-Methyl-2H-pyrazole-3,4-dicarboxylic acid 3-{[2-(3-fluoromethoxy-phenyl)-[1,2,4]triazolo[1,5-a]pyridin-7-yl]-amide} 4-[(2-methoxy-ethyl)-methyl-amide], and
4-(Azetidine-1-carbonyl)-2-methyl-2H-pyrazole-3-carboxylic acid {2-[3-(2-fluoro-ethoxy)-phenyl][1,2,4]triazolo[1,5-a]pyridin-7-yl}-amide,
or a pharmaceutically acceptable salt thereof.

19. The compound of claim 1, selected from the group consisting of:
4-(Azetidine-1-carbonyl)-2-methyl-2H-pyrazole-3-carboxylic acid [2-(3-fluoromethoxy-phenyl)[1,2,4]triazolo[1,5-a]pyridin-7-yl]-amide,
2-Methyl-2H-pyrazole-3,4-dicarboxylic acid 4-[(2-hydroxy-ethyl)-methyl-amide]3-[(2-phenyl-[1,2,4]triazolo[1,5-a]pyridin-7-yl)-amide],
{Methyl-[1-methyl-5-(2-phenyl-[1,2,4]triazolo[1,5-a]pyridin-7-ylcarbamoyl)-1H-pyrazole-4-carbonyl]-amino}-acetic acid methyl ester,
2-Methyl-2H-pyrazole-3,4-dicarboxylic acid 4-[(2-hydroxy-ethyl)-methyl-amide]3-[(2-morpholin-4-yl-[1,2,4]triazolo[1,5-a]pyridin-7-yl)-amide],
{Methyl-[1-methyl-5-(2-morpholin-4-yl-[1,2,4]triazolo[1,5-a]pyridin-7-ylcarbamoyl)-1H-pyrazole-4-carbonyl]-amino}-acetic acid methyl ester,
2-Methyl-2H-pyrazole-3,4-dicarboxylic acid 4-[(2-fluoro-ethyl)-amide]3-[(2-phenyl[1,2,4]triazolo[1,5-a]pyridin-7-yl)-amide],
2-Methyl-2H-pyrazole-3,4-dicarboxylic acid 4-dimethylamide 3-{[2-(2-methoxy-phenyl)-[1,2,4]triazolo[1,5-a]pyridin-7-yl]-amide},
2-Methyl-2H-pyrazole-3,4-dicarboxylic acid 4-(ethyl-methyl-amide)3-{[2-(2-methoxy-phenyl)-[1,2,4]triazolo[1,5-a]pyridin-7-yl]-amide},
2-Methyl-2H-pyrazole-3,4-dicarboxylic acid 4-[(2-methoxy-ethyl)-methyl-amide]3-{[2-(2-methoxy-phenyl)-[1,2,4]triazolo[1,5-a]pyridin-7-yl]-amide}, and
2-Methyl-2H-pyrazole-3,4-dicarboxylic acid 4-dimethylamide 3-({2-[2-(2-fluoro-ethoxy)-phenyl]-[1,2,4]triazolo[1,5-a]pyridin-7-yl}-amide),
or a pharmaceutically acceptable salt thereof.

20. The compound of claim 1, selected from the group consisting of:
2-Methyl-2H-pyrazole-3,4-dicarboxylic acid 4-(ethyl-methyl-amide)3-({2-[2-(2-fluoro-ethoxy)-phenyl]-[1,2,4]triazolo[1,5-a]pyridin-7-yl}-amide),
4-(azetidine-1-carbonyl)-N-(2-(2-methoxyphenyl)-[1,2,4]triazolo[1,5-a]pyridin-7-yl)-1-methyl-1H-pyrazole-5-carboxamide,
N4-cyclopropyl-N5-(2-(2-methoxyphenyl)-[1,2,4]triazolo[1,5-a]pyridin-7-yl)-N4,1-dimethyl-1H-pyrazole-4,5-dicarboxamide,
N5-(2-(3-fluorophenyl)-[1,2,4]triazolo[1,5-a]pyridin-7-yl)-N4,N4,1-trimethyl-1H-pyrazole-4,5-dicarboxamide,
4-(azetidine-1-carbonyl)-N-(2-(3-fluorophenyl)-[1,2,4]triazolo[1,5-a]pyridin-7-yl)-1-methyl-1H-pyrazole-5-carboxamide,
N-(2-(3-fluorophenyl)-[1,2,4]triazolo[1,5-a]pyridin-7-yl)-1-methyl-4-(morpholine-4-carbonyl)-1H-pyrazole-5-carboxamide,
N-(2-(3-fluorophenyl)-[1,2,4]triazolo[1,5-a]pyridin-7-yl)-4-(3-methoxyazetidine-1-carbonyl)-1-methyl-1H-pyrazole-5-carboxamide,
N-(2-(3-fluorophenyl)-[1,2,4]triazolo[1,5-a]pyridin-7-yl)-1-methyl-4-(4-methylpiperazine-1-carbonyl)-1H-pyrazole-5-carboxamide,
N5-(2-(2-fluoropyridin-3-yl)-[1,2,4]triazolo[1,5-a]pyridin-7-yl)-N4,N4,1-trimethyl-1H-pyrazole-4,5-dicarboxamide,
4-(azetidine-1-carbonyl)-N-(2-(2-fluoropyridin-3-yl)-[1,2,4]triazolo[1,5-a]pyridin-7-yl)-1-methyl-1H-pyrazole-5-carboxamide; and
N-(2-(2-fluoropyridin-3-yl)-[1,2,4]triazolo[1,5-a]pyridin-7-yl)-1-methyl-4-(morpholine-4-carbonyl)-1H-pyrazole-5-carboxamide,
or a pharmaceutically acceptable salt thereof.

21. The compound of claim 1, selected from the group consisting of:
1-methyl-N-(2-morpholino-[1,2,4]triazolo[1,5-a]pyridin-7-yl)-4-(2-oxa-6-azaspiro[3.3]heptane-6-carbonyl)-1H-pyrazole-5-carboxamide,
N4-cyclopropyl-1-methyl-N5-(2-morpholino-[1,2,4]triazolo[1,5-a]pyridin-7-yl)-1H-pyrazole-4,5-dicarboxamide,
4-(3-fluoroazetidine-1-carbonyl)-N-(2-(2-fluoroethyl)(methyl)amino)-[1,2,4]triazolo[1,5-a]pyridin-7-yl)-1-methyl-1H-pyrazole-5-carboxamide,
N-(2-((2-fluoroethyl)(methyl)amino)-[1,2,4]triazolo[1,5-a]pyridin-7-yl)-1-methyl-4-(pyrrolidine-1-carbonyl)-1H-pyrazole-5-carboxamide,
N4-ethyl-N4,1-dimethyl-N5-(2-(pyridin-3-yl)-[1,2,4]triazolo[1,5-a]pyridin-7-yl)-1H-pyrazole-4,5-dicarboxamide,
N-(2-(2-fluoropyridin-4-yl)-[1,2,4]triazolo[1,5-a]pyridin-7-yl)-1-methyl-4-(morpholine-4-carbonyl)-1H-pyrazole-5-carboxamide,
4-(azetidine-1-carbonyl)-N-(2-(2-fluoropyridin-4-yl)-[1,2,4]triazolo[1,5-a]pyridin-7-yl)-1-methyl-1H-pyrazole-5-carboxamide,
4-(azetidine-1-carbonyl)-N-(2-(6-fluoropyridin-2-yl)-[1,2,4]triazolo[1,5-a]pyridin-7-yl)-1-methyl-1H-pyrazole-5-carboxamide,
N5-(2-(6-fluoropyridin-2-yl)-[1,2,4]triazolo[1,5-a]pyridin-7-yl)-N4,N4,1-trimethyl-1H-pyrazole-4,5-dicarboxamide,
N-(2-(6-fluoropyridin-2-yl)-[1,2,4]triazolo[1,5-a]pyridin-7-yl)-1-methyl-4-(morpholine-4-carbonyl)-1H-pyrazole-5-carboxamide, and
2-Methyl-4-(2-oxa-6-aza-spiro[3.3]heptane-6-carbonyl)-2H-pyrazole-3-carboxylic acid (2-pyrrolidin-1-yl-[1,2,4]triazolo[1,5-a]pyridin-7-yl)-amide,
or a pharmaceutically acceptable salt thereof.

22. The compound of claim 1, selected from the group consisting of:
2-Methyl-2H-pyrazole-3,4-dicarboxylic acid 4-(cyclopropyl-methyl-amide)3-[(2-pyrrolidin-1-yl-[1,2,4]triazolo[1,5-a]pyridin-7-yl)-amide],
2-Methyl-2H-pyrazole-3,4-dicarboxylic acid 4-(ethyl-methyl-amide)3-[(2-pyrrolidin-1-yl-[1,2,4]triazolo[1,5-a]pyridin-7-yl)-amide],
5-[2-(Cyclopropyl-methyl-amino)-[1,2,4]triazolo[1,5-a]pyridin-7-ylcarbamoyl]-1-methyl-1H-pyrazole-4-carboxylic acid,
2-Methyl-2H-pyrazole-3,4-dicarboxylic acid 4-(cyclopropyl-methyl-amide)3-{[2-(cyclopropyl-methyl-amino)-[1,2,4]triazolo[1,5-a]pyridin-7-yl]-amide},
4-(Azetidine-1-carbonyl)-2-methyl-2H-pyrazole-3-carboxylic acid [2-(cyclopropyl-methyl-amino)-[1,2,4]triazolo[1,5-a]pyridin-7-yl]-amide,
2-Methyl-4-(morpholine-4-carbonyl)-2H-pyrazole-3-carboxylic acid [2-(cyclopropyl-methyl-amino)-[1,2,4]triazolo[1,5-a]yridine-7-yl]-amide, 4-(1,4-Diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide, 4-(Azetidine-1-carbonyl)-2-methyl-2H-pyrazole-3-carboxylic acid {2-[2-(2-fluoro-ethoxy)-phenyl]-[1,2,4]triazolo[1,5-a]pyridin-7-yl}-amide, 2-Methyl-4-(morpholine-4-carbonyl)-2H-pyrazole-3-carboxylic acid {2-[2-(2-fluoro-ethoxy)-phenyl]-[1,2,4]triazolo[1,5-a]pyridin-7-yl}-amide, 2-Methyl-2H-pyrazole-3,4-dicarboxylic acid 3-({2-[2-(2-fluoro-ethoxy)-phenyl]-[1,2,4]triazolo[1,5-a]pyridin-7-yl}-amide)4-[(2-methoxy-ethyl)-methyl-amide], and Methyl-4-(morpholine-4-carbonyl)-N-(2-(2-oxopyrrolidin-1-yl)-[1,2,4]triazolo[1,5-a]pyridin-7-yl)-1H-pyrazole-5-carboxamide, or a pharmaceutically acceptable salt thereof.

23. The compound of claim 1, selected from the group consisting of:

4-(azetidine-1-carbonyl)-1-methyl-N-(2-phenyl-[1,2,4]triazolo[1,5-a]pyridin-7-yl)-1H-pyrazole-5-carboxamide, N4-ethyl-N4,1-dimethyl-N5-(2-phenyl-[1,2,4]triazolo[1,5-a]pyridin-7-yl)-1H-pyrazole-4,5-dicarboxamide, 4-(azetidine-1-carbonyl)-1-methyl-N-(2-morpholino-[1,2,4]triazolo[1,5-a]pyridin-7-yl)-1H-pyrazole-5-carboxamide, 1-methyl-4-(morpholine-4-carbonyl)-N-(2-phenyl-[1,2,4]triazolo[1,5-a]pyridin-7-yl)-1H-pyrazole-5-carboxamide, 1-methyl-N-(2-phenyl-[1,2,4]triazolo[1,5-a]pyridin-7-yl)-4-(pyrrolidine-1-carbonyl)-1H-pyrazole-5-carboxamide, 4-(3-fluoroazetidine-1-carbonyl)-1-methyl-N-(2-phenyl-[1,2,4]triazolo[1,5-a]pyridin-7-yl)-1H-pyrazole-5-carboxamide, 2-Methyl-2H-pyrazole-3,4-dicarboxylic acid 4-[(2-fluoro-ethyl)-methyl-amide]3-[(2-phenyl-[1,2,4]triazolo[1,5-a]pyridin-7-yl)-amide], 1-methyl-4-(morpholine-4-carbonyl)-N-(2-morpholino-[1,2,4]triazolo[1,5-a]pyridin-7-yl)-1H-pyrazole-5-carboxamide, 4-(azetidine-1-carbonyl)-N-(2-(dimethylamino)-[1,2,4]triazolo[1,5-a]pyridin-7-yl)-1-methyl-1H-pyrazole-5-carboxamide, and N-(2-(dimethylamino)-[1,2,4]triazolo[1,5-a]pyridin-7-yl)-1-methyl-4-(pyrrolidine-1-carbonyl)-1H-pyrazole-5-carboxamide, or a pharmaceutically acceptable salt thereof.

24. The compound of claim 1, selected from the group consisting of:

N-(2-(dimethylamino)-[1,2,4]triazolo[1,5-a]pyridin-7-yl)-4-(3-fluoroazetidine-1-carbonyl)-1-methyl-1H-pyrazole-5-carboxamide, 4-(azetidine-1-carbonyl)-1-methyl-N-(2-(pyridin-3-yl)-[1,2,4]triazolo[1,5-a]pyridin-7-yl)-1H-pyrazole-5-carboxamide, 1-methyl-4-(morpholine-4-carbonyl)-N-(2-(pyridin-3-yl)-[1,2,4]triazolo[1,5-a]pyridin-7-yl)-1H-pyrazole-5-carboxamide, N4-cyclopropyl-N4,1-dimethyl-N5-(2-phenyl-[1,2,4]triazolo[1,5-a]pyridin-7-yl)-1H-pyrazole-4,5-dicarboxamide, N4-cyclopropyl-N4,1-dimethyl-N5-(2-morpholino-[1,2,4]triazolo[1,5-a]pyridin-7-yl)-1H-pyrazole-4,5-dicarboxamide, N4-cyclopropyl-N4,1-dimethyl-N5-(2-(pyridin-3-yl)-[1,2,4]triazolo[1,5-a]pyridin-7-yl)-1H-pyrazole-4,5-dicarboxamide, 2-Methyl-4-(morpholine-4-carbonyl)-2H-pyrazole-3-carboxylic acid [2-(ethyl-methyl-amino)-[1,2,4]triazolo[1,5-a]pyridin-7-yl]-amide, 1-methyl-4-(morpholine-4-carbonyl)-N-(2-(pyrrolidin-1-yl)-[1,2,4]triazolo[1,5-a]pyridin-7-yl)-1H-pyrazole-5-carboxamide, N-(2-(2-methoxyphenyl)-[1,2,4]triazolo[1,5-a]pyridin-7-yl)-1-methyl-4-(morpholine-4-carbonyl)-1H-pyrazole-5-carboxamide, and 2-Methyl-4-(morpholine-4-carbonyl)-2H-pyrazole-3-carboxylic acid [2-(3-methoxy-phenyl)-[1,2,4]triazolo[1,5-a]pyridin-7-yl]-amide, or a pharmaceutically acceptable salt thereof.

25. The compound of claim 1, selected from the group consisting of:

2-Methyl-2H-pyrazole-3,4-dicarboxylic acid 4-[(2-methoxy-ethyl)-methyl-amide]3-{[2-(3-methoxy-phenyl)-[1,2,4]triazolo[1,5-a]pyridin-7-yl]-amide}, N5-(2-(3-fluorophenyl)-[1,2,4]triazolo[1,5-a]pyridin-7-yl)-N4,N4,1-trimethyl-1H-pyrazole-4,5-dicarboxamide, 4-(azetidine-1-carbonyl)-N-(2-(2-fluoropyridin-4-yl)-[1,2,4]triazolo[1,5-a]pyridin-7-yl)-1-methyl-1H-pyrazole-5-carboxamide, 2-Methyl-4-(2-oxa-6-aza-spiro[3.3]heptane-6-carbonyl)-2H-pyrazole-3-carboxylic acid (2-pyrrolidin-1-yl-[1,2,4]triazolo[1,5-a]pyridin-7-yl)-amide, 2-Methyl-2H-pyrazole-3,4-dicarboxylic acid 4-(cyclopropyl-methyl-amide)3-[(2-pyrrolidin-1-yl-[1,2,4]triazolo[1,5-a]pyridin-7-yl)-amide], 4-(Azetidine-1-carbonyl)-2-methyl-2H-pyrazole-3-carboxylic acid [2-(cyclopropyl-methyl-amino)-[1,2,4]triazolo[1,5-a]pyridin-7-yl]-amide, and 4-(1,4-Diaza-bicyclo[3.2.1]octane-4-carbonyl)-2-methyl-2H-pyrazole-3-carboxylic acid (2-phenyl-[1,2,4]triazolo[1,5-a]pyridin-7-yl)-amide, or a pharmaceutically acceptable salt thereof.

26. A pharmaceutical composition comprising a therapeutically effective amount of a compound of formula (I)

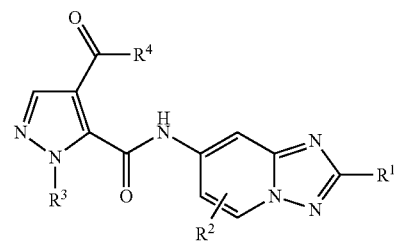

wherein

R$^1$ is halogen, lower-alkyl, lower-haloalkyl, lower-hydroxyalkyl, lower-alkoxy, lower-alkoxy-lower-alkyl, —C(O)—NR$^9$R$^{10}$, aryl, heteroaryl or NR$^7$R$^8$, wherein said aryl and said heteroaryl are each optionally substituted by 1 to 3 substituents independently selected from the group consisting of hydroxyl, halogen, lower-alkyl, lower-alkoxy, lower-alkoxy-lower-alkyl, lower-haloalkyl and lower-haloalkoxy;

R$^2$ is hydrogen, halogen, lower-alkyl, lower-haloalkyl, lower-hydroxyalkyl, lower-alkoxy or lower-alkoxy-lower-alkyl;

$R^3$ is hydrogen, lower-alkyl, lower-haloalkyl, lower-hydroxyalkyl, lower-alkoxy or lower-alkoxy-lower-alkyl;

$R^4$ is hydroxyl, lower-alkoxy or $NR^5R^6$;

$R^5$ and $R^6$ are each independently hydrogen, lower-alkyl, lower-haloalkyl, lower-hydroxyalkyl, lower-alkoxy-lower-alkyl, cycloalkyl or heterocyclyl, or $R^5$ and/or $R^6$ are lower-alkyl substituted by a substituent selected from the group consisting of heteroaryl, lower-alkyl-heteroaryl and lower-alkoxy-C(O)—, or $R^5$ and $R^6$, together with the nitrogen atom to which they are attached, form a heterocyclyl, bicyclo-heterocyclyl or spiro-heterocyclyl, wherein said heterocyclyl is optionally substituted by 1 to 3 substituents independently selected from the group consisting of hydroxyl, halogen, lower-alkyl, lower-alkoxy, lower-alkoxy-lower-alkyl, lower-haloalkyl and oxo;

$R^7$ and $R^8$ are each independently hydrogen, lower-alkyl, lower-haloalkyl, lower-hydroxyalkyl, lower-alkoxy-lower-alkyl or cycloalkyl, or $R^7$ and $R^8$, together with the nitrogen atom to which they are attached, form a heterocyclyl optionally substituted by a substituent selected from the group consisting of hydroxyl, halogen and oxo; and $R^9$ and $R^{10}$ are each independently hydrogen, lower-alkyl, lower-haloalkyl, lower-hydroxyalkyl or lower-alkoxy-lower-alkyl, or a pharmaceutically acceptable salt thereof
and a pharmaceutically acceptable carrier.

\* \* \* \* \*